United States Patent
McNally et al.

(10) Patent No.: US 9,873,739 B2
(45) Date of Patent: Jan. 23, 2018

(54) MITIGATING TISSUE DAMAGE AND FIBROSIS VIA LATENT TRANSFORMING GROWTH FACTOR BETA BINDING PROTEIN (LTBP4)

(71) Applicant: Ikaika Therapeutics, LLC, Oak Park, IL (US)

(72) Inventors: Elizabeth McNally, Oak Park, IL (US); Ahlke Heydemann, Oak Park, IL (US); Ermelinda Ceco, Chicago, IL (US)

(73) Assignee: Ikaika Therapeutics, LLC, Oak Park, IL (US)

(*) Notice: Subject to any disclaimer, the term of this patent is extended or adjusted under 35 U.S.C. 154(b) by 0 days.

(21) Appl. No.: 13/957,100

(22) Filed: Aug. 1, 2013

(65) Prior Publication Data

US 2014/0037637 A1    Feb. 6, 2014

Related U.S. Application Data

(60) Provisional application No. 61/678,564, filed on Aug. 1, 2012.

(51) Int. Cl.
| | |
|---|---|
| C07K 16/26 | (2006.01) |
| C07K 7/08 | (2006.01) |
| A61K 45/06 | (2006.01) |
| A61K 39/395 | (2006.01) |
| A61K 38/10 | (2006.01) |
| C07K 16/18 | (2006.01) |
| A61K 39/00 | (2006.01) |

(52) U.S. Cl.
CPC ............ *C07K 16/26* (2013.01); *A61K 38/10* (2013.01); *A61K 39/3955* (2013.01); *A61K 45/06* (2013.01); *C07K 16/18* (2013.01); *A61K 2039/505* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,816,567 A | 3/1989 | Cabilly et al. | |
| 5,057,540 A | 10/1991 | Kensil et al. | |
| 5,270,163 A | 12/1993 | Gold et al. | |
| 5,399,363 A | 3/1995 | Liversidge et al. | |
| 5,466,468 A | 11/1995 | Schneider et al. | |
| 5,637,459 A | 6/1997 | Burke et al. | |
| 5,720,950 A | 2/1998 | Poiani et al. | |
| 6,004,937 A | 12/1999 | Wood et al. | |
| 6,096,506 A | 8/2000 | Lee et al. | |
| 6,369,201 B1 | 4/2002 | Barker et al. | |
| 6,465,493 B1 | 10/2002 | Burgess et al. | |
| 6,468,535 B1 | 10/2002 | Lee et al. | |
| 6,906,089 B2 | 6/2005 | Gaster et al. | |
| 7,192,717 B2 | 3/2007 | Hill et al. | |
| 7,202,210 B2 | 4/2007 | Wolfman et al. | |
| 7,261,893 B2 | 8/2007 | Veldman et al. | |
| 7,320,789 B2 | 1/2008 | Dunham et al. | |
| 7,572,763 B2 | 8/2009 | Hill et al. | |
| 7,960,541 B2 | 6/2011 | Wilton et al. | |
| 7,973,015 B2 | 7/2011 | van Ommen et al. | |
| 8,084,601 B2 | 12/2011 | Popplewell et al. | |
| 2003/0166633 A1 | 9/2003 | Gaster et al. | |
| 2004/0039198 A1 | 2/2004 | Bender et al. | |
| 2004/0063745 A1 | 4/2004 | Gellibert et al. | |
| 2004/0138118 A1 | 7/2004 | Wolfman et al. | |
| 2004/0181033 A1 | 9/2004 | Han et al. | |
| 2004/0223966 A1 | 11/2004 | Wolfman et al. | |
| 2011/0151490 A1* | 6/2011 | Hillman et al. | ............ 435/7.92 |
| 2012/0039806 A1 | 2/2012 | Lahoud et al. | |
| 2012/0046345 A1 | 2/2012 | Collard et al. | |
| 2012/0058955 A1 | 3/2012 | Kichler et al. | |

FOREIGN PATENT DOCUMENTS

| | | |
|---|---|---|
| WO | WO-1990/14837 A1 | 12/1990 |
| WO | WO-00/043781 A2 | 7/2000 |
| WO | WO-01/05820 A2 | 1/2001 |
| WO | WO-01/53350 A1 | 7/2001 |
| WO | WO-0268650 A2 | 9/2002 |
| WO | WO-02/085306 A2 | 10/2002 |
| WO | WO-2004/083241 | 9/2004 |
| WO | WO-2005/084699 | 9/2005 |
| WO | WO-2005/094446 | 10/2005 |

(Continued)

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Brown et al. (J Immunol. May 1996;156(9):3285-91 at 3290 and Tables 1 and 2).*
Vajdos et al. (J Mol Biol. Jul. 5, 2002;320(2):415-28 at 416).*
Kringelum et al (Molecular Immunology 53 (2013) 24-34).*
Altschul et al., Basic local alignment search tool, J. Mol. Biol., 215(3):403-10 (1990).

(Continued)

*Primary Examiner* — Brian J Gangle
*Assistant Examiner* — Andrea McCollum
(74) *Attorney, Agent, or Firm* — Marshall, Gerstein & Borun LLP

(57) ABSTRACT

The disclosure relates to compositions and methods of mitigating tissue damage and fibrosis in a patient by modulating latent transforming growth factor beta binding protein (LTBP4)-induced proteolysis of a Transforming Growth Factor-beta (TGFβ) superfamily protein.

12 Claims, 11 Drawing Sheets

(56) References Cited

FOREIGN PATENT DOCUMENTS

| | | |
|---|---|---|
| WO | WO-2006/012627 | 2/2006 |
| WO | WO-2006/025988 | 9/2006 |
| WO | WO-2006/116269 | 11/2006 |
| WO | WO-2012/006181 | 1/2012 |

OTHER PUBLICATIONS

Banker (ed.), Pharmaceutics and Pharmacy Practice, Philadelphia, PA: J.B. Lippincott Co., pp. 238-250 (1982).
Berkner, Expression of heterologous sequences in adenoviral vectors, Curr. Top Microbiol. Immunol., 158:39-66 (1992).
Bernasconi et al., Expression of transforming growth factor-beta 1 in dystrophic patient muscles correlates with fibrosis. Pathogenetic role of a fibrogenic cytokine, J. Clin. Invest., 96(2):1137-44 (1995).
Bernstein et al., Role for a bidentate ribonuclease in the initiation step of RNA interference, Nature, 409(6818):363-6 (2001).
Burks et al., Role of TGF-b signaling in inherited and acquired myopathies, Skeletal Muscle, vol. 1, pp. 1-13 (2011).
Bushby et al., Interventions for muscular dystrophy: molecular medicines entering the clinic, Lancet, 374(9704):1849-56 (2009).
Caplen et al., Specific inhibition of gene expression by small double-stranded RNAs in invertebrate and vertebrate systems, Proc. Natl. Acad. Sci. USA, 98(17):9742-7 (2001).
Chang et al., Adjuvant activity of incomplete Freund's adjuvant, Adv. Drug Deliv. Rev., 32(3):173-86 (1998).
Chen et al., Early onset of inflammation and later involvement of TGFbeta in Duchenne muscular dystrophy, Neurology, 65(6):826-34 (2005).
Cohn et al., Angiotensin II type 1 receptor blockade attenuates TGF-beta-induced failure of muscle regeneration in multiple myopathic states, Nat. Med., 13(2):204-10 (2007).
Crawford et al., Peptide aptamers: Tools for biology and drug discovery, Briefings in Functional Genomics and Proteomics, 2(1):72-9 (2003).
Davis et al., Preparation and characterization of antibodies with specificity for the amino-terminal tetrapeptide sequence of the platelet-derived connective tissue activating peptide-III, Biochem. Int., 10(3):395-404 (1985).
Derynck et al., Smad-dependent and Smad-independent pathways in TGF-beta family signalling, Nature, 425(6958):577-84 (2003).
Erickson et al., The Proteins, 3rd ed., vol. 2, pp. 257-527 (1976).
Finn et al., The Proteins, 3rd ed., vol. 2, pp. 105-253 (1976).
Goldstein et al., SMAD signaling drives heart and muscle dysfunction in a *Drosophila* model of muscular dystrophy, Hum. Mol. Genet., 20(5):894-904 (2011).
Grant, Synthetic Peptides: A User's Guide, Oxford University Press (1992).
Heintz, BAC to the future: the use of bac transgenic mice for neuroscience research, Nat. Rev. Neurosci., 2(12):861-70 (2001).
Hersh et al., Genetic association analysis of functional impairment in chronic obstructive pulmonary disease, Am. J. Respir. Crit. Care Med., 173(9):977-84 (2006).
Heydemann et al., Genetic background influences muscular dystrophy, Neuromuscul. Disord., 15(9-10):601-9 (2005).
Heydemann et al., Latent TGF-beta-binding protein 4 modifies muscular dystrophy in mice, J. Clin. Invest., 119(12):3703-12 (2009).
Hoffman et al., Restoring dystrophin expression in duchenne muscular dystrophy muscle progress in exon skipping and stop codon read through, Am. J. Pathol., 179(1):12-22 (2011).
In Mice, CpG Outstrips Classic Vaccine Adjuvant 5-Fold; Clinical Trial Coming Soon, Bioworld Today, Nov. 5, 1998.
International Search Report and Written Opinion, PCT/US2013/053255, dated Dec. 19, 2013.
Javelaud et al., Mammalian transforming growth factor-betas: Smad signaling and physio-pathological roles, Int. J. Biochem. Cell Biol., 36(7):1161-5 (2004).
Kensil et al., IN: Powell et al., Vaccine Design: The Subunit and Adjuvant Approach, Plenum Press, NY (1995).
Kisseleva et al., Fibrogenesis of parenchymal organs, Proc. Am. Thorac. Soc., 5(3):338-42 (2008).
Kohler et al., Continuous cultures of fused cells secreting antibody of predefined specificity, Nature, 256:495-7 (1975).
Lan, Diverse roles of TGF-?/Smads in renal fibrosis and inflammation, Int. J. Biol. Sci., 7(7):1056-67 (2011).
Larsen et al., The Merrifield peptide synthesis studied by near-infrared Fourier-transform Raman spectroscopy, J. Am. Chem. Soc., 115:6247 (1993).
Lu et al., The status of exon skipping as a therapeutic approach to duchenne muscular dystrophy, Mol. Ther., 19(1):9-15 (2011).
Massague et al., Smad transcription factors, Genes Dev., 19(23):2783-810 (2005).
Mayer (ed.), Nucleic Acid and Peptide Aptamers: Methods and Protocols, Humana (2009).
McNally et al., Mild and severe muscular dystrophy caused by a single gamma-sarcoglycan mutation, Am. J. Hum. Genet., 59(5):1040-7 (1996).
Merrifield, Solid Phase Peptide Synthesis. I. The Synthesis of a Tetrapeptide, J. Am. Chem. Soc., 85:2149-54 (1963).
Moustakas et al., Mechanisms of TGF-beta signaling in regulation of cell growth and differentiation, Immunol. Lett., 82(1-2):85-91 (2002).
Nelson et al., Inhibiting TGF-? activity improves respiratory function in mdx mice, Am. J. Pathol., 178(6):2611-21 (2011).
O'Donnell et al., Solid-Phase Unnatural Peptide Synthesis (UPS), J. Am. Chem. Soc., 118(25):6070-1 (1996).
Powell, Drug delivery issues in vaccine development. Pharm. Res., 13(12):1777-85 (1996).
Rafael-Fortney et al., Early treatment with lisinopril and spironolactone preserves cardiac and skeletal muscle in Duchenne muscular dystrophy mice, Circulation, 124(5):582-8 (2011).
Rosenfeld et al., In vivo transfer of the human cystic fibrosis transmembrane conductance regulator gene to the airway epithelium, Cell, 68(1):143-55 (1992).
Ruiz-Ortega et al., TGF-beta signaling in vascular fibrosis, Cardiovasc. Res., 74(2):196-206 (2007).
Saharinen et al., Identification and characterization of a new latent transforming growth factor-beta-binding protein, LTBP-4, J. Biol. Chem., 273(29):18459-69 (1998).
Schmierer et al., TGFbeta-SMAD signal transduction: molecular specificity and functional flexibility, Nat. Rev. Mol. Cell Biol., 8(12):970-82 (2007).
Smith et al., Comparison of biosequences, Adv. Appl. Math., 2:482-9 (1981).
Smith et al., Solid-phase peptide synthesis and biological activity of bovine thymopoietin II (bTP-II), Int. J. Pept. Protein Res., 44(2):183-91 (1994).
Stewart et al., Solid Phase Peptide Synthesis, Freeman (1969).
Stoute et al., A preliminary evaluation of a recombinant circumsporozoite protein vaccine against Plasmodium falciparum malaria. RTS,S Malaria Vaccine Evaluation Group, N. Engl. J. Med., 336(2):86-91 (1997).
Stratford-Perricaudet et al., Evaluation of the transfer and expression in mice of an enzyme-encoding gene using a human adenovirus vector, Hum. Gene Ther., 1(3):241-56 (1990).
Stratford-Perricaudet et al., Widespread long-term gene transfer to mouse skeletal muscles and heart, J. Clin. Invest., 90(2):626-30 (1992).
Swaggart et al., Distinct genetic regions modify specific muscle groups in muscular dystrophy, Physiol. Genomics, 43(1):24-31 (2011).
Trissel, ASHP Handbook on Injectable Drugs, 4th ed., pp. 622-630 (1986).
Tuerk et al., Systematic evolution of ligands by exponential enrichment: RNA ligands to bacteriophage T4 DNA polymerase, Science, 249(4968):505-10 (1990).
Yan et al., Aptamers and aptamer targeted delivery, RNA Biol., 6(3):316-20 (2009).
Zhang et al., PowerBLAST: a new network BLAST application for interactive or automated sequence analysis and annotation, Genome Res., 7(6):649-56 (1997).

(56) References Cited

OTHER PUBLICATIONS

Ausubel et al., Current Protocols in Molecular Biology, Greene Publishing Associates and John Wiley & Sons, New York, N.Y. (1994), Table of Contents Only.
Bushby et al. "Diagnosis and management of Duchenne muscular dystrophy, part 1: diagnosis, and pharmacological and psychosocial management," Lancet Neurol 9:77-93 (2010).
Bushby et al. "Diagnosis and management of Duchenne muscular dystrophy, part 2: diagnosis, and pharmacological and psychosocial management," Lancet Neurol, 13 pages (2009).
Estiarte et al., Burgers Medicinal Chemistry, 6th edition, vol. 1, Part 4, John Wiley & Sons, New York (2002), Preface and Table of Contents Only.
Ge et al. "BMP1 Controls TGFβ1 Activation Via Cleavage of Latent TGFβ-Binding Protein," J Cell Biol. 175:111-120 (2006).
Rafael et al., "Testing of SHIRPA, a mouse phenotypic assessment protocol, on $Dmd^{mdx}$ and $Dmd^{mdx3cv}$ dystrophin-deficient mice," Mamm Genome. 11(9):725-8 (2000).
Rogers, et al., "Behavioral and functional analysis of mouse phenotype: SHIRPA, a proposed protocol for comprehenisve phenotype assessment," Mamm. Genome 8:711-713 (1997).
Sambrook et al., Molecular Cloning, a Laboratory Manual, 2d edition, Cold Spring Harbor Press, Cold Spring Harbor, N.Y. (1989), Cover and publisher information only.
Sterner-Kock et al. "Disruption of the gene encoding the latent transforming growth factor-beta binding protein 4 (LTBP-4) causes abnormal lung development, cardiomyopathy, and colorectal cancer," Genes and Development, Cold Spring Harbor Laboratory Press, 16(17):2264-2273 (2002).
Sinha et al. "Cellular and extracellular biology of the latent transforming growth factor-beta binding proteins," Matrix Biology. 17:529-545 (1998).

\* cited by examiner

A.

B.

A.

B.

SEQUENCE LISTING

```
<160> NUMBER OF SEQ ID NOS: 13

<210> SEQ ID NO 1
<211> LENGTH: 1624
<212> TYPE: PRT
<213> ORGANISM: Homo sapiens
<220> FEATURE:
<221> NAME/KEY: MISC_FEATURE
<222> LOCATION: (357)..(586)
<223> OTHER INFORMATION: TP2E fragment
<220> FEATURE:
<221> NAME/KEY: MISC_FEATURE
<222> LOCATION: (483)..(565)
<223> OTHER INFORMATION: TP fragment

<400> SEQUENCE: 1

Met Pro Arg Pro Gly Thr Ser Gly Arg Arg Pro Leu Leu Leu Val Leu
```

-continued

```
  1               5                  10                 15
Leu Leu Pro Leu Phe Ala Ala Thr Ser Ala Ala Ser Pro Ser Pro
                20                  25                 30

Ser Pro Ser Gln Val Val Glu Val Pro Gly Val Pro Ser Arg Pro Ala
                35                  40                 45

Ser Val Ala Val Cys Arg Cys Pro Gly Gln Thr Ser Arg Arg Ser
 50                  55                  60

Arg Cys Ile Arg Ala Phe Cys Arg Val Arg Ser Cys Gln Pro Lys Lys
 65                  70                  75                 80

Cys Ala Gly Pro Gln Arg Cys Leu Asn Pro Val Pro Ala Val Pro Ser
                85                  90                 95

Pro Ser Pro Ser Val Arg Lys Arg Gln Val Ser Leu Asn Trp Gln Pro
                100                 105                110

Leu Thr Leu Gln Glu Ala Arg Ala Leu Leu Lys Arg Arg Pro Arg
                115                 120                125

Gly Pro Gly Gly Arg Gly Leu Leu Arg Arg Pro Pro Gln Arg Ala
                130                 135                140

Pro Ala Gly Lys Ala Pro Val Leu Cys Pro Leu Ile Cys His Asn Gly
145                 150                 155                160

Gly Val Cys Val Lys Pro Asp Arg Cys Leu Cys Pro Pro Asp Phe Ala
                165                 170                175

Gly Lys Phe Cys Gln Leu His Ser Ser Gly Ala Arg Pro Pro Ala Pro
                180                 185                190

Ala Val Pro Gly Leu Thr Arg Ser Val Tyr Thr Met Pro Leu Ala Asn
                195                 200                205

His Arg Asp Asp Glu His Gly Val Ala Ser Met Val Ser Val His Val
210                 215                 220

Glu His Pro Gln Glu Ala Ser Val Val His Gln Val Glu Arg Val
225                 230                 235                240

Ser Gly Pro Trp Glu Glu Ala Asp Ala Glu Ala Val Ala Arg Ala Glu
                245                 250                255

Ala Ala Ala Arg Ala Glu Ala Ala Ala Pro Tyr Thr Val Leu Ala Gln
                260                 265                270

Ser Ala Pro Arg Glu Asp Gly Tyr Ser Asp Ala Ser Gly Phe Gly Tyr
                275                 280                285

Cys Phe Arg Glu Leu Arg Gly Gly Glu Cys Ala Ser Pro Leu Pro Gly
                290                 295                300

Leu Arg Thr Gln Glu Val Cys Cys Arg Gly Ala Gly Leu Ala Trp Gly
305                 310                 315                320

Val His Asp Cys Gln Leu Cys Ser Glu Arg Leu Gly Asn Ser Glu Arg
                325                 330                335

Val Ser Ala Pro Asp Gly Pro Cys Pro Thr Gly Phe Glu Arg Val Asn
                340                 345                350

Gly Ser Cys Glu Asp Val Asp Glu Cys Ala Thr Gly Arg Cys Gln
                355                 360                365

His Gly Glu Cys Ala Asn Thr Arg Gly Gly Tyr Thr Cys Val Cys Pro
                370                 375                380

Asp Gly Phe Leu Leu Asp Ser Ser Arg Ser Ser Cys Ile Ser Gln His
385                 390                 395                400

Val Ile Ser Glu Ala Lys Gly Pro Cys Phe Arg Val Leu Arg Asp Gly
                405                 410                415

Gly Cys Ser Leu Pro Ile Leu Arg Asn Ile Thr Lys Gln Ile Cys Cys
                420                 425                430
```

```
Cys Ser Arg Val Gly Lys Ala Trp Gly Arg Gly Cys Gln Leu Cys Pro
        435                 440                 445
Pro Phe Gly Ser Glu Gly Phe Arg Glu Ile Cys Pro Ala Gly Pro Gly
    450                 455                 460
Tyr His Tyr Ser Ala Ser Asp Leu Arg Tyr Asn Thr Arg Pro Leu Gly
465                 470                 475                 480
Gln Glu Pro Pro Arg Val Ser Leu Ser Gln Pro Arg Thr Leu Pro Ala
                485                 490                 495
Thr Ser Arg Pro Ser Ala Gly Phe Leu Pro Thr His Arg Leu Glu Pro
            500                 505                 510
Arg Pro Glu Pro Arg Pro Asp Pro Arg Pro Gly Pro Glu Leu Pro Leu
        515                 520                 525
Pro Ser Ile Pro Ala Trp Thr Gly Pro Glu Ile Pro Glu Ser Gly Pro
    530                 535                 540
Ser Ser Gly Met Cys Gln Arg Asn Pro Gln Val Cys Gly Pro Gly Arg
545                 550                 555                 560
Cys Ile Ser Arg Pro Ser Gly Tyr Thr Cys Ala Cys Asp Ser Gly Phe
                565                 570                 575
Arg Leu Ser Pro Gln Gly Thr Arg Cys Ile Asp Val Asp Glu Cys Arg
            580                 585                 590
Arg Val Pro Pro Pro Cys Ala Pro Gly Arg Cys Glu Asn Ser Pro Gly
        595                 600                 605
Ser Phe Arg Cys Val Cys Gly Pro Gly Phe Arg Ala Gly Pro Arg Ala
    610                 615                 620
Ala Glu Cys Leu Asp Val Asp Glu Cys His Arg Val Pro Pro Pro Cys
625                 630                 635                 640
Asp Leu Gly Arg Cys Glu Asn Thr Pro Gly Ser Phe Leu Cys Val Cys
                645                 650                 655
Pro Ala Gly Tyr Gln Ala Ala Pro His Gly Ala Ser Cys Gln Asp Val
            660                 665                 670
Asp Glu Cys Thr Gln Ser Pro Gly Leu Cys Gly Arg Gly Ala Cys Lys
        675                 680                 685
Asn Leu Pro Gly Ser Phe Arg Cys Val Cys Pro Ala Gly Phe Arg Gly
    690                 695                 700
Ser Ala Cys Glu Glu Asp Val Asp Glu Cys Ala Gln Glu Pro Pro Pro
705                 710                 715                 720
Cys Gly Pro Gly Arg Cys Asp Asn Thr Ala Gly Ser Phe His Cys Ala
                725                 730                 735
Cys Pro Ala Gly Phe Arg Ser Arg Gly Pro Gly Ala Pro Cys Gln Asp
            740                 745                 750
Val Asp Glu Cys Ala Arg Ser Pro Pro Pro Cys Thr Tyr Gly Arg Cys
        755                 760                 765
Glu Asn Thr Glu Gly Ser Phe Gln Cys Val Cys Pro Met Gly Phe Gln
    770                 775                 780
Pro Asn Thr Ala Gly Ser Glu Cys Glu Asp Val Asp Glu Cys Glu Asn
785                 790                 795                 800
His Leu Ala Cys Pro Gly Gln Glu Cys Val Asn Ser Pro Gly Ser Phe
                805                 810                 815
Gln Cys Arg Thr Cys Pro Ser Gly His His Leu His Arg Gly Arg Cys
            820                 825                 830
Thr Asp Val Asp Glu Cys Ser Ser Gly Ala Pro Pro Cys Gly Pro His
        835                 840                 845
```

-continued

Gly His Cys Thr Asn Thr Glu Gly Ser Phe Arg Cys Ser Cys Ala Pro
850                 855                 860

Gly Tyr Arg Ala Pro Ser Gly Arg Pro Gly Pro Cys Ala Asp Val Asn
865                 870                 875                 880

Glu Cys Leu Glu Gly Asp Phe Cys Phe Pro His Gly Glu Cys Leu Asn
            885                 890                 895

Thr Asp Gly Ser Phe Ala Cys Thr Cys Ala Pro Gly Tyr Arg Pro Gly
                900                 905                 910

Pro Arg Gly Ala Ser Cys Leu Asp Val Asp Glu Cys Ser Glu Glu Asp
            915                 920                 925

Leu Cys Gln Ser Gly Ile Cys Thr Asn Thr Asp Gly Ser Phe Glu Cys
930                 935                 940

Ile Cys Pro Pro Gly His Arg Ala Gly Pro Asp Leu Ala Ser Cys Leu
945                 950                 955                 960

Asp Val Asp Glu Cys Arg Glu Arg Gly Pro Ala Leu Cys Gly Ser Gln
                965                 970                 975

Arg Cys Glu Asn Ser Pro Gly Ser Tyr Arg Cys Val Arg Asp Cys Asp
            980                 985                 990

Pro Gly Tyr His Ala Gly Pro Glu Gly Thr Cys Asp Asp Val Asp Glu
            995                 1000                1005

Cys Gln Glu Tyr Gly Pro Glu Ile Cys Gly Ala Gln Arg Cys Glu
    1010                1015                1020

Asn Thr Pro Gly Ser Tyr Arg Cys Thr Pro Ala Cys Asp Pro Gly
    1025                1030                1035

Tyr Gln Pro Thr Pro Gly Gly Gly Cys Gln Asp Val Asp Glu Cys
    1040                1045                1050

Arg Asn Arg Ser Phe Cys Gly Ala His Ala Val Cys Gln Asn Leu
    1055                1060                1065

Pro Gly Ser Phe Gln Cys Leu Cys Asp Gln Gly Tyr Glu Gly Ala
    1070                1075                1080

Arg Asp Gly Arg His Cys Val Asp Val Asn Glu Cys Glu Thr Leu
    1085                1090                1095

Gln Gly Val Cys Gly Ala Ala Leu Cys Glu Asn Val Glu Gly Ser
    1100                1105                1110

Phe Leu Cys Val Cys Pro Asn Ser Pro Glu Glu Phe Asp Pro Met
    1115                1120                1125

Thr Gly Arg Cys Val Pro Pro Arg Thr Ser Ala Gly Thr Phe Pro
    1130                1135                1140

Gly Ser Gln Pro Gln Ala Pro Ala Ser Pro Val Leu Pro Ala Arg
    1145                1150                1155

Pro Pro Pro Pro Pro Leu Pro Arg Arg Pro Ser Thr Pro Arg Gln
    1160                1165                1170

Gly Pro Val Gly Ser Gly Arg Arg Glu Cys Tyr Phe Asp Thr Ala
    1175                1180                1185

Ala Pro Asp Ala Cys Asp Asn Ile Leu Ala Arg Asn Val Thr Trp
    1190                1195                1200

Gln Glu Cys Cys Cys Thr Val Gly Glu Gly Trp Gly Ser Gly Cys
    1205                1210                1215

Arg Ile Gln Gln Cys Pro Gly Thr Glu Thr Ala Glu Tyr Gln Ser
    1220                1225                1230

Leu Cys Pro His Gly Arg Gly Tyr Leu Ala Pro Ser Gly Asp Leu
    1235                1240                1245

Ser Leu Arg Arg Asp Val Asp Glu Cys Gln Leu Phe Arg Asp Gln

```
                    1250                      1255                      1260
Val  Cys  Lys  Ser  Gly  Val  Cys  Val  Asn  Thr  Ala  Pro  Gly  Tyr  Ser
          1265                      1270                      1275

Cys  Tyr  Cys  Ser  Asn  Gly  Tyr  Tyr  Tyr  His  Thr  Gln  Arg  Leu  Glu
          1280                      1285                      1290

Cys  Ile  Asp  Asn  Asp  Glu  Cys  Ala  Asp  Glu  Glu  Pro  Ala  Cys  Glu
          1295                      1300                      1305

Gly  Gly  Arg  Cys  Val  Asn  Thr  Val  Gly  Ser  Tyr  His  Cys  Thr  Cys
          1310                      1315                      1320

Glu  Pro  Pro  Leu  Val  Leu  Asp  Gly  Ser  Gln  Arg  Arg  Cys  Val  Ser
          1325                      1330                      1335

Asn  Glu  Ser  Gln  Ser  Leu  Asp  Asp  Asn  Leu  Gly  Val  Cys  Trp  Gln
          1340                      1345                      1350

Glu  Val  Gly  Ala  Asp  Leu  Val  Cys  Ser  His  Pro  Arg  Leu  Asp  Arg
          1355                      1360                      1365

Gln  Ala  Thr  Tyr  Thr  Glu  Cys  Cys  Cys  Leu  Tyr  Gly  Glu  Ala  Trp
          1370                      1375                      1380

Gly  Met  Asp  Cys  Ala  Leu  Cys  Pro  Ala  Gln  Asp  Ser  Asp  Asp  Phe
          1385                      1390                      1395

Glu  Ala  Leu  Cys  Asn  Val  Leu  Arg  Pro  Pro  Ala  Tyr  Ser  Pro  Pro
          1400                      1405                      1410

Arg  Pro  Gly  Gly  Phe  Gly  Leu  Pro  Tyr  Glu  Tyr  Gly  Pro  Asp  Leu
          1415                      1420                      1425

Gly  Pro  Pro  Tyr  Gln  Gly  Leu  Pro  Tyr  Gly  Pro  Glu  Leu  Tyr  Pro
          1430                      1435                      1440

Pro  Pro  Ala  Leu  Pro  Tyr  Asp  Pro  Tyr  Pro  Pro  Pro  Gly  Pro
          1445                      1450                      1455

Phe  Ala  Arg  Arg  Glu  Ala  Pro  Tyr  Gly  Ala  Pro  Arg  Phe  Asp  Met
          1460                      1465                      1470

Pro  Asp  Phe  Glu  Asp  Asp  Gly  Gly  Pro  Tyr  Gly  Glu  Ser  Glu  Ala
          1475                      1480                      1485

Pro  Ala  Pro  Pro  Gly  Pro  Gly  Thr  Arg  Trp  Pro  Tyr  Arg  Ser  Arg
          1490                      1495                      1500

Asp  Thr  Arg  Arg  Ser  Phe  Pro  Glu  Pro  Glu  Glu  Pro  Pro  Glu  Gly
          1505                      1510                      1515

Gly  Ser  Tyr  Ala  Gly  Ser  Leu  Ala  Glu  Pro  Tyr  Glu  Glu  Leu  Glu
          1520                      1525                      1530

Ala  Glu  Glu  Cys  Gly  Ile  Leu  Asp  Gly  Cys  Thr  Asn  Gly  Arg  Cys
          1535                      1540                      1545

Val  Arg  Val  Pro  Glu  Gly  Phe  Thr  Cys  Arg  Cys  Phe  Asp  Gly  Tyr
          1550                      1555                      1560

Arg  Leu  Asp  Met  Thr  Arg  Met  Ala  Cys  Val  Asp  Ile  Asn  Glu  Cys
          1565                      1570                      1575

Asp  Glu  Ala  Glu  Ala  Ala  Ser  Pro  Leu  Cys  Val  Asn  Ala  Arg  Cys
          1580                      1585                      1590

Leu  Asn  Thr  Asp  Gly  Ser  Phe  Arg  Cys  Ile  Cys  Arg  Pro  Gly  Phe
          1595                      1600                      1605

Ala  Pro  Thr  His  Gln  Pro  His  His  Cys  Ala  Pro  Ala  Arg  Pro  Arg
          1610                      1615                      1620

Ala

<210> SEQ ID NO 2
<211> LENGTH: 18
```

```
<212> TYPE: PRT
<213> ORGANISM: Mus musculus

<400> SEQUENCE: 2

Glu Pro Arg Pro Arg Pro Glu Pro Arg Pro Gln Pro Glu Ser Gln Pro
1               5                   10                  15

Trp Pro

<210> SEQ ID NO 3
<211> LENGTH: 17
<212> TYPE: PRT
<213> ORGANISM: Homo sapiens

<400> SEQUENCE: 3

Glu Pro Arg Pro Glu Pro Arg Pro Asp Pro Arg Pro Gly Pro Glu Leu
1               5                   10                  15

Pro

<210> SEQ ID NO 4
<211> LENGTH: 18
<212> TYPE: PRT
<213> ORGANISM: Mus musculus

<400> SEQUENCE: 4

Glu Ser Gln Pro Arg Pro Glu Ser Arg Pro Arg Pro Glu Ser Gln Pro
1               5                   10                  15

Trp Pro

<210> SEQ ID NO 5
<211> LENGTH: 19
<212> TYPE: PRT
<213> ORGANISM: Homo sapiens

<400> SEQUENCE: 5

Glu Pro Arg Pro Glu Pro Arg Pro Asp Pro Arg Pro Gly Pro Glu Leu
1               5                   10                  15

Pro Leu Pro

<210> SEQ ID NO 6
<211> LENGTH: 43
<212> TYPE: PRT
<213> ORGANISM: Homo sapiens

<400> SEQUENCE: 6

Phe Leu Pro Thr His Arg Leu Glu Pro Arg Pro Glu Pro Arg Pro Asp
1               5                   10                  15

Pro Arg Pro Gly Pro Glu Leu Pro Leu Pro Ser Ile Pro Ala Trp Thr
            20                  25                  30

Gly Pro Glu Ile Pro Glu Ser Gly Pro Ser Ser
        35                  40

<210> SEQ ID NO 7
<211> LENGTH: 155085
<212> TYPE: DNA
<213> ORGANISM: Homo sapiens

<400> SEQUENCE: 7
aagctttata ttataaatac aaagtaaaca tgaaaataaa acccaaacat agcagtgtta      60
ttaaactctg gcctgtagca gtggctcaca cctgtaatcc tagcagtttg gaggccgaga     120
caggtggatt acttgagacc tggagtttga gaccagccca ggtgacacag caagacctca     180
```

```
tctctactaa aaataaaaaa aaattagcca ggtgtggtgg tatgcacctg tggtcccagc      240
tacttaggat gctggagtgc gaggatcgct tgagcccagg aggtcaaggc tgcagtgaac      300
tatgatcact cattacaccc cagcctgggt gacagagcga gatgctgtct caaaacaaaa      360
caaaacgaaa aacaactctg gctagatgct attgcttgcc aagggtgcag tcttccattt      420
attaaaagtg aaaattaggg ccaggcacat ggctcatgc ctgtaatccc agcactttgg       480
gaggctgagg tgggtggatc acctgaggtc aggagttcga ccagcctg gccaacatgg        540 tgaaaccttg tctctgccaa aaatataaaa gattagccat gtgtcgtggt gggtgcttgt      600
aatctcagct acttgggagg ctgaggcagg agaatcactt gaacccagga ggcagaggtt      660
gcagtgagcc aagattgtgc cattgcactc cagcctgtgc aacgagcgaa actccaactc      720
aaaaaaaaaa aaaaaaaaa aaacggaaaa ttaggtaata ctgcagattc attaatatca      780
cagcagcact aaactcagtc ttcctctgtg ctgggctcaa gggaactgaa agggaagtaa      840
cttgctatgt ggttcagtgt catttcatgc tgtgtcactg caccacttaa aatcttcacc      900
cggagactat gtcccacaca tggggaaatc aatcaccgtc atattttaag tgcttgctgt      960
gtgacagcca cgattacaat gactgttact ctacctctta ttctcactgt agtgttccca     1020
gtgaagcggc ggaaccggca cagcctagtg gggcctcagc agctaggagg acggccagcc     1080
cctgtccgac ggagcaacac gatgccccc aaccttggca atgcagggct gctgggccga      1140
atgctggatg agaaaacccc tccctcaccc tcaggtacgt ttctatctcg tggaaggttg     1200
gggcagctgt ggggtccctg tgaccctctt ctgatcccta ctcttcccct caaggacaac     1260
ctgaggagcc ggggatggtg cgcctggtgt gtggacacca taattggatc gctgtggcct     1320
atacccagtt tctagtctgc tacaggtgct tggggaggga gtggcaggag gtcccagccc     1380
tgttgatggg aagggcatgc ggtgagggtt ggtgatgtcc cctcgatcct acaggttgaa     1440
ggaagcctct ggctggcagc tggtgttttc cagcccccgc ctggactggc ccatcgaacg     1500
actggcgctc acagcccggg tgcatggtgg ggctttgggt gaacatgaca agatggtggc     1560
agcagccacc ggcagcgaga tcctgctatg ggctctgcag gcggaaggcg gtggctccga     1620
gataggtatg accccaagcc ttttccagaa ccctctgtcc tttaaattct actgcctgtt     1680
aaaatgaccc accccataaa atcctcaaac ccataagaat tctctgctct attagatctg     1740
tttgtgtcat tagaatgctc cagcccttca gaattctgta tcctgttaga attccctggc     1800
ttcctagaaa aatccaccca catacaattc tccctccatc agaattccct gccctgttag     1860
atctcttggt tttgttagaa tgcgctattc tgtgtggcca tgagaaatgt ctgacttggc     1920
ccggtgcggt ggctcatgct tgtaatccca gcactttggg aggctgaggc gggcagatca     1980
cttgaggtca ggagttcgag acccccttgg ccaacagggt gaaacccagt ctttatttca     2040
aaaatacaaa aaattagct gggtgtggtg gcacgtgcct gtaatcccag ctactcagga     2100
ggttaaggca ggagaatcac tggaacctgg gaggcagatg ttgcagtgag ctgagatcgc     2160
accactgcat tccagcctga gcgacagagt ggacagagtg agacaccatc tcaaaaaaaa     2220 aaaaaaaca aaaaagaaa tctctgactt atggctgggc acagtaactc acatctgtag      2280
ttccagcact ttgggaggcc atggcaggag gattgcttga ggccaggagt tcgaggctgc     2340
cgtgagctat gtaagccatg attgcaccac tgcactccag cctggacaac agagcaagac     2400
cctgtctcaa agccacagca acaaatctcg gacttattaa tctgtcccca aataaatctc     2460
agccctcgta agaatcccct gccaccagtg gaggtttttt tgccttattg caaatctcag     2520
```

```
tgctgttaga attccagacc gttttagaat cccataccccc atcagaaatc ttctggccca    2580
ttttatcttc tctaattcct gctggaatct tcactttttt tttttttgaa atggagtcat    2640
tctctgttgc ccagattgga gtacagtggt atgatctcgg ctcactgcaa cctctgcctc    2700
ctggggtcac gcaattctcc ttcctcaacc tcccaagtag ctgggctac agttgtgtgc     2760 taccacactc agctaatttt tatatttttt agtagagatg gagtttcatc atgttggcca    2820
ggctggtctc aaactcctgg cctcaaatga tccgcccacc tgagcctctc aaagtgttgg    2880
gattacaggt gtgagccact gtgcccagcc cctgatggaa tcttctatcc ttcaaggatt    2940
ctgtggtccc actgaaccct ctggtccttg gagttcttcc tcccacctct cctcctccat    3000
gaggcagggt tccagctgag ccctttttgc ccactgcagg ggtctttcat ctgggggtgc    3060
ctgtggaggc cttgttcttc gtcgggaacc agctcattgc tacaagccac acagggcgca    3120
tcggggtgtg gaatgccgtc accaagcact ggcaggtcag agttctggcc agcctggctg    3180 ccccttccc agttttccag actgtacaga cccaggaagg ggttcacgtc tgcccccacc     3240 cccacccct aagcctggag gaagccagag aaccagcagc tggccagagc tggggatgt     3300 ctgtgataaa ggcctaagga gcaccaggga agccttcctg gaggaggtgc tgcagagccc    3360
acatgaagca tgaatgggtt tgaaaaggag tagggaggat tgtcttggga ctgggtgaga    3420
gagcaggtta ggggggatgc tgtagaagac aagaactggc ttggctcggt ggctcacact    3480
tgtaatccca gcactttggg aggctgaggt gggaggatgg ctttgggaga agacagaca    3540 gaggcagaga aagagacaga gaggcagaaa accaggcaaa tagaaataga aaatcagaaa    3600
gaggtgacag agaagggtag acagagtcaa accagactga accactgtgg cagatggggg    3660
aactcagaga gataaatgga gatgaattag agtcatgtca gaagtacata gtggaggccg    3720
ggtgcagtga ctcccgcccg taatcccagc actttgggag gccgaggcaa gaggatggct    3780
tgagcccagg agtttgacgc cagcctggga aacataataa gactctgtct ctacaaaaaa    3840
tttaaaaaat taaaacttta aaaagtacag agtccaggag aggccaagag tcagacagac    3900
agatgcatca aagggaggaa gggagggaac aagacaggga caaaggcagg cctggggtgg    3960
acggggctgg ggagcagtgg gtgggttctg gaggtggagg agagggccca tcctctgtga    4020
ggggtcacca cggaaggaaa ggaatggaag ggctcccggc tgcagcctgt cctgcccac     4080 ccccaggtcc aggaggtgca gcccatcacc agttatgacg cggcaggctc cttcctcctc    4140
ctgggctgca caacggctc catttactac gtgggtgagc agcagcctgt gtcccgggtg     4200
cccgagaccc tccctggga gaggggaagg gaggagaga ggctggggca cttggaacaa      4260
acccgctcca ccctccctgc ccaccccaga tgtgcagaag ttcccttgc gcatgaaaga     4320 caacgacctc cttgtcagcg agctctatcg ggacccagcg gaggatgggg tcaccgccct    4380
cagtgtctac ctcaccccca agaccagtaa gctatgaccc ggcttccct gctgctgtca     4440 cctgccagcc ccagccccag cctgcagctg tccccaact tgtgtagcat gacccagagg     4500
ggtttatcga ggggcggcag attcaactct ctctcatttt tttttctgag acagactctc    4560
attctgttgc ccaggctgga gtgcagtggt gcaatcttgg ctcactgcaa cctccacctc    4620
ctgagttcaa gcgattctcc tgcctcagcc tcccaagtag ctaggattac aggcgcccac    4680
tgccacgcct ggctaatttt tgtagtttta gtagagatgg ggtttcacca tgttggccag    4740
gctggtcttg aactcctgac ctcagatgat cctcccgcct cagccccca aagtactggg     4800 attacagacg tgagccaccg cgcccagcca gattcaactc tcatccagtc attcaacaaa    4860
tatttactga gtatccctgt atataagcac gttctaggtg ctagatggtg gccaccctct    4920
```

```
ccactagggg cagaatggac cattaggagt taatctttgt gtttctttcc cacctttgtg   4980
attaaggcat gatgttcaca tgttcataaa acaacacaga tgcaggtttt acagcagatg   5040
aacctgagtt ctcttacttg agacagtttt ttgttttgtt ttcttgacat caaatgcaga   5100
atgggttaat ttttgagacg taattctcat accataaaat ttcccatttg aacgtgcaca   5160
attcagcgga ttttagtata ttcacaaggt tgtacaacta tcaccatgaa caaattccag   5220
agtatgttca tcaccccgt aagaaacccc ctgatcttta gcagtaactc cacatttctc   5280
acttctgata ccctctagaa atcactaata tgctttctct ttttgtttga dacaaggtct   5340
cgctctgctg cccaggctgg agtgcagtgg catgatctca gctcactgca atctctgcct   5400
cttgggttca agcgattctc atgcctcagc ttcctgagta ggggaggatt acaggtgtgc   5460
atcaccatgc ctggctaatt tttctacttt aagtagagac tgggttacgc cacgttggcc   5520
aggctcaata tgcttcctat acctatggat ttgcctgttc tggacaattc ctgtaaatgg   5580
gatcatacat tatatggtct tttgtgtctg cattttttcac ttagcatatt ttttaaatg   5640 gttagtgttt tctgggtctt aagatatcct tacctattct aggttacaaa gatcttctcc   5700
tgaatttctt ctagaagatt tacagtttag ttttacatg gaagtctgtt ctatcagaaa   5760
ttaaatttta tgtatggtgt gaagcaggga ttattctttt ttaaaaaaaa atagagacag   5820
ggtcttgctc tgttgcccag gctagagtgc agtggcatga tgtgagttct ctgccacctc   5880
cgccactcgg gctcaagcga ttcttctacc tcaacctcct gaacagcaga accacaggca   5940
tgcatcacca cacctgtcta atttttgtat ttttttgtag agacagggtt ttgccatgtt   6000
gcccaggcta ctcttgaact cctgggctca agtgatcctc cactttggc ctccaaagtg   6060 ctggaaatac agactgagt cactgtgctt ggccatagct gctgctgctg cttttcttt   6120 tttttaaag cagaaataag ttaataatac cctaacttc atgacacatt atcacctttc   6180
ttctttgtaa ggcccttttc ttattctctt tttttcttc tttctttttt ttttttttg   6240 tcttttcctg agacagagta tcgctctgtc attcaaccca ggctggagtg caatggcgca   6300
atctcagctc actacaacct ctgcctcctg ggttcaagca attctccaga ctcagcctcc   6360
caagtagctg ggattacggg tgcctgccac catgcccagc taattttgt gttttagta   6420 gaggcagggt tttgccacgt tggctaagca agttttgaac tcctgggatt ctcctctcgt   6480
cgtctcccaa agtgctggaa ttacaggcat gggctgctgc acccggcctc tttcttattt   6540
cacttactta ctcatttcct cctcatctcc cttcccgcca catgccacta ttatgtcatt   6600
tttctttgtt ttttgagaca gtctcgcttc gtcacctagg ctggagtgca gtggcgcaat   6660
catagctcac tgcagcctca ccccctgggc tcaagtgatc ctcctacttc agcctcttga   6720
gtagctggga tcataggtga atgccatcac acccaactag ttttttaaaa atcttttgta   6780
gagatgaggg tctcactatg ttgcccaggc tggcctcaaa cgcctggcct caagcaatct   6840
tcctgcctcg gcctctgttc tctgttttac ttttctcttt ctctcttatt tgctgtttca   6900
ctgttacaat ttctgtctct gggcctctcc tcctttgacc tgtgcctttg tctccctgtt   6960
cctccatttc ccacatctca tcaccatctt tttgtgtcct tccctctctc cttgcttttct   7020 gactgtgtct ctgttctgtg tctctttctt tctttctttc tttttttttt tttgagacag   7080
agtcacattc tgtcatgcag gctggagtgc agtggcgtgg tcttggctca ttgcaacctc   7140
tgcctcctgg gttcaagcaa ttctcatgcc tcagccttct gagtagctgg gattacaggt   7200
gcgtactacc accaccagct aattttgta ttttactag agacagggtt tcagcacgtt   7260
```

```
ggccaggctg gtcttgaacg cctgacctca agcgatccac ccgcctcagc ttcccaaagt   7320
gatgggatta cggcgtgagc caccgtgccc ggcctctcct tgctttctga ctgtgtctct   7380
gttctgtgcc tgtttctttc tccctgccct ggtttctgtc tctgtggccc aggccctctc   7440
ctcatccttg gcccctcacc aggtgacagt gggaactgga tcgagatcgc ctatggcacc   7500
agctcagggg gcgtgcgggt catcgtgcag cacccggaga ctgtgggctc ggggcctcag   7560
ctcttccaga ccttcactgt gcaccgcagc cctgtcacca agatcatgct gtcggagaag   7620
cacctcatct caggtgagcc tctgtggggt gctccagtgc tgggagagac agctcagatg   7680
ggagtgtgga gacaggagga tgagaatttc cactggggag ggacattgtg taggaagaga   7740
gctctggcgg agaggattga cctgggatgg gactgtaatt gcagaagtga gagaatacca   7800
taggggatca gtctggggaa gagtgaatct gtgtgtgttt gggaatccat caattcagca   7860
acgatttacg gggcacccac catgtgccag gcatagggga tacagtgatg aacaagacag   7920
gccaagtccc tgccctcgtg gagctgacat tctagcagcg atggcagaca ataaatctat   7980
aaaaatggac atcaatggcc agctgcggtg gctcacacct ataatcccag aactttggga   8040
ggccaaggcg ggtagattac ttgaggtcag gagttcgaga ccagcctggc caacatggtg   8100
aaaccccacc tctaccaaaa atataaaaaa ttagccaggt gtggtggcac gtgcctgtaa   8160
tccccgctac tcgggaggcc gagggaggag aattgcttga acctgggagg cggagattgc   8220
agagagccca gatcatgcta ctgcactcca gcctaggcaa cagagcgaga ctccatctca   8280
aaaataaata gataaaaatg caaatcaggc tgggcactgt ggctcatgcc tataatccca   8340
gcactttggg aggccaaggt gggaggattg cttgaggcta ggagtgtgag accaacctgg   8400
acaacaaagt gagacattgt ttctacaaaa aattttttaaa aaattagcca agtatggtgg   8460
catgcacctg gggtcccagc ttcttgggag gctgaggtgg agggatcact tgagcccaag   8520 agtcagggc tgcaatcagc tatgattgca ccctgcact ccagcccagg caacaaagca   8580
agactctatc tcataaaata ttaataaaat aatctaaatc aacaccaggc aatgataagg   8640
gctatgaata aacatgaagc tgtgtgtggc tagagagtgt caagtcgctg gagaggggtc   8700
attcagggaa ggcctgagga aggacctttg agcagaaata acagaatgag cagtgcagat   8760
tggtagggac aagcattcag gccgagggaa caggcattgc aaaggctctg aggtgagagg   8820
atgcctgagg aagtgcaggg agccacttgt gcctggaaca gagtaaatga ggggagaat   8880 gggaggagat gagggtatgg aggtgacaag ggcaggagcc acagagggct ccgagcaggg   8940
gagggacatg actagcttca ggtgttcaca ggctccacct ggctgcccgt gggagcacac   9000
tactgggata ggacaggagc agggacctct gggaggggcg tgctgatacg gtccaggcag   9060
gtgacgaaat ggaccaggac cggtgtgggg cagaggatag ggcaaggtga gatcaggctc   9120
tggaacagtt ttggaggcag aggcaacagg gtttttaaca tttggaattc tggggaggaa   9180
aggattctct gaaagggaag aactcagcaa gggctgaccc tcctgaaacg gggctgtcct   9240
gaggctctgg acgggcaggc agcattgatg cctgcaccag gcctgacttc ctgctctcct   9300
tgtgcccctc agtctgtgcc gacaacaacc acgtgcggac atggtctgtg actcgcttcc   9360
gcggcatgat ttccacccag cccggctcca ccccactcgc ttcctttaag atcctggctc   9420
tggagtcggc agatgggcat ggcggctgca gtgctggcaa tgacattggt gcctactggc   9480
tcctggcctt cccaccccac tgaccccctt acctgacccc tgttgacctc cgctgattcc   9540
cacttgcgga cacctgaccc aggagcctgc aacgattggg gtgtcctgat ccttgaggca   9600
cctgagctcc actgactgcc acaaccccccc agccctctct ggccctgccc aactctaaca   9660
```

```
acctggggat gggactgggg tcttggggtg gtgggtttca tcagtgggga aggaagtctg    9720
aggctgaggg aatcccagct ggccctgacc cctgcccctg cctggcccag gcccctacgg    9780
tgagcgggac gaccagcaag tgttcatcca gaaggtggtg cccagtgcca gccagctctt    9840
cgtgcgtctc tcatctactg ggcagcgtg aggacagtcc tgtccaacag ggagggagga    9900
cagtcctgtc caacagggag ggaggtcagg ggagaaggca agatgctagc cagatcactg    9960
aggccagaaa gggtcccag ccaaggagca ttgaaggagc aaaggctggg agggaggaca   10020
ggcctggtag gtttgtcttc tggtatcaaa ggtgtgacag gtgttggtgg gactgacctg   10080
gcgcagtgcc agcccagtgc aggcagggcc aggttgaagg cacaggggt ggggtcaggg   10140 tgggatgggg ggcccaggcg gaggggagg ggtgggatgg gggccaggg ggagaggtcg   10200 gggtgggatg gggggaccag ggggaggggt tggggtggga taggggggacc aggggcaggg   10260 gtcgggatgg gatggaggag acccaggag ctgtaggagc cttgcttcag ctgggaaagg   10320
ggcctcggag gatgttctgg atgaaggga tctgagcaga gacctagagg acaagtagga   10380
aggagcagaa gaaagaaggc aggggaaggg ggccccagcc tgagggaact gtatgtgcag   10440
aggctgagaa gggccaaata gggtcacatg gaaggacac gtgggctcct gggctggagc   10500
acagaacagg aggtgaggat ggggtgcaga tgcgggcggg ccttgtcagg ctgtggaagg   10560
gctgaggctt tgtcctgtgc ggggagccgt ggccactgca tggggatga aaggaggctt   10620 gatgggagc caggagccca gggaggaggc caggaggctg ataggaggtg ggggagcagc   10680
tgggacgggc ctcaggtctt ccctgcagtg ggagcaggga agagcagaag ctctgggaga   10740
ctccctgggt gtttgggct gcggtgtcca agagctgctg gacccttggg actggaactc   10800
aaaagcaggc tagggatgga taaagattgg gatggcccct ggagaggcag gaactgcagc   10860
cacagtggtg gggactggga cgaggaaggg tgagaaagcg agggtgacca cctcccccac   10920 tgcaccccc agggtgtgct ccgtgcgctc cgtggacggc tcaccacga cagccttcac   10980 agtgctggag tgcgagggct cccggcggct cggctctcgg ccccggcgct acctgctcac   11040
tggccaggcc aacggcagct tggccatgtg ggacctaacc accgcatgg acggcctcgg   11100 ccaggcccct ggtactccct gccccacccc aatcccgtcc caagccccac agcctcaccc   11160
agaaccactc tccactgcca actgcttgat ctctctccca ggcccttgcc ctctgacccc   11220
ttttcctttg accccctctc tgctccccat cccttcctgc ccttgttttt caacccctgt   11280
ctcagcctct ggcccccatg cattgatctc tgcttcctct ctcctgtcct gaccctcggt   11340
gcttgcactg caatgcaacc caggcccttg ccctatgacc cctgtcttgc cccctgaccc   11400
tgcttccgtg ccccccagca ggtggcctga cggagcaaga gctgatggaa cagctggaac   11460
actgtgagct ggccccgccg gctccttcag ctccctcatg gggctgtctc ccagcccct   11520 caccccgcat ctccctcacc aggtagccac aactccactg ccccttctgt gcaatgaggg   11580 gagagggac agcatggtgt cccggggac agagtggccc agctgccccg tgatgacgtg   11640
cacttactgt ccttacttcc tcagcctcca ctcagcctcc agcaacacct ccttgtctgg   11700
ccaccgtggg agcccaagcc ccccgcaggc tgaggcccgg cgccgtggtg ggggcagctt   11760
tgtggaacgc tgccaggaac tggtgcggag tgggccagac ctccgacggc cacccacacc   11820
agccccgtgg ccctccagcg gtctcggcac tcccctcaca cctcccaaga tgaagctcaa   11880
tgaaacttcc ttttgaacaa cgcagctgcc atgatgcctt gggatgccct ggtcctgggg   11940
gactcaggtg cctccctgat tcctgtggga accccgggtt cagggccagg gcctccttgg   12000
```

```
aataaatggt tattgttact aggtccccac cttccctctt ttctggaagc caaagtcacc   12060
ctccccaata aagtcctcac tgccaacatc ttgcttattc ttagcaggtt tgggactccc   12120
caggaaaggg gtggggaaga tgtgggaccc aacccgatat atgcaaaatc aggaacatct   12180
acctctcttg tttaagcaaa gggaggccag gcatggtggc tcacatctat aatcctggca   12240
ctttgggagg ccagtttgct tgtgctcaga agtttcagac tagcctgggc aacataacaa   12300
aaccccatct ctacaaaaaa atacaaaaat taagcaggca tggtggtgca tgcctgtggt   12360
cccagcttct tgggaggctg aggtgggagg atcgcttgag cctaggaggc caaggctaca   12420
gtgagccatg atcacaccac tgcactccag cctgagtgac agagtgagat cctgtctcaa   12480
aaacaaaaca aaacaaaaaa ggtgttgcag gggaggaatg tgttggcttt tactctgcct   12540
tcaggcatgg ctggatccgg ggcttcaaac actaattcag aatatctttt tttctttttt   12600
cttttctttt ttaaagtctc actctgtcat ccaggctgga gtgtagtggt atgatctcag   12660
ctcactgcaa cctccacctc ccgggttcaa gcaatcgcaa tcctcctgca tcagcctccc   12720
gagtagctgg gattacaggt gtgcaccacc atgcccagct aatttttttta tttttagtag   12780 agacagagtt tcaccatatt ggccaggctg gtctcgaact cctgacctca ggtgatctgc   12840
ccacctcagc ctcccaaagt gctgggatta caggcgagag ccactgtgtc cggcccagaa   12900
tatcttttta tctcctaact tcacttacct ctggaataca tcttcaatca ggttttctct   12960
ctgtggcaag gtgactctaa gcagctgctt agcaactctt tcttccctag caacagcaaa   13020
aatcacaaga ctgattttca ttggcttgaa ttaagtcagg tggccattcc tgaaccaatt   13080
actgtggcca gtgtgatgaa ggccttccat tattgcagcc tggatcatgt gtcctgctgt   13140 attttagta gaggcagggt ttcaccatgt tggccaggct ggtctcaaac tcctgacctc   13200
agatgatcca cctaactcgg cctcccagag tgctgggatt acaggcgtga gccaccttc    13260 ctggctggcc ttgggatttt ttttcccccaa ataatgcccg ttcctacggc acttccttga   13320
ggagattttc tgcatctttt ttccttgtgc caataaaaaa gggacagaaa gtggggacag   13380
actaggagta gagaatacta gaacatgcta attctagaat tccatagttt ctggaatgcc   13440
agagcttctg aaacatagta gagaggggtc tcgaacatta ggacatctcg gacacaagga   13500
tattctggag tgctcatgga ttaacaatat tagagttctc ccctgcttat cagagaatcc   13560
agaatataga agtttctgac aaaaaggacc tgaaaaatca ctgattctag aatagggag    13620 tgtcaagggg agttcatacc catgaatctc caccggtagg aatatcttgc atgccaggat   13680
gtctggaatg ctgagaatta taggatacag aaaggaacct ggattactag gaaatctaga   13740
gaatgggaga gatcctggac tatccgccct tccagagcac tggaaggttt gtttgcgttc   13800
caagaaatcc ataatggcag gagattccgg attatcagag aatctggaac acaaatggga   13860
gacgtaaaag gtgagtgcct ctgaaaccgg ggtgttctga aatagctgtg cacctcaaac   13920
cctaattttg tttttgtttg tttgttttg agacagggtc ttgctttgtt gcccgggcta   13980
gggtgcagtg gtgcaatcat ggctcactgc agcctcggcc ttctgggctc aagtgatcct   14040
cctgcctcag cctcctgagt atttgggact acaggtgtgt gccaccacag ccagctactt   14100
tttaagtttt tttgtagaga cattgtctca ctatgttgcc caggctggtc tcaaactcct   14160
gggctcaagc cattctcctg ccttagcctc ccaaagtgct gggattacag gtgtgagcta   14220
ccatgcccag cctcacactc tagaaaattt tttacatgcc aggatattca gaatattggg   14280
ggatattggc atgttaggaa atctagtatg tagggggagg gcctgaaagg tcaggaaatc   14340
tagaatatgg tggtgttttg taatgctcac agatctagaa tattagagtc attttttttt   14400
```

```
ccaggccgga gaatccagaa cgctcgtgtt gctgaaatgc tggtcattct attcttattt    14460
catgtttaaa tttttattat tttctttatt tcttttttt gagacagggt ctttctctgt     14520
tgcccgggtt ggagtgcagt ggtgtgatct cagctcacct caacctctgc ctcccgggtt    14580
caagtgatcc tcccaccttag gcctcttgag tagccgggat tacaggcgtg cgccaccatg   14640
cctggataat ttttgtattc ttagtagaga cagggtttca ctgtgttggc caggctggcc    14700
tgaaactcct gacctcaagt gatctgccct cccacctcgg cctcccaaag tgctgggatt    14760
acagacgtga gccggcctta ttctgggggga ggggtgggg gggagagag agagagggag     14820
agagagagga gaatttggga tgttagcaaa tctagaacac tgaagagctg ggtttttaa     14880
atgctagaga tagtattatc ctagtatagt attaactctg tgtgttttg tgcgtgagag     14940
ggcatggggg gaggggtgga agattctgga atgcgggggg actagaactc tgagggattc    15000
tgaagggttg agatgagtta ggattcaaga ggtgacatag acacgatcct gggagatagt    15060
gacactgatg ggagggatgg ggagctgggg actccaaatt ctaggggggag gggaggctaa    15120
cgccggaagt tgcagtggtg agccagagga tgttgcctag caacaagcat tgaagatgcg    15180
ctggatcccg gacagaaggg agaaatttca gcagcgcccc cagcaaatgc tccagccaca    15240
gggtaggagg tggtgagggg ggaagcgggt agggatatgc tgtcctgcag ggtcatgtga    15300
gcaggggtct tgggggttat acaaaaacag ggtcatggag tacagtcatg gggcagagcc    15360
gggctctggg acagcccacg aatagctgtg aatggagtgt gagtgccgtc gtcacctgcc    15420
ccagggactg tgtgtccctg gacggtgctg gacccagatt tctgggtgtc agtgtgggat    15480
ggaggcatgg attgctgtag gtggcagtaa tggtgtgtag ccgtgtgagt cagcctgtgt    15540
gtctcacagt gagcggggggt gaagggcttc cccgtcagtc ctgcacaccc tcctggattg    15600
gaagaaggag caggagtggg gggtggggggg tgcaactgga tcagttgcca ttcttggtct    15660
ggggtgggct ctgtggtcac ggcgtgtggc ctagtaccct gtgtgggtgg agcctgggat    15720
ccacgaggtg ggggcggggc taacgctaca gaactgggaa gcttaagaat ccaactgctt    15780
tgggatatgg ggcctggaac cccaaagcga agcaaacatg aaaggggtgg gcttgggatc    15840
ctacatgtgg tcacgtccca gttttctgtg ggaaagggtg tggcctgaaa ctctggaaaa    15900
agaggtgatt aggggcagag tgaagctctg agggtggtgc cttagggaga gaaggggctt    15960
gtatttcaga gaatatagggg tggagccttg aatttataat gatcttctca aagaattgat    16020
cccttctcaa ggccctaggc ttcaggggtt ccaggctcac catctgcaaa agcttgctcc    16080
ccgaagctct gtccctcagt gaacccagcc aggctctgcc cctgacccac aggatctgct    16140
cccaggggggt cctgggggct cctggctctg cccctcctg cacctcactt attgccatcc   16200
ccagagggta tcagaccccc ttccttgcct gagtctttga atgctcccaa gagctttgag    16260
tctcaagctg ggcttgagac cctgagtttg aaggcttgaa gcctggaacc ccggtgtgga    16320
cggggtttaa gggcccctgt ggcttgcagc tcctagtggt ggagactctt aggcaaggaa    16380
gggatcggta ctctctttta tatagtttta tgtatttatt tattattgag atagggtctc    16440
actctatcgt ccaggctgga gtgcagtgca gtgcagtggt gccatctcaa ctcactgcag    16500
cctccactta ccaggctcaa gtgatcctcc tacctcatcc tcccgagtag ctgggactac    16560
tggctcatgc caccataccc ggctaatttt tggattttt tttttttttt tttttttt      16620
ttttttgag acagagtctt gctctgtcgc ccaggctaga gtgcagtggt gtgatcttgg    16680
ctcactgcaa cctccacctc ctgggttcaa acgattctcc tgcctcagcc tcccgagtcg    16740
```

```
ctgggattac aggcgcccac cactgcaccc agctaatttt tgtattttt agtagagatg    16800
gggtttcacc atcttggcca ggctggtctc gaactcctga cctcatgatc cacccgcctc    16860
ggcctcccaa agtgctggga ttacaggcat gagccaccgc gcccggccta attttggat    16920
ttttaataga gatggggtcc tatgttgtac tatgttgctc aggctcacct caaactcctg    16980
gactcaagcg atccacctcg gccttccaaa gtgctgggat tacaggcccg cgccagggca    17040
cctagccgga actgggaact ctctaaggag aaagtctgca attctgggtg gtgggaggct    17100
gctcttggga gcattcaaag actcaggcaa ggaagggggt ctgatacct ctggggggcgg    17160
cgataagtgg ggtgcaggag ggggcagagc caggagcacc ctgggagcag agtttgtgga    17220
tcaggggcag agcctggctg ggttcactga gggacagagc ttcggggagc aagcttttgc    17280
agatggtgag cctggaatcc ctgaagccca gggtcttgag aagagatcaa ttctttgaga    17340
agatccaatg tgaacttggg accctcagag gggcaggacc tgggggctgg tgcagggttg    17400
gtgctccatt tgcagaatcc tcagtctctc tcgtggaaag gggtacccgt gggggggcttc    17460
cagcttctac gccagcgagg gagctaaatt ctgaccgaat tctcccagaa ctgggagcag    17520
agagctgagg actgccagat ggagtccagc ttaggggacc ctgcccccaa ccccgctccc    17580
gtatccctcc cattttaag cacccctacg cctgggacct ctgttccacg agaaggttca    17640
cggagccagt atccgagtcc taatttcccc ccaccgcgtg gggaactcga ggtccccgc    17700
gcccctagtc cggcacctgt ccctgctgcc tcctgattgg ccgcgcggcg agcgctggcg    17760
gcgccgggct gtgattggcg ggaagttcgc agcccgtggc tggactgtgg agaaagtgag    17820
tcggcctcgg gcggggggcgg gggcggggggc aggggcgggg ccggggctag cctgacccgc    17880
tggacagacc gcccgcccgg agcgggactc ggcgcccgac acgatgccga ggcctggcac    17940
cagcggccgc cgccccctcc tgctggtgct gttgctgccg ctcttcgcag ccgccacctc    18000
cgccgccagc cccagcccca gcccagcca ggtcgtcgag gtcccgggggg tccccagccg    18060
cccggccagg taagccccct gcttccttgt gccccttcca cccaataagt ctggtggtcc    18120
aggaggacca cggctttcgg attcagggga aactcgaacc cactgcttcg atgtggagat    18180
gcaaagaggg cccttggatt tattaggcgc cctcaatttg taggggttag attcgggag    18240
tactgagatt tttaggggaa agagtcccct ttattgtggt ggagaaggct aagtctccag    18300
agaatcctgg ggttagttcg gggaaaaggtc tctagttat tggggcaggg ggtgggggc    18360
tgagctctcc tagaatgata gagacgtgtg gggtcttcga gctaggatgg agcgcccaa    18420
gtttcttggg cgcgtaagga ggaaaggtgt tggggattc tggagggact ttatgaggcc    18480
gctgagttgt cctggtttc taggatttgg gggctctgtg ttcatgaaaa gcgacctttg    18540
ggttttcga attggtcagg aagacataga ctcttgcgtt gatggtggag gggcttgtgg    18600
ggagtggggt cgggtgggggg agtcctcagg cttcagaacg gttgggatg ctcaagtttc    18660
ctagaattag aggactctgg gattgaatga ggctccagtg atttcaccgc gagagatcca    18720
ggattcccta tagatctggg ggctataggc gcccttcctg tctgcgggtg acggactga    18780
aggaagccgt ctgcccagca cccccaccca ccctccccgc ctggcggccc agcgctccgt    18840
tacaaaggcc ccgggctcct ctcccgcctg ggtctctgcg aatgcgttta gtaacccgag    18900
ccgcggcggg ggcggggccg ggaagggggtt aacctggaga aaaggcggga gggatgacgg    18960
caagatcggg gatccccgag gctccccacc agatggcctc atcctccact cggccccacc    19020
cacctgagag gggccacgc gctggacacc ccctctctg cacccccccca ctgctctcct    19080
ctcggggtct gggcgcgcgc cctcgtctct agacccccctt agcctgggga taatggactt    19140
```

```
gtctgggggg cccottcatt gcgacgcact tgaaccggag ctggaagctc cgccactgag   19200
accctctggg ctgggagatg tctgcaagaa cggcaccttt ctcctggtca ggcgggaaac   19260
tgaggcccaa agaccaagaa acgctggctt ctggacacac atcgtggaag ggcaagaacg   19320
ggctagaact caggctctgg gattctcagt cctggactgt gactcccgtt atcccctcc   19380
acctcagcac cctgctggac ccacagtcag agggaagagc cttccctccc cagctgccga   19440
ggcctgtgaa aatggcgcca cctgtcggcc aggctcagga tggcgtctga gtcccggacc   19500
gggatgtgcg ggagggcggg gttctagatt cccagacagt gcgggcttag aaatgctctt   19560
agaaatcgag tcttttgttt ttgttttttgt tttttaatca cttttaaaag gctttaaaat   19620
aacgtatttt ttcaataaaa tcgtacgcca aaatctcttc ataagacaaa agtacggttt   19680
ctgtgccctt cagcccgaag tctaagccaa tttgcctccc attgtacaga tggagaaact   19740
gaggcgtggg gagaagaacc tcgttagtca tatacctgtt tcaagccccc tcaggatgcg   19800
tcttggtttc ccctccccga ttgccctcct ttgcagagtt ctggggtgct aggggcctga   19860
gtgacttcca ctccactatt tatagcgttg ctgtttgtcg ctgctgcccg gccagacgt   19920
ctaggaggag ccgctgcatc cgaggtgggt tctggaagat ggagtatgag tagggggcaa   19980
aagggaatag gaggagaggg gcagggagct ccccatccct cccctcatcc cagtgggaga   20040
gctggatgca tttggtagag aagtacttgg tcccctcctt ccccacttag tccctggctg   20100
tctccgaagc cttctgcagg gtccgaagct gccagcccaa aaagtgtgca ggcccccagc   20160
ggtgcctgaa cccagtgcct gcagtgccca gtcccagccc cagcgtgagg aagagacagg   20220
tgtccctcaa ctggcagcca ctgacgtgag tgggcagtcc ctcccctacc aaatcctccc   20280
tcaggaactc ctagctttgc cccgtttcc gctcctcctc ccttccctc tccctctctc   20340
tccccctcc ctccccggct cttctttg ctatcagcct gtctgtccgt ttctatttca   20400
tcccttgcct gcctatctca ggctcttccc atctctgcat tatttctgtc tctttctgtt   20460
tctttctagt tacctgtctc ttttcctctc tctctttctc cctgtgtctc actgcctgcc   20520
tctatgtcta agtctctctg cccttctct ctttctctcc cccaaccccc atcatctctc   20580
tttctctcag ggtctttgtt tctctcccac tagaggcctg gtccccataa ataggtgttg   20640
tgggggagg gttgggcaga gccgctactg aaagacattt tcctggcatg gaggcccttt   20700
ggtggggagg tcagtttaac ccggtgacag cagcttttcc gtcctctccc acccaggctc   20760
caggaggcca gagctctact gaagcggcgg cggccccggg ggccaggggg ccggggacta   20820
ctgagaagga ggcccccaca gcgtgccccc gctggcaagg ccccgggtaa gcacatccgc   20880
cttcctccg cctgggggcga gggggttcc gggccagata aagccgtctg gttcccacgg   20940
tccagccgcc gcctacccgc ccccgttgt agctcagcac ccaccccag gacgaggccc   21000
cctctaggga ccccagcgtc cggccgtgcg aggtgagccc gggacaggac cagacacagg   21060
ccagaggcac tgaccgcgg gggtggggcc gggaagccag gcgtccggc tccccgcggc   21120
cgaagaggga gggcgctggc ccgttagaaa gctccgccga accagcccag acaacaaaag   21180
cgattgtgcg ggttggcgcc tgcctgggca ccaaatgctc aagattgtgg ggcggctggg   21240
ggccaaaggc ctcctcctgt ttcccgaatc ttccccctgc cctcctcccg ctccagctct   21300
tgacccctag tctagaacac ccctcatctc aaacacccctc aaaaccctcc tcttgctgta   21360
gccttcagcc cagatgtgac ccctcccct aaagtcttcc agatgtgagc ctcgggccag   21420
atgttagtac ccccgcccac agcctccctt tatccattgt gacttctccc gccaggtgtg   21480
```

```
gcgttctggc cagatgtggc tacatcttca catgtatccc cccacctcc agcctcctgc   21540 ccaggatcta gacgcccaat tcctttatgt gcccaggtgt agcgacccct ctcccatccc   21600
tcagatgtcc cacctggctg tccagatgta ccatgatagc ccctatcaa gatgaagccc   21660 ctttctctgt gccccgggca gaagaggatc aactcttagc tgtctcccca aatgtggccc   21720
ccactactct taatggattt cctctttatg gattcagctc tgtctggggg gaaacccgcc   21780 cgccccacc tgttcccttc cccgccgctc cctacaggc ccggtccact tgttggtgcg   21840
cggatgggga cagaggggc gccccgctca ccctgcgag tctagcgccc agcctgcgag   21900
cctctggcta gcgcccagc ccacgcgcc ccgcgcggc cgccggggag ggagtggtga   21960
ggaggggggg cctgagcggg ggcgcgggcg acctccccg cgggcgggcg ggcgggtgcg   22020
gccgggcccc tcgggcggc tggggcgcg gcgcggcgga gcgcggcgct gcagccatgg   22080
cgggcggcgt gcggctgctc tgggtgtcgc tattggtgct gctggcgcag ctagggccgc   22140
agcctggact gggccggctc ggagagcgtc tccgcgtgcg cttcaccccg gtcgtgtgcg   22200
gcctgcgctg cgtccatggg ccgaccggct cccgctgtac cccgacctgc gcgccccgca   22260
acgccaccag cgtggacagc ggcgctcccg gcggggcggc cccgggggga cccggcttcc   22320
gcgcctgtga gtgcggggtg gtggtcccga gagagcggct ccgggggga ggaggatccc   22380 tggggatgga ggagacagtc ctccagggag agggagccca gattccatat gcaatagtgc   22440
aagggaatat caggggctat ttgaggaagg ggccccaaa ttcctggctt ttggggttgg   22500
gtcctgaggg ttccgatttt gcaagcaatg agggttctta gaggcctgtg atgtcccacg   22560
tgagggaatt ggcgccagct ttcatgcttt gcgtcaaaat ggggatctca gaattgaggg   22620
gcctgagaac ttttgggagg ggggctcgaa ttctgagacg ctgagtaagg agtccccggg   22680
gaccaagcaa gagtctcagg accgcatggg ggacgtctca gtttctgtgt gtttgggtgg   22740
gaaggttctg tatgggaatg cctgtgaggt ggggtactag agagaagaaa gttaatccga   22800
agaactaaga gggagagggg acagagacg gggttgtgtg tgtgtgtgtg tgtgtgtgtg   22860
tgtgtgtgtg tggcggcggg ggtggggtgg gggtgtctcc gcaggacctg agttgcaggg   22920
gtcccacgtg cgacagaaat ccagataaga gggcttacgg aagggcgcc ccctgggggc   22980 ggaggggaca ggaggtgtat gcaccaggca ctcctagaga tggggagcct tgggggttca   23040
ggtgaggtgg gggagggcgc accacctgtt gttccaggat gcaaaagtgg gcagactctc   23100
tgggatcggg ccttcctgcc ccctaccccg cagaccctat ggagtgggga gtgggggccc   23160
ctggagcgga gaactcgccc agcctggccc ccagccagcc cagcccggcc ggcgtgagct   23220
catctcccgc ctgagccccc gcccgctgcc actccctctc tcctcccctt cctccctctt   23280
tctttcactc tttcccggcc cagccccaac gtgcctgtgc caggcgccat gcccaggcgg   23340
gtgccaagcc cttggggtg caaggagtgg catgtgaagt gggggctgac ctcaaaggga   23400
cccctatgtc ctcaactccc cgcttggcca gggctgtggg gcatgacgtt ggctgtggcc   23460
atctagtggc ccaccctggg tgtaggcacc cccagggagc tggcctgcgg gcctgcattc   23520
aggccaagag aaggcagaga aatgcctctg gagcctggga ataccctca gacctggctg   23580 gtttcccacc ccctccatca gagacccctta ccattctgca attttgattc ctagttaagc   23640
ctctcctagg ccccactact caattaaaag ccccattag accaccctgg agtcatggcc   23700
ccacactcct acctaaggga gctgagtttt tgctccaggc cctagacccg ctctccaacc   23760
atggcaacag actttagaga ccactcctcc agtgaaattc cctctcattc ttccctccca   23820
cctcccaaac tgtgcctttc cccagataac tctgtagtat tgtccagaag tcctgttctt   23880
```

```
ctagctcacc cccttcccca ggaacttctg atcccattta tcttcagaga accccagggt    23940
tggtcttgat aagtgggttc tcgcaagagg actccagaca ttgtgctcct tacaggcagc    24000
cattaataaa aagcctttgg cacttaatcc ttagctggga ggggagggga ttccacagag    24060
ggactcggcc aattgagcct cttaagtgct gatgacttcc aggaattcca cttcactatc    24120
taaaccctgt tttcagcacc gtcaaactgg ttgtctccta ggcggcacta gagtcctgtt    24180
ttctaggtaa ctgtccacaa aaggactcct gctgaaagga cgcctcagtt tcctctgagc    24240
taggttcctc catcccagaa acctccagcc gtctttgaac tcgagaggac tgcccttttag   24300 tcgatctcct cccaggactc cagtcccttt atccttctaa acggaggtgg ctctctgcgt    24360
cctttcctct ctacagttgt ggctcagaat cccacacgcg cctcccccgg ccgcctgcct    24420
cctccctccc ctccgcacag ctgtctccag ctgttctctg cagccccggg agagagaggg    24480 aggggggtgcc ctcgcaggac agcccggcct cctttggctc aaaggtcccg ggctcccca    24540 agggtccgga atgtggagcc tccgcccctgc ccccgccgca cctctctctt tgtttacccc    24600
gccgcacagc tggcagtgcc ccgcccagag gtggcctggg gcccagcgag ggcgcgcaga    24660
ggggagtgga ggcgcgttcc cgctcgtggc tccgccccgg tgctactgga ggctgtaagg    24720
ccgagctaga actctaaagc cccagccaga aagaagttgg gcggagacac agcgcggtgg    24780
gcggaactag ggcacccgga cagcctggag gtgggggtggg aggggcgtga acaagtgagc    24840
cgggcgaatc agagtgcgga aaggaaggtg ggaggggcta gaggcagcag gttaagctcc    24900
tggataggcg gggtttagaa tcccgcgggt agaaggtaat gtgagagggg ctacaaaggg    24960
ggcacagcca gggggcggag gtaggacttc gtggaccaag cagagggagt gtgggcgggc    25020
atagaatgcg aaggagacag agttgggcgg ggagttatgc cagggagtgg ttaaaatgtg    25080
gtttgagtca atggaaggga tcagcattgg gtcggagggg ctggaacagc aaagggttcc    25140
gtcggactac ggaatgggcg gggtcagcgc cgtctgggct ggtctggaac tccgtggact    25200
cagccagaaa ttgggatccg agaggttgac atgaaagtga ataaacagcc tgagggctgg    25260
ctgggctcac gcctgtaatc ccagcacttt gggagactga ggcagaagga ttgcctgagc    25320
ccaggagttc aagaccagcc tggccaacat agtgagaccc cgcctctacc aaattttttaa   25380 aaaacgtagc ccgatgtggt gcacgcctgt cgtctcagct acttaggagg ctcagatggg    25440
aggatcactt cagcttagga ggtcgaggct gcagagccat aatcacgcta ctgcattcca    25500
gcctgggcaa tagagcgaga tcctgccgac ttagtgggtg ggaccgtacc tctgatggct    25560
gaacaactgg actgggccaa tgctgatgcc agaattgggg cggggccaca tgacagctaa    25620
gggcggagcg acttagaaat gaatgatacc ttgagggagt agggaccccca ggagaacctg    25680 ccaggaatgg tggcgcccct gagtgtcctc gttctcctcc cagtcctgtg tcccttgatc    25740
tgtcacaatg gcggtgtgtg cgtgaagcct gaccgctgcc tctgtccccc ggacttcgct    25800
ggcaagttct gccagttgca ctcctcgggc gcccggcccc cggccccggc tgtaccaggc    25860
ctcacccgct ccgtgtacac tatgccactg gccaaccacc gcgacgacga gcacggtgag    25920
gaaagggtgg ccagagtccc ctccgacccc tgtcaagcat ttcactttgc ccctgaccct    25980
catatttccc gccttcccga gcacctttgc ccagctcgcc ctcccgcct tgtctagccc     26040 caccccgtaa gaacccgtgt agacatccgt ttgcccggcc gtgcctcccc taggcgtggc    26100
atctatggtg agcgtccacg tggagcaccc gcaggaggcg tcgtggtggg tgcaccaggt    26160
ggagcgtgtg tctggcccctt gggaggaggc ggacgctgag gcggtggcgc gggcggaagc    26220
```

```
ggcggcgcgg gcggaggcgg cagcgcccta cacggtgttg gcacagagcg cgccgcggga    26280
ggacggctac tcagatgcct cgggcttcgg ttactgcttt cgggagctgc gcggaggcga    26340
agtgagagga ggcccgtggg gaggggcccg gagcttgcct ccgcgcgggg gcgcgctcac    26400
ccaacacttc cccgcagtgc gcgtcccgc tgcccgggct ccggacgcag gaggtctgct     26460
gccgaggggc cggcttggcc tggggcgttc acgactgtca gctgtgctcc gagcgcctgg    26520
gtaagcccca ggacgtcccc gaagtgctcg gagctgggga gtggtgacaa cctcaccgtt    26580
cctcctactc tgccctagat aaacccagtt cacaaattgt agccacgcct accccattgt    26640
ggaggcgact tccagtcctg agcttttcat accgctctgg gaccaccac cccattttct     26700 gactttggcc actctgttct caccctgcct ttgtgccttg gccccccacc atatactttg    26760
ggagtctcca atgttgccat ttcaactgcc aacctaaggc tgtccctgca cttaaactac    26820
agccaacatc ttttagtccc tcccacccg tcttcgtctc tgcccactcc attctcgctc     26880
tgcccacctg tccctggccc acccctctcc tctcgccaca gggaactccg aaagagtgag    26940
cgccccagat ggaccttgtc caaccggctt tgaaagagtt aatgggtcct gcgaaggtgc    27000
aacggggcag gggtgggagg ggcttggttc tggggcggg atttgcaggg atcaagttcc     27060
tgactccacg gtgacctccc caaccctggc agatgtggat gagtgcgcga ctggcgggcg    27120
ctgccagcac ggcgagtgtg caaacacgcg cggcgggtac acgtgtgtgt gcccgacgg    27180 ctttctgctc gactcgtccc gcagcagctg catctgtgag caaccagcag ggagctgagg    27240
ctgggtcccg ccctccctgc cctcagaagt cccagagcat cctggggcct ttaattccct   27300
cggacccccc cagactcccg ggttcctctg tcagccttag agccccctca gaacttctca    27360
gattcttata cagcttcagc atccctggac cacctttaga cctttcaagc cttttggatc    27420
cagatccctc cagactccca gactttttt tttggagatg gagtctcgct ctgtcgccca    27480
ggctggagtg cagtggcgcg atctcggctc actgcaatct ctgcctcctg gtttcaagtg   27540
attctcctgc ctcggcctcc cgagtagcta gaactacagg cgggcaccac catgcccggc    27600 taaattttt tgtattttg gtagagacag ggtttcgcca cgttggccag gctggcctca     27660
aacccctggc ttcaagtgat ctgcccacct cagcctccca aagtgctggg attacaggcg    27720
taagccactg cgcccagctc tcccagactt tctggaatcc ttctcagacc cccaaatcct    27780 ctcgtcccc tcaacgactc gactatcttc agatcttgag atccttctca gagtctctca     27840
ttcaccactg acacccatt gaggctccaa gcccttctca gacctccaga gcccactgct     27900
ctccttcaga ccctctcaga cctctcccaa atgcccctcg cacccaccaa ccccccaccc    27960
ccaaccccag aaccattccc ctctctccca aatccctcag tgctacagca ttcccagccc    28020
cgccctgaag gatttcctcc ctgctcctcg cagcccaaca cgtgatctca gaggccaaag    28080
ggccctgctt ccgcgtgctc cgcgacggcg gctgttcgct gcccattctg cggaacatca    28140
ctaaacagat ctgctgctgc agccgcgtag gcaaggcctg gggccggggc tgccagctct    28200
gcccacccct cggctcaggt gagcccctgc ggcagtgcct agccctacgc gcaacacatg    28260
tggcgctcat tctacgcccc accctccaac cctgagttca ctgccccaac ctgactggct    28320
gggctccagc cttggccacg cagcagcctc tgagacccgc aggcctcaga ctggacagca    28380
tccatggctc cacctccatc tgtagccaca gccacccctc cattcgtagc cacagctacc    28440
ccggagctcc caagttagtt tttgtctcct gagcgtcaac gcccagtccc accctgtccc    28500
tgaactttga ccaagtcctt ggcttctgag acactgcctt cagcttagcc ccaccccagg    28560
catgcccctc cctgagacac ctccctggca ttctatcttc tgcttaaaac taaatctcac    28620
```

```
aagggagcta tttcctagcc tccaactctg tccctgtaga cccaaccgga ccctgccctc   28680
aaccctgttc ctaccaccat cccaaatgtg ggaaaacgct cttggcccca cctgtagcct   28740
ctaagacatt ctactctttg gccaggacac caccccatcc cagcctccag ctcaaacccc   28800
tgacactctc cagccaagcc ctgcccctag ccaaggccag agtctgggct ggccatcgtt   28860
ttcttcccgc tctcttgtcc tctctctgtc tctcttacct attcccagag ggtttccggg   28920
agatctgccc ggctggtcct ggttaccact actcggcctc cgacctccgc tacaacacca   28980 gaccctggg ccaggagcca ccccgagtgt cactcagcca gcctcgtacc ctgccagcca   29040
cctctcggcc atctgcaggt gagctggctc tggcagaagt gggtgccatc ttcaaggggc   29100
tgccccagcc ccatagtgaa aggaggcaag agaggatttg gctccactc gttgataccc   29160 cttctttatc aggcttctg cccacccatc gcctggagcc ccggcctgaa ccccggcccg   29220
atccccggcc cggccctgag cttcccttgc ccagcatccc tgcctggact ggtcctgaga   29280
ttcctgaatc aggtttgcta gaaagaactg agggcattgg gcctgcagca gtggctcacg   29340
cctgtaatcc cagcattttg ggaggctgag gagggtggat caccaggtca ggagttcgag   29400
accagcctgg ccaacatggc gaaaccctgt ctctactaaa actacaaaaa ttaactgggc   29460
gtggtggcag atgcctgtaa tcccagctac ttgggaggct gaggcaggag aatcacttga   29520
acccaggagg cagaggttgc agtgagctga gatcgtgcca ttgcactcca gcttgagcga   29580
cactccatct caaaaaaaaa aaaaaaaaa gaattcaggg cattgatggg ggtattacag   29640
gtgggattct ggggtaaaag actccaaggt gaagattcca ggttacagca aataggaatg   29700
gtatgggcag agataagcgt ttgaagggtt gggtggtagt tagatcagga gctggagtca   29760
cagttgggct cttctgtgtc aatcgagcaa gccatttaac ctctgagact cagttttctc   29820
attggtaaaa tggggatggt tgttgagatg cctctgaagt gtctgacacc tagtaagtgc   29880
tcagataaat acttatggta gataattatt tttcattatc taatattaga taattatttc   29940
tcaggtaggg cactaagaat gtatctcagg cggagggttg gagagcaaac tattcaaagc   30000
cagagacctt ggggtggcat gatgagggga ttcggccaag gatctgatga gaacgttcca   30060
ggataaaaaa gatggagatc agaagaagac tgggcttgct tggggaggag acatccatga   30120
aggtgtttta tggatgtctc cggggtggg ggttttactg ggatgaaagg aacggaggat   30180
tcagagatgg gggaaccctg gctgactgga cccccaggt ccctcctccg gcatgtgtca   30240
gcgcaacccc caggtctgcg gcccaggacg ctgcatttcc cggcccagcg gctacacctg   30300
cgcttgcgac tctggcttcc ggctcagccc caggggcacc cgatgcattg gtgagcaaga   30360
cggagggcgc ggaaggaggc ggggcggggg gctttgcctg gtcaccttgt caccagcccc   30420
ctccgtgtcc tcagatgtgg acgaatgtcg ccgcgtgccc ccgccctgtg ctcccggggcg   30480 ctgcgagaac tcaccaggca gcttccgctg cgtgtgcggc ccgggcttcc gagccggccc   30540
acgggctgcg gaatgcctgg gtgagaaatt tgccccaccc ggctccaggc ccaccccagg   30600
gtctcgctcc tgctctcact ccagagcctc tccagccctc ccacgcttcc cctctcgggt   30660
cccgccccag gactgctctg ccctggccct tggccctgcc cttccctgac ccgcctccac   30720
ccagctccag cctccctttg accccacccc tacccagctc ccaaactgcc agtttctatc   30780
ggggcctggt cgcaactcgt attgctccgc cccacgccc aggccccgcc cttattggcc   30840
acgcccctcc ctgactaact ccctccccca ggccccgcca ctgtcctgca actgcggcaa   30900
ccaatctcct gaccgcgacc ccgattccaa ccctgccaca ccagagccct atccccaaac   30960
```

```
tgctcctttc ttctctagcc cctaccccac cttcccttag cttggtcccc aaagctctcc    31020
tttctgccct tgcgctacca aaccctgccc tccacaattg cctctctcac tgtgcccctc    31080
tccggctgtc ctggccgggt ccccatcctg gctctggccc aagcttggtc ccgctcccgc    31140
ttccctctac ccctgcctcc ttgcgtcgct ctcccgggg ctgtctgccc cagtcccagc     31200
cgcctggtct gtgcctacag atgtggacga gtgccaccgc gtgccgccgc cgtgtgacct    31260
cgggcgctgc gagaacacgc caggcagctt cctgtgcgtg tgccccgccg ggtaccaggc    31320
tgcaccgcac ggagccagct gccagggtga gggcctggga ggggcagctg ggaaggggtg    31380
tgagcggttg ggtagagcgc agtgatgagg gccagagaga ctgaacaata gggcaaagcg    31440
agttgatttg gagacagagg ccaggctctc gagcagacgt gtggcctgat ggcagtagag    31500
agagacctgg gatgcagagg ccaagtgatg ggaaacagaa aggctgagtc atgaaagatg    31560
gagaagcaga atgaggaggg atggagatgt cagtaatcgg gtaaggggag cagagttatg    31620
gaggaagggg gagaaggagg ccttctcatg gggactacag agacagaacc agccaggcag    31680
cttagtaggg attggtggag gatgcagagt cagatgatgg tgacaaggag gaatagagat    31740
ggggtcacgg ggacagaatg ttggagggtg gaaagccaaa gtgacagagg tcaggaggc     31800 agaggggaac aagtgacccc gggcccctg ccctgtgcag atgtggatga atgcacccag      31860
agcccaggcc tgtgtggccg aggggcctgc aagaacctgc ctggctcttt ccgctgtgtt    31920
tgcccggctg gcttccgggg ctcggcgtgt gaagaggatg tggatgagtg tgcccaggag    31980
ccgccgccct gtgggcccgg ccgctgtgac aacacggcag gctcctttca ctgtgcctgc    32040
cctgctggct tccgctcccg agggcccggg gcccctgcc aagtgagggg tgctgagccc     32100
agccctactc catcactgtt tgctgtggag actggagaga gattattgag gggcagagag    32160
gcagagtgat ggggctcagg gatggagaac aggggctgag ggatggggac ctcactccag    32220
agtcttctct cctttcaaca aaataaggca gtcctcccca cccctcctcc cttttgaaa     32280 gatactcttg tgcttatggg aaccctgagg aggggtcac ctgaggcagg gcaggcaaca      32340
tggagttggt gccttagccc ccaccttagt agctggagag accattgaat ggggacacga    32400
ggaaggtgtc tgtcttcctg ggaagaggga gcagcctgag gcaagtccag aaggcaggct    32460
caagactgga atgctggggt gggtggtgat ggccatggga atggattcag gccccttcct    32520
cagcctcatt ggtccctct gccccagatg tggatgagtg tgcccgaagc cccccaccct     32580
gcacctacgg ccggtgtgag aacacagaag gcagcttcca gtgtgtctgc cccatgggct    32640
tccaacccaa cactgctggc tccgagtgcg agggtgaggc cggggaggga gggaggagtg    32700
tggatgggtg agggggagt tggaccactt cttcaaggcc accctctccc ctgcccccca     32760
gatgtggatg agtgtgagaa ccacctcgca tgccctgggc aggagtgtgt gaactcgccc    32820
ggctccttcc agtgcaggac ctgtccttct ggccaccacc tgcaccgtgg cagatgcact    32880
ggtgagacca ggccctggct gtgacttgg gcctgcatca tgaccccga ccctcgaccc      32940 agatcacaac tatgacctgg ccgtaacctc ctgacctgga cctcagtccc tcagtcccca    33000
gagcctgtga ctcctgaccc tgacctggac cacaactctt gaccctgaat gtgactcctg    33060
agacccaact tgacagtaac atttgaccct aaccatcacc cttgatgata gtccctgccc    33120
ataccctgat agcaattgtg accctcatga ctctggccct gaatgtgacc tataactcct    33180
gaatttgact gtgacatttg accctaatca taaccactaa ccatagcact gaccataacc    33240
ttgactgtgt gactcttggt cctatctctt tcacagcccc tgcctcttct cagaatccct    33300
tctctggaac ctggttgggt tcataatccc tgaccctggc ccctgacttg aggcagaatt    33360
```

```
ctggaccctg actataactt ctgatcctaa ctggattcag attccagtca ctaactctga   33420
cccatggctc agccgaatcc catccaatga tcctagttta taatacttga ctggtccctt   33480
gccctagttg atttctgatc cctgtctgat ccctctcctg actccaaaat cctggcacag   33540
gtagttccta gaaacctaga cccacaggac ttgcaaccat ggtccccgga acccgagaac   33600
cttggtcagc cctacccacc tctgccatag agccctcccc cagcctccaa ctcatgagac   33660
ttcccaccac ctcccccaga caccctactc caagggggatt ggtcgggtgt gtcccgagac   33720
tggacccttt ctgaacaccc cacccccca cagatgtgga cgaatgcagt tcgggtgccc   33780
ctccctgtgg tccccacggc cactgcacta acaccgaagg ctccttccgc tgcagctgcg   33840
cgccaggcta ccgggcgccg tcgggtcggc ccgggccctg cgcaggtgag cagcataggg   33900
acccgccaga gagtctggga gtagggcctg ggttccaggg caaagccggc tggaaaggtg   33960
gaggcgggac caaggcgctg tgggaggagc ttagaaacct ggcattggtg ggggcggggt   34020
tactgcgatg tgggcggagc ttgtctggga ggccgggtcc cgtgactccg cccaatctcc   34080
cgcgtaccct agacgtgaac gagtgcctgg agggcgattt ctgcttccct cacggcgagt   34140
gcctcaacac tgacggctcc tttgcctgta cttgtgcccc tggctaccga cccgaccccc   34200
gcggagcctc ttgcctcggt tcgtacccgg gctgatcctg gccccggaaa gggtgggctt   34260
agggcaggaa aaggcgggac ggggagaaga gggcgaaaag gggaaaacga gtttttagcc   34320
ggggtattcc agcaggatca gggggcagct ggtgggagtc tcgaggcagt gagggggggc   34380
ggggcgtgga gatgaaaggg ccgagtctgg gtatttggac cgtgattgta aagaagctgt   34440
tctaaacccg tcgggggggcg gtgtttgcag ggagggaagt agcgtgaggc aggttgggga   34500
aggcgtgaga ggcctaggag agccgagggg cggtggaggg gtgtggccta gaatgttagg   34560
cggagcggga ggtgggccgg gccttcggac gccctgtccc gcagacgttg acgagtgcag   34620
cgaggaggac ctttgccaga gcggcatctg taccaacacc gacggctcct tcgagtgcat   34680
ctgtcctccg ggacaccgcg ctggcccgga cctcgcctcc tgcctcggtg agaggccccg   34740 cccccggcctg atccctcctc ccttcgactc cccgactcgc cgattggcct ccacctctg   34800 tctttcctcc tccgcttctc ccctcccctt acctctttcc cccgcctcct ctcctagcct   34860
ccccaactct cctctacccc aatcttctcc tgccctctcc tctgcttccc cggcctcccc   34920
cttctgactc tcctctcccc tctttgtatc ccccatcttg cctccctgct tcccacatcc   34980
gaccacccga cctctctcct cagacgtgga cgaatgtcgc gagcgaggcc cagccctgtg   35040
cgggtcgcag cgctgtgaga actctcccgg ctcctaccgc tgtgtccggg actgcgatcc   35100
tgggtaccac gcgggccccg agggcacctg tgacggtgag cctgcccca cccgccttcg   35160 ctagcgcttg caacgcggtg ctggaggctg ctcccttggg gactgaggag gggcgccctg   35220
cttcccagac ttaggcggag ggaaagaaca ccctctcacc gtatctctgt agtggaaata   35280
agccgccacc gtgtccatgt atttttcttgt gtcaggatca cggccaagcc tcccttccag   35340
ccgcagtcca ttcccctct gcagctgaag cccggtccac attttaggct atgcccccag   35400
taagacaccg ccccaaaact gttaggcccc gcccctcca atcggcctct ggattaaaac   35460
cccctcttca ggcccttct cttcctaaca gaagtttgga cgtgccctt ccgcgccctc   35520 caccagtcct acttccagcc ttccctccaa agaggcccaa tcccggtggc cctaggcccc   35580
attctttccc aatgagaaat tcccaaggtg aaattctcct agcattggcc cccgcccgtt   35640
taagctctgc ccttccttgg tctctctaga cagggctttc cattcgctcg gatggctcca   35700
```

```
gtctctcgaa cacttaggcc ctcccttcct atctttgctc cgcccacaga cccgcccctt   35760
gccttttctt actttccagg ccttccctcc cgccccgctc tttcacccct cccgggtcag   35820
gctccagcga ggcaggaggg tggggctaat cttccataca gtatatattt ttttgtgtcg   35880
gcgggggggg gggggcggtg atggtgtgtg agtccgcatc ttgtggaaca catgaaacaa   35940
aacatctgtg ggctgccgtt gactctgcta gacctctgac tcatggaaat ctagcttcat   36000
aagatctcat tcattaattc cacaagaatt cactaagcac ctactctatg ccagcgtctg   36060
gaaaaggtaa taagagcaac aggaaataag tcatataaaa acccctgcct tcctggagtt   36120
attgtggggt aataaatatg taaataaatt caagatttat acagcaggcc aggagctgtg   36180
gctcatgcct gtaatcccag cactttggga ggccaaggcg gatggatcac gaggtcagga   36240
gatcgagact agcctggcca acatggtgaa accccgtctc tactaaaaat acaaaaatta   36300
gctgggcatg gtggcatgcg cctgtagtcc cagctactca ggagactgag gcaggatact   36360
cgcttgaacc cggaggcgg aggtggcagt tgagccgaga tcgcgccact gcactgcagc   36420
ctcggcgaca gagtgagatt gtctcaaaaa aaaatttat acaacaaaaa actgggggc   36480 accttactat atgttgggca ctggagatgt agcaggaac aaaatagaca caaatccctg   36540
ctattgtaga gtttgtattc tagagaggcg acagttggca taccaataaa tacatacgta   36600
taacatcagg tttaggaagg aaaacaaagc aagacaaatg ggacagagat gacagagcag   36660
tggatggagg agtgctagga gggcttgacc tagacaccag acagaagcga gggaggcagc   36720
catgcagaga gctgagggga gactgttcct ggcagaggga agagccagtg caaaggctct   36780
gaggcaggac catgcttttg agaaatggca gtgaggactt gagagttatc aactatgcta   36840
ggtgtggtgg cacaagcttg taatcccagc tactcaggag gctaaggtgg gagaactgcc   36900
tgaacccggg aggttgaagc tccagtgagc catgatcctg tcactacact ccagcctgag   36960
caacagagca gaccccatt taaaaaaag aaaaaaagc tggatggggt ggctcatgcc   37020
tataatccca gcactttgga aggctgaggc agctagattg cctgaggtca gaagttcatc   37080
accagcctgg ccaatatgat gaaaccccat ctctactaaa gaaaaaaaaa aagatagtg   37140 gctgggcgtg gtggctcaca cctgtaatcc taggacttga ggaggccgag gtggacagat   37200
cgcttgaggt caggagttcg agaccattct ggtcaacatg gtgaaatctc atctctacta   37260
aaaatacaaa aattagctag gcatgatggt gcatgcctgt agtcccagct gctctagaag   37320
ctgaggtaga attgcttgaa cctaggaggc aaaagttgca gtgagctgag attgagccac   37380
tgcactccag cctgagtgaa agagcgagac tccgtctcaa agaaaaaaca aagttttcaa   37440
cattgttgat cttcagaagc tcaggctcct agaataccag attgctaaag acttcttagt   37500
cttgggcacc ggaagtggtg ttagaacttc tgaattcagg cctttgactc ccctttcatc   37560
tcctccacac tctgcagatg tggatgagtg ccaagaatat ggtcccgaga tttgtggagc   37620
ccagcgttgt gagaacaccc ctggctccta ccgctgcaca ccagcctgtg accctggcta   37680
tcagcccacg ccaggggcg gatgccaggg tgggtgtcca tcaggcatcg ggtgagatgt   37740
ggagatggta gaaggtccag aaatggcctg actgtctggt ggttgcagat gtggacgaat   37800
gccggaaccg gtccttctgc ggtgcccacg ccgtgtgcca gaacctgccc ggctccttcc   37860
agtgcctctg tgaccaggtt acgagggggc acggatgggc cgtcactgcg tgggtacggg   37920
acttcaggag gtggatggga ccaaggggg tgggggaggt tggtcaggcc ctgtccctcc   37980
ccatatatct gaacaaatgg gaattttcgg gttgtggaat ttagactttg gaatataaga   38040
tcatcttcat gccaggcacg gtggctcacg cctgtaatcc cagtactttg ggaggccgag   38100
```

```
gcgggcagat cacttgaagt caggagtttg aaaccagcct ggtcaacatg gtgaaacccc    38160
gtctctacta aaaatacaaa aattagccgg atctggtggc aaatgcctgt aatcccagct    38220
actcaggaag ctgaggcaca agaattgcct gaacccaaga ggtggaggtt gcagtgagcc    38280
aagattgtgc aattgcactc cagcctgggt gacagagtga gaccctgtct caaaaaaaaa    38340
aaaaaaaaaa aaaaaatcag aactgttgta gtggctggtg acagaaacct gacttaatca    38400
ggttttattt ttgtgtgtgt tcttttaaaa atgtataaag tataaatgta taagtacta    38460 atcttaagtg ttcataaaca ttaatctttc ctaacatttt atgaggaaaa tttctaaaca    38520
caaagcaaat tgagagaatc atagaatgaa cacctaccta ctcatgatct agattatatt    38580
atcattttat tacacttgct tcctcacata tctatccatt aatccatcta atttttggga    38640
cagagttaaa agtaaattgc aggcaccagt ctgcttcccc ataaattctt caatatgcat    38700
atcactaacc agaattcaat atgtgtttac caatgtattc ttctcttctc tctttttttt    38760 tttactttg aggtggggtc ttgctctgtt gcccaggctg gagtgtggtt gtttgatcat    38820
agcttactgc agcctctaac tcctgggctc aagccatcct ccctccagaa ctgagcttcc    38880
gagtagctgc taccacaggc acacgcaacc acgcccagct aatgttttta attttttgtag    38940 agatgagttt tttttttttt tttggagaca gagttttgct ctagttgtcc aggctggagt    39000
gcaatggcat gatcttggct cactgcaacc tccacctccc gggttcaagc aattctcctg    39060
cctcagcctc ccaagtagct gagattacag gtgcccacca ctatgcccag ctaattttttt    39120 gtactttgag tagagatgga gttttgccat gttggccagg ctggtcttga actcctgacc    39180
ttaggtgatc cgcccaccgt ggcctcctaa agtgctggga ttataagcat gagccaccac    39240
gcctggcctg tagagatgag ttattgctct gttgcccaga ctggtctcaa actcctggct    39300
ttaagcaacc ctccctcctt ggcctcccaa agcactggga ttacaggcat gagccattgt    39360
accctacaga tattttcatt caacgttcaa tttatataca gtgaaatgca gcaatcttaa    39420
ttatacattc tgtaaatttt cacaaatgca aacacaacag gttttatttc tttaaaggga    39480
attaaaacta taaagtcttg ggatatattt gaactccagg cataactgga tccaggaatt    39540
ttaacaaggc tatttctatc ttctctgagt tctgctttct tctattgcat gattttcagg    39600
cagattattt ttcacaatga tgaaggtggc cctagaacct ctgggctaac atctccagtg    39660
ggccacccga gagctaaaaa gggaggtttt tttttcaata tttctagcaa aagcgccagg    39720
cctggctttg attgacccag catgatcact gcctatgtct gaaccagaga aatgccgtca    39780
tctgtttggt cattcctgga acttgtgccc acctctcaga gtagatatag ccctactcaa    39840
agaacaggat tgaaaataga ggagcacagg gttcccaagg gaaattcaag gtttctcact    39900
agaagaaaaa cagatgatgg gatctgggcc attaaatata cacattatat ttgaaagctg    39960
agactttcgg acctttggaa tcatagaagc ttataaccac tgagtccctc tcccctgttg    40020
tctcctgctt acagatgtga acgagtgtga aacactacag ggtgtatgtg gagctgccct    40080
gtgtgaaaat gtcgaaggct ccttcctctg tgtctgcccc aacagcccgg aagagtttga    40140
ccccatgact ggacgctgtg ttcccccacg aacttctgct ggtgagactg atgtgtctat    40200
ttaactgatg gcggctggcc ccatgggaaa atcacgtggt ctaatcattc ctgatgtgga    40260
cagctaccat cagctaaata ctgttgtttt aaacatcaac aaaagacaca taagttaaca    40320
tgggtagtga gactgtgtca ggagaattag accctggtcc tgactctacc agattctttc    40380
attcaacaaa tgttcacagg gtgtgcactg tgttcaggcc atcttctggg cactgagaac    40440
```

```
atagtagtga ccagaaggga tcactgtctg tcctcaaggg gctcacaagc caatggggca   40500
gacagagata tcaccagata gtgacaaccc agagaaatca acaagactgt gacggggaaa   40560
gcccaggggg gttttggagg aggcgcctgg cccagcatga aagaggatt agggagttct    40620 tcctgtagga gacgacatct gaactgagag ctgtgggatg aatagaaatg agccaggccc   40680
gatgagtgag gagggcattc tgggcagagg acacagcaag ggcaaaggcc tggcaaagcc   40740
agagagcatc tggcatgtga gaagaactga aacaggttca acatggcatg atttagagag   40800
caaaggaagg ggtagggaga gatggggcca gggaaagagt caggtgcccg atcacactga   40860
cttatcacag taagagagca ctgcggtacc gtggaagggg tttcggcgtt tttttttga    40920 aaatttttt taaatgtttt tttttaaga cagggtcgta ctttcaccca ggccggagtg     40980
cagtggcgtg atctcagctc actgcaacct ccacctcctg tgctcaagga atcctccaac   41040
ctcagcctgc tgagtaactg ggactacagg cacatatcac cacaacagct aattttgta    41100 tttttgtag agatgtggtt ttgtcatgtt gcccaggctg cagtattttt tttttttaa     41160 tttttaaatg ttacatattt aggctaggat tggtggctga aggccataat cccagctctc   41220
tgggaggcca aggcgggagg atcacctgag gtcaggagtt cgagaccagc atggccaaca   41280
tggcaaaacc ctgtctctac taaaaataca aaaattagct gggtgtagtg gtgcacgcct   41340
gtaatcccag ctattcgaaa ggctgaggca ggaaaatcgc ttgaatccag gaggcggagg   41400
ttgtgggatt gcaccactgc actccagcct gggtgagaga ggaagactcc gtcccaaaaa   41460 aaaaaaaaa aaaaagcta tgtatttatt tatttttaat aatttccatc tttacttag     41520 attcagggga tacatgtgca ggcttttac ctgggtatat ttcgtgatgc tgagctttgg    41580
gatacaaatg atcccgtcac ccagatagta agcacagtac ccaacagcca gttttttt     41640 ttctttgaga cggagttttg ctcttgttgc ccaggctaga gtgcagtggc gtgatctcag   41700
ctcactgtaa cctccacctc cctggttcaa gtgattctcc tgcctcagcc tcctgagtag   41760
ctgggattac aggtgtccgc caccacgccc agctaatttt ttgtattttt agtacagacg   41820
gggtttcatc atattggtca ggctggtctc gaactcctga cctcaggtca tccacctgcc   41880
tcggcttccc aaagtgcagg gattacaggc gtgagccacc atgctcggcc aacagccag   41940 ttttttcaacc cttgtacctc tgtccctccc ccatctagtg gtccccagca actattgtgg   42000
gcatctttac atccatgagt acccactgtt tagctctcac ttgtaagtga aacatgtgg    42060 tatttggtct tctgtttctg cattaatttg cttaggataa tggcctccag ctgcatccat   42120
gttgctgcta aggacatgat ttcattcttt ttcatggctg tgtagtattc atggaagggt   42180
tctaagcagg aaagatagaa tcagatttg aaacctccct ctggccgcca tgtgaaggtg    42240
attgaagcgg gtgatatgga ggctgggagc tcagggaaca ggctggggca ggggcctgga   42300
caggagagaa cagggctgga ccaaggcagg ggctgtggaa ggggaggaga aggtggtggg   42360
agaaaaaccc aagaggccat gtggacaagc tgtggatgtc tgggtgggga agctgtgtcc   42420
aagacaaggc ataggttttt tgtttgtttg ttttgtgaca gagtctcgct ctgtcgccca   42480
ggctagaatg cagtggtgtg atctcggctc actgcaactt ccgctcccgg gttcaagcga   42540
ttctcctgcc tcagcctccc aagtagctgg gattacaggc atgcgccacc acacccggct   42600 aatttttct attttagta gagaccgggt ttcaccatgt tggtcaggct ggtctcgaac     42660
tcctgacctc aagtaatcca accgcgtcgg cctcctgaag tgctgggagg acaggcagga   42720
gccactgcac ctggcgacaa attgtaggtt ttgagatgaa gactcagcca gtttgccaca   42780
cactggataa gagacccaga gaggcatcca ggaagccagg gaagttccct caccacccac   42840
```

```
ccaagctgtt agctgcagtg acgggaaagt gtgaggtggg gaggcaagag atgcagaaat   42900
gacaggaggt gacagtggga gaaagagaaa cagtgacaga ggagcgtgag aggtgtggag   42960
tctggttctg ccactgatgg ctgccaccct ctgtttccct atctatgcca gcctcagttt   43020
ccccatctat gatagtggcg gggctgggga ttcagcccac actgggctaa agctccttgt   43080
ctccccaggc acgttcccag gctcgcagcc ccaggcacct gctagccccg ttctgcccgc   43140
caggccacct ccgccacccc tgccccgccg acccagcaca cctaggcagg gccctgtggg   43200
gagtgggcgc cgggagtgct actttgacac agcggccccg gatgcatgtg acaacatcct   43260
ggctcggaat gtgacatggc aggagtgctg ctgtactgtg ggtgagggct ggggcagcgg   43320
ctgccgcatc cagcagtgcc cgggcaccga gacaggtggg catgggctga tggggacaca   43380
gggctgaggg cttgggtgga aatactgggt ggggtgtggg cctgggacag gggacacttt   43440
tggacagggc cttgaggtac tagtactgtc agggcaaggg cgagctgcca ggcaggtggg   43500
catgggcaga cataaggctg agaggtgggc actaacaggc acagggccag agggactttt   43560
gtgacaagtg ggcacgagca ggtcagggct ggggctgggg ctctggtgtc ctggctcagg   43620
cttgtctctg tgtgtagctg agtaccagtc attgtgccct cacggccggg gctacctggc   43680
gcccagtgga gacctgagcc tccggagagg tgaggccagc ctttgaccct ccaccccact   43740
cagctctgag gcccagcttc gtctcttcct gttttctttg cctctgtctc tcacccttc    43800 tgtttctctg tatctgtctc cccgacccca cccatactct gtctctttct ttcttttctt   43860 tcttttttt ttttttctta agatagagtt ttgttcttgt cgcccaggct ggagagcaat    43920
ggcgagatct tggctcactg caacctttgt ctcctgggtt caagcgattc tcttgcctca   43980
gcctctggcg tagctggcta cagacactag ccactacgcc tggctaattt ttttgtattt   44040
ttagtagaga cagggtttca ccatgttggc cagattggtc tcgaactcct gacctcaagt   44100
gatccgccca ccttagcctc ctgaagtgct gggatttcag gcatgagcca ccgctcctgg   44160
cctctccatc tttctttccc tgtctctact tcttggtcta tcaccagctc tgtctctgtc   44220
ttcccacgtc atgccctcac acactccacc catccagccc gccccatctc tctctctgc    44280 ttttcgcaca gacgtggacg aatgtcagct cttccgagac caggtgtgca agagtggcgt   44340
gtgtgtgaac acggccccgg ctactcatg ctattgcagc aacggctact actaccacac    44400
acagcggctg gagtgcatcg gtacaagccc cacctccccc aaccccggc aactctctcc    44460 aaccccctagc cttgccagct cccctctgga atgtggccac caccagcggg aagtcttttcc  44520 tggagtctag actccatcca tcacactgcc aatgtgctgg gaagagaaat gggaaagggt   44580
ggggagagtt gaaggggatg cctcttaatc atcctctccc tagacaatga cgagtgcgcc   44640
gatgaggaac cggcctgtga gggcggccgc tgtgtcaaca ctgtgggctc ttatcactgt   44700
acctgcgagc ccccactggt gctggatggc tcgcagcgcc gctgcgtctc caacgagagc   44760
cagagcctcg gtaaccccgc ccacgccatc caggccctcc ttcccttggc tcggcctcac   44820
acccgcaccc gggccacacc tttgcgacgg ccacgccctc cgaaggccac gccccatgct   44880
cctggctcga ccacgcccca ctgagccctc actcagtctc tgtcccactg tctgtctctc   44940
tgaggcgagc tggctaggtg gttaaaggca aaagttttag gcaaccttt gcatgttgcc    45000 tcttggactc caggtttctt tctgcacact gggtgaatag cccctacctt atagggtggc   45060
tgtgaggaat tttatttaat tttattt att tattttttga gacggagttt cgctcttgtt    45120
gcccaggcta gagcgcagtg gcgccatctc agctcactgc aacctccacc tccggggttc   45180
```

```
aaacgattct cctgcctcag gctcccgagt agctgggatt acaggcatgt gctaccacgc   45240
ccagctaatt ttgtattttt ttctttagta gagacagggt ttctccatgt tggtcaggct   45300
ggtctcgaac tcccgacctc aggtgatccg cctgccttgg cctcccaaag tgctaggatt   45360
acaggtgtga gccaccacac ctggctgatg aattttattt tattttattt tattttaat    45420
ttttaatttt tagttttatt atttattttt tactaagtac cacatgagtg ctgcctgtta   45480
ttatttatct gcatctctag gtctctgtct ctttccagct gtttgtggat ttctgtcttt   45540
ggggttttct ctgaatttct gacaccctct ggatctttgt tttcaggtcc ctttctcctg   45600
cctctgtatc tttgttttcc tgttttgagt ctttgactct ttggatgtgt ttctctctct   45660
ctctttgggt ctttttttctc cctttttcgtt tctgactatt ttcctatctc taggcccta   45720
acaacttctg ctgaagctct gtctcttgaa cactctactt gtcgttgttt gttttcattt   45780
ttgagacaag atctcgctct gtcatccaag ctgaagtaca gtggcacaat cacagctcac   45840
tgcagcttcc acctctcatg cccaaatgat cctcccacct cagacttgca gtagctggga   45900
gtccaggagc ccgccaccaa gcctggctaa ttttgtatt tatatatata tatatata     45960
tatatatata tatatata tatatata tatatata tatattttt tttttaaaga          46020
tgggttttg ccatgttgcc caggctggtc ttgaactcat gggctcaagc aaccccccca    46080
cctcagcctc ccaaagtgct gggattacag gctccaacac actctctctg tgcttcttgc   46140
cacctctctt tttgcccact gtcccaacca ctcttctctc atttcctgtg ccttcagcac   46200
ttaccccat acagtgagat gtcagacaat gctcagagaa gcaaagcaac tgccccgagg     46260
ccacacagcc ctccagaggc cagacttggg tagaccctc tcaggcccta cctcccagtc    46320
attggacacc ttcttctgcc ctctcctcct atatgacagt ctccttgttc ctcaatccag   46380
aaccctggag tgacctcaga gaacttccag agttagatca cagctgatga gaaggatttg   46440
ctgataggca gagggtgcct gggctgctca gcagggaag ggtccagccc ctgggaggac    46500
ctgagtgcca ggcccactct gacacatgct gtctccacct acagatgaca atctgggagt   46560
gtgctggcag gaagtggggg ctgacctcgt gtgcagccac cctcggctgg accgtcaggc   46620
cacctacaca gagtgctgct gcctgtatgg agaggcctgg ggcatggact gcgccctctg   46680
ccctgcgcag gactcaggtg ctggcactgg cctaggctga actcagaggc cttgccccat   46740
gggctccaaa tctaggccct cagatcccca gtcgcagaac ccccagactc tatccaaact   46800
ctgtccccta gaccaacccc tatgtcgcag cccatcccaa aatcttggtc cccgattcac   46860
actccaaaga cttccaagtc tcagccacag acatccaag gcctgaccca gcagatccca    46920
tagtaccaga cccacaggcc cctgaggtct ggtctctcat atgctcagct cctggtctct   46980
agaaccacca gacacagcct atgagatgtc ctccctaaa tcctgggccc ttagacctga   47040
aatgccagtt gctcagacct caccatcctg gccccagacc ccctggtcac agccccacag  47100
acctccaagt cccattgcct tagacaccct ccaagtccca ttgccttaca caccacatcc   47160
gggtgcctaa gaccccaaca cacagcccca gagattccca agtcttggtt tctacaacct   47220
ctgagtccct cagtcctcag cccttaggaa cccagttcca aagcccagt cctgggtcct    47280
cagacctcca ggtcccagtg cctcagactg tctcccatgc atcctgcccc ctcaggtccc   47340
cagcagcaat ccctgggatt cccccagtcct ggtccacaga acaccccat ctaatttctt   47400
caggtcccta gtcctagctc ccatgggtcg ctccaattcc agcctctcag accctgattc   47460
ttagcaggct tcattaccct tgatctcagc acgtccgaat cccagtctca gccttcgat    47520
tctcagcgct ggctccagaa accccgggc cacccaggac cctccccatc cagtcctctg    47580
```

```
cctcctctcc caagggggt atgtgagtgg tgggtgtggg ggccagcagg ggctgattgt   47640
ttgccttggc tcctgttccc agatgacttc gaggccctgt gcaatgtgct acgccccccc   47700
gcatatagcc ccccgcgacc aggtggcttt ggactcccct acgagtacgg cccagactta   47760
ggtccacctt accagggcct cccatatggg cctgagttgt acccaccacc tgcgctaccc   47820
tacgacccct acccaccgcc acctgggccc ttcgcccgcc gggaggctcc ttatggggca   47880
ccccgcttcg acatgccaga ctttgaggac gatggtggcc cctatggcga atctgaggct   47940
cctgcgccac ctggcccggg cacccgctgg ccctatcggt cccgggacac ccgccgctcc   48000
ttcccagagc ccgaggagcc tcctgaaggt ggaagctatg ctggtgagca ctgccagcgc   48060
atgatgagac tgagatgagg ggtgaggtgt gcacggagag aggagggagg gaaacagaag   48120
gcgggaggag agacggaaca caggtgcaac tggagagagc cacagaaagg gacagagaag   48180
tgtctatagc ccggcaaaga aagagaaggt ggcagaggga aagctggcga gagaatgagg   48240
taagcttact ggccccgcag cacccgccac agccctggag cgggatggac agtttacagc   48300
gagaaagatg gagccaagga cgcgcaccca ccgttgtggg taagggtga aggcagggac   48360 ctcaagtcat agggtccccg catttcccac aggttccctg gctgagccct acgaggagct   48420
ggaggcggag gagtgcggga tcctggacgg ctgcaccaac ggccgctgcg tgcgcgtccc   48480
cgaaggcttc acctgccgtt gcttcgacgg ctaccgcctg gacatgaccc gcatggcctg   48540
cgttggtgag ggcgggcccg gggccagcat gcgcaggag aggcgaggct tgtccaggga   48600
gggtggaagc cctgactagg gggtgctggt caggacggg aaaggacctc actacagggg   48660
acgggccagc gcaaaaggga ggagtaattc ttccacctgg gtggggcttg actgaagaag   48720
gcggagtcag ggtgccagca gggcagggct taaccacggg gctggagccg gcccttgaag   48780
caggatagag gaatagaata gtgctggtgt gacttgcagt gctaccttgg gcagtctgca   48840
ggacctcttt ggagagcctc agtcttccca cctgtaaaat gggaatatta atcaagtctg   48900
cctaatttgg atggcagtaa agccaagtga ttaaaatcaa gaacatagcc gggcgcagtg   48960
gctcacgcct gtaatcccag cactttggga ggccgaggcg ggcggatcat taggtcagga   49020
gtttgagacc agcctggcca atatggtgaa accccgtctc taaaaataca aaattagccg   49080
ggtgtggtgg tgcatgcgtg taatcccagc tactcgggag gaacccagga ggcagaggtt   49140
gtggtgagcc aagatcgcgc cattgcactc cagcctgggc aataagagca aaactccgtc   49200
tcaaaaaaca aacaaaactc gaggaggtca catagacctc agactcagtc cagcaacttg   49260
ctgtgtgacg ctggacaggt cactgtccct tacctaattt ttctgatatg aaaaatggct   49320
acagtcaaag atcccatttc atagaattgc gaatattatt aacactgatt tacaataaca   49380
ttgagagtca tgtgcaaatg gaggcacatg cgtaaaacga attacagtac ctacctaata   49440
ggggtattag aaggacaaag ttaatacttg taatgtgctt aaaacaatgc atgaacattt   49500
attgttgttg acaccatcat cagtattttt ttcttctttt tttttctttt tcttggcgac   49560
agagactcac tctgtcgccc aggctggagt gcagtggcct gatctcggct cacagcaacc   49620
tcctcctccc aggttcaagc gattctcctg cctcagcctc tcgagtagct gggattacag   49680
gcgcccgcca ccatgcctgg ctaattttgt tattcttagt agagacgggg tctcaccatg   49740
ttggccaggt tcgtctcgaa ctccggcctc aagtgatcca cccgcctcag cctcccaaag   49800
tgctgagatt acaggcatga gccaccgcgc ccggccatta ttattttctt aacaaaatcc   49860
tagtgcggta tgggccacca tatccatctt acagaacacg aaactgaagc acagtgaggt   49920
```

```
taagccacct ggccgggctc acacagttag cagatggcag aggccagatt ggactccaaa    49980
ctgctcagca tctgtgctcc tctgttccaa gaacttaagg ggccaaggag gcgagcttct    50040
ggggcccag  ccttcagcag cgatcgttgt ctcccctccg cagacatcaa cgagtgtgat    50100
gaggccgagg ctgcctcccc gctgtgcgtc aacgcgcgtt gcctcaacac ggatggctcc    50160
ttccgctgca tctgccgccc gggattcgca cccacgcacc agccgcacca ctgtgcgccc    50220
gcacggcccc gggcctgagc cctggcaccc gctggccgcc cacccgcgcc cgccactcgg    50280
ggcccctgcc gcgcatcctg cagcccgctt atgcgtatgt gcacggggcc gcccgcctgg    50340
acctggagaa gggacctacg gacgcctgga agctgcgacg ccctgcactg ctcccgcctc    50400
caccagcgcc tcccactgat gtcgtggtcc cgggcctggc ccaggggccc ctttacatgc    50460
cctctccctt ttataaaatt ttccattaaa aaccacctat tttctatctt ttgcctcctc    50520
ctgtctattt ctccaagtct accccagttt gtgctttgag tcactaaatg acattccctt    50580
cccttctgac ccctagtttc gtctgtctct ctgcctctct tggtctctgt cttccttctc    50640
tctctgtctc tgtcgttcta tctcatctct gtctctttct gatttgtttt ctctgcctaa    50700
cctctacatc ctgtcttttc atttctgttt ctgcatgcgt cttttctctt tcccttctct    50760
ttgtttggtt ctttcatctc gagagcaatc ttgcctctgg atttttttt ttttttttt     50820
ttttttttg  agatggagtc tcactctgtc acccaggctg gagtgcactg gcgccatctc    50880
catccactgc aacctctgcc tcccggtttc aagcgattct cctgccttag cctcccaagg    50940
agccgggatt acaggtgcac actacaaccc aggctaattt ttgtattttt agtagagacg    51000
gagtttcgcc atgttggcca ggctggtctc aaactcctgg cttcaggtga tccacccacc    51060
ttggcctccc aaagtgctgg gattacaggt gtgagccacc gcacccagct tttatttttt    51120
agagatgagg tctccctatg ttgcccagtc tggtctcaaa ttcctgggct caagtgatcc    51180
tcccacctcg gcctcccaaa gtgctgagat tatagatgtg agccaccgtg cttggcctag    51240
aagtcttaag ctgtcctgga acaagtgggg caagagcagg gagcaggagt ccctggaggg    51300
ccaaacccag acctgacgct ccagctagga gttggctgtg gatggagtat ggagcggcag    51360
tcctgacagc tggaggcggg aatgagctct gtgtgtgatg gtggagtgcc cagcacggac    51420
ctcctccatg tgccctgcct gcttactggc catgttccta gtccagactc ctcctcccta    51480
aaaaacaaga acggcctaga tcagcataaa cttgggcag  gagtaggggt cgggaatcgt    51540
gggtgatcaa cttggcactg ggccaagctg ggaaaaaaaa aaaaaatgta cctcagccag    51600
gcgcgatggc tcacacatgt aatcccagcg ctttgggagg cccaggcagg cggatcacga    51660
ggtcaagaga tcaagaccat cctggccaac atggtgaaac ctggtctcaa ctaaaaatat    51720
aaaaattagc cgccatggt  ggcatgcaac tgtaatccca gctatttagg aggcggagat    51780
aggagaatca cttaaaccca ggaggcagag gttgcagtga gccgagatga cgccactgca    51840
ctccagtctg gcgacagagc cagactgcat ctcaaaaaca aaaacccaca aaactgtacc    51900
tgtcattctt cacccacctg tcaattcttg tgtccccagg gtttcaaact catatgctgc    51960
aaagaccaga accggaatgt tagcaggaag cagggaaaat tgaggcacac attaccttct    52020
gcctaaggct tggttagact aggaagggga attttcccca ttgttaatac ttttttttgg    52080
cctggcgggg tggctcacga ttgtaatccc agcacttcgg gaggccaagg caggatgatc    52140
acttgagctc gggagtttga gaccagcctg gcaacatagt gagacccat  ctctacaaaa    52200
aagtagctgg gtgcgatggt acatgcctgt agtcccaact acttgggagg ctgaggtggg    52260
atgattgctt gagcccagga ggtcgagact gcagtgagct gtgatcgtgc ctctgcattc    52320
```

| | |
|---|---|
| cagcctgggt gacaaaggca taccttgtct ccaaaaaagt tttttttaat gtatattttt | 52380 |
| ataaactatc tgatattgtt tggctgtgtc cccacccaaa tctcatctca aattgtaatc | 52440 |
| agaattgtaa tccggggaag gacctggtgg gaggtgattg gatcatgggg acagtttccc | 52500 |
| ccatgctgtt atcgtgatag tgagtgagtt ctcacaagat ctgatggttt tataagggc | 52560 |
| tcttctccct tggctcgctg tctctcctgc cgccttgtga agaaggtgac tgcttcccct | 52620 |
| ttgccttctg ccatgattgt aagtttctga ggcctcccta gccatgcaga actgtgaatc | 52680 |
| aagtaaacct ctttcctta taaattaccc agtcttgggt ggtatcttta tggcagagta | 52740 |
| agaatggacc aatagggccg ggcacggtgg ctcatgcctg caatcccagc actttgggag | 52800 |
| gctgaaacag gtggatcacc tgaggtctgg agttcaagag cagcctggcc aacatggtga | 52860 |
| aaccccatct ctactaaaaa tacaaaaatt agcagagcat ggtggtggat gcctgtaata | 52920 |
| ctacctactc gggaggctga ggcaggagaa tcgcttgaac ccaggagccg gaggttgcag | 52980 |
| tgagctgaga ttgggccact gcactccagc ctgggtgaca gagcaagact ctgtctcaaa | 53040 |
| aaaaccaaaa acaaacagaa aaagactaat atagtaccct atgggcctg tttggcctat | 53100 |
| gaggctccag ttttaatcct ctaggcactg ctgaaattgc ataaattgtg gattggaggc | 53160 |
| tgcttcctga cctgatctcc agcccacccg ctgagtgtca ggagggtca catgcccagc | 53220 |
| agcctcctgt gctacatcgg ggaatcatac taagagcgcc tacctgcag gattggtggt | 53280 |
| ggtggttaaa tgaattgtca tatatgtgct tagaatgtca cctggtacag agcaagggct | 53340 |
| cagtcattgt tggcataacc ctgggcctcc caggatatgc tgagccctgt ggctgggcag | 53400 |
| atagtaaggt cttgttcttt tctctttcc tttccttct cctttctttt tctttctttc | 53460 |
| tttctttctt ttttttttt gacatagggt cttgctctgt tgcccaggtt ggagtgcagt | 53520 |
| ggtgccacca tggctcactg cagcctcaac ctcccaggct caagtgatcc tcccacctca | 53580 |
| gcctctcaat tagctggaac tgcaggcatg tgccaccatg ctcagctaat ttttaattt | 53640 |
| ttatttttg tagagagggg accttactgt gttgcacaag ctgatctcaa actcctgggc | 53700 |
| taaagtgatt ctcctgcact ttggcctgcc aaagtgctgg gattacatgt atgacccacg | 53760 |
| gcacctggcc tggctaggtc ttttttcttta ccaattctcc ctcccagggt ggaggaggag | 53820 |
| gccagacccc atccccttca acaggacagt gagaaacacc taacacaagg ccttggtggg | 53880 |
| gaggagtgtc agacaaggag tggctcaagg ctccacaaag gggtgacagt tgcacaaaac | 53940 |
| tgtctgtacc aaaaatcatt gaattataca ctacacatgg gtgacttgtg tggtatgtga | 54000 |
| atcataagtc aataaagccc ttcttaaaa acgccgactc tacaaagcgt ttcagaaagt | 54060 |
| taccctccag ctgatacagg gaacccgacc caaccactaa ttcctcagtc attcattcaa | 54120 |
| caaatatttt cctgctttgc aataagtgaa ttcgaggaac acaaacttta acccagcctt | 54180 |
| ggggggtggt tagggagggc tcctggagga ggagatgttg gagctgagag ttgattactg | 54240 |
| tagggaaatg agcaagatga aagggtgga ggtgcctata atcccagcta ctccggaggc | 54300 |
| tgaggcagga gaatctcttg aacccgggag gcagaggttg cagtgagcca ggattgcacc | 54360 |
| gctgcactcc agcctgggca acagagtgag actctgtcag aaagaaagag agagagagag | 54420 |
| aggaaggaag gaaggaaaga aggaaggaaa agaaagaaag aaagaaagaa agaaagaaag | 54480 |
| aagaaagaa agaaagaaag aaagagaaag aaagaaagaa agagagagaa aaagaaaaga | 54540 |
| gaaagaggtg gagaaccatg ttccaggtgg aggggacagc acttccgaag gcctagaagt | 54600 |
| aagagagcaa gtgtctgtta gatgtctttc ctttggtatc taaggcctgt attggacaac | 54660 |

```
aatggtgaca atcttggtgc ctgagaaatc ccaggcccct tgccttcatgg gggacaccga   54720
cacatcacca cacatgagag cctgtgctgt atggggagg  cacaggcagg ggtcaggctg    54780
cggtgggga  agatcagagg gcatgcatgc ccagaggaga cacttgatcc agtctgagag    54840
atgatcaggg aaggctttct ggagaaagag acaaagctct gaacagtctc tgtttgggcg    54900
tctagatccc tttgagaatc tgtcgaaagc tcattcacag aagaaaaact cacacaaaca    54960
aaggttgcag gcaatttcca agtattctca tccttcctcg gaatcttctg tgggtatccc    55020
attcccaccc cgcccccaca accaccttgc tgcataaatg tcccaggaat tgcgacaggg    55080
ctggccaaca gtgctggaaa actgcaatcg aatttcagca tcctgggagt gggatctttc    55140
ttctgagatc tcgcccgccg ccgggcctgg agggtgtgcc ccatggatct aattgttatc    55200
ctgcctgcat cccctgcact aaccccccaga cctggcgttg gggcttctgg cactggccgg   55260
gaccgacgcg ttctcctctg gaatgttcag agggaggtag tccaggcggt caccgcgctc    55320
gccagacaag caacgcagcg ccccccgatg gccaccgcgc gccggcgcag cccaagccgg    55380
ctgcgccccc tagtggccga tgctcgtaaa gtcttcagcg agcccgagc  ttttgctagc    55440
cagcccttgg ttttgcaggc tggggtcatc gtcgttgtca tcgttggcat catcatcatc    55500
atcatcatca tcatcatcat catcaatagc tagtaggctt ggcgtggtgg cccacacctg    55560
taatcctagc actttgggag gccgaggcag gtggatcact tgaggccaga agttcgagac    55620
cagcctggcc aacatggtga aacccccgtct ctacaaaaca gtacaaaaaa gcaaccgggt   55680
gtggtggtgg gcacctgtaa tcccagctac tcgggaggct gaggcatgag aatagcttga    55740
acctggaagg cggaggttac agtgaactga gatcgaacca ctgcactcca gcctgggcaa    55800
cagagtgaga ctctgtctca aaaaaaaaa  aaaaaaaaa gctatgatca tccaggcagt     55860
gattcatgcc tgtaaccgca gggctttggg aggccaaggc aggaggatgt catgaggcca    55920
tgagttctag actaacctgg gcgacagagc aagagctgtc tctataaaac aaaacaaaat    55980
gctatagacc agacgcagta gctcacacct ataatcccag tgctttggga ggccaaggca    56040
ggcggatcac ctgaggtcag gagttcgaga ccagcctggc caacatggtg aaaccccatc    56100
tctacacttt gaaaaccact actttaactg tctctcccac agggagagct gcctccttca    56160
ctctcagctc atttggttca catgttgacc ctactggaag actccagacc tggccagtga    56220
gagaatccct tcccttcagc cttttgcaact ggcttaggga caggtgtgtc cctgaagctg   56280
gactgatgag cattggctct ggaactactg ctgattgttg aagaaggggc ttcctagaca    56340
tactgtgctg aaagggcaca ggcttggaac actgggttct tacatgggag aagagctggc    56400
ctgaaaatgc agccaacacg aggggaagca gcgctgggag aggaacagag agactggtgc    56460
ctggcgcacg tcatctgcac ctctgtctca cccttctcca gaacatttct ttgcatctta    56520
catcaaattt gtcagcaaat tctgtcggct ctagttagaa aaggtgtccc attctgtgtt    56580
ggaggaaaag cgatgctgtc tatcaggacg ttacccgggtc agttgacaga actgaaatac   56640
gaacagtcga ttagaaaaat tcacatacta atattaaatt tactgaagtt gatcactata    56700
ttgtggtcat gtaagagaat atccctattc ttttgttttg ctttgttctg tttttgagac    56760
ggagtctcgc tctgttgccc aggctggagt gcagtggtgc aatctcagct cctgcaacct    56820
cctcctcctg ggttcaagca attctcctgc ctcagcctcc cgagtagctg ggactacagg    56880
tgtgtgccac catgcccagc taattttcgt attaatattt ccagtacaga cggggtttca    56940
ccatgttggc cagggttctc gaacttacgg cctcaagtga tctgcccacc tttgcttccc    57000
aaagtgctgg gaccacaggt gtaagccacg tcgcctggcc agaaatatcc ctattctttt    57060
```

```
cttttcttttt cttttttgag atggagtttt gctcttgttg cccaggctgg agtgcaatgg    57120
cgaaatctcg gctcactgaa gcctctgcct ctggggttcg agaaattctc ctgccttagc    57180
ctcctgagta gctgggatta caggcaccca ccaccacacc cagctaattt tttgtatttt    57240
tagtagagac agagttttgc catgttagcc aggctggtct tgaacttctg acctcaggtg    57300
atccgccccc ctcggcctcc caaagtgttg ggattacagg catgagccac cgctcccggc    57360
caaatatccc aattcttaag aaatacatag ggcggctgag cacattacct catgcttgta    57420
atctcagcac tttgggacac tgaggtggga cgatcccttg agcccaagag ttcaagacca    57480
acctgggcaa catggcaaga acccatctct caaaaacttt aaaaatgatc caggtgtggt    57540
ggctgcagtg tcaaggctgc agtgagccag gatcatgcca ctgcactcca gcctgggtga    57600
cagagtgaga ccctgtctct acggaaaaaa agaaagaaaa gaaaagagaa tacattacag    57660 aagttttttgt ttgtttgttt gtttgtttgt ttgagacagt cttgctctgt cgcccaggct    57720
ggagtgcaga gtgcagttca gttcactgaa atcctggttc actgcaacct cacctcccgg    57780
gttcaagtga ttctcctgcc tcagcctcct gagtagccag gactacaggt gtgtgccacc    57840
acacccaggt aattttttgta ttttttagtag agacaaggtt tcttcatctt ggctgggctg    57900
gtctcgaact tctgacctca gatgattcgc ctgccttggc cttccgaagt tctgagatta    57960
taggcatgag ccaccgtgcc cagcccatta tagaagcttt tagggggtgat gttgtttgta    58020 acttagcctc aaagattttt ttaaaaatca gaaaagaaa atacataaca gagaagagag    58080
caagtgataa aggaaatgag gtagaaatgt taccaatcca tgaacctgag tataaaatac    58140
aagagagttc tttgtcctat tatttgtctt gcaacttttt ggtaaatttg aaattatttc    58200
caaaggaaaa gttaaaacac tttctaaaat tgagagatct aaaatcttag gccaggcgtg    58260
gtggctcaca cctgtaatcc cagcactttg ggaggctgag gcaggtggat cacatgaggt    58320
caggagttgg agaccagccc ggccaatatg gtgaaaacct gtctctgcta aaaatacaaa    58380
aatcagctgg gcatggtggg aggtgcttgt aatctcagct actcaggcac gagaatcgct    58440
tgaacctggg gagcggaggt tgcagtgagc cgagatggcg ccactgcact ccaccctggg    58500
taacagagca agactccaac tcaaaaataa tatgaaataa aataaaatct tagacaacac    58560
tatcattata agtaggattg gggagatcaa aaacaacatg ctctgtgctc caggtactgt    58620
ttggtgtgat gttgaaaata ttagatttta aacttgattt tttctttttt tttttttga    58680 ggcagagtgt tgctctgtcg cccaggctgg agtgcagtgg cgtcatctcg gctcactgta    58740
acctccgcct cctaggttca gcgactctt ctgcctcagc ctcctgagta gctgggacta    58800
caggtgtgcg ccaccacacc tggctaattt ttgtattttt agtagagacg gggtttcacc    58860
atattggcca ggctgatctc gaactcctga cctcatgatc tgccctcctc ggcctcccaa    58920
agtgctgaga taacaggcgt gagccactgc gcctagccta gacttgattt tttaaatttc    58980
tgtcctccaa tagaaataga cctgatttt aaaaatgtgc atggccaggc acagtaattc    59040
atgcctataa tcctaggact tgggaggcc aatgtgggag gatcacttga gcccaggagt    59100
tggagatcaa cctggacaac atagctagac cctgtctcta caaaaataaa aatattaggt    59160
gggtgtggtc ttgtacacct gtagtgccag ctacacaggg ggttgaggag ggaggatcca    59220
ttgagaccag gagttccagc ctgcaacgag ctaggatctc accactgcac tgcaggctgg    59280
gcaacagagc aagaccctgc ctcaaaaaaa aaaaaaaaa aaaagcatg ttaaaatttc    59340 aaagattgct acaaaaagaa agaaatggtg catagattcc aaactagtag agggaaaaca    59400
```

```
aagaataaga aaacataaga caaaactaaa caaaaaatgc agccaattca aagaagctta    59460
aatgagcatg aaaaaataaa taaacgtaga aaaatgagga cactagaatc acaaagcaaa    59520
atggtagaag taaataaaat acatcattaa tcacatacac aaaaaatgta ttcagggcca    59580
ggtatggtgg ctcacacctg taatcccagc actttgtgag gctggggcag acggatcact    59640
tgaggcaaca agtttgagac tagcctggcc aacatggtga aaccccatct ctaccaaaaa    59700
tacaaaaaaa aaaaaaaaaa aaagaagaa gaagttatcc aggcattgtg gtgcacgcct    59760
gtaatcccag ctacttggga ggctgaggta ggagaattgc ttgaatccag gaagtggagg    59820
ttgcagtgag ctcagattgc accactgcac tccagcctgg gtgacagagt gagactccct    59880
ctcaaaaaca aacaaagaaa aaatgtattc agaggccaaa tacttcttac cacctccata    59940
gctgccaccc atatcttacc ctcctcctag ggtttggagt tcctactcct ggccccacaa    60000
tctctccccg tcatgcagat agagggactc tgggaataac caagtcaact caactccctc    60060
tgctgctcaa aactttcctg tggctccatc tcactcaaag attattttgc tcattttttt    60120
tttgtttttt tttgagacag ggtctcactc tgttgcccag gctggagtgc agtggtgcaa    60180
gtcatgactc actgcagcct agacttcctc ggctcaagcc atcctccagg cctccagggc    60240
taccacaacc cagccaattt tttgatagag acgaggcctc ccttattgcc caagctggtc    60300
ttgaacttat gggctcaact tatctaccca cctcggcctc ccaaaatgct gggattccag    60360
gcctgagcca ctgtgttccg ccaatctcat tcaaagtaag agccaaagtc ctcactgtgg    60420
tccagcagac tctgcaccgt ctgcttcttg ttccctctct gacctcacct cccctccacc    60480
ccccacacgc tcctctgcag caacacggat ctccttgttg tttctctaag atccagacat    60540
gttcccatcc caccccagga ccttggcact ggctgttccc tctgcctagg ggactctttc    60600
cactaggttc agtttctctt ttttttttt tttgagacgg agtttttca ctcttgttgc    60660 ccagactgga gtgcagtggc acgatctcgg ctcacagcaa gctcctcctc tcaggttcag    60720
gcaattctcc tgcctcagcc tcccgagtag ctgggactac aggcacccgc caccaccccc    60780
agctaatttt tgtattatta gtagagacgg ggtttcacca tgtggccagg ctggtctcga    60840
actgctgatc tcaagtgatc catctacctc agtctcccaa agtgctggga ttacaggtgt    60900
gagccaccgc gcctggcccc cttggctcag tccctcacca ccagcagaag aatggataaa    60960
ctgatcccac agtggcctgc aatgtgtgtg tgctgcaatg agaataacct gtaactgcac    61020
acgacaacca ggatgaattt ttttcacggt gctgactgaa aaaagccaga tgctaaaaag    61080
aacatatttt cagattgcat ttacatgaat tcaaaacagg cacaaccaat ctatgctgtc    61140
agaagtgagg gtgataatga ccttggaggg agggcaggtg ataagggagc gccgaggggg    61200
cttctggggg gctggagata ttgcttcttg ggctggtggc tggtgacaca ggtgtgttca    61260
atcggtgata attcctccag cggttacact tacggtttgt actttcctga atatgggtct    61320
acttcaagaa accactgctg aaaacgagga gctgcaccca ccaccagtg tccctccat    61380 ccagtttaag caacaggaca ttctcagccc cccggggtcc ctccctccca atgcaatgtg    61440 ctttatgtc ttcaaggggc ctggccacca ccttggttgc ttccccagc ttgctatgca    61500 tgtcacccca cgcatgttcc aggcagctcc acagaggtcc ccagagagaa ggcaggctgt    61560
gggtgggagg aagggcaggg gtgggggacg tggcttccca gcggagcccg ggcaggggga    61620
ggaaacattt ctgcaacacc ccacaccaag tcctgacttc gggggggctt tgcagggtga    61680
attctaagtg cccagggccc catgtgaagg ggtcaactgt gtctcactct gtgtctgtct    61740
ctctgtctgt ctctcttcct gtttcctccc tccctcccag tctctctctc ctcaagaaga    61800
```

```
aaaaaactca caactatttta cataacaatt ttatatcaga ctgtaaccca aaaacccaag   61860
ttccaacttc gaattttttca ataaactttg aataaatagt agtgctattt ttcttctctt   61920
ttttttttag tactgtaatg tttactttta aatttaattt ttactggcag actttacgta   61980
tatgaggttc aagaaaagaa aatctccact gtttacattt cttttctgac tattaatatt   62040
gttcatttca tttcctgatt attactggca ataattttgt cctatgggga agggaggcgc   62100
ttggcaggcc tcgagttatc ctttgagaca tgggggtctg tggtcagatt tagaaagtgc   62160
ttgtgggtgg ctgggtggga gtgggtcatg ggagacataa gggcaggctg gagtccaggg   62220
aggaggccgg ccgggcaggg acccaggcag cggagatgga cagggccatg gagaatctgg   62280
gaggcgcagg ccctggggac tgtggattgg ggaaggagat aattttattt tattatattt   62340
ttttgagaca gagtttcagt ctgtctccaa gactgtagtg caatggcacg atctctgctc   62400
actgcaacct ctgcctcccg agttcaaggg attttcctgc ctcagcctcc caagtagctg   62460
ggattacagg cacgcaccct cacacccagc taattttttaa tattttttggt agagacgggg   62520 tttcaccata ttggccaggc tggtctcata ctcctgacct caagcgatcc acctgccccg   62580
gcctcccaaa gtgctgggat tacaggcatg agccacgacg tctggcctaa ttttttgtat   62640
ttttaggaga gacagggttt tgccatgttg gccaggctag tcttgaactc ctggcctcaa   62700
gtgatccgca cacctcaacc tcccaaagtg ctgggattac aggtgtgagc cactacgccc   62760
cgccaaggga aggggagaat ttgagtgcta ttgaaggtag aaaacacaga acataggctg   62820
ggtgtggtgg ctcatatctc taatcccagc actttgggag gccaaagtgg gaggctggct   62880
taatcccagg agttcgagat cagcctgggc aacatagtga ccccctgtc tctacaaaaa   62940 attaaaaatt agccaggcat ggtggcaccc acctgtactc ccaaggctac ttaggaggct   63000
gaggtgggag gatcgctgga tcccaggaga tctgaggtga gccgtgatca tgccactgca   63060
ctccagcctg ggcagcagag taagaccctg tctccaaaaa taaaaaataa tttaaaataa   63120
agcgcggaac actgtcaggt tgtctgtggg ggagcagcgg gcaggcgacc aggagggctg   63180
gctgctctgt gcagggctag tgcctgggtt gggatgactc ggcctcagag ctgtaaataa   63240
agaaggaaga gggccgggcg cggtggttca cgcctgtaat cccagcactt tgggagggcg   63300
aggtggacta atcacctgag gtcgggagtt cgagacaagt ctgaccaaca tagagaaatc   63360
ccatctctgc taaaaataca aaattagccg ggtgtggtgg cacatgcctg taatcccagc   63420
tactcgggag gctgaggcag gagaatcgct tgaacccggg aggcagagat cacagtaagc   63480
cgagatcaca acactgcact ctagcctggg cagcaagaac aaaactccat ctcgaaaaaa   63540
aaaaaaaaaa agtagaagaa agaaagagct gccacagttg agagcttcct ggatgccttt   63600
gttaactctt ggggttttca catcccatc ttacagatgg ggaagctgag gctcagagag   63660
aggaaggccc aagtggaaga gcaagcctgg agcccaggtc tcctcctgcc taatcctggg   63720
cttttgctgg tggactcccg cccaatcttg aataacttca ggccttaaac aacctcccac   63780
gattgctttt cctcccatta gaacaataaa tgcagataca aaaccaact atgcttgtct   63840 acaaagccca agagaatttt tgaagtaata aaactgtcat gaatgcagac tgtggtgatt   63900
acatgactta cgaattttttc aaaactcaga atcgagccag atgaaatgat cctgcctgca   63960
atcccagcac tttgggaggc tatggcagga ggatcatttg aggccaggag ttcaagacca   64020
gcctggccaa catggtgaaa ccccgtctct actaaaaata caaaaattag ctgggtgtgg   64080
aggcacatgc ctgtaatccc agctatttca gcagctaagg caagaaaatt gtttgaaccc   64140
```

-continued

```
ggaggctgag gttgcagtga gaaatgatcg tgccactgca ctgtagaccc tgtctcaaaa    64200
accaaaacca aaaccaaaaa aagaaaaaaa aaccccttaag aatcaggatt atacacgagc    64260
acacgcacac tcacccataa attttaccat ttgtagaaaa gaagaagaaa attcaaaacc    64320
aaatacaatg aatgtacttt ctctggattc caattcacac caaacaactg taaaaatctg    64380
tttttgagac aattggggaa cacaaactgg cttttaggag atattaagga atttcggtta    64440
attatgctag acttgataat gccattgtgg ttgggtaatg cccacatacc atgccttggc    64500
tgggcgtggt gactcacacc tgtagtccca gcattttggg aggcccagat gggaggattg    64560
cttgagctca agagttcgag accaacctaa gcaacatagt gagacctcat ctctacacaa    64620
aattttaaaa aacattagcc gagtgtggtg gggtgcgcct gtaatctcag ctactcagga    64680
ggctgaggtg ggaggagtac ttaaacccag gagtttgagg ttgcagtgag ctgagattgt    64740
gtcactgcac tccagcctga gcgacagagc aagaccgtca aaaaaataaa gaaagaaaag    64800
aaaatgtacc ctattcttct cttcaaggtg ctcattgaag tatttacaaa tgaaacaaca    64860
taatacctct cacctgtaat ttttttaaaat ttttatttat taatttttta gagatggggt    64920
ctcattctgt tgctcaggct ggagtgcagt ggcatgatca cagctcactg taacctcaaa    64980
cttctaggct caagtgatcc gcccgcctca gtctcccaaa tagctgagat tacaagcact    65040
ggccaccatg ctttgctaat gttttaaaaa ttattttttgt agacacaaga ctatattgcc    65100
caggctggtc tcagactcct ggcctcaagt gatcctccca acttggcctc ccaaagtcct    65160
ggaattacag gcctgagtca ccgtgcctgg ccaatttttt tttttttttg aggtggagtc    65220
tcgctctgtc gcctaggctg gagtgctgtg gcctgatctc ggctcactgc aagctccgcc    65280
tcctgggttc acgtcattct cctgcctcag cctcccgagt agctgagact acaggccccc    65340
accacgcctg gctaattttt tgtatttta gtagagacgg ggtttcacca tgttagccgg    65400
gatggtctcg atctcctgac cttgtgatct gcctgcctcg gcctcccaaa gtgctgggat    65460
tacagacgtg agccactgcg tcctgccctg cctggcctat tttttatttt tatgtttttt    65520
acagacaggg cctcactatg ctgcccggac tcgtctcaaa ctctgggctc aagcgatcct    65580
tctgcctcag cctcctgagt agctgggact acagggtgtg atttttttc aagtattcaa    65640 aaaaatgggg aggggaaaga agatgaaatg gcaaaatatt gatggttctt gaacctgggt    65700
gatgagtata tgtaagctta ttgtctcttg acttttttgtg tctgtttgaa aatttttcatg    65760 atataagagt ttaaaaactg aaaataaaat ttattgaagg agagtttggg ccgggtgcaa    65820
tggctcgcgt ttataatccc agcactttgg gaggccaagg caggtggatc acctgaggtc    65880
agaagttcaa gatcagcctg gccgacatga caaaacactg tctctaccaa aaatacaaga    65940
atcaggctgg gtgcggtggc tcatgcctgt aatcccagca gcactttggg aggctgaggt    66000
gggtggatca caaggtcagg agttcaagac cagcctggcc aagatggtga accccgtctc    66060
ctactaaaaa tacgaaaatt agccaggtgt tgtggtgggc gcctgtaaat tccagcaact    66120
tgggaggctg aggcagagaa ttgcttgaac ctggaggca gaggttgcag cgagccgaga    66180
ttgcgccact gcactccaac ctgggggaca gggcgagact ccttctcaaa aaaaaaaaa    66240 agaaaaagaa aaagaaaaat tagccaagcg tggtggcagg cacctgtaat cacagctact    66300
cgggagctga ggcatgagaa tcgcttgaac ccgggagacg gaggttgcag tgagccgaga    66360
tcgtgccact gcactccagc ctggggtata agcgaggct ctatctcaaa aaaaaaaaa    66420 aaaaaaaaaa aaaaaaaaa aggagagttt ggcgttcatc aagcaacatt tggaaactac    66480
agagaactag caaggcaaag acgcccctcc catccctaag tcctgtacca ctatggttgt    66540
```

```
tgacattttg atatatttcc tttcagcctt ttctattctc tgtgagcttt ttaaatgcgt    66600
gtgttgtgtg tgtgcacgtg tgtgttttac ataactgtgt gagcaaattg tttatacagc    66660 cctgttttt ccctcttaa aatgtaagct gttccctgt taaaacatct ttggataaac       66720
acaatctcta atgtttgcac tatgtttatt caaaagggca gcattgccag aggttgaagc    66780
tgtttccaat ttcctcccat tataaataat cccctcatgg acctccttgt gtgtcccaga    66840
ggagggattc ttgggccaaa gggtgcggac cctttggcag agctcatggt caaaaatctc    66900
ggcagagttt cagcctgacc cgaagctaag atgacctcat acggttaaag tgagattgga    66960
ctgctattta tttcctgaac gtttgattca tgactcaggc ttgtcagggg atctttttt     67020 ttttttttctt ctgtatgtgc ttggttgcaa gaaacagaaa tccattcaca ctagctcacg   67080 tcaaagggc aagagaatcg cttgaacgcg ggaggcggag gttgcagtga gccgagatcg     67140
cgccactgca ctccagcccg ggcgacagtg cgagactccg tctcaataac aaacaaacaa    67200
acaaaaaaag ggcgggggt gttgtatcct tcagcaagta aagctcatat tcagcttgga     67260
ctagctgtct gcggagcatg ttgttggggt atatctaggc tatgttgatt gttgaaatac    67320
tgaattattt ccgtattggt tggtaaatca ttctgtctca agtcgctcca atgacgtcct    67380
ccaccaaggc cactctagct gccctggtcc ctctcccagg acttcccaga cctctccaca    67440
atgcaggaag taaagggtca atatcgggca cagaagtgaa ccatgctgct cggtcagtgc    67500
ccaaagtatt ggttgtgaaa ttcattttt cttttctttt tttttttt ggagacaaat       67560 tctcactatg gaactcaagc gatcctcctg ccttggcctc ccaatgtact gggattaagg    67620
tgtgagccac tgcacctgga ctgcttgtaa aatatttgat gattcgccta gatgcaagta    67680
ccagaacagc tgactcaaat ggcttaaatt gtaaggggaa tctgtggctg gaaaatccac    67740
acttgtgctg gcttcagcca aagttgacac aatggctcag ccatgtcacc aaggactttc    67800
ttttctttct ttccttctt ctttcttctt tcttttttc tttctttct ctctcttct        67860 ttctctctct ctttttttt ttttttttg acgtagtctg gttctgttgc ccaggctgga     67920
gtgcagtggc acaatcttgg ctcactgcgc aacctccaa ttccccggaa ttcaagtgat    67980
tctcctgcct tagcctcccg agtagctggg actataggta tgtgccacca cgcccagcta   68040
atttttgtat tttatttt ttatttatta ttttttaat cattcttggg tgtttctcgc       68100 agaggggat ttggcagggt cacaggacaa tagtggaggg aaggtcagca gataaacaag     68160
tgaacaaagg tctctggttt tcctaggcag aggaccctgc ggccttccgc agtgtttgtg    68220
tccctgggta cttgagatta gggagtggtg atgactctta acgagcatgc tgccttcaag    68280
catctgttta acaaagcaca tcttgcaccg cccttaatcc attcaaccct gagtggacac    68340
agcacatgtt tcagagagca cagggttggg ggcaaggtca cagatcaaca ggatcccaag    68400
gcagaagaat ttttcttagt acagaacaaa atgaaaagtc tcccatgtct acctcttcct    68460
acacagacac agcaaccatc cgatttctca atcttttctc cacctttccc cattttctat    68520
tccacaaaac tgccattgtc atcatggccc gttctcaatg agctgttgag tacacctccc    68580 agacgggtg gtggccgggc agaggggctc ctcacttccc agtaggggcg gccgggcaga    68640
ggcgcccctc acctcccgga cggggcggct ggccgggcgg ggggccgacc ccccacctc    68700 cctcccggac ggggcggctg gccgggcaga ggggctcctc acttccagt aggggcggcc    68760 gggcagaggc gccctgacc tcccggacgg ggcggctggc cggcggggg gccgacccc     68820 ccacctccct cccggacggg gcggctggcc gggcagaggg gctcctcact tcccagtagg   68880
```

-continued

```
ggcggccggg cagaggcgcc cctcacctcc cggacggggc ggctggccgg gtgggggggct    68940 gaccccccca cctccctccc ggacggggcg gctggccggg cggggggctg acccccccac    69000
ctccctcccg gacggggcgg ctggccgggt gggggggctga cccccacctc cctcccggac    69060
ggggtggctg ccgggcggag acgctcctca cttcccagac ggggtggctg ccgggcaaag    69120
gggctcctca cttctcagac ggtgtggctg ccgggctgag gggctcctca cttctcagac    69180
ggggcggttg ccaggcagag ggtctcctca cttctcagac ggggtggccg ggcagagacg    69240
ctcctcacat cccagacggg gcggcagggc agaggcgctc cccacatctc agatgatggg    69300
cggcctggca gagatgctcc tcacttccta gatgggatgg cggccgggca gagatgctcc    69360
tcactttcca gactgggcag ccaggcagag aggctcctca catcccagac gatgggtggc    69420
ccggcagaga cgctcctcac ttcccagacg gggtggcggc cggcagaggg ctgcaatctc    69480
ggcactttgg ggggccaagg caggcagctg ggaggtggag gttgtagcga gccgagatca    69540
cgccactgca ctccagcctg gcaccattg agcactgagt gaacgcaact ccgtctgcca    69600
tcccggcacc tcgggaggcc gaggctggcg gatcactcgc ggttaggagc tggagaccag    69660
cccagccaac acagcgaaac cccgtctcca ccaaaaaaat acgaaaacca gtcaggcgtg    69720
gcggcgcctg caatcccagg tactcggcag gctgaggcag gagaatcagg cagggaggtt    69780
gcagtgagcc gagatggcag cagtacagtc cagctttggc tcagcatcag agggagaccg    69840
tggaaagaga gggagaggga aaccgtgggg agggagag ggagagcgag agcgcatcag    69900
agtattttaa cagcagaatt gatcaaacag aagaaagaat tagtgagttt gaagacaggc    69960
tatttgaaaa tacacagtca ggccgggccc agtggtcat gcctataatc ccagcatttt    70020
gggaggctga ggtgggcgga tcacctgagg tcaggagttc aagaccagcc tggccaacat    70080
ggcaaaaccc cgtttctagt acaagtacaa aaattagcca ggaaatggtg gcatgtacct    70140
gtagtcccaa ctactcagga ggctgaggca caagaatgac ttgaacccag gaggcagagg    70200
ttgcaatgag ccgagtttgt tccattgcac tccagcctgg gtgacagagt gaggctcttt    70260
aaaaaaaaaa aaaaaaagtc caggcgcagt ggctcatgcc tgtaatccca gcactttggg    70320
aggcggaggc gggcaaatca cctgagatcg ggagttcaag accagcgtga ccaacatgga    70380
gaaatcctgt ctctactaaa aatataaaat tagccgggcg tggtggcaaa tgcctgtaat    70440
ctcagctact caggaggctg aggcaggaga attgcttgaa cccaggaggc agaggttgtg    70500
gtgagccaag atggtgccat tgcactccag cctgggcaac aagagtgaaa ctcttgtctc    70560
aaaaaaaaaa aaaaaaaaaa aaaagatgaa agaaagaaa gagaaagaca cagagacaaa    70620 aaagaagag aagaaaaag aaagaggaag aaagaaagag agaaagaat aaaaaaaaag    70680 aggaagaaag aaaggaaaga aaaaagaaa agagaaagga gggagggaag gaaggaagaa    70740
aggaaggaac gaacaaacac agtcacagga gacaaaagag aaaaagtttt ttgtattttt    70800
aatagagacc gggttttacc atgttggcca ggctggtctt gaactcctga cctcaagtga    70860
tctgcctgcc ttggcctccc aaagtgctgg gattacaagc gtgagccccc gtgcccggcc    70920 agacccccatt tctcccatttt ctttttatct ctctgcttta tcttttccag tggaagctcc    70980
caagatgact acctccagcc tctggccaca gggaaccttc ttcatatccc acaagcaaag    71040
gagagcacct ttggctcagg tttcctgcca aagtaatgag gctaactctg attgggccaa    71100
cagagggcac gtgttcatgc aagagccaat cactgtgatc ggaggacag aaggaaaaac    71160 cataatggca agattggctg agccaagtca catgttcctc aaatagtaag gtgagtggct    71220
cacactaggg ctgcaggagc cacacctggg ttcaatttcc attccaaaca aatttctgtc    71280
```

```
ttctctgccc tgtttcccgt cagtaacata gagataatga aggcactcat atggtagagt    71340
tcccgtgagg attaaatgag ttagttaatg caaagcactg agaatggtgc ccatatacag    71400
aaagcgttca aatgttagct tctgttatcg tcattacatg gccattctca cctcttaagg    71460
ctgcttttct ttgcaagctc cttatgctcc acacatttcc ctctttctag ttactattgc    71520
ttggtaacaa atcactccaa aatatggtgg cccaaaacaa caacagtcat cctattattt    71580
ttcactgtgt ctgtggtcag agttttggga aggacccaac tgggcagttc tgacttggaa    71640
tttcatatgg ttgcagtcac ttggcagctg aaactggaac agggaagcag ctgggggtgg    71700
atggatctct ctctctctct ctttctctta ctctctcccc actccatgtt gtctcagggc    71760
ttctcaatgt ggtctctcca cgcgaactgg tttgggctcc ctcacatcat gacagcctct    71820
gggcagttgg acttacatgg cagcttcggc atccagtaca agtgttttat gaaagtagca    71880
gccgcgactg ggtgcggttg ctcacgcctg taatcccaac actttgggag cttgaggcag    71940
gtggatcacc tgaggtcggg agtccaagac cagcctggaa acatggtga aatcccgtct    72000
ctactaaaaa tacaaaaatt agctgggcat ggtagcacgg gcctgcggtc ccagctactc    72060
aggaggctga ggcaggagaa tcgcttgaac ctgggaggcg gaggttgcag tgagccgaga    72120
tcacgccact gcactccagc ctgggcgaca gagtgagact ccatcgaaat gaaagaaaga    72180
aagaaagaa gagaaagaga gaaagaaaga aggaagaaa gaaagaaaga gagagaaaga    72240
aagaaaggag ggaaggaggg agggaaggag ggaaggaagg aaggaaggaa ggaaagaagg    72300
aaaggaaggg gccttatctc ttctgatcta gccttggaat catgcagcat tacttctgcc    72360
acatagtctt ggttacaagc aagtcacaaa ctgcctagat gtaagggag cttacacaaa    72420
ttccacttcc caatggaagg ggtatcaaag ttctagagga atatatggc tgggaaacat    72480
tgttgccacc atctttggaa gttacatctg gcttttactg gtactgattt aagacccacc    72540
tctatacagc ctgtgcccaa taacatccac ctgggcacag ctccaactcc ctgttctaaa    72600
cagaaatagt ttattgagaa atctcaatcc cttgggatca aaaacatgac agtttccatt    72660
tgttctgcag tgactgctct ctacctgcta tctattgttt tccaagacta tgatccaaaa    72720
tcacagcatc caagactgtg tcttttttat ttatttattg ttttcgagac agggtctcac    72780
tctgtcgccc agactgtagt gcagtggcgc aatctccact caccgcaacc tctgcctccc    72840
aggctcaaga gattctcctg cctcagcctc ctgcgtagct gggattacag gtgcaccacca    72900
ctactgcctg gctaattttt gaattttcag tagagacagg gtttcaccat gttggccagg    72960
ctggtcttga actcctgacc tcaaatgatc cacccacctt ggcctcacaa agtgctggga    73020
ttacaggcat gagccaccac agctggcccc aagactgtgt ctttattatt attattattt    73080
cgagacagag tctagtctg tctcctaggc tggagtgcag tggtgcgatc tcagctcact    73140
gaaaccttca ccttgccagt tcaagccatt ctcgtgcctc agcctccgga gtagctggga    73200
ttacaggcac gcaccactac acccggctaa ttttcgtatt ttcagtaggg acggggtttc    73260
cccatattgg ccaggctggt cttgaactcc tgacctcaag tgatccaccc acctcggcct    73320
cccaaaggtg gctcacagaa gtgagccacc acgcccggcc tgtctattat ttttatttt   73380
aaaaataaat gtattgttaa tttccttttt cctgttggat aaaggctaca gggaaactta    73440
atgacaattt tgctagagtc tttaatattt ctctcatttt cattcattta aaaacatagc    73500
cttcaggcca ggcacggtgg ctcacaccta taatcccagc actttgggag gccgaggcag    73560
gtggatcact tgaggtcagg agttcaagac cagcctggcc aacatggtga aaccccgtct    73620
```

```
ctactaaaaa tacaaaaatt taaaaattag ccgggcatag tggcatgtgc ctgtagtccc   73680
agctactcag gaggctgagg caggagaatc acctgaaccc aggaggtgga ggttgcagtg   73740
agctgagatc gcaccactgc actccagcct gagcgacaga gtgagactcg gtctcaaaca   73800
aacaaataca caaaaaaacc cacaaagttc atggggaggg aaaggtgtag cctctcttga   73860
gaactttcct ctctcatttt cccccaaac aggatgatgc ttcctttctc ttctctatcc    73920
ttttctggac agccttgggt cctctcagta acttatttgg gtaagtggct ggttataatg   73980
gcagtgacct cgaacttagg ctctggggta gttggccact tttgtcctca gttttgggca   74040
gtagtagcaa ttctggaagt tctgggaaaa atccaatttg acatcatagt acgaacctga   74100
aggaaaggtc ttgatcccaa agagctctcg gcagctcatg gctgtgactg tcatccaggg   74160
cctgggcctg ggaaatgtt tggggatctg tgggatcctt tagggactgt cacagtgact    74220
cgggaaatgt tgctataggc aactgttctg gaacttttg gtcttaggac tcttttacat    74280
tcttaatagt atcaaggacc ccaaacagct tttatttgtg tgggttataa ctttttttt    74340 tttttgagat ggagtttcat tctagtcgcc caggctggag tgcaatagtg tgatcttggc   74400
tcactgcaac ctctgcccca caggttcaag caatcctccc acctcagcct cccgagtagc   74460
tgagactaca ggtgtgcgcc atcacgcctg gctaatttt ttgtatttt attagagaca     74520 gggtttcacc gtgtcggcca ggctggtctc caactcctga cttcaggtca tccatccgcc   74580
tcggcctttc aaagtgctgg gattacaggc atgagccact gcgccggcc tgtgtgggtt    74640 atagctattg atatttacca tattagaact taaaactggc catttaaaca aattttttat   74700
tattgattga ttttgagac agggtctcac cctgttgccc agagtggagt gcagtggcat    74760
gatcacagct cactgcagcc tcgaactcct ggcctcaagt gatcctctcg cttcagcttt   74820
ctgagtggtt gggactacag gtgtgcacca ccacacccaa ctaatttatt gattttttg    74880 tatacacagt cttgctgtgt tgcctaggct aaaactgaca atattaaat ccagccatcc    74940 acaagcacac actggcagag caattatgtc atcacatgtc atggagccat tgtatgctca   75000
taagtgaatg agattgaaat acgcaaaaa agtcctggaa ttattatgaa agtaattttg    75060
gccgagcgcg gtggctcacg cctgtaatcc cagcactttg ggaggccgag gcgggcggat   75120
cacgaggtca ggagatcaag accatcctgg ctaacatggt gaaacccgt ctctactaaa    75180 attacaaaaa aaattagcc ggggtggtg gcgggcgcct gtagtcccag ctactccgga    75240
ggctgaggca ggagaatcgc ggagcttgca gtgagccgag attgcgccat tgcactccag   75300
cttgggcgac agagcaagac tccatctcaa aaaaaaaaa aaaaagaaa gtaattttaa    75360 cttttgtggac aaagtctcag ggacctccag gaaaccctgg accaaacttt gaaacttgct  75420
ctaaaagcat ttgtaagcct gggatggtta ggtatgttca acgtgcagcc atgtaggaga   75480
tagtgcatgt caaaagggcc cctttggatg ggttaatatc actttggttc agttatctgt   75540
ggcctggaag gggtcccttg tgtacaaaca aagctgggga gtaggaggga agaattttt    75600 tttttttttg agacagagtc ttgctctcgt ccccaggct ggtgtgcagg ggtgtgatct    75660
tggctcaccg caacctctgc ctcccaggtt caagcaattc tcctgcctta gcctccctag   75720
tagctgggat tacaggcacc tgccaccaca cttggctacg ttttgtattt ttagtagaga   75780
cggggttttg ccatgttggc caggctggtc aaccctgacc tcaggtgatc caccctcctt   75840
ggcctcccaa agcgcaggga tttacaggcg tgagccactg cgcctggccc aggagggagg   75900
aatcttaacc ataatgctca tcttgtacta tctactggaa accctaaaaa tacagagacc   75960
ctggagccac tttctgggtt ctgctcccct tcattgcttt ctagctgtgt gactttgggc   76020
```

```
caagttcctt aaccactctg tggctcagtt tctcttctgg aaaatggaga caataatagt   76080
atctgcctct cagcgttgtt ataagagtta ccttggcaca cagtgttatg tgggtgttta   76140
cgctgagtat tactgttatt acagtaatca ttcaaatcca agaagccatc aaaggtaaga   76200
tgcattgttt tttattttat tttattttat tttttatttt tattttgaga cagagtcctg   76260
ctctgttgcc caggtgggag tgcagtggtg cgatctcagc tcactacgac ctccacctcc   76320
caggttcaaa caattctcct gcttcagcct cctgagtagc tgggattaca ggtgtgccct   76380
accacgccta agttttgtat ttttagtaga gatggggttt caccatgttg gccaggctgg   76440
tctcaaactc ctgacctcaa gtgattcacc cgcctcagcc tcccaaaatg ctgggattac   76500
aagggtgagc caccacaccc agccaagatg cattgtcact tcaaatcccc aggggagaaa   76560
aaacagctgc cagttaaact atgacacata atcatttata agacacatcc tgatttccaa   76620
gtcattgaaa aggggtgggg aggataaata agtcaattaa aaatggtttt attcggcctg   76680
gcgtggtggc ttacgtctgt aatgccagca ctttgggagg ctgaggtggg tggatcacga   76740
ggtcaggaag ttcgagacca gcctggccaa cgtggtgaaa ccccgcctct actaaaaata   76800
caaaaaatta gccatgccta gtggcacagg cctgtaatcc cagctactcg ggaggctgag   76860
gcaagagaat ctcttgaacc cagaaggcag agattgcagt gagccaagat cgtgccattg   76920
cactccagcc tgggtgacag agcaagactc catctcgaga aaaaaaaaaa aaaagatggt   76980
tttattctgg aataggagag tatttaagga aagaaaataa aaaataaagg aaaaaaagaa   77040
attttaaaat taaaaaaaat gatttcatgt gtacagaaga atttagcaac aaggatgtcc   77100
accacagcac ttgtcataat ggcaaacctg ctgaaacccc aaccattatg gattaactgc   77160
acaagttaag agagagccac aaaatattgt gactgaaggg gttttcaaag attgttccaa   77220
aaccctgggg atcctcaaaa gtgaatcaat ttctctcttt cataatcttt ttcatcttca   77280
ctctcctatg agtgcataaa gcaaaaaata ataagcaggt gacttctaaa aagaaaaaac   77340
ctctggaaac tatgcctcaa ccccattcta gagcctgctg ggccactgct cagaaaagga   77400
aatgtgtgcc ccaggctgac ccactcttaa gacaacccat tctccacatg cctctgcctt   77460
cagttacaca gctgtaccca gagaggggtc ttgtctttac tcagctgtcc atccacccta   77520
cctgtgttgc aatgaataca tccctggtat cttctgtgcc tggccccagc ccacccctc   77580
ctcagagctc cagccacaca ttccagtgcc ttcgagactc acctgctttg aaaggtagat   77640
ccttacattc aattttcttg ttgaaatact tcatgtggtt tcttttttct tgacaagcct   77700
ctgaccaaca cttggtggtc attcttaaac cgttgatttt tccccttcac acctattccc   77760
ctccacgatc acaatcttcc cagtctcaaa aatgtctcta cctgggacct caagccagaa   77820
acccaggcaa tatggaggca cttcctctcc tcattccaca tatgccactc atggacaatt   77880
cctgctttcc tctaaggcag atgcttacca caccctacc ccacccttc tatttagaaa   77940
atttctaaac atgcaaaaga attgcaagaa agtagaagaa tataataata tactgtggat   78000
atggattcac taggtttttg cagttttttg tttgttttg ttttgagacg gagtcttgct   78060
ctgtcaccca ggctggagtg caatggtgcg atctcagtgc aagctctgcc tcccaggttc   78120
aagcaattct ccctgcttca accttccaag tagctgggat tacaggcacc caccaccatg   78180
cccagctaat ttttgtattt ttcagtggag atagggtttt gttacgttgg ccagctggtc   78240
ttgacctcct gacctcaggt gatccgcctg ccttggcctc ccaaagtgct ggattacagg   78300
cgtgaaccgt cacacctggc cttttgtgtt tttgtttttg ttttggtttg tgtgtgtgtg   78360
```

```
tttgtttgtt tgtttttgag atggggtttc actctgttgc ccaggctgga gtgcagtggt    78420
gtgatcacag ctcactacag cctcaacctg ctaggctcaa gcgatcctcc cttctaagcc    78480
tcttgagtag ctgagactgc aggtgcccac caccacaccc agctaatttt tgtattttt    78540
gtagagacgg gttttcacca tgttgcccag gctgttctca aactcctggg ctcaagtgat    78600
tccccccacc ttggcctccc aaagtgcttg gattacaaac gtgagccact gtgctgggcc    78660
tatttctttg tgttttaaga ggcagggtct ttctctgttg cccaggtgga gtacgatgat    78720
tcgatcatag ctcactgcag cctcaaactc ctaggcacgg gagaccctcc tgcatcagcc    78780
tcccgagtag cccagactac aggtgtgtgc cactatacct agctaatgaa aagaattttt    78840
ttgtagacat gagttcttgc tatgttgtct aggctggtct ggaacctcca gcctcaggcg    78900
atccccttgc ttcagtcttc caaagcagtg gggttacagg cgtgaaccac ctggcctggt    78960
ctcgctcttt ctctttcgac atctacattg atctgtagct atctacgtac tatagatatc    79020
taaaagttat gtaaatgtct acttaagctt ataggtatga gctactgtat gctatctaag    79080
cttataggta tgagctacaa attgctattg tgttatgagg ggaattcaaa aagttgatgg    79140
agaatggaat taagagataa aaattttaaa aaaatcttta tttctcacca taaactccat    79200
caaggtcaaa gtcaagacac ttttgtaaac cattatacca gccatttagt ctatccctaa    79260
ataactgagg gtcccaggaa tttaatcatg tcagtgcagc cttttacat tttctctttc    79320
ttttttttt tgatggaatc tcactctgtt gctcaggctg gagtgcagtg gtatgatctc    79380
ggctcactgc aacctctgcc tcccgggttc aagccattct cctgcctcag cctcctgagt    79440
agctgggact acaggcatgt accaccacat ctggctaatt ttttttttt tagtagagac    79500
gaggttttgc caagttggcc gggctggtct caaactccta acttcaggtg atctgcccgc    79560
ctcggcctcc caaagtgcta gcattacagt tgtgagccac tgtgccaggc ctttttttt    79620
tgttcttgtt gcccaggctg gagtgcagtg gcatgatctc ggctcactgc aacctccacc    79680
tcctgggttc aagtgattct cctgcctcag cctcccgact agctgggatt acagtcatga    79740
gccaccacac ctggctaatt tttgtatttt ttttttagt agagacaggg ttttgccatg    79800
ttggtcaggc tggtcttgaa ctcccaacct caggtgatcc accctccttg gcctcccaaa    79860
atgctaagat tacaggcgtg agccactccg cccagcccag tcttttttaca ttcttaactg    79920
aagaaaaatg ggtgcccttc aaagatttta agattaggaa acaaaaagtc agaaggagcc    79980
aaattgggac tgccaagtgg atgcctaata atttcccatc aaaacttgta aaattgctcg    80040
tttgatgagg agaatgagca gaagcgtaga catgctggag aagaactctc tggtgaagct    80100
tcccaggctt atttctacta aagcttcggc taactttctc aaaacactct cataataagc    80160
agatcttatt attctttgac cctacagaaa gtcaaccagc aaaatgcctt gagcatcccc    80220
aaaaactgtt gctatgacct ttgctcttga ccagtgtgct tctgccttga ctggatcact    80280
tccccgctct tggcaatcat tctctgatta cgatttgtct ttaggattgc acccgtgaaa    80340
ccatgtatca tttcccgtta caatccttca aggaaatgca ttaggatctc gatctcactt    80400
gtttagcatg tccatggaaa gctctgctct tctctgcagc tgatctgggt gcgaccgttc    80460
tggcacccat cgagtggaaa gtttgtttag ctttaatttc agtcagaatt gtgtaagctg    80520
aggccgggtg aggtggctca agcctgtaat cccagcagtt cgggagaatg aggcaggagg    80580
atcacttgtg tccaggagtt caagaccagc ctgggaaacc taatgagacc ccatctcta    80640
caaaaaatac gaaatttag tgtcaggcct ctgagcccaa gctaagccat catatcgcct    80700
gtgacctgca cgtatacatc caggtggcct gaagcaactg aagagccaca aaagaagtga    80760
```

```
aaatagcctt aactgatgac attccaccat tgtgatttgt ttctgcccca ccctaatgat   80820
caatgtactt tgtaatctcc cccaccctta agaagtttct ttgtaattct tcccatcctt   80880
gagaatgaac tttgtgagat ccgccccctg cccgcaaaac attgctccaa actccaccgc   80940
ctatcccaaa acctataaga attaatcata atcccaccac cctttgctga ctctcttttt   81000
ggactcagcc tgcctgcacc caggtgaaat aaacagcctt gttgctcaca caaagcctgt   81060
ttggtggtct cttcacaggg acgcgtgtga cacttagctg aacgtgctgg cacgcacctg   81120
tagttccaac tacttcggag gctgaggtgg aaggatcgct tgagcccagg aggttgaggc   81180
tgcagtgagc cacaatctca ccactgtact cagcctgggc gacagtatga gaaccctgtc   81240
tcaaaaaaaa aaaaaaaaa aaagaaaaaa gaattgtgta agctgtacca attgagatgt   81300
ctatggtgtt ggctattgtt tctgctgtta actgtaagtc ctctttaatt aaggcataaa   81360
caaatttaat ttttttctgc aaaaattgat gtggatggta tgccacggtg ggcttcatct   81420
tcagcatgac ccaggctgga gtgcagtggc gcaatcacgg ctcactgcaa cctctacctc   81480
ccagactcaa gtgatcctcc cacctcagcc tcctgagtag ctggaactac aagtgtgcac   81540
caccacaccc agctaattta tgtatttttt gtacggatgg ggtttcacca tgttacccag   81600
gctggtctcg aattcctgag ctccaatgat ccgctggcct cagcctccca agtattggg   81660 attacaggcg tgaaccacca cgcccgaact tgtcccttct taaaacgagt tatccatttg   81720
taaatggctg atttctctgg ggcactgtca agttttgga aaacatcaat gatttcatca   81780
ttcttccacc caagcttcac catcaatttg atgcttgttc ttgcttcaat tttagaattc   81840
gtgttgctct gatagggget cttttcaatc tgatgtttta ttttagtgtc tcaaactagg   81900
tcctgttcag acaagttata acaagttagt atgaatttat tttggtgcaa aaaaaaaaaa   81960
ttgaactcca tgcatagttt tttcataata cacattttcc atgaattttt ggaagaccct   82020 tcttttctc tctttttttt tttttttttt ttttctgtag agatggtctt gttctgtcac   82080
ccaggctgga gtgcagtggc acaatcatgg ctcactgcag cctcgacctc ctgggctcaa   82140
gcaatcctcc cacctcagct tcctgttact gggactatag gtgtgcacca ccacaccttg   82200
ataattaaaa aaaaaatt ttttgtagag atcggggtgg gggggggggt ctcactatat   82260
tttccaggct ggtcttgaac tcctggcctc aagtgaccct ccccaatcag cctcccaaag   82320
tgctgggatt acaggcacaa gccacagtgc ctggccaata aatgtttttt gaatgaatga   82380
agaaattagt gcatggacat attttcccat cagctattac aataaccaga ctctgagttc   82440
cctgaaggca gggcctgtga gtttcattgt gtaccctcag ccctcaatag ctgataaaaa   82500
taaatattca gaaatgcttt gtaaaatgaa gaagagaata tgtatgggac agaaagtaga   82560
ccagtggttg cctggggctg ggacaggaa tagggagcga ctgcaaatgg gcagaaggga   82620
tcttttcaga gtgatggaaa tgttcttgaa ttggctgtga tggctgcaga actgtaaaat   82680
cacccaaaat cagtaaatca cttataatag gtgaatttta tgacaggtag attataccte   82740 agtaaagctg ttaaaacaaa accagtgttg agggaggaaa taaatgttac cttggtaata   82800
ctgaggactc agtagttatc aagacagctc tcttccctgc cctcatgagg ttttctgtgc   82860
agggcgggga cgccgaccca ttatagacag tgacagccta gagccatcac ggcgggatgg   82920
tggggagggg acaggcagag gggtgggagg ccaggatggg ggaagcccgg gcagagaggt   82980
tgggctggaa tggggggcac aggcagaggg gtcgggcgg ggactggtga ggtgcaggca   83040
gagggcaaag gggtcgaggt ccagatggga gatgtacagg cagacggatc cgggccaggg   83100
```

```
cggggaggta caggcccagt tgaggagcat aaggaaccat aggagcccaa aggaggcgcc   83160
cgaccagtca gggaggactt cccagagggg tgaatggctg agccaggcc  tgaagtataa   83220 tgttcatgaa tgcgacagca attttttttt ttttgagacc gagtctccct ctatcactgg   83280
agtgcagtgg ctcgatttcg gctcactaca acctccacct accgggttca agcgattctc   83340
ctgcctcagc ctcccgggta gctgggacta caggcgcccg ccccacgtc  cggctaatgt   83400 ttgcattttt agtcgagacg gggtttcgcc attttggcca ggctggtctt gaaccccctga  83460 cctcaggtaa tgcacctgcc tcggcctccc aaagtgctgg gattacaggc gtgagccacc   83520
gcgcccagca caattttaat ttttcttaaa cacttttcct gccttagcaa agtcttggag   83580
gggcggccgc ccaggcgccg cgagcgcaag accacgaggg ggcgctgctt caccacgcta   83640
gaggagcgct cccggcaacc acgtggcccc acaggtgcgg gaggtcggcg agcgcgcctg   83700
gagggtggac ggggtaggtt acggccaggc agcccggggt ggcgcgtggc cctgcgcagg   83760
gcagtggaag cagcgggccc caggagcat  gagacgccgc gctccgtggg gcggtcccag   83820
cgctgtgcag cgaggggcca gggctgtccc cggtcctgcg cggccggctc ccggagaaac   83880
tgtggcctcc tgggggtgga gctttaaaaa acaaaacaaa acaaaacaaa atcacccaac   83940
aggaagcggg gtgggggcgc ccggctctgt cacccgtgga atgcatcaaa atagcctgcg   84000
cggccggggg cggttccggg aaaggggggcg gccgcgaggg gcggggctgc aacggagggc   84060
ggagcttccc aaagaacggg agagaggagt gcagaaccgg ccccaggggg acgtcctcct   84120
gttcccccaa aatgaccctcg ataggcgttt gtgtgggatg gggttcctgg gtagggcggg   84180
gctttccagt gcgatgtccc tggtctattc ttagcgggct gaaacctgga gaagtgggag   84240
tgggcggttg atccgggttc cagggcctct ttggagcgaa aagctccgtg gagagccaga   84300
gtctccatcc tgggcgtggg agggaagatg ggaaatgggc caagaggagc ctgtgggagg   84360
tcctccccgg gacggccccc ttccatctgc atccgcggga accgttgtgg gggcagctct   84420
gagaaaggct gctctgggcg caaggaaggg tggttgaacg aagagatcag tcagggacgg   84480
ggtgggggtg ccttgactgt gtcccagatt tgctgcgtgc ttctgacctc agttccccat   84540
ccttccagtt gctcaaatcc tctctgtccc agtcctaggc cgtttctgcc cctctcactt   84600
cctagtggtt tgcagagggg aaacactgag gctgcctctt ctgtgcctgg ccctgtgttg   84660
gcacggggaa gtgactgaga cgccccagac ccccttctcc ctcacagtcc agtgaggcag   84720
acagacctgc caccagatag tgacagccca gaatgagtca ttgagaggac gggggaggca   84780
caggcagatg ggtcagggct gggataggggg aggagagggg cctgtaggat ccaagggggag  84840 agtgggtgct gctgactcag tctgggggggg ttgaagagcc gtctgaactt agaccaaaaa   84900
ggtaggatgg ggccgggcgc ctgttatccc agcactttgg gaggcagaga caagaggatc   84960
gcttgaggcc aggagttcca gaccagattg gacaacatag cgagacccccc atctctacaa  85020 aataatttaa aaatcagttg ggcatagtgg tgtacgccta agtcccagc  tactcaggag   85080 gctgaggtgg gaagattggt tgagcccagg aattcaaggc tgcaatgagc tatgattgcc   85140
ccactgcagt ccagcccggg tgacagcgtg agacccctgc ctccaaaata ataatagcaa   85200
aaatactggg ctgggcgcgg cggctcacac ctgtaatccc aacactttgg gaagccgagg   85260
tgggcaaatc gctgaggtca ggagttccag accagcctgg ccaacatggt gaaacccagt   85320
ctctactaaa aatacaaaaa ttagctaggt gtggtggcaa ggcatctgta gttccagcta   85380
cttgggaggc tgaggcagga gaatcgcttg agcccaggag gtgagggctg caatgagatc   85440
acaccactgc actccagcct gggcgacaga gtgagactct gtctcaaaaa ataaataaat   85500
```

```
cctaatgaaa ggataggatg gggctcaggg ccttggaaga gggtcacctt ctaacaaaag    85560
gtatttgaac ggagtcctaa agaatgagta gcattcttct gggaagtgct gtgtcaccat    85620
gaaggaaagg gtgttctagg cagaaagaat gacaaatgca aaagcttgga ggtgagagtg    85680
tggcttatct ctggcagggt cctctgctcc ctgcctggga cattccccca acgtcatacc    85740
ccgacagagc tgtcttaggt ctcctagtcc tggagtccac aagcaggtta atgggatgta    85800
atggaaacgc tatagagggc agaccccag gcttgttccc tcacagcctg atgcttttt    85860 gtttttgaga cagagtctcg ctctgttgcc caggctggag tgcagtggcg tgatcttggc    85920
tcactgcaac cttggcctcc caggttcaag cgattgtcct gcctcagctt cccaagtagc    85980
tgagattaca ggcacccacc accacgcctg gctaagtttt gtattttag tagagacgga    86040 gtttcaccat gttggccagg ctagtctcga actcccaacc tcaggtaatc cacttgcctc    86100
ggcttcccaa agtgctggga ttaaaggcat gagccaccac gcccagcctt ttgttttgtc    86160 tgcttttta dacaggtct cacgctgtca ccctcacagg ctggagtgca gtgactgcat    86220
cacggaccac tgcagcctgg acctcccagg ctcaagcaat cctcccacct caacctctcc    86280
agcagctggg actacaggcg tatgccacca cgcccaccta attttaaaat tatttttgtag    86340 agacagggtc tcattatgtt gcccaggctg gcctcgaact cctgggctca gcgatcctc    86400 ccaccttggc ctcccgaagt gctgggctta caggtgagag ccacctcagt gcccggcctc    86460
agcctgatgg tttcacgact gcctttgact ttggcccaca ctaatcaaat gtatcaccgt    86520
gggccactga ctcaacttcc ccatctatcc agtgggaata gaatattgga ctgcacaaaa    86580
tcaaccacct cattttaaag agctataacg aaacaaaatt tatatgttat atatttttaa    86640
aaatacatct tatagattaa aggactcaag aaacaatagc aagactgtaa aacgttgcca    86700
catcaggtga cacttttggcc agagttatgg aaaatgctga caaaacaaga atttgccagc    86760
atgggcaaag atatactgtt accaacccaa cttgttaaaa tattaatatt gagctaatta    86820
gaagtagttt tttttttttt gttttttttt tttgagacag agtctcattc tgttgcccag    86880
gcaggagtgc aatggtgtga cctcaggtca ctgcaacctc tgctgcctgg gttcaagcga    86940
ttcttgtgcc tcagcctcct ggaattacag gcgcctgcca ccacgcccgg ctaattttttg    87000 aattttttggt agagactggg tttctccatg gcggccaggc tggtctcgaa ctcctgacct    87060
taagtgatct gcctgcctcg acctcccaaa gtgctgggat tacaggcgtg agccactgtg    87120
cccagccagc agttcataat atttgttttt tattccttga ttctaactct gtaaggaata    87180
gaaatggggt gattaatttt ggctcctttta atacccgcct ggcaggtgct gagtcagtgg    87240
tacctgttac cacgctatga ctcagaggtt atcactcagg gacatccttc tgactctgtt    87300
tcagtccatg actcaggagg aaaggttcta gggcctcacc agcgccctac acacaccctc    87360
gtttcccgag gggcaccatt atattcttcc tttattggct gtccttgtat aatacaaatc    87420
ttcaagttta gatacaaaaa aaatctggaa ataaaagata gaaagtacc cgccaggcac    87480 cccttcccct tcttcccgga ccccttccca gcgggcaccg acatgaggta actgcgcatc    87540
ttctcctcct cctccctccc cgcctcctgg gcccccaact tggccctagc ccccatgaga    87600
ccttggccca aggaagacat gggcccccaaa gttggaggt gatggaggtg agtacagcat    87660
tggcagtgaa cgcagcgtgt gggcagaggg cagcccttag cttgtgctgt gcatgggggg    87720
aggagacgac cagattttggg gtgggcactg gtgtgggggcc caggagagcc cctaagcaag    87780 tgtccccct ccatcctgtc caacactgga aggtgggggt caacagaaac tgggaaatgg    87840
```

```
agtgtgaacc aagggcattc agtgggattg tggccaaccc ctgtgtctgg ggttggggaa      87900
ggggcattg ccagcctaag tccggcagtg aaatggttcc cttagccagg ctgggtccgt       87960
ccctgaattc catcctgttg caacctgggc gtcacaatgt tggttctgta gtggttgtcg      88020
gggtggttga gggagggggg tgttgagagg gtgttgaggg gcgcagcccc agggagcagg      88080
gttaggggag aggttgtgcc tccacccca ggcgtggggc acctggagat gatggagtgg       88140
gtggggcggc tcgggctaca gttcaatctc gaatgtcttt tgcaggtcgc cagaaagggg     88200
gttggagggt ttctctacag tggctttgcc ttctaatgcc gcccactggg cctcaaaggg      88260
gtccaactct ggagctgggg caggcgctgg ctcaggggc caggggccc cattggggcg        88320
agggcgggcc tggctcccag gggcactggg tatggcaggg ggcgggaagg ccccagcttt     88380
cccaagcaga gtggcaggct gaggctgag ctggcggct gagcagaagg cgtttgccac        88440
catctgtgag ggtgtgatgc ccaccacggg cacccggggc atcggtgggt agcccaagcc     88500
cgggtaggcg ggcacaaaag ggggctgcat gtgtgggggt ggcaggaaca cggccacttg     88560
ggcaggtgca gcgtcaaagg gccccacggg ggcggggaaa ggctgcaggg caggaggcat     88620
ggtgggcact ggggccactg aggctgcttg ctgctgttgc tgctgctgct gctgctgctg     88680
ttgctgttgc tgctgctgct gctgctgggc cttggccacc tgtgacacct cctccagcca     88740
tcgctcagcc tctgaaggtg tccgcttgtg cccaggctgg aaggcagctg caggggcac     88800
ggagggctca ccccaggcag aagtccctgg agagaggaga gggacaggtg agggaggggg    88860
caacggcttc agcagaagaa ccccaggctg ggaactggca tggtgtgggg atcagagcac    88920
ggactctgga gccagaccgc ctgcctctga atcccagctc tgcacctccc gagcttgctg    88980
acttcaggcg agtgacttca ccattctgga ccacgtaatg gttctggagt gctaagaaca    89040
tacaattctg agcttctaag gccctatgat gagaaagtct aagtaggact gacatcctcc    89100
tagccccact acccttctga ctggtcagtg ccaagcctag gattcactat tttgttttgt    89160
ttgttgtctg ttcgttttga gagtctcact ctgttgccca gggatgccct atctgggctc    89220
actgcaacct ctgcctccca ggttcaagca attctcgtgc ctcagtctcc tgagtagctg    89280
ggattacagg cgcgcaccat tacgcccggc tgatttttg tatttttagt agaggcgagg     89340
tttcaacatg ttgcccaggc tggactcgaa ctcctacctc aagtaatccc cctgcctcgg    89400
cttcccaaag tactaggatt acaggcatga gccaccacac ccagctggta ttcactattt    89460
tgaatatcac ccttgatttt ctaataccttc cagaatgtat tgttttagga gttaagattc   89520
taagattgca tggatctttc tccacatgta aatagtatc ctaacatagt aaggtttgac     89580
agtttagggt tgggctttct aagattctcg agttctacat ttacagtgtt tgagattcta    89640
aggtgcacct gtggttctag gataagccca tggctctaag atgatacatg gttctcaagg    89700
attccatggt tctgaaacga tctctgggct ctaaggtgat cccaagattc tagcatgagc    89760
acatgcctct gaggtgaccc cgtggctcta caatgatccc gtatctctaa gataattcat    89820
ggttctaaag tgatcacttg attctcaggt aatcccacgg ctctaagatg atccttggtt    89880
ctaggatgat cctctggttc taagatgatc tgtgtttcta aggtgatcct atggctctaa    89940
gatgatccat agttctagga tgatcccatg gttctaaggg gatcccgtgg ctctaaaatg    90000
atcaagggct ctgagatgat ccatggctct aaggtgatca catgattctc agataattcc    90060
atggctctaa gatgatccat ggttctagga taatcccctg gctctaagat gatccctggg    90120
tctaaggtga tcacatgatt cttaggtaat cccatggctc taagatgaac cacggatcta    90180
ggatgatccc ctggctctaa gatgatccat ggctctaaga tgatcacacg attctcagat    90240
```

```
aatcccatgg ttctaggctg atccctggc tctaagatga tccctgcttt taaggtgatt    90300
gcatgattct caggtaatcc cgtggctcta agatgatcca tggatctagg atgatcccct   90360
ggctctaaga tgatccatgg ttctaaagta atcgcatgat tctcaggtaa tcccatggct   90420
ctaagatgat ccatggttgt aggatgatcc cctggctctg aggtgatcca tggttctaag   90480
cctgtaggat cccaagaccc ctggagtgtc tgggtagccc tggatagagg aggggataca   90540
ggagggacat gcagggtgtc tgcccagcag aaagcctggc tttacctgtt gtggcaggtg   90600
gtggccctgg tgctggcgct ccagcactgg caaaagatga actgatctgt gtgcacagag   90660
cgttgatgct gtcactgtcg ccggcaccag gaggctccat ctcaggcact gggaagcagg   90720
gcaggacaga ggtcagcaaa caggcccaga ccctgccgca gccccgccct ctaccccccg   90780
ccctcggtgg ccctctcttc tgacctggat cctttcccac tgtagtaact aagtggccat   90840
gaccgccaaa taactgtgca tatgtgtgtg tcacatctga gcggcagaac gactgagtta   90900
gtgtgtgaca tttgacggct gacagtaaca gggaccccaa accaaggacc tcaagatttg   90960
tgtgtggcca caaaccagaa gagttgtcta aaacacttag caacatatat tagtttaaaa   91020
atatgcccaa ccacgtgcat ggcaaggaca tgggcccagt ctgaatgggc tgtggcatgg   91080
ccgctcactg gctggggatc atttgtccag cttgggcag agaagtgggg tcctgtccac    91140
cccacccagg ctgatctatg gcaaacatca tgagagcaga gatacacctg tgccagcaag   91200
gcaggagaca ctgagcaggc atggcggccc cgtgagggct tgtgatgagc aaaggtacca   91260
tccaaataaa caattaagga ctcccatgtg tggtgtgtga cacatgtctg tgatgtttta   91320
gccaatggct gtctccaagg gaccatgtag atgctccagt gaacatcaga actggccgta   91380
ggagtctgca ggtgtgctgc gggggcgccc gggtgggaca gccaatgtcg acaatgattg   91440
tgcatgttcg tccaaacagg aatgcagctt ctgagagtgt gactggggtc cgggtgtgtg   91500
gcgtcctgat gcgtgactcc caggtgtgag tgcatctgcc gtgtgatgta tgagtgtgtt   91560
tgcaggtgtg catggatctg cacatgtggc tttggagttt gcataaatct gggtgtgtgg   91620
tctgtgaagg tgtgtaaatc tgagtgtgtt tcttttttaa aaatatttat ttatttattt   91680
ttgacacagg gtctcgctct gttgcccagg ctggagtgta gtggcacaat cttagttcac   91740
tgcaacctcc gcctcccagg ctcaagcaat cttcctgagt agctgggact acaggtgcat   91800
gccactgcac ctggttaaca ataaaggtta attttaaaa tttttttgtg gagatgagat    91860
cttgctgtgg tgcccaggct ggtctcaaac tcctgagctc aagtgatcct cctgcctcag   91920
cctcccaaag tgctgggatt acaggtgtga gccaccacgt ctggccatgt gtgacttctg   91980
actctgtgat tttggagtgt gtgtgacttg agagtatacc tgactgtgag tttgtgactt   92040
ctgagcatgt gtgacatgtg tgtggggggg tgcaatgtct atgtgagtat gtgaaatttc   92100
tgtgtggcaa gtcacatcca aataagcgtg cagctggcca caggagtgtg aggcttccaa   92160
ataaagcctg gagctcctgc cacctctcag gagcacgtgt gacagcctgg ggagtgtgcc   92220
tgatgtcagg ctgcgttaag gacagcaaat gtgagggtgt gtgatggccc aggaatgctg   92280
caggcatgga gggagcgtgc gtcactctca acaagggttg gcatctgctc accggttacc   92340
ttttggagca gcccagcctc ctggatacag ctcaacaccc tcccacatca atccccgagg   92400
acataacggg taggcgatgc agatttggca tccaggagca agagagtggg ccagaccaca   92460
tgggttcact ggctgctggt ggggaagaca gcccttctgc ctgcctccct caggcaaaaa   92520
ctcagtagcg tgccacctct atcttccttc cctatggcag agattgctct taatttttt    92580
```

```
tttttttgaga caggttctca ctctgttgcc caggctggag tgaagtggcg caatcttagc   92640
tcactgcagc tgggctgaag caattctcct tcctcagcct cctgagtagc tgagactaca   92700
ggcatgcgcc accacaccag gctagttttt gtattttttt gtagagacag ggtttagcca   92760
agtgatctgc ctcaagggat ccttgagccc ctcttgggct caagtgatct gcctgccttg   92820
gcctcccaaa gtgctgagac cacaggcatg agccactgca cttggctaga catcacttt   92880 agatcatgat gtacaccacc tgtctccttt ccctggccca tggcagacat tagtaatcaa   92940
acacaatgct ttttttcccc acggagctct ttgctcacct tacccgtcac ctgtccagac   93000
ctcatggctc ccctggccaa gtgctagaag aaacagatcc ttgtaactcc atcttccctc   93060
caagtaaaac aggaccttta tatctcctct ctcttaccac cagccatggc agacaatgcc   93120
aatcaattat gatgtgctgc tccttttcgt gatgggtact gcctctgctc aactctgtgc   93180
ctacaacaaa tgttcctgat ccatcactat gcccctgacc cctgggatct ctgagctcac   93240
tggtgccctg catgtcatgt ttctactgac caaattctgg gagtctcccc tttgggtaaa   93300
aacataacac tcttgctact ctttcttctc ccttgcccat gacacacact gcatggagat   93360
catgactgct aaccgatcat gatgtgtgcc atctttctcg tttcccttaa ccacagcaga   93420
cattgctaat tgatcatgac ttgtgatgcc ttttttgcca tccttgatg ctccctgccc   93480 taggcagaca tttctaatcc atcacaatcc tcctttcctc agagcctgag gaatacctgt   93540
atccttcacc tagccagatc tcataggtga atgcttggag ggaggagca ttaacctgta   93600 gtgcttcagt ctactcctga gcaaaacag gccaatggtg ttgcttctct tctttccctg   93660
gcccatggca aacttcctta tccatgcccg acttctttgt ccatagccga ctttgctaac   93720
taatcatgat gtgtgtcatc ttttctcctttt tccttaacca caccagacat tgctaactga   93780
tcataacttg tgatgccttt ctactatccc ttactcagag cagacacggc ttatcaatcc   93840
tgatttgtgc tatctctttc ctctcccttg cccactgcta atcgatcatg acatgttccc   93900
actctctctc ctttgcccat ggcagacagt gcaaatcaat cacagtgtga accatctcgc   93960
ctccatccct tgcccacatc agatagtgcc aattgattcc aacgccgttt cccactgggc   94020
ccagggctca cctgtgccct tcacctggaa gtcagtgcgg cgctgcagcg tggatggcag   94080
ctcattcagc cgtaggctca gctgccgttt gaaaggcgag ttcttctggc tgagtgctgg   94140
gaacccacgg aaggagccct ggcgaaccag ctgctccagg ggtgcatggc gccgggggat   94200
ggcggccgca gtggtgcctg cagccacagg ggtgcctgcc tcacccttct caccagggga   94260
tgtggtggct ggtgtcgggg acacgtgccc aggctgggca gggccaggag ccacagtggg   94320
ggcagctgct gcctctgctg gagacatggg ggagatggat ggttagatat ctcaccatgg   94380
catgcaaggc ctctcccacc tggttctctt gatcattctc caaggctgcc ttccttgccc   94440
agtgagtcct gcccttaaga caagctagtc aaagccctga gatatccctc accccacc   94500 aagtcatgat ccccttcccc aggaggctct tggaaaaccg tccccaggc tcaccctctg   94560 tgtctctcca gcttcctgcc cctttctgtc ttgccctgct gctctcacca ttcttccctc   94620
taagaccctc tatctcccctt tttgatcact aacaaacac tgatttggtg ctggaacaac   94680
gtatcaggca ttgttccaga tgcttttcaa gtattcactc attcaatcca cacgactacc   94740
catggggttg atatgattct cattttacag atgtggaaac tgagacccag caaaggccca   94800
gtgtgatgtg cccaagtcct actgctagga aggggcaggc tgactctgga ccccatgctc   94860
caaatgactg cccgccctgt ctccctctga cctgtctctc catatcatgt tgtctttctc   94920
tgtcactgtc tgttcccctc tgtctcccac ctcccagcct tcttcccacc tcaagtagct   94980
```

| | |
|---|---|
| cctcccttcc tccagtcatt ctagacatgg cttggatgct tcatcctctg agaagctttc | 95040 |
| cagattgttc caggctctca gcctggctcc ctccactctg agactgttct ctgtactctg | 95100 |
| ggaggaaacc tgacctcccc actcagcagg agaggcaggc tcttcaaggg cagggctgcc | 95160 |
| ctcacccctg ccaaaccaca aacacacatc taccctccta ccagggcctc cccgagctgc | 95220 |
| agcctgaatg ccatggagat taaactcagg cccagagaga ccctcccata aggatgtcgc | 95280 |
| ccagtgctgc ttctcccatc gtgacacaat ggggcaccca tgcaggcctg cccaaggca | 95340 |
| gtggaaacag cccaggacag gttggaacca ggaaacctcc tctgcctcca ctcactgtgt | 95400 |
| gacctcagga agtcccctcc cctctctggg ctccagtttg ccaactagaa acctgggata | 95460 |
| aacatctcag tgctacctcc caagcctctg agagggtcag tttaggtagt gaatgttaaa | 95520 |
| tgttttggaa tccaacaaaa gcatgcctgg acacagtggt tcacgcctgt aatcccagca | 95580 |
| ctttgagagg ccaaggtggg gggatcagtt gaagccagga gttcaagacc agccttgcca | 95640 |
| acatggtgaa acaccatctc tactaaaaat acaaaaaaag attagctggg tgtggtggca | 95700 |
| cacgcctggg attccagcta ctctggaggc tgaggcagga gaatcgcttg aacccgggag | 95760 |
| gcagaggttg cagtgagccg agatcgcacc attgcactcc agcctgggca acagagcaag | 95820 |
| actctgtctc aaaaaaaaaa aaaaaaaaa aaaaaaact tagctggacg tggtggcggg | 95880 |
| cacctgtaat cccagctact caggaggctg aggcacataa atgtcttgaa accaggaggc | 95940 |
| agaggttgca gtgagctgag atggcactac tgcattccag cctgggtgac ggagagagac | 96000 |
| tctgtctcaa aaaaagatg ttcttttttt tcccttaca atccaggatc taattcagga | 96060 |
| tcacatctcg catctattaa tacctgttaa acctcattag tctcccttaa tcaggatcag | 96120 |
| ttcccaatgg taaattcttt gtaaattcta agtagtgttt tcccaaagaa cttaaattca | 96180 |
| cagtaaaata aataaataaa ttaattaatt aataaataaa ttaattatat ggtgactcag | 96240 |
| gacatacata caattatatt ttaaacacac acacacacac acacacacac acacacacac | 96300 |
| acagagtttt agaacttaca aagtatttaa ccatttacct agaaagttag ttttaccaag | 96360 |
| tatgtttcaa actttcttga tggcaatcca gagttaagag atatctttta tatggtagcc | 96420 |
| tcttacacac gcgtgcacac acacacacac tctctctctc aaataaaagt atcattaaat | 96480 |
| tatatttaac ccttatgcca ttcaatatac tctgatattt tctatgattc tctatttcat | 96540 |
| tgttttttaaa ttaattttt ttttttgag acagggtctc actctgtctg tcacccaggt | 96600 |
| tggagtgtgg tggtgcaatc gcagctctct gcagcctcta cctcctgggc ccaggtgatc | 96660 |
| ctcctgcctc agcctcctga ggagctggga ccacaggttg caccaccacg cctggctaat | 96720 |
| tttttaatga tttgtagaga cagggttttcc ctatgttgcc caggttgatt tcatttttt | 96780 |
| aaatgtcagc cacatgggct gggcccagtt gtccacacct ataataccag tgctttggga | 96840 |
| ggctgaggtg ggaggatcgt ttgaggccag gagtttgaga ccagcctggg aaacacagca | 96900 |
| agatcccagt tctacaaaat ataaaaataa aattagccag atgctgtggc ttgtgcctat | 96960 |
| attcccagct acatggaggc tgaggcagga ggattacttg agcccagcag tttgaggctg | 97020 |
| cagggagctg tgatcgcacc actgcactcc agcctgggca acagaattag acctcaactc | 97080 |
| agacaacaaa acaaaacaaa aaatgccagc cacagtacag caaattggct tcccaggtct | 97140 |
| taatacacag gttgaaaagc cctgagaagg ccaggcgcgg tggctcacct gaggtcagga | 97200 |
| gttgaggcca acatggtgaa accccatctc tactaaaaat acaaaaatta gccatgcctg | 97260 |
| taatcctaac tactcgggag gctgaggcag aattgcttga acccgggagg tggaggttgc | 97320 |

```
agtgagccta gatcacacca ttgcactcca gcctggttga cagagcgaga ctccgtctca   97380
aaaaaaaaaa aaaacaaaca aaaaagaaa agcctcgaaa agccccgaat tggtggatag    97440
taaaccactt ggtgcgccct tagaatattg cccagagaac tctttccatg gaagttgctt   97500
tatttattta tttatttttt gagacagagt ctcactctat tgcccaggct ggagtgcagt   97560
ggcgtgatct cggctcactg caacctctgc ctccagggtt ccagcgatcc tcctgcctca   97620
gcctcccaag tagttgggat tacaggcgta ggccaccatg cccagttaat ttttgtattt   97680
tagtagagac gaggttttac catgtcgcgc aggctggtct caaacttctg acctcaagcg   97740
atccgcccat ctcggcctct caaagtgctg ggattacagg tgtgaaccat ggcgcttggc   97800
ctgaagcatc ccctactttg taaactgttg agtctctgca cctctgcagc tccctgcccc   97860
ctgatactgg gtaccctgtg cccactctgt gctctgctgg cgcttggggc aacacccacc   97920
tttcttcttg tccggggcct ctcgctcagc aggccgccca ccccagaca ggcggaagga    97980 gccctcgcgg gcgaagctgg tgcggctggc atcgaaggcg gccgtgaccc cacattcctt   98040
ctcccgtcgc tgttttcgct ccaggcaggc ggcaaaagca cagcccacag cgtggctcag   98100
cctctcgccc tatggggaga ggatgggcgg gggggttaga ggcgctgggc agtgcggaca   98160
ggggccaggg gcactgggtt atagccgcta ggtactgggt tgcccggat gagtctctgc    98220 acttctctgg gcctcagtgc tcatctgcac cacaaggaag ggctggaaat gacagctcca   98280
agtgagagaa gccagaaacc aatgagcctg ttgtgtggct ccacttactg gaaattccag   98340
aagaggcaaa actaatctat ggttctatgg tgaaaaaag tcagaacagg ccaggagtgg    98400
tggctctcgc ctgtaatcct agcacttggg gaggctgagg cggaggttc ccttgagccc    98460 aggaggtcaa ggctgcaagc agctatgatg gggcaactgc actccagctt gggtgacaga   98520
gtgagattct gtctaaaaaa aagtcagaat agtggtagtt tcctatgggg tgggaatga    98580 ctggaaagtg tatgagggga tgaccgggtg gtggcaatgt tctagatatt gatagggtt    98640 tcgttacatg ggtgtatgca gttgtcgaaa ttcgttgact gtacaccaaa ggcttgtgca   98700
ttgctataga ctaaacgtgt gtgtctctct cagttctaac gctgaagccc tcatccacaa   98760
tgtgctggta tttggaggtg ggcctttgag agacaataaa agttatgtta gatcatgagg   98820
tggggtcctc atgatggaat taatgccctt atttatttat ttttttttctg ggacagggtc   98880 ttactctgat gctatgctgg agtgcagcgg catgacctca gctcactgca acctccacct   98940
cccggcttca gcgattctc ctgcctcagc ctctcaagta gctgggatta taggcatgcg    99000
ccaccacacc tggttaattt gtgtattttt agtagagatg ggatttcatg atgttggtga   99060
ggctggactc gaactcctga cctcgagtga tctgcccacc tgggcctccc aaagtgttgg   99120
ggttacaggc gtgagccacc atgcccggcc gggattaatg cccttaaaaa ggaaaaagag   99180
acaagagatc tcccctccac cttgagaggt gaagatacag aaagcaggca tccatctgca   99240
aaccaggaaa agagccctca ccaagaaatg agccatttga caccctgacc tcaggtatcc   99300
agcctctaga actgcggcaa acaaatgttt gtcatttaag ccacacagtc tacactatct   99360
ggttatagca gcctgaacta agacaatcat atctttcgct ttgaagaaaa aaaaaatctg   99420
gaaacaaata cgaattctac ttaatggtgt gcatgctgaa gtagtccaat gcctacaaat   99480
ttgacataca aaaagaatca gacggtgtga ctgcagtcgc tcacacctgt aatcccagga   99540
ggccgaggca ggcaaatcac ttgaggccag gagttcgaga ccagcctggc caacatggtg   99600
aaaccccatc tctactaaaa atacaaaaat ctgccaggtg tggtggcgtg cacctgtaat   99660
cccagctact agggaggctg tggcaggaga atcacttgaa ggttggaggc ggaggtttca   99720
```

```
gtgagccaag atcgtgccac tgtactccag cctggggcaa cagagcgaga ctccgtctca   99780
aaaaaaggaa tgaaccactg atacaagcag ctcacgcctg taatccgagc actttgggag   99840
gccaaggtga ctggatcgct tgagtccagg agttcgagac cagcctgggc aacatggcga   99900
aatcccatct ctacaaaaaa ttagccaggc atggtggcgt gtgcctgtag tcctagctac   99960
tcaggaagct gaggtgggag aatcgcttga acccaggttg cagtgaggcg agattgcacc  100020
actgcacacc agccttgatg acagagagag acgctgtgtc attaaataaa ttaattaaaa  100080
acattgccgg gcagggtggc tcacacctat aatcccagca ctttgggagg cagaggcagg  100140
cggatcacct gaggtcggga gttcaagacc aacctgacct gcatggagaa accccatctc  100200
tactaaaaat ataaaattag ccagctgtga tggtgcatgt ctgtaatccc agctacttgg  100260
gagactgaga caggagaatt gcttgaaccc gggaggcaga ggttgcagtg agctgagatt  100320
gctccattgc actccagcct gggtaacaag agcgaaactc tgtttcaaaa acaaacaaaa  100380
acacaacatt acactaagta aagaagccag acacatatta tatgattcca ttaaatgaaa  100440
tatccagaat aggtaaatcc acagagagac aaagcagatt agtggttgcc aggggctgg   100500 ggtagtgggg agacggggtg aattgatgaa tggagatggg gtctccttta gcggtgatga  100560
aaatgtttca ggactgctaa agtcaatggt taaacaacac tgaaaatgta ttaaatgcca  100620
ttgaattgta cacttttaaa tgattaattt tatgtgaatt tcacctcaag aaaaaaaaaa  100680
agttgaactt ggggaattct actgcttaat ggttaaaact tccttcagaa gtaggaagga  100740
attcatccaa catcacattc tttacccaca ggagatggtc ctgctctttt ctggctttca  100800
ttctcatccc caaatagttt tttttttttg ttttcttgag acagagtctc gctctgtcac  100860
ccaggctgga gtgcagtggt gcagtcttgg ctcactgcaa cctccgtctc cagggttcat  100920
gtgattctcc ccacatgtga ttctcctacc tcagcctctg gagtagctgg gatcacaggc  100980
gcctgccacc atgcctgtct actttttttg tattttagt agagatgggg ttttaccagg  101040
ttggccaggc tggtctcaaa ttcctgacct caggtgatct gcctgccttg gcctcccaaa  101100
gtgttgggat tacaggcgtg agccaccacg cctggccaat actcttttt ttttgagatg  101160 gagtctcact ctgtctccca ggctggagtg cagtggtgca attttggctc actgcaacct  101220
ccacctcccg ggctcaagtg attctcctgc ctcagcctcc caagtagctg ggactacagg  101280
tgtgcaccac cacacctagc taattttttg tatttcagta gagatggggt tttaccatgt  101340
tgtccagggt ggtcttgaac tcctgagctc aggcaatccc cccgcccag catcccaaag  101400 tgctgggatt acaggtgtga gccactgcac ccggccctca cgtgaatact ctaaattggg  101460
aaccgtgagt atactttctt ctccagatga ggaaactggg cacacagagg ttagtgatgt  101520
gcctgaatgc aggaagcttg taggggtggg gctgggatgc cagggcatgg gagggaagag  101580
ttggccagct gtggcaatac tcacggagtc cttcagtgcc agaaaacagt ggcagatcca  101640
gcggcgggta gtcccgtcac gacagatata ggagaaagcc ttgtccaggt tgcggtcagg  101700
agcacaaaag gagacctttt cgatggtctg gtcgaccaga agatcctagg aggggccggg  101760
gaggccagga gaagagtgtg aactctcttt caagtgttca ctcaacattc tctctgtgtc  101820
tgctgaaatc cagtcctgaa cagggtgggg acccagcagt cactgagaca ccctgtgcct  101880
tgcctgcaga gggctcccag gtcagcggga agatcagacc catcacgaga tgggcagccc  101940
agagtcatag ccaggatgtg atgaaggagg cccaggcaga ggggtcaggg ccaggaccat  102000
ggaggcacag gcagagggt cagggccagc atggcagaag ccagcttggg gtcagtcagg  102060
```

```
caaggcttcc tggagcaggt actaactaag aaaaaaagtc aaggaacagt attttgggct 102120
gagggaactg ccttgcaaag gtggtgatct tgttctgtta ttaacccaac tctcagcatg 102180
tcctgggcac ctcctagggc agtctctggg ctgggggcag cagattcaag gtgagcaaac 102240
agatacctag attgtggcct catagtgctt ccttctgact gggcagggtg acaataaaca 102300
cttaatggct aacattcatt gatctgagca gttacgatgt actagacccc atttaaatat 102360
atatatatat ttttttccca gaaggagtct tgctctgtca cccaggctag agtgcagtgg 102420
catgatcttg gcttactgaa acctctgcct cctgggttca agtgattctc ctacctaagc 102480
ctcccaagta gctgggatta caggcacgca ccaccacgtc tggctaattt ttgtattttt 102540
agtagaggtg gggtttcacc atcttggcca ggctagtctc gaactcgtga cctcaggtga 102600
tccaactgcc ctggcctccc aaagtgctgg gattacaggc gtgagccacc gtgcccagcc 102660
cacatttaaa ttttttttaaa aattattttg tatagatgga gccttgctat gtttcacagg 102720
ctgatcttga actcctggct tcaaggggcc ctcccagcca ggcaccattt caaataactt 102780
gcatatgctt tctcacttaa tggtagggtc tattataatc cctgttttc tgcgatggag 102840
tttagctctt gttgcccagg ctggagtgca atggcatgat ctccgctcac cgcaacctcc 102900
aagtctcggg ttcaagagat tctcctgcct cagcctccca agtagctagg attacaggta 102960
cacaccacca tgtccagcta attttgtat ttttagtgag atgaggtttc accatattgc 103020
caggctggtc tcgaactcct gacctcaggt aatctaccct ccttggcctc ccaaagtact 103080
gggattacag gcgtgagcca ccactcccgg cctataatct gcattttca gatgacacaa 103140
ctgagactca gagaggttaa atctcatgcc cagggtccct aagctgggat cggagctgag 103200
gcagctgctc cagtctctct cacccacagc ctatgccagt tcccaaataa tcacagcatt 103260
tattcctgag ttatgacgac agaggggagca cacggcatcg tctagaaggt ccctgaggga 103320
gggatgtgca gaggaggcgg gaaggtgtcc tccgccctga ttccagcagg gtgagcagac 103380
aggcccctg gcgtccaccc ccacaggcct cctaccttgg ttttgtcgtc caccactcgg 103440
agcccatcgg ctgacaccca caggacagac ttcacggact ttcggcccat ctggagggag 103500
gcaaggggac aaaggagccg ggtcagggtg cctctccctg tctgaccttg cccctcct 103560
catggcagcc ccctcactca ccgccttcag cttcttcacc gcatcttcac acacgtgcat 103620
tccccgggac tcctctacct ccacgtgacc caggtacttg ggttggaggg aatgggggggg 103680
gggacatgaa acagcacagt aatcactcat tctcagtgtc cactgagcat ctgccatgca 103740
gtagacaata ttttaagcac atgatgtgta tgcaatcatt tattctgcat ctcaactcta 103800
caaggtggag accccattcc tggtctagac atgcagatgg ggaaactgaa gcacagcacg 103860
tagtagtgat tccagtctag ctataccct gggccctaac ccggcaccgt ggtcctcccg 103920
agagctagta tttgcatctc tgtgcgtgag gactggccac aggccatgca aagctgcttt 103980
gcctacccta aagcagctag aaagagcctg ggccagtccc cacaatgact gaagggagtt 104040
agggtacctg agcccagct ccctcatctg caggtgggat gactgttgcc tcgagtttcc 104100
caggggaaag ctcagttgca cactgctgca gttttaataa cacacccttt actggctgcc 104160
ttactttcct cactcccaac accatttcct gcacctccca aatgaagccg tcacattcaa 104220
agtctgcttc cagggaaggg aacgtaaggt ggtggagggg ctgtgaccat ggtcagtcat 104280
cacccagcca ggaaggggct gagctccaca gtccacgccg tgaatcctgc tctccccctc 104340
acaggaatgt aaaagcgtag ggtatggcta aaccagaacg tccttatcgg tagagcgctt 104400
tgcaaatgct acaccacatg acggcttcca ggtaatagtt tgctggtaca aaaaaatgtg 104460
```

```
ttctggtttt ttgtttgttt tcaagattgg gtatcactct gttgcctagg ctggagtgca    104520
atggcacaat taaggctcac tgcagcctcg accttcctgg actcgagtga gcctcccacc    104580
tcagccttgt gagtagctgg gactacaggt gcgtgccact gtgcctattt tttgtagaga    104640
cagggtctcc ctgtgtttgc ccaggctggt cttgaactcc ttgactcaag caatcctccc    104700
accacagcct cccagtgtgc tggaattaca ggtgttagcc accactacgc ttcaagtttt    104760 ttttttttt tttttgaaac agagtctgct ctgtcgccca ggctggagtg caatggcgct    104820
atctcggctc actgcaatct ccgcctcccg ggttcaagcg attctcctgt ctcagcctcc    104880
ccagtagctg ggactacagg cgcccgccac cacgcgaggc taatttgttg tatttctagt    104940
agagccgggg tttcaccgtg atagccagga ctgccggcct cacgcttttt aacaccaact    105000
tcaaacgact tgggctggtg tcccagccag gccgcgcacc cgcacagcac agcacagcgg    105060
cccccgtccc cctcgccccg ccgcaccctg ccgcgcccac tcaccctgac cgggaagctg    105120
cacgtgccct tccgcaccgc gtcctcgtct gcctgccact ggtgcgggcg cgacgcctcg    105180
ggcacgtagg ctggcttcct ccgccgcagg ctctgccgta acttgttcat ggtgcccgcc    105240
ccgtctggtg acacaggaca gtgatgtggg tcaagggtgg gggtcagaag gtatggagct    105300
caacggggag ggaccagtgc tcagggagca tggggtcaga taacaagata actggaagcg    105360
gggttacagg gtcagttggc agcgcacatg ggatcagcag ctcaagtcag gggacagtga    105420
ggaaaggagc caacagaagc caggggagtg cgaaagttgg gcactgggga ttcagaacca    105480
tggggctaag gggctggagg tctggggtgg ggggtatggg gcacaggctt cagggcattg    105540
gagggcttct tgtccatgtg gtggatgctt cctcattccc agggccgtga ggacacaaag    105600
ggtgggaaat cagacgtagg agggcatggg ggctagaggg catagaagtc aggggccgca    105660
cggtcagggg ttttaggggt atgagagtca ggcagtgggg tgatcagagg gcagcagagg    105720
agttgggaat tgcatgggtc aggggtgcag gagtcaggtg catggggtat ggggatggt    105780 ggcttgtctc tggaactctg agacacagcc attctgtgac aactgtgtct agtccccagg    105840
caaggcttct ggggccttgc actgatgact gtcagaggca gggctgtggg tgtgtggagt    105900
gggtgtggag gtggccagcc actaggacag tcttcactga tcagccatcc tgacagtccc    105960
aggactggga gcaccaacag cagaggggga tgtgtgtgtg tgtgtgtgtg taagcaagtg    106020
tgcaatggta tgttctggaa cgctgtctat gaggggctct atatctgagc aggcaagtaa    106080
tgtctgtgag tgtgtttctg aaggctgtct ggaagaacgc atgtctgaga atggtgtagg    106140
atagtgtgca tctgtgaatg ctgtccgtga gggatgcatc caaaagtgtg gttgttgtct    106200
gtgagtctga ggccctgaag gttgttgctg aagggcatcg atgtctgaga gtggttgtga    106260
gtgtgtgtct gctgtctata tccgagagtg ccgttgttgt ctatgagaac ttgtggctca    106320
gtgcctgttg cctgtgaggg tgtgtctgtg tttgagatga ggctgtcgtc tttcaaaggg    106380
tgtgtccatg gctgttatcc atgtagctat gtctctgtgt gaaggtgtgg ctattgtctg    106440
tgatgacatt gcctcggaga gtgcatctga gggatctaca agactgtctg tgtccaagag    106500
tgcagctgtt ggcggtgagc ctgtgtgact gtggctgttg ccttagagtg tgggtgtgtg    106560
ggtattgcac agagggtgta tctgtgtgca gtggtgcatc cgttagggtg tgtgggaaca    106620
tgaggttgtc tttgagagtg ttttcatgag ggttatttgt aagggtgtga ctgttgcctg    106680
agagagtgct gggtgttctt tgtgagactg tgtgcatgtt tgtacacaac cgtagctccc    106740
tgtgagagcc tgggcccgcg ggtgctgtct gtgaaagtgt ggctgtcgtc tgtagaaatg    106800
```

```
tgggtctgtg tgtgttgtca gactgtgcaa gagtgtgtct cttttttttt ttttgagac   106860 gaaattttgc tcttgttgcg aatgaaggct ggagtgcaat ggcatgatct cagctcacag   106920
caacctctgc ctcccaggtt caagcgattc tcctgcctca gcctcccaag tagctgggat   106980
tacaggcatg tgccaccacc cctggctaat tttgtatttt tagtacagac agagtttctc   107040
catgttggtc aggctggtct cgaactcctg acctcctgac ctcaggtgat cctcccgcct   107100
cagcctccca aagtgctggg attataggca ttgagccacc acgcccggcc aagagtgtgt   107160
ctcttgagag tgtgtatctc agagtctgta tccagcgagc gtctgtggtc acctgtgaat   107220
ctgggtgttg tctaggaatg tgtgtgtgtg tatatatgtg tgtacattag tgtgatgaac   107280
atctacttca gcatgtgttc aagtgtgtca ctgcattagc aagtgtgtgt gatctgaaag   107340
agatctgtgt gtgtgtgtgt gtctctaacc gtatatctac agatgtgagt gtttgtgact   107400
ctgcacttga ggctgtaagg gtgtcagggt gtgggtctgt gcatgagtgg ggctctgaca   107460
gtcgctgagg aagatgcctg agggtgtcca ctcatgagtg tgattaagcc tgtgtgaccg   107520
cagggacagc tcctctggtc gtgttaggca agaccacata cccattcagc cctgccctgt   107580
cccaggctgg tcgctcacct ggctccgtcc tgcaggtttc tgggggcccc ggggcccac   107640 aggggctggg ggcaggtgc cgctcaggcc tccggggtcc gccctgcccg agtaggggag   107700
gagaaggtga gaagtttgtc tgggttgggg ctcagtctga tacttcaccc cgactttgga   107760
cttcggccag ccccctccat cttgggctcc ctgatgagag tcctagttgt cctagcaact   107820
gttaccaggg agatcagcca cctggttcca agggcccagg aaggagtagg tatgtttggg   107880
gggcatatgt tggggatgtg ctggcctcag gagagcctca ctgcccaagg ggatgctgtg   107940
agagtggcct tgccctccag atgcatgtgc agggctacac acatacgcag ccaactcata   108000
tctacaggtg tccctagcat ctggccacag ctttacacac ttggttacac atagacgcaa   108060
tcacagctac acacctcaga tcgcagatac acagaaacag tcccaaaccc agaaagctgc   108120
cactgtaaac atctggccgc atattcatgt tcggacacac acagtctcta ctacagacat   108180
ttgtccacat acatgcagca tgtcctggcc cactcagttc ccaccgcaga cacctggtca   108240
caccacccac tgaaatttgg tcacttccac attctcagcc atacaaaag aacgggccc   108300 agacaaccca ctagagccgc acatgcgtgg ccacacccag tgacagctat gtttcctcag   108360
gcacccgccc aagatactga cgtcacaggc ccacccagat agaatcacac ccagagttca   108420
cccatttgct gacccagtcc cacacgacac aatcgcagct atatacactt gttacacgta   108480
tctccactgc tgcacactga catctggtca cagatgcaca cggacagaca cacatttggt   108540
cccacggaga ccacatgcag cctcaaccag accagtcaca ccaacacact gttttttggcc   108600 acacactgtc acgtggtcac acatactcag tcataggtgc tcaaatctgg tcacagcatc   108660
agtcacacag tctattgtga cagccacact catagggaca gtcctctata cacaaccaca   108720
tacagaggta ctgatggcca cagcatgcaa ccacccacaa acaactgtcc ccaaggatgg   108780
cctccctcaa gacacagcca tggtggtcct ataggcatgg ccacagcatc aatgtccatg   108840
tgacccagcc acctatcatg gtcataatcc cgtcacccag tgtccataca cagctgtacc   108900
atgtcactcc aatgcagcga aacatatagc ctttcttcat gcaggcacac aagtcacaca   108960
gacaagtatg tggccatata gaatcacagc cccgtgtgga caggtgcaca aagtcacaag   109020 cccccacctac acacatatct cacacataga gacataagca cacagtttta gtttcccatg   109080
tcacaagtac acagtccagt gtatgcacat aaatgcagtg accaggatgt ggcatttata   109140
gctgggttta cacagaagac acaggtcctg acggagccat gtgcacagtc agggccaat   109200
```

```
ctcatcacca aatcacacat tctaacacag gtagtccagc acatacacac agagacaaaa   109260
acaggcacac agctacagac cccacactct cacagatgat gacatagaca cagacatcta   109320
tagtcaccca gggtcagaca tgcaggtcaa acacaataat atggaagcca taatcatata   109380 cacacccta caaacataat ttcctggcac cagcacggag acacatccac agctttagtc   109440
acacacaaat aatccctcta aatagccagg gtttcagaca ccaagtcaaa tacataaccc   109500
aaatcacaca tgcaaggcta gaaatacaca caatcactcg ttatcacaca cactgctaga   109560
tacagtcatt tatattaata caacctcagt cacacactca gacatggttc tgcatacgca   109620
accactgtca tacacaatac tgtcacacaa ccccagtcac acagatacaa tgtgacttca   109680
gacacaatgg cagtcacaca ggcagagttg cacagacagg tgtgtgtcac tcacgtatat   109740
aaaatcaggt agagacacaa ctataaacat tgtcagtcac tgggagggtc acacatgcac   109800
atggagccat agacaactcc actcacacac agtcacaact ccacccacgt cctgtcagtc   109860
acacgcatgc ccaccccag actcaacaca tactgtcaca tacccagtta tagttaccga   109920
ggcatacaaa cacagggtca caaaagacac aatcacagac aaccacagtc acaaccatgc   109980
acacctccaa acacagacag actaaaaagt acaggattct gcacagtgag cagctgtcac   110040
acacacatac acagtcacac agatactagg gtcacagaca caatcataga caccaccaca   110100
agcacacaca cacgacacag gattcctcag tcaccagctg cagcgtacgc gtgcacacac   110160
acacacacat acacagccac agtcacacaa acacagggca cactcctagc cacctcccca   110220
tcgcttgctt ccccccttcc ccccaggtac cacacacaaa gccgccgtca ccgtcaccgc   110280
agacactgca gacagacagg gctgcacccg gtccctgggg agccgccccc agcccagcct   110340
gtatcctgga gcctgagggc caggtccagg aggggggaagc ggtgcattgt ctgcgggtgg   110400
ggccactctt ggacagctgg gcagccctgg ggacaaaggg ggtggcctag ggatcctgtg   110460
ccctgggacc catgaccaag ccaggggggtg gagggattgg gggttgcctg aaattgtcct   110520
tattttattc aggctggggt ggggtggagt cccaggcaca gggaccttgt tttgagaagt   110580
ggctgtgcct gggactccgc ccaaggattg ggggatgct gtgccagggg tgcctctgag   110640
acctgggggc aggctgtgct tggagtcccc ctaggccttg gcgtggtggg aacgctgtac   110700
ccagtgaccc catcctcgag accgtaccta ggcagttgtt gtgctgagac ccccttaggc   110760
agggagaggt agggattgtg tctggaatcg cgtcctggag gccttggttt gatacgggg    110820 ctgtgtcccc gaccccatct ccatccccat ctagttctag gagttgtacc tagaatctct   110880 gtaccctgt ccttggtttt gtgggggggtc tgtgtccagg atccctatttt ccagggcctt   110940 ggcaagagat ggcccagggg tctgtgccca agaccccggt ctcctgggct ttggcttgtt   111000
gggcctgttc ctggaccccc acccgggacc acctctccca gccttggcac cctctctcca   111060
tccgggcgcc gcggccgcct cccaccctcc gccacatcag cagcggcgcc gccccgacc    111120 cgagcccccc tctcccgccc ttctcacgct ggccgccgcg ctgcgggaca tccagggccc   111180
gggcgccccc gcctcccgcg gccctggctg ggcctggctc cccgactgct gctgctgcgg   111240
tggtggcggc ggcagctcgg tctgacgccg gccaggggcc ggggccgggg gatggtgcgg   111300
gatgcacgcg cgcgagcctc ctcggctccc gggaggattc cgttccgggg gcggggagc    111360 gtccctcggc ctcggctccc cgccccgacc ccgcccattg gcccgccgcc tgccgtatat   111420
gcagaaaggt cccgcccccgc cccgcccctt ggcctgaaga cccgcccac acgcagacac    111480 catcccgcct tccccggcgc ggccaccgcc ccgccacgcc cattggccag tcccgagctg   111540
```

```
agcatgccta tgaacatcgc cgagtccttt cccccggtcc gtcctggcct gggctccctt 111600
tccctccgtg acacctgacc tcagatcccc tccagctccg cgtccgaaag agttgcttct 111660
agaggcgcct tgccgcccca cacccccaaa tcttcccgct aaccccatgg ttccccagcc 111720
cggcggggc gggcaggagc ggtgacgagg cactttttgc aaggaagggg aggggtgtg 111780
aacagaccaa ggcgtcctga tgcgcgatcg gttcggcttt gggaacgggg gcgccggggt 111840
gggaccaggg cgcggttctg gccgctacgg cgccccgcc gcccctacg ccaatcctgt 111900
gggtttggca aagcagctgg cagggacatt agagcccatt agtaaaggcg aggttgccag 111960
gagtgagggg agggagcccg cagccaagag gcactgtgtg tgtgggaggc ctcagctgcc 112020
acagcccta gagcaggtgg tcagcacgtg ggggggggtg gggaaggcga aaggaggtt 112080
cccggcaaca gatggcacag gcagggctga ggctttcaga caaggggtg caggggggct 112140
ggccatctgc acctggaggc cgctggcgag ctcctccccc tctcccccca acctagcgc 112200
agagaaaaga gctgggggaa ggggagggct gcttttattc cgattgaaga ttcagctccc 112260
ccccaccccg cacccctacc tctccaacac actgagagcc tggaacccgg agaaggcag 112320
ctgttggagg agcgagggag gcagaggtga ggactgcctc caggaccatc tcgccttcca 112380
cgggaggctt gaggcagagg tgagggctcc ccctgatgag tctgatctgc ataacgacat 112440
gcagcggccc aaggctccct caaatgttgg caaagataag ttaaccgctt ccctggctta 112500
gttttcggat acccactttc gagtggggag gtgcaggatc tagggcacga agttgggagt 112560
tccccagccc cagggatcct gagctcctgg gccaaggagg agagccaggc aagactggga 112620
agcccaaggg ggctcctctg acccagggca gacgggaag ggataagagg cactacagca 112680
gggtacggcc tgctctgggg actgaatccc ccatggaggc tgtcatgagg gatccaccca 112740
ggagtcccct ttggtgggga ggctgccggc agtggctgcg tctggctggc gactggccca 112800
gtagcggtgg taggtgtcct ggaagaggtc cctgcaggcg atgtgggctc ggaggtgggc 112860
acaggccagg aaagccctg ccagcttgcg gtgcagggca taggtctcct cgggtgggg 112920
acacagccgg tgccgcagca gcaccgggat gaggtcctgt atgcggcggg ccgtttcccc 112980
cgacccaaag tcataagggc cctgggtggc gaaaggctcc cccaggatca tcactgcctc 113040
cacgtgggcg tcggagaatg cctgggagtg ggggtggggg gagagcaaag gcagccagtg 113100
tggacataga gccctctgca taacccagaa acaacgtgta gcctccactc cctccagtct 113160
ccaccatcaa cacaagcccc gactccccca agagtgagca gcttccactc cttccagagc 113220
ctggactaga caagcagctg cctattcccc gagtaagcac cccttacttc cctgcagagc 113280
ctccaacaga caagtagccc tctactctct ctacaacaga gaagcggcct tcgcccctcc 113340
tgaacagatc cacggtgccc atgttcccag ggttcctgag aagtcaggca gccacctccc 113400
cccactcctc cccaaagccc ccagcatgga taagcatccc tcctagagtc acccactccc 113460
caggtataga cacacagcct ccattctccc tagtggagac aagcccctcc tagagtcccc 113520
cagtccccgg gtatcgacat gccccatcac ctactcgagt tcctcagtgg agataagcag 113580
cccccactg caccccacca acagacacca gcccctttct ccccagtgt ctccccacct 113640
tggtttcaaa gcctgtgagg aatttgaggt ccctggactt ctgcaggaca cagtctctgt 113700
ctccatcagc tgcagccttc accacctggg gagacgggtg ggagttagag ggacaaaggc 113760
cggggctcaa gggggctctg gagaagagga gctggaagcc tgggcctccc atgtaccac 113820
ctccattctc atctgcctgg gccctccctc acctggaagc ttcctgctcc caactttgcc 113880
tgtctgtgac tcccttaaag actcttccag agcctgggag tggaggtggt tagggatcct 113940
```

```
gcccacctag agggcaatgt ggggcctgcc cgggaactgc cacagtgaaa cagtgcaaga    114000
aacaagtgtc agggctgctg gtgagtccaa acactcaact ggacgggtat gagcgtgacc    114060
cagaactgca tccaaagttg ccaggggcca tctctctgtc tcccacactg gactttgagc    114120
cccgtgagag caaggatccc agttgggttt agtcgcacgg ggcacagggt ctggtgctga    114180
ggaggccctg ggtgaacctt gctttagcaa atgagcgtgt ggagcagagc agctctccag    114240
ccatgagctc acacacacag ggcaggagtt gtgggcatgg agagatgccc agctggggcc    114300
agctggctag ggttccgtcc cagctctgcc acctgccggc ctgttgggcc tccactttct    114360
catctgtgaa gtggggatgc caaaagtgcc ttcctcatgg ggctgttggg aggataaaga    114420
aggtgatgcc tgtggcctgc ctggcgctgt gtctcatgca ggaagcaccg taaatactat    114480
aatctaccat tattaagagg tgggcacggg ggtccctatt tcacagaagg ggaagcagac    114540
ccggagtagg gagtggaacc gggtcacacc actcactact gggttgccct ttttgtgag    114600 gaggggatt cggattaat tccattccct ctctgctccc cctgcccgag catgtctggc    114660
catctgtcag gcctgtggtc ctcagaagcc agggctttta taaagtggca aaggctgcag    114720
gcctgggtgg gaggggaggg tgtcagtggg gagaagaagg gtctcagctt tgtgcctcag    114780
tggccggcag agagggcccc aaggggcctg tgtgtaaggg gttatcacct cctcttcctg    114840
ttcctgtctc agaggtggcc ccaccagtcc ccagaccaga ccctagaca cctctgtccc    114900 caacttctag cccgtctgct cccatggact gccagctggg catctcccag ccacccctct    114960 gccccctctcc acagctgccc tgagctccca ccccaggct tagagaccac ttcttattca    115020
gagggagttt tcaaattctg actgcatccc ttccctgctc aaatcttttc cacggctccg    115080
cagggcacct ggatacagta cgagctgtag agcgcagcct ctaaaatccg cagtgatttg    115140
ctgcagcctc gtcactgtgc tgccccccga cctgccctcc cactcagaat gggagcttcc    115200
tttgggtgct ctagggcctt actactacca gtgtggtccc catacgggta gccctggcct    115260
cacatgggtg cgtgtcagaa catagcatct tacacccacc tccagaccag aatctgcact    115320
tgcacaggat caccaggctt cacatgcaca tccaagtctg agaaatgctg ctctaatggg    115380
actgtccctt atcactgcct cgtcttggca catgttgtct atctgaaata ccctccgagc    115440
cttttcccag ttggcccccc tcatccctca ggtctcaatg ctgacactcc ctcctccggg    115500
aagccctcct tggctcccca ggctggctca ggctcctcct ctgggctcac agtgccctgc    115560 gcttcccca tcccagccct gtccatgcta ggtcctcact gtcgcctcac tgactatgag    115620
ttctgtgagg agggccctag gctgggccca ggtcactgct gtgtctccag ctttgcctag    115680
aatagagctg ggcacagagg agggtcaga aaacatttag attggctggg caggagggct    115740
catgcctgta atcccagcac tttgggaggc caaggcagga ggatcacctg aggtcagcag    115800
ttcgagacca gcctgggcaa catggtgaaa ccccatctct actaaaaata caaaaattag    115860
ccgggcgtgg tggcacatgc ctgtaatccc agctactcga gaagctgagg caggagaatc    115920
gcttgaaccc aggaggtgga ggttgtggtg agccaagatc gagccactgc actccagcct    115980
gggcgacaga gcaagactct gtctcaatta aaaaaaaaa aagaaaaga aaaaaagga    116040 aaagaaaacg tttagattga tggctacatg attagaggac ccaggcaaa tgtccaatct    116100 caacaacgaa tgaaatggta ttctctgcag cctctaagac aaactgaccc cagtgggtgg    116160
gagagacgag ccaagtacgt gaggaaacac ctcctgtaga cagagttgcc cccagggaca    116220
cacacctggg ctggacacca gggccctgga cagcatgggg tctggagagg tgacaagatg    116280
```

```
gtcactgtgg gcctttctct taggagggag ctgggcagtg gttggaagct tgggctctgg   116340
acctggacca cctgaatttg aatcccaagt ctgctgtgat cttgggcacg tgacttaacc   116400
cctccaggac ccagttactt catctggcct aaaacgggcc taaaaacggt cctttctcgca  116460
ttgtgttgct gtgtggttta tatcggttcc tatacgtaag cactaaagat ggagcctgac   116520
atattaagtg cttggtgtgt gctagttgct acgagtatta ctattattta ttatttctta   116580
attccagaaa ctgcatttcg ccttcttact cctctgcctc agtatatggc ttgagcctca   116640
gcctttcaga ggccctgggg tctgggggag actcacctcg atgtaatggt ctgtgaactc   116700
tgtcccaaac tcccggcttg caccaaagtc cagcagggtc acctggaagc aaggaatggt   116760
gaaaggaatg ctgggatccc attcacaccc tcactgtcta ttggggcagc caggatctgt   116820
ctccctcccc atgaccctgc ctgctcctgc cagagtccct gcctggctgc ctcactgggc   116880
tcctggcctc atctcccgtt ccaaccgac  cccctagctg aaggcttttt tttcttttag   116940
ttctaattgt ttatgcaata acaaatttta gacccagaaa aaaaatccag agaataataa   117000
aagatataga aaagtaaaat gaatactcac aaatcctgcc acccagccta aaatataaaa   117060
tactccccat ccggccacac gtggtggctc acacctctaa ccctagcact ttgggaggcc   117120
aaggtgggtg gatcatgagg tcaggagttt gagaccagcc tggccatcat ggtgaaatcc   117180
cgtctctact aaaaatacaa aaattagcca ggtgcggtgg tgcgtgcctg taatcccagc   117240
tacttgggag gctgaggcag gagaatggct tgaacctggg aggtggaggt tgcagtgagc   117300
cgagattgtg ctattgtact ccagcctggg caacagagtg agactccgtc tcaaaaaaaa   117360
aaaaaaatac tccccatcca cgtggagcct cctgtgtatc ccgccctgat cacacctccc   117420
ccaggtcccc agggtcacct cttttcctaca atcattatta aattatttcc tgaaattctc   117480
atttatgcat ttctatattt tctatgtatg tgtacagctg taaacaatct agagtaatgg   117540
tgtgcatatt ttcaaacttc acagaagtgg tatttactgt cgttctcctg caacttgtgc   117600
ttttttgccca gcatggtttt gcgatttatc cctgttgcca tgtgtcgctc cagctcagtg   117660
actcatttca cactgctgtg taaggacttc gttgcgtgaa tctatcacag tgcatttatc   117720
tggctgagga atactgtggt tgtttctgat ttttttttcct tcttttttaaa tatgtttatt   117780
agttataaac tctgttctga cattttttttt ttttttttgag acagggtctt gatctgttgc   117840
ccaggctgga gtgcagtggc acgaccatgg cttactacag cctcaaactc ccacgctcaa   117900
gtgatcctcc cgcctcagcc tcctgggtag ctgggaccac aggtgcaccc caccacacct   117960
ggctaagttt gaaacatttt ttgtagagat agggtttcac tacgttgccc agactggtct   118020
cgaactactg ggctccagtg atcctcccac ctcagcctcc caaagtgcag agattacatt   118080
agtgagtcat ctcacctggc ctgtttctaa ttttttgtgct caatgaacac ctgtaagaat   118140
gtttctaggg cagtagagtt tgaactgacc acaacccaca gtaagaaatt gtttctactg   118200
gtggctgggc gtgatggctc acacctgtaa tcccagcatt tgggaggct  gaggggggcg   118260
gatcacctga ggtcaggagt tcaagatcag actggccaac atggtgaaac cccacctata   118320
ctaaaaatac aaaattagct gggtgtggtg gcgcacgcct gtagtcccag ctagttggga   118380
ggctgaggca ggagaatcac ttgaacccag gaggtggagg ttgcagtgag tcgagattgt   118440
gccactgcac tccagcctcc attctcaaca agagcaaaac tctatctcta aacaaacaaa   118500
taaataaaat tatatatata tatatatata tatatata gagagagaga gagagagaga   118560
gagagtttct actgggcgtt catgcaaatg cacacaaaaa cgtcaaacaa aagtgtccca   118620
aggccaggcg caatggctca tggctgtaat cccagcactt cgggaggcca aggcaggcgg   118680
```

```
atcacctgag gtcaggagtt cgagaccagc ctggccaaca tggtgaaacc ccatctctac 118740
taaaaataca aaaattagct gggcgtggtg gcaggcacct gtaatcccag ctacttggga 118800
ggctgaggca ggagaattgc ttgaacctgg gaggcggagg gtgcagtgag ccgagatcac 118860
accattgcac tccagcctgg gtgacaagag cgagacttca tctcgggaa aaaaagaaa 118920 agtgtcccaa aataatatgg atccctccca tctgtgacat actgacatca tctattccat 118980
aaaaaaaaaa aaagtgctgg tggatcatga ggtcaggagt tcaagactag cctgccaaa 119040 atggtgaaac ctcatctcta ctaaagatac aaaaaattag ccaggtgtgg tggcgggcac 119100
ctgtaatccc agctacttgg gaggctgagg tgggagaatt tctcgaaccc cagaggcaga 119160
ggcttcagtg agctgagatc gtgccattgc actccagcct gggcaacaag agcaaaactc 119220
tgtctcaaaa aaaaaaaaaa gtcctgttgg aaaccaataa attgatgtca ggactcctat 119280
cacttggagt tgggtaaaca tatccctggg gtatgaacct aggaggggac acagggtgta 119340
tgcacattgt ggagaaagaa gaggcaaggg actagggctg gagactccgt ggggccacag 119400
gatgctcagc aaagggttca gacttgattc tgaggggggct gtgaagctgt aggagggata 119460
tcttgaccag atttgtgctt tagaaagacc cctctgggga caaatggggg atagaccact 119520
ttggaaaaca gttggcaacc cctgataaag gtaatgatgt atccaccaac actcaagtct 119580
gcaggtccaa accttcacta caggtctttg tacaccccct gccctctgct gggaacactc 119640
tgctctctgg atggttgtct ccttttcccc tgtcccatct cagccttttt ttttttttta 119700
aatagagccc aggctggttt taaattcctg gcctcaaggg atcctcctgc ctcagcatcc 119760
caaagtgctg gaattacagg catgagccac catgctcagc ctctggtctc agcttttttt 119820
ttttttcttt ggtgagacag agtctcgccc tgtcacccag gttggagtgc agtggcatga 119880
tcttggttcg ctgcagcctc gacctcctgg gctcaagcca tcctcccacc tcagcctctc 119940
agtggcctca gctttaatgg cacttgcttt aagaagcctc ccttaatccc tgctcacccc 120000
acagtgagtc aggcactttc cctgggatcc cataacttcc tgtgcctccc ccaactccag 120060
cccccacccc tctgcctgtg cctcccccat cccggtcctg acccatctgg cctgtgctcc 120120
tcattgtggt tggtacgaac cactctaggt catcgctgtg tggtgccagg tccccccact 120180
ggactgggca ctctgagaag gcaagggtca gggatgtctt tttattgctg tcaagaggca 120240
agggcaggtg atggtgtgtt ctgtatggat gacgagtgtg gtagtgatgg ctaactgcct 120300
tccaaaagct gtacttcccc tctgtgctgt cacattgcca ccaggaacca ctgcctagcc 120360
agggactcca tttccagca tgccttgcac ctaggcaggc tatgtcacta gctctcactg 120420
atggaatggc aacggaagtg ctatgtccat tgccccagga tgagcttagt gtatttagcc 120480
tgggcattac ttttttccact tctggccaaa gcagttaggc aggggctac cctcaacctc 120540 tcttacccctt tccttgggaa gcagagcgtt gcaaggcccc agggatggca aaaccacaaa 120600
agggaaggag ctgggtccct gaatcccact tggaaaggg ccaccctgc ctattgtggg 120660 ggtaatcaac tgctattttg ttgagctacc gaaatatcaa ggaatatttg ttacaacagc 120720
aaatgtaccc agacacacat cactaggaac caacctggtg gctggaggca tcatacagga 120780
agttggccca gttgggggtca gtctgcatga atcggaactc aaacagctcc cgcagacaca 120840
gcgtcaggag ctggaagcaa atctggggtg gggagaatta acaggcatct cagtgtgatc 120900
tcccttgtgg tgccactgct ggcctggaga gagaccatga gcctggccca cccgccctgg 120960
ggccatgccc ttcccactgt gccaccagac agcatacctg gttccgcagg tcctggctta 121020
```

```
ggccctggca ctggtccagg gggacccctc cagccagctc catgcccagc acccgtgtcg 121080
tgcacagctc cttaaccacg gctgggaccc ggaagaaggg gtcatttgcc agcagctgcc 121140
tggggcagaa ggaaagggag aaggggact tcgtgcttca ggcttgtgac ccagcttgag 121200
acctcctcct tgtgctctca gaagtcctcc atgaacagtc tgcgccatgc cctccctcct 121260
gcccatctct tgctgctgtc tgccctgggt gatgaccaac acctggctgg actgagattt 121320
aacaagtatc tccaaggtgc ctactctgca cctgcctctc aactgggtgc tgctggaaac 121380
ccagtcacca cttccctacc cgaaaccctt ctatgacttc tggttgcccc agaaggatga 121440
gttcaggtgt atttcagcct ttgcattact ttttcattaa tttattaatt cattcatccc 121500
aaaagtagtc actggtatca aaatctgtga agtctatagt gatacccatg ggtcagtcct 121560
tgcaatcact actctgaaca caggtaaata gcgggaaaga atcttctgtg tccatccttg 121620
tgctaaatga tgctggggac agagcagtga atgaaccagt ccctggacct ggcccccaac 121680
cccgagacca cactctcaca aacagacgga ttatagattg aggtaagtgt gttggctggg 121740
tgcagtggct tacacctgta atcccagcag tttgagacac cgaggtggga gaatcgcttg 121800
agcccaggag ttcaagacca gcctgggcaa catggtgaaa cctcgtcttt atgaaaaact 121860
acaaaaatta gctgggcgtg gtggcctgcg cctatgttcc cagctactca ggaggctgag 121920
gtgggaaaat cacttgagcc tgggaggtcg aggctggagt gagctgtgat ctcaccactg 121980
tattccagcc tggaaaacag agcgagaccc tgtctcaaaa aaataaaaga agtatgtcta 122040
tgtaagattt gggaggcaga gaatatgagc aaggtctctg gttgaggatc cgtgggatgg 122100
ctggaggaga gtgagggaga acaggagggt ggtgtggggt tttatcctaa gggcacccgg 122160
gaatcctgtg ggggacgggg gggtctctgg cccatcaccc cacttcacac tctcttcctt 122220
gagctcctcc tttggggttt gtattttgt ccttgttgat aaaaatctct gatgtttgaa 122280
ctgctcctca tgaaccggag ccatgtgggg catttaatcg gcacactccc ctttcatcct 122340
cactccacag tgaggggatg ctctctggag gccactgtac agattgtatg gatgcaggcc 122400
acgtaacctg ttaagggctg acccaggatt tcatcccgca tctgagtcta gggtgtgtgc 122460
ctctaaccac tgccttctac tgagcttca ctctctgtct acagagcttg gcacgttta 122520
ggctgtcaat aaatgtgtga gccacactgt ggaggacccc actgaggtgc cattaattgc 122580
tacacatcag gatgcttcca agatataacc acattgttcc acgtagccat agttcatgca 122640
ttttcactgc tacgtaatat tccacagatg aatataccgt tgcttatttg tccaccctgc 122700
tggataaact tgatggatat gggttgtttc cagtttgggg ctgttgcaga caagcgttct 122760
agaacagtct gatgatggat actggcaaaa gggtccctag agtgttcagc agggagggca 122820
atcgttggct tgcagagttc ttgaatataa gggcttatgt gatgatgcca acctgttctc 122880
aaaatgcttc taccaccttc tcccacaacc tgcagtgcag aagggatgct gtggagccca 122940
ctctctctac ctcccagtgc tgtgggctcc ttgctctccg tcagtccagc agaggtaaga 123000
gtgtgtcatt gtgtaattaa ttaagtgcct gtgtcggacc acagtggata tgcggcccat 123060
ctgacacagg agaagactgc cgcttgggaa gtgacctgcc caagctcaca gaggacaaag 123120
ggggtaagcg aagtgatgga tgagtggaag gatggatgaa caatgattga agaaagaga 123180
gagtttgccc taccccacag ctccagctgc cagaagctga gggggcagct acttcccacc 123240
cagcctggga gggagggaag gagggaagct cagggcactc agctcacctg aaattctggg 123300
cacaagccgc ctcacgacgg tagtcacact cccaagccag ctcctgctgc aaggcctgca 123360
ggctctgctc ggcaaacagg cctgtggggg aggtgtgtca gccagggaag ggccccgagc 123420
```

```
gcccactggt ggatgccttc tcctgccaac cctctctctc ctgtctcccg cgctgtccct 123480
cacagctcct actctaggcc tgtgacccac atctgtccct ctcctgtctc ccacgcagct 123540
cctgctcctg cctctgacct gcatctgtcc ctctcctgtc tccccgctg ccccttgcag 123600 ctcctgctcc aggcctctga cctgcatcgt atcatctgtc tacacatttc cctcgtcctt 123660
catagcacca cagggttccc cggggtcttc cgaagccttt tctgggctct gtctcttgca 123720
catgcctgca ccccagtccc tggcagctct ttcagagtca cgcctgcctc tattctgtct 123780
ccttttcata ctgactctca cgttgctcac tgcatctgaa tctcacttct gggcctggct 123840
ttccctctcc ctctccgtct cttacacaaa cacaacccac cctcctttct ctaggcgcct 123900
cctcacgtgc catccccagg actgtccttt tctgctctgc cgcacctaca atcccgctcc 123960
ctgcatgcac accctctgag agtctgctgc tgtatcttgg ccctgggctc ccgtctctct 124020
aaggctctgt taaaatccat aaggcttttc ccacacctgc tcatgctccc tgggctctcc 124080
ccgccttggt gtccttctg tctctgacac tcccgctcac aacgccagca caccctgccc 124140
gtgctctcct ctgggctccc cctcctgctt tctctctctg ggcatagccc ctttggagg 124200 tcagcagagg agtgggtggg cgcctcaccc gcgggcaggg ccgcgctcat cttgagtacc 124260
gccagcaggt tctggacatc gctctgaatg ctctgggcta tgccggggta ctgtaaaggg 124320
agaagggagg gagagaaggt gggagtcact tctctgggct agcagggtgc ccgcccctac 124380
cctgcccagc ctcccctctc acctggatct tcacggccac ctccgtcccg tccctcagca 124440
ggccctggtg cacctgccca attgaggcag cggcaaaggg cacctcctcc aaggaggcca 124500
ccttggcctg ccagtccctg ccgagctcct cttcaagaac tctctgcggg gagtggtcac 124560
agccatcatc attgtggcag agttcattcc ccaggctgag tgctttacgt gttgataacc 124620
ccagcactca ccacatgcag ggccctgggc taagctcttg gctgccaccc cctttgcaga 124680
tgaggaaact gaggctcaga gagagctccc ttgtgcaagt gactagccag gcactggcag 124740
actgtgaggc tcagcctagc ctgtgtcccc tgaacctgga ctccctgggc tgttgtgggg 124800
attgctatta tttatagtta agactcataa caatccttt ttttttttt ttttttgagac 124860 agggtcttgt tctgtagccc aggctggagt gtagtggcac tctcacggct cactgcagca 124920
tcaacctccc gagctcaagc catcctcctg cctcctgaat agctgggact acagatatgt 124980
gccactgtgc ccagctaatt attactgtta ttatgtttag tagagacaag gtctcactat 125040
gttgcccagg gtggtctgga agtcctgagc tcaaatgatc ctcccaccgc agcctcccaa 125100
agtgctggga ttacaggcat gagccattac acgtggccaa ccatccttta ttatgctctt 125160
atatgttatt attaactcac agttactgtg atcaagaaga gctaaaattt acaatgggct 125220
tcctgtgggc caggtcctat tcagagtggc cagagagag gcagtacctg cctggggccg 125280
catggcgaat aagcagaaca gggatgggag agcaggtggg tggcggaatc ctggattcca 125340
tgccttaccc agttattaga acagctcatg tcctgggcac ttacttggtg ccaggcgccg 125400
tgccaaccta ttacagacac gatctccttt aattaaaaaa acagtaataa tcacagctaa 125460
cacctgcatg ttgctcacag tgaatcaggg gccgttctca gtgctcagtg taaactgatt 125520
tatgtgaccc tatgatgtgg gtgtggctgt cactatcgcc atttcccagg aagggaact 125580 gaagcacaga gaggtcaggc tgctgttccc tgttttaatc accacagcaa tgctaggagg 125640
tgtgtactct ggtgattccc attttacaga tggggaaagt gaggctcaga ggcagggagt 125700
ggggcagtga agccaggaag gtcaggcagg tcagaggaga tggagcctgc ctccctcacc 125760
```

```
gccctcccccc actgggcact caccagcatc tgccagcggg gcatgaagtc ggcgctctgg  125820
cggacccgct caaagatgtg ctgcagctga gggctgatga agctgttgtc ttgggagaca  125880
gtggaaccag gggggaagta agcgaagagg tgaggaggga ccccgtgtga gtatctgaag  125940
ttggggcctg ttggtgggta gggctgqqqt agaagqqagq tcaggqgtca ggagtcgagg  126000
gtcatgctgt accctggatg ctgagcatct ggccaacctt gagggcggcc cctcgaactg  126060
tacataaggt ctgcacaatc cgctcggcat tggcctccga caggaagggg ctggagtcca  126120
gcccagaacc accctctggg gagagaacaa ccattagaat tataaccaca aatatcatca  126180
ctgcggccag gccggcggc ccacgcctgt aatcccagca ctttgggaga cccaggcggg  126240
atgaacacag gagtctgaga ccagtctggg caacagtgac atcctttctc tattaaaaaa  126300
aatatatatc atctgcacac caacaggaat ggctaaaacg aaatacgagg ccaggcttg  126360
ttggctcgcg cctataatcc caacactggg aggtcaatgc aggaggatgg cttgagtcaa  126420
ggagttccag accagcctgg ataacaaagc aagaccctgt ctctaattag ctgggtgtat  126480
ggtggcatgt gcctgtagtc ccagctactc aggaggctga ggcaggagga ttgcttgagc  126540
cctggaggtt gaggctgcaa tgaactgtga tcgcaccatt gcactccagc ctgggcaacc  126600
aagcaatacc ctgtctcggg aaaaaaaaaa aaaaagaaa agaaagaaag aaaaataaac  126660
ataagttaaa acaaattgca ggagagtcaa agagtaacta ctacagtatt gaatagatga  126720
gctatcacta cacacaacag cccaggtggg tctcaaaaat gtaatgctga gtgaaagcag  126780
ccgggtgcat gaaatcatca cccagttaca ctgatataaa gagcaaaaca aggccaaaca  126840
aatccagggt ccaggagcca agacagaggt caccettggt gaggggagtg accaggtggg  126900
gacatgagaa gggcaacgat tctcgaaatg tgggccaggg acccctgagg gtccctgaga  126960
ccattcagag gggtctgaga gatcaaacta tttttatcgt aacattaaga tgttattttc  127020
cccttttctgc tctcatgcgt ctaagaacat tcactggagt tctccagagg ctccaggaca  127080
tgtgaggaca ccatcagact gacagctgat ggaatgtgta cgtgtgtact cttgtgtttt  127140
aaaaatatct ctgtattttt gttgtgtttt tgagacagtg tctcactcta tcacccaggc  127200
tggagtgcag cggcacaatc atggctcact gcaacctcct gggcccaagt gatcctcctg  127260
ccttaacctc ctgagtagct gggactacag gtatgcacca ccatgcttgg ctaatatttt  127320
tactttctgt aaaaatgggg cctcgctatg tcactcagac tggtctcaaa ttcctgacct  127380
caagggatcc tcccgcccca gcttcccaaa gtgttgggat tacaggcgta agccaccgca  127440
cctggcctaa aaatttctca gttttaattt ctaatatggt agacattgat aactataatc  127500
cacataaata agctctttgg aggctcattc taacagtttt attgagaaat aattcacata  127560
ctgttataat tcaccattta agttatataa ttcaatgatt attagtatat tcacagagtt  127620
gtgcaagcat caccagaatc aattttagga cagttacacc acgcaaaaaa gaaacctggc  127680
tgggagtgct ggctcatgcc tgtaatccca gcactttggg acgtcggggc gggatcactt  127740
gagttcatga gtttgagacc agcctggca atatggtaaa accctgtttc tacaaaaaat  127800
acaaaaatta gctgggcatg gtggtgcatg cctatagtcc cagctactca ggaggctgag  127860
gcaggaagat cacttggacc caggaggtag aggttacagt gagccgtgat cccgccaccg  127920
cactccagcc tgggtgacag agtgagacct tgtctcaaaa aagaaaaaa aaaaagaaa  127980
ccctataccc attagcagtc actcttcatt tcccccaatc tccccaggcc ttgacaacca  128040
ctaatctact ttatgtccct acagatttc ctatttgta catttcatat taatggaatc  128100
attcaatatg tggtttttca gtgtgtggtt gcttttactt agtgttttt tttttgaaa  128160
```

```
cagtgtctcg ctctgtctcc aaggctggag tacaatggca tgatcttggt tcactgcaac 128220
ctccgcctcc ccggttcaag caattctcct gccttacccc ccacccaagt agctggggtt 128280
acaggcaccc accaccacat ccagctaatt ttttgtattt ttagtagaat caggatttcg 128340
ccatattgga caggctggtc ttgaactcct cacctcaggt gatccacctg cctcggcctg 128400
ccaaagtgct gggattacag gcgtgagcca ccgcaaccgg cctcacttag tgttttcaag 128460
attcatctac attgcagcat gtgtcagccc ttcattcctt tttatggctg gataatattc 128520
cattgtatgc ctatcacatt ttattcatcc attcatcagt tttaaaggtg tgcagggatc 128580
ctgagaccaa gaagtttgag agcagctatt ctagggtttc ttactctggg tacggacaaa 128640
tgtactttgt gaaaacgcac caagccatac acttacaggt atgtgtacct gggtttatat 128700
gcaaattaca tttcagcttt ggcaaaacat ttatttttct ttttttaata tgaacacttt 128760
atgaatttat gtgtcatctt tgcacagagg ccgtgctaat tttctctgtc tcattccaat 128820
ttttatttat atgtgatgct gaagcaagca cagcacaaca aagcaattct taagccttta 128880
ttaattttga aggccagttg tggtggctca cagctgtaat cccagcactt taggaggcca 128940
gggtaagagg atctcttgag cccagaagtt caaagctgca gtgagccatg actcaccact 129000
gcactctagc ctgggtgaca gcaagactct atctcttaaa ataaaattta aataaaata 129060 aaatgttatt gagctcatta ttgagctgtt ccaggcagaa tcctaagtgt ctttgtggat 129120
tctctggctg aatgcccaca atcacacctg gaagtaagaa ttatcaatcc tttaattttc 129180
aaggtgagaa agcaagagac tcaaagaggt gcagcaccta tccctgggtc acatagcatg 129240
gaagtggcag agtggggtgt agactcaggc tggtcatacc caaaccctaa tcctccacct 129300
accctcaact ttttatttg aaaaaaatat ccaggctggg tgtggtggct catgcctgta 129360
atcccagcac tttgggaggc tgagcaggga ggatcacttg aggctaggag ttccagaccg 129420
gcctgggcaa catggcaaaa ccttctctct acaaaaaata caaaaaatta gccaggcgtg 129480
gtggcacgtg tctataatcc cagctatgca ggaggctgag gtgggaggat cacctgagcc 129540
tggggaagtc aaggctgcag tgagccatga tcgtaccatt gcattccagc ctgggtgaca 129600
cagcaagacc ctgtctccaa aaaaaaaaag acagaaaaaa atccaaacag aaaagttgca 129660
tgcataatat cgtgaacacc tgcacacccg cacaccctcc acctcgattc aacatggtac 129720
cattctgctt cgtctgcttt atctgtgcgt gtacccacac acttactatt attattttt 129780 gctgacccac ttgcatgtag ttgcacttaa gctttgctaa gaataaggat attcccctac 129840
acaatcacag taccataatc acatgtaaga aaattaacac caattcctta acatctgcca 129900
tgcagtccat attcagattt tccatttgtc tccaaaaagt ctttcatggc tgttttttcc 129960
aaactgatat gcaatcatgg ttcagatgct ccatttgtca aataatgtct ctttcatctg 130020
tttttaatct ggaatatcca cccccacttg tttcaagaca ttgacttgtt gagggaacct 130080
ccacctaccc tcaactttt attttatttt ttataacggc aaatgctaca catctcaattc 130140 catctctgat gtacacagac cctcgctggc acttctattt tcagctttct gctcctgctc 130200
caagttagga actcccaatg gcttaaatgt tttctcagat aatctaatat gtggctgggc 130260
acagtggctc atgctataat cccagcactt gggaggcca aggcgggtgg atcatgaggt 130320
caggagttga agaccagcct ggccaacatg gtgaaaccgt ctctactaaa aatacaaaaa 130380
ttaaccaagc gtggtggcat gtgcctataa tcccagctac ttgggaggct gaggcaggag 130440
aattgcttaa acctgggagg tggaggttgc agtgagccaa gactgcgcca ttgtactcca 130500
```

```
gcctgagcga cagagtgaga ctccatctca aattaaaaaa aaaaaatcta atatgcttct 130560
cttaatcatg accctgatag tggtttaggc ctgttcaaag cacttcacaa tgactctaag 130620
aggtgggtaa attatcacca cctccatctt ccgcatgagg aaactggagc tcagagggt 130680
gaagtcactt gccccaggtc acacagcaaa gccaggatct gaacccaggc agtgtggctc 130740
actcacctga ctgcagacga cctcctggca tggacttctt agccatctcg gccagtactc 130800
ctagccccaa gcccacagcc agtcctgag tgcaagagaa gaacatgagt gcccgtttgc 130860
ctggggtgcc cccagcctaa cccactctcc tttctcagtt tttctccaag aatgcttgtc 130920
tcccaactct tttttatttt tcttttgttt gagatggagt ctcgctctgt tgcccaggct 130980
ggagtgtggt ggcacaatct tggttcactg caacctccac ctcccgggtt caagcgattc 131040
tcctgcctca gcctcccgag tagctgggat tacaggcacg cgccaccac gcctggctaa 131100
atttttttg tatttttagt agagacgggg tttcaccgtg ttggccaggc tggtctcgaa 131160
ctcctgacct caggtgatcc tcccgcctcg gcctcccaaa gtgctgggat tataggcatg 131220
agacaccgca ctcagtcttg tctcccaatt ctttgtatct ctgtttccaa atcagtctct 131280
gactctgttc ctgcatgggg ctccctttaa ggtgcagctt cctctttctt taaccctttc 131340
tccatgtctc tgtctccctc ccagcagttc tcagccctgg ctgcacattc cagttaccag 131400
aggagctccg gtaaatataa tgcccagact ccactcccca aattctgatt aaattggcct 131460
gagacatggg aatttgtgtt ttgttaaaaa gcacctcaga taattctaat gtgcgatcaa 131520
ggttaagaag gcccctcggc cgggcacagt ggctcatgcc tatgatccca gcactttggg 131580
aggccgaggt gggcagatca tctgaagtca ggaggtcgag accagcctgg ccaacgtgga 131640
gaaaccctgt ctctactaaa aatacaaaat cagccgggcg tggtggtgca tgcctgtaat 131700
cccagctact caagaggctg aggcaggaga atcgcttgaa cctgggagac agaggttgcg 131760
gtgagccgag atcacaccat tgcactccag cctgggaaac aagagagaaa ctccgtctca 131820
aaaaaaaaaa aaaaagaag gccccgaaac aattgtccta ggtccctctg tcttctggtg 131880
actcttcttt ctctgtccac acctcctctt ctttatgctt atctcttttt cttttagag 131940
acagggtctc actctgtcgc ccaggctgga gtgcaatggc accatcataa ctcactgcag 132000
cctcaaattc ctgagctcaa gtgatcctct tccctcagcc tcctgagtag ctgagaccac 132060
acgtgcatac caccacgctc acctaatttt ttattgagac agggtctcac tatgttgccc 132120
aggctggtct ggaactccag aactcacgtg atcctcctgc ctcggcctcc caaagtgctg 132180
ggattacagg tgtgggctac caggcttgac ctctcccttt ctaagccagt tatttctgca 132240
tctcttgcct tctccccatt tgtcctatct atctagatct cttttctctct tttcctccct 132300
ttgatgttat ctctccatct ctgatttcct ctgctacctc tcctcttgtc cctaaagacg 132360
tctcgggtct ctctccttct tttgttgtca ccatctctgt caattaccat atctggcatt 132420
ttctgtgtcc tttctacatg tcaggggctg ttcccagtgc cttctgtgca cttactaatt 132480
tttgtcctta catgaggtct ccaccttcat aaaatgtatt ttacagaaaa cttccatttt 132540
acagaaaagg aaattgaggt tcagagaagt gaagtaattt gcccagagtc acgtcacaaa 132600
gcgaggacac agcagagtca tcccttaatc cctgggcagc ctggtgccaa agctctaacc 132660
agtgcctttg actgcctctg cagactgtga atctatctat gtatatatat atagattttt 132720
ttttttgag acagagtttc actcttgctc cccaggctgg agtgcaatgg tgcgatcttg 132780
gttcactgca atctctacct cctgggtaca agcaagtgaa tctatatttt taaaacttga 132840
accaggcggg gcatggtagc tcacgcctat aatcccagca cttgggagg ctgaggcagg 132900
```

```
tggatcacga ggtgaggagt tcgagatcag cttgaccaac atggtgaaac cccatctcta 132960
ctaaaaatac agaaattagc ggtcaggcac agtggctcac gtctgtaatc ctggcacttt 133020
aggaggccaa ggcaggcgga tcatgaggtc aggagatcga gaccatcctg gccaacatgg 133080
tgaaaccctg tctccctaag aaaaaaaaaa aaaaaaacaa caaaaaatag ttggacgtgg 133140
tggcgtgcat ctgtaacccc cgctactcag gaggctgagg caggagaatt gcttgaacct 133200
gggaggtgga ggttgcagtg agctgagatc atgccactgc actccagtct gggtgacaga 133260
gcaagactcc atctcaaaaa caaaaacaaa acaaaacttg aaccatgat cagcaataag 133320 aagacattta cgttataacc agtgcagacc aaggtatatg tttcacgaaa caagactttc 133380
ccttgctcta caggtgcatg catattttct gtcctattct tcttttttaaa tgctggttgc 133440 aacccactaa attatttcat gtgacttgca cgacatccgg ctgtgtaacc caaagtcaag 133500
tgacctcccc tttgttagcc tcaatgtcct catgtacgga atagaacact cattgattca 133560
gtgcagcatg tgtgtatatg ggacactgca cattacaggt tctcagtaaa tgttattatg 133620
gccaggagca gtggctcatg cctagaaccc cagcacttcg ggaggccgag gcaggaggat 133680
cgcttgagac caacttgagc aacatagggga gaccctatct ctacaaaaaa atatttttta 133740
aattacccag gccaggcaca gtggcttccc gggcaccgtg gctcacatct gtaaatccca 133800
acactttggg aggccgaagt gggtggatca cttgaggtca ggagttcaag accagcctgg 133860
ccaacatggt gaaattctgt ctctactaaa agtacaaaaa ttagccaggc ggccaggtgt 133920
ggtggctcac gcctgtaatc ccagcacttg ggaaggctga ggcaggcgga tcacaaagcg 133980
aggacatagc agagtcatcc cttgaaccct gggcagcctg gtgccaaagc tctaccactg 134040
cctgacaaac atggtgaaac cccgtctcta ctaaaaatac aaaaattagc cgggtgtggt 134100
ggatgcatgc ctgtaatccc agctacttgg gagtgtgagg caggagaatc ggcttgaacc 134160
cgggaggtgg aggttgcagt gagccaagat ggcgccactg cactccagcc tgggtgacag 134220
agggatactc cgtctcaaaa aaaaaaaaaa aaaatagcc aggcatagtg gcaggcacct 134280
gtaatcccag ctactcagga ggctgtggca ggagaattgc ttgaatgtag gaggcagagg 134340
ttgcaatgag ccaagacggt gccactgcac tccagcctgg gcaacagagc gagactctgt 134400
ctcaaaggaa aaaaaaaaaa aaattacccg ggcggatggt gcacaactgt ggtcccagct 134460
actcaggagg ctgaggcgag agaattgctt gagcccagaa gtttgaggct gcagtgatcg 134520
cgccactgca ctccagcctg ggtgacaaag tgagactctg tctcaaaaaa aaaaaaaaaa 134580
attatcattt atgttcctct tgatttctct tggccttgca ggcccttgcc tttgtctctc 134640
tttttttgtc tctctctctt tcctgtctct gattcatcct ctcccttgct tcaatctgta 134700
aatgttgccc tttctaattg aggtcacacc aagatccccc aaagtcacac ctaccccaa 134760 agttggccaa gcggctgatg cgggaggcag gcaccttgcg ttctcgagag cggtcactca 134820
gctgggaaat ggggacaagg tctgagggtg ggaaagtggg catcgtggcc agagagtgca 134880
gccactctgc caccacaccc ttccccaagc tcaggggggcc agcagtattc gtgggtgtt 134940 gctgggtggg tgggggtaat gatacctggg gccggggtgt cttcctggga cgggcctccc 135000
gtgccctgcg aatgtcctcc tcacccagcc ctctcccagg cccatcctgg taaaacttt 135060 gggcccaaga acctccacat ggtccctgca agagatatac tttgataagg aggggaggac 135120
atgggatcac ctgcccctt ctggaccctc ctgtcctttt accctctgaa gtctccctca 135180
gcctcttccc cttggggacc tgctccctag cctcttaccc agcggtgggg cccaggcccc 135240
```

```
agggccccac aaggccaacc aacagtctgg cccagctgtc caccggtccc ccgaagtagg 135300
ccccccacct tcagccacat tgcctggagg agaagaggag ggattattca ggtgggagtt 135360
gcctggcttc ttggccaggc cccatgttc ctctgtgtcc accctctctc attcccaccc 135420
actaaatact tcctccacta ttaatagatt cccacagttt ctcctggttc tcccctggtt 135480
gctaggaacc cttagctctt cctgcaggcc tcccaaaacc cactttcccc cctctcccaa 135540
ccctcgccgt tgctagggtc cgccccgtt actagacacc cacagttcct caggggctac 135600
ctctccactt ctctgaaacc cccctcgttg ctatgcaccg ccttcccctc tgttggccct 135660
gtaggcaccc gcaattcctc cggtgtcccc ccgcccgatc cccacccgt tactgagcac 135720 ctcccccgt tgctaagcac ccactgctct cagcctccga gtccgcaacc tgctgggcc 135780 ctcctgtgct tccgggagcc tctgtatgcc cgcccccttc ggccagccaa ccaatgcgc 135840 ggcagcaact cgctgactgg cacggagttt ctccatctgt gcgcggggga aggggccaga 135900
gagaggccct agcgatggag cctggaatta aggtgggcat cggggggccca tctgggggga 135960 ttgctgaggc atcgcgggag cgcaagcgtg ccctgtctgc ccttccactc acctcaaagt 136020
gccttgtacg cgacagaccc ttctgttccc tacactttct tgcaaagtct cccttacaaa 136080
cctgacgcct ctcttctgca cgaatatctt gccaaccccc cttcttattt ttaccctgg 136140 caggctcaac acaattcctt tgaatacaca ttcttcccag caaacatttc ccttgcacat 136200
ggagcccctc cactttgcac aaacacccac attctggcac ccaacctcct tccttgtgca 136260
tataaatccc ttgccttgct tgccaactgt ttcccgctca cgccttcaac tctctcgtgt 136320
acataccctc cccccacctt gcacactgag tctctgttcc ctcacacacc ctgttctctc 136380
cgctccccgc ccacctgcgg aatggtgcga ctgggagccc tctgcttcct gtaggcctga 136440
catttcccag aacacactca gccaagattc ccagtgctga gtcaggaacc ttggcatccc 136500
agaaaaccac ctcccatcct atctttcttt ctctgtgtgt gtgtgtgtgt gtgtgtgtgc 136560
gcgcgcgcgt tggaaagcct gctctcccca caacaggctg actcacccac ttctcacagt 136620
ctggaataga ggcatctggt tggggcatct ttcccaccac tgggagaggg agggatgccg 136680
atgcttcccc cacagaaccc cgctgcccca accctcttg tcgggaatca ggcctctttg 136740
tctctattcc cgtactgtgt gacctcagaa aagccctcat ccctctctgg acttctcctt 136800
cccaacctgt atgaggtact aggtgggctc ctgccttcga tttctctcat tggtctgtga 136860
aaaggtgact cattttagag ccttggacct gtgcccaatg tctcccccag ttgactcaat 136920
ttcaagacaa accacctcct ctccccttc agaggtgaac ggctgactca ggagctgggt 136980
ggcagctcag ccttgggggc aaaatatatc aaaatcacct aggacaataa ataatcctac 137040
tgggctacaa ctgacagtgc caggcccggg gccacatgct tcacatacat gagatcatgt 137100
cagatagccc cgtagctgca agcaaagggt agaggccggc agatctctga gcctctgttc 137160
tcacgtgtaa aatggagccc tggcatccct attgttcagc cttggagaat gaactgaaat 137220
cgtgtcaggg tctgatacag aacaagtact ctatacatga cagagatttc ttacggaaaa 137280
tccaatggag cgtaagtcat ttgctcaggg tagcggagct gggaactggc agaggaaggt 137340
ctcgaaccca cacccgtggg aactccaagt ctttgaaagt ccgtcccgcc cctgcgtgaa 137400
gaatgggcgc gcggctggac tcgtcaccgg gggttttagg gaaggttgaa cttgtcattc 137460
aaccgtgtag ggagggtggt ttagtcacag gggtggaggg agggggccca ctggcgcgcc 137520
accaggaccc cggtgcccta gatgcatacc tggccgcgct tcgatgctc agaggcaaac 137580 cccctcccct tgggaggcgg agtcggacaa ggctccgtct cgttccgttc cgtcacgtcc 137640
```

```
ggtgggcgg   ggcttcgggg   cttcccctt   tgagggagt   atcggttaac   ccttgcgcgg   137700
cggggcgggc   tggagctccg   cgggccggaa   cccgggagtc   ggggctcccc   agccacaccc   137760
ctcgcgggat   ttaaagggat   aggaggggcc   gggtcggccg   aagcccgaac   cgaaggagcg   137820
ggcatgaggc   gctgcccgtg   ccgtgggagc   ctgaacgagg   cggaggccgg   ggcgctgccc   137880
gcggcggccc   gcatgggact   ggaggcgccg   cgaggagggc   ggcggcggca   gccgggacag   137940
cagcgacctg   ggcccggcgc   aggggccccg   gcggggcggc   cggaggggg   gggcccctgg   138000
gcccggacag   aggggtccag   cctccacagc   gagcctgaga   gggccggcct   cgggcctgcg   138060
ccggggacag   agagtccgca   ggcagaattc   tggacagacg   gacagactga   gcccgcggca   138120
gctggccttg   gagtagagac   cgagaggccc   aagcaaaaga   cggagccaga   caggtccagc   138180
ctccggacgc   atctagaatg   gagctggtca   gagctggaga   cgacttgtct   ttggacgag   138240
accgggacag   atggcctttg   gactgatccg   cacaggtccg   acctccagtt   tcagcccgag   138300
gaggccagcc   cctggacaca   gccagggtt   catgggccct   ggacagagct   ggaaacgcat   138360
gggtcacaga   ctcagccaga   gagggtcaag   tcctgggctg   ataacctctg   gacccaccag   138420
aacagttcca   gcctccagac   tcacccgaaa   ggagcctgtc   cctcaaaaga   gccaagtgct   138480
gatggctcct   ggaaagaatt   gtatactgat   ggctccagga   cacaacagga   tattgaaggt   138540
ccctggacag   agccatatac   tgatggctcc   cagaaaaaac   aggatactga   agcagccagg   138600
aaacagcctg   gcactggtgg   ttccaaata   caacaggata   ctgatggctc   ctggacacaa   138660
cctagcactg   acggttccca   gacagcacct   gggacagact   gcctcttggg   agagcctgag   138720
gatggcccat   tagaggaacc   agagcctgga   gaattgctga   ctcacctgta   ctctcacctg   138780
aagtgtagcc   ccctgtgccc   tgtgcccgc   ctcatcatta   ccctgagac   ccctgagcct   138840
gaggcccagc   cagtgggacc   cccctccgg   gttgagggg   gcagcggcgg   cttctcctct   138900
gcctcttctt   tcgacgagtc   tgaggatgac   gtggtggccg   ggggcggagg   tgccagcgat   138960
cccgaggaca   ggtctggggt   gagtgggacc   catcctgccc   ttgagccaca   tcacgcaaaa   139020
ctccttattc   ctccgccttt   gcttaggaag   ttctctaccc   atttactgtt   agttgcccac   139080
cagcaatttc   atctccggga   acctcttcca   tccactgacc   tcctccctct   gacagccagg   139140
ttactaattc   actccaggca   ccccttctta   attctctcct   ttccccttcc   tgcactgtct   139200
ccactcctgg   gggtctacaa   tggagggcca   ctgaccgact   ttatgggggcc   caggaacccc   139260
tgaaattgta   ggactaagga   gcctgccgtg   cgtgttcaca   tacattgttg   cagcgacggt   139320
ctgacatctg   tctaatcctc   tggaatctga   agaaacactgg   gataggggaga   caggcagggt   139380
gcactttcta   ccccacattt   cttaatctgg   ggcctgtggc   tgtcttaaag   ggtcacaaac   139440
cttcaccacc   ccttagccta   tttgtatgta   cattttcta   gggagcaaag   cgattccccc   139500
agcttgcatc   agattcgcaa   aagggctgtg   tgaccccaaa   cgccaaagga   tccttggcct   139560
agccgggagc   ccacctggtc   tcccctgtga   ccctacatc   cccaaggagc   ccctgaaca   139620
ctcttgttta   ctttgtccac   cgtcacccc   agcttgggtg   tggctctccc   ctggtgaatc   139680
aggaggaccg   gccgggcagg   ttcagggagg   gcgggacaga   gcagaggccg   gtgtgaaact   139740
ggagagcctc   acgtggggct   gggagccgtg   gggctgggag   ccgagtccgg   agtccatcag   139800
cttgccagct   tgcctgctga   ggcctctttt   tgctctgggg   ccctggctg   gagtctgccc   139860
tgagccccgc   ttcaccccac   atgccttcct   tggggacgtg   ttcacacatg   tggccctagc   139920
tgtgagagac   agacctgcct   tgacgtgcct   gtgcctgtgt   gcaggggctg   accctcctgg   139980
```

```
gccccattgc ttttttctct ctgcctgccc tctcacttcc ttggcatctc agaacagctg   140040
agctggaagt gggtgaataa taataataat aataataata ataacaacaa caattagcac   140100
tcactcatgt ttagccctgt gctaagtgct gtgcttttat taactcactc actcctcgca   140160
gcaaccctaa tgaggtagat acttttttt tttttctgag acagtctcgc tctgttgccc   140220
aggctggagt gcagtggtgc catctcggct cactgcagcc ttcacttcct gggttcaagt   140280
gattgtcctg cctcagcctc ctgagtaggt gagacaccag gtgcccgcca ccacacctgg   140340
ctcatttctg tattttgagt agagacaggg tttcatcatg ttggccaggc tgacctcaag   140400
actcctgacc tcaagtgatc cacccgcctc agcctcccga agtgctggaa ttaccagcat   140460
gagccactgc acccggctga ggtagatact attattatcc ccttttacag atgaggaaac   140520
tgaggcacag agaattcaag tcacttgtcc aaggatatca ccttgcaaga tgcagatcaa   140580
ataattctaa tccttactgt acaccagaca ctgttttaag ttttttcttc tttttttttt   140640
ttagtctttt ttgtcaattt ttttctgtca tttttatct taaaatagca tctatcttaa   140700
ttaagggctt tgtatgtgtt aactctgagt ccttatgaca gcactgagat tgtctccatt   140760
caacagatgg gggccaggct cagtggccca agcctgtaat cccagcactt tgggaggccg   140820 aggcagggg atcacctaag gtcaggagtt caagaccagc ctggccaaca tgatgaaacc   140880
ctgtctctac taaaatacaa aaattagcca ggcgtgtgat ggcgggcacc tgtaatccca   140940
gctacttggg aggctgaggc aggagaatcg cttgaatgtg ggaggcggag gttgcagtga   141000
gccgagattg caccactgca ctccagcctg ggtgacagag caagactcgg tctcaaaaaa   141060
aaaaaaacaa aaacaacaga tggggaagct gaggcataga gaggtgagag attctttgct   141120
tagggttggc cacgtcaagt cagagccagg attctaactc agttctggct gagtttcaaa   141180
cccatcgttt aaaccctcca gtgtgtagat ctgttcctaa cttgtctccc tcccaggcct   141240
ccctatctcc agttttttc tcatccttcc agaatctgcc tccatggccc agctttgtct   141300
gctcaggtgc cctctctgag agcagtcagg ggctcagtgc tgcgtttgga gcctccggtc   141360
tccaggcgcc ttcccagaat cgacttcctt ccctcctcct gaccccctct gctgtaacta   141420
ggcctgagta cacactgttc cttgaacact cttctgttgt cctgcctcca cgcattgctc   141480
aagccgttcc cactgcccag catacccgtg cttccttctc ccttaatttt gaaatcctct   141540
ctgaccgtaa aggctcagct tcctttctcc cttttcctcct tccttccttc tcaccatcct   141600 gtccttttttt taaaattgtg ttctctttct ttttctttt ttggtaggga tggggtcttg   141660
ctatcttgcc caggctggtc ttgaactcct gggctcaagt gatcctcctg cctcagcctc   141720
ccaaagtgct gggattacag gtgtgctatc ctattcttct aatgagacaa aaatcactcc   141780
ctaagcccct accatgtatt tggtcctatg ttagctttgc tggggaaaca gcagtgacca   141840
agacactcat ggagctccca ggcccatgaa agagacagac caatcagccg acagtcacag   141900
ttcagagtgg tcaggaggat gtgtgagccc agaaggaggt cactggccag acacagggta   141960
tcagagaggg cttcctggag gaagggcat ataagctgag accattgtga aaaaaatccg   142020
agaaagccca gataaaccat tggatctaac tttttttttt ttttggagg gcgtgcagtg   142080 cggagtttca ctctgttgcc taggctgaag tgcagtggcg agatctcagt tcactgcaac   142140
ctcagcctcc cgggttcaag tgattctcct gcctcggcct cccaagtagc tgggactaca   142200
agcgcacgcc accacgcccg gctaattttt ttttttagta gagagtgggt ttcactatgt   142260
tggccaggct ggttctgagc tcctgacctc aggtgatcca cccacctcag cctcccaaag   142320
tgctgggatt acaagcatga gccactgtgc ccggcccgga tctaacataa aacagagaga   142380
```

```
gaagatatta tgtttatgat taagggcca ggtgtggtgg cttatgccta taatcccagc 142440
actttgggag gctgaggtgg gaggattgcc tgagcccaga aatttgagac caccctgggc 142500
aacacagtga gacctcatct ctactaaaag gaaaaaagaa ctagctagat gtggtggtat 142560
atgcctgttt tccagctatt cgggaggcta agcaggagg attgcttgag cctgggaggc 142620
agaggttgca gtgagccaag atcacacctc tgcactccag cctgggcaac agagtgagat 142680
cctgtctcaa aaaaaaaaaa aattactatt aaaaaaatcc caactaacat tcttcagtcc 142740
aagcatcaaa gaatgtttct ggagcgtctg tcgtgtgcca ggccatgtgc tggggacata 142800
atcataacca tgacaaccc agtctctgcc atcatgagct tgtagtccag caagtgtgta 142860
ggggataagc cccaaggcac tgggatccaa ccagagctag aaccccagcg ctgtgtgggg 142920
tgatgttagg taagtggctt cacctctcag accctctgtt tcctcctttg taacaccgag 142980
acgataatct ccctgggggtt gtgtttttag aaattaagta ggttgtggca cactgagtct 143040
ttgtcattgt gtctggaatg ttccaggtac ttagtaaaca ggaaccttta ttaatcatct 143100
cttccccagg gccggcagct ggattgggga gggactagcc cttcccgaac cctgactccc 143160 tcttaaccttt cccactgtca aagagatgtc tgtgaggtag ctgggctctg aggggggcggg 143220 agagatgaac acgtccctga tcctggggta ggagagggat gagccataca gtttccttct 143280
ctggaggtga cccactcttc cagtacttgc taagggactt gacatgcttg tggggtgcag 143340
aatgtattcc tgtgtgtgta tgtgttcatg aatcagacac taaccctgtc tcaaaaagct 143400
catagtttag tcggcatgat acaacgaaaa ccctgttttc tatttgcttc tctggttttc 143460
tttctttctt tcttattttt ttgagtcagg gtctcactgg gtcacccagt ctggagtgca 143520
gtggcacaat cactgctcac tgcagcctca ccctccaggg ctcaagtgat cctcccacct 143580
tagcctcctg agtagctggg actacaggtg cacaccacca cgcctagctg attcttaatt 143640
ttttatttat ttatttattt atttttttgag atggagtctc gctttctcgc ccaggctgga 143700
gtgcagtggc acaatctcgg ctcactgcaa cctctgcctc tcaggttcac accattctcc 143760
tgcctcagcc tcccgagtag ctgggactgc aggtgcccgc caccatgccc agctaatttt 143820
ttgtattttt agtagagacg gggtttcact gtgttagcca ggatggtctc aatctcctga 143880
cctcatgatc cgcctgcctc agcctcccaa agtgctggga ttacaggcat gagccactgc 143940
gcccggccta attttaaac attttgtaga gatgggtct tgctatattg cccaggctgg 144000
cctcaatctc ctgggctcag tggtcctccc accttggttt cccagtgttg agattacagg 144060
cgtaagccat cgtacccgct gcttttgtgg tttccttttgt tctctctctc tttgtctact 144120
tctgttcatc ttttcttttt catcattact ttgtatctct ctcttttagt cttcctatat 144180
ttgtttgttt tttttttgt ttttgagaca gtcttgctct gtcgcccagg ctggagtgca 144240
gtggcgtgtt cttggctcac cgcaacctct gcctctcggg ttcaaacgac tctcatgcct 144300
cagcctcctg agtagctggg actacaggtg tgtatcacca cgcccggcta attttttgtat 144360 ttttagtaga ggtgggggttt caccatgttg gccaggctgg tctcaaactc ctgacctcag 144420
gtgatctgcc cacctcaccc tcccgaaatg ctgggattac aggtgagagc caccacaccc 144480
ggcctatttc tttatctttt agcaattcta tacctgtctc tgtattagtc agggtaggtc 144540 aggatttttct gcagtaacaa agagcccca aatcttagtg acttagaaca acaaaggatt 144600
attttgcttt atactacaca ttggtcacag gtcagtggtg ggtcaagggc tctgcttcat 144660
gctgtcttca ctcagggtcc caggctgagg gagcttccat ttcttttctt actccctccc 144720
```

```
ccactgggga acaaacgtgg cgagtcataa actggctctt aaggctccta cccgaaagtg   144780
acacttctgc tcccagttaa ttggccaaag caaggccagg tgtggtggct cacacctata   144840
atcccagcac tttggagacc aagatgggag gattgcatga ggccaggagt tcaagaccag   144900
cctgggcaac atagcaagat gccataaagt agctgggcat ggtggcacac gcctgtagtc   144960
ctgactactc aggaggctgg gatgggagca tcgcttgagt ccaggagttg gaggttgcag   145020
tgagctatga tggtgccatt gtactgcagt ctggctgacg gagtgagacc cggtctctaa   145080
aacaaaacaa aacaaacaaa aaacaacaat ccccagttca ggagggcagg gacatccctg   145140
aactaatagc tggagctatg tggtgaacag ctgtcatgac tgccacggtc tctgtcgctg   145200
tctctgtctc tctgtcatca ctatgtcatc tgcctctctg tttctgtctc tctctgtggt   145260
ccatctccat ccatcaactc ctgcctctat aattttcccc aaaaggtctg acctggttta   145320
gggacagaga tggggcttcc aatatttgac actggtccct acataatggc ttatgcctga   145380
aaccccaaca ctttgggaga ctgaggcagg tggactgctt gaggtcagga gctcaagacc   145440
agcttgggca acatggtgaa accccatctc tactaaaaat acaaaaatta gccagacatg   145500
gtggcatgca cctgtagtcc cagctactcg gagggtgagg caggaggatc acttgaacct   145560
cggaggcaga ggttgcagtg agccaagatc ataccactgc actctggact aggtgacaga   145620
gaccctgtct caattaaaaa aaaaaaaaaa agaagatttg gaactgtgta tgtgcagtgg   145680
aagatgtaag ggttgtttgt taaaccacaa caaaacctag cctgtcctta ctcataagat   145740
ccttactcat aagagaagga cagagagaca tagatacaaa gaaagtgatg acagagggga   145800
gaaatgggca aagaatttcc cctatcttgc tgagggcttt gggcgatcat gtgattgccg   145860
aactaagtgg ggctcactca ccccaacaag cctgggaaca gtgatcccag gaagcccctg   145920
gccctggaaa gactgcaggt cccctttcgt tccctctcat ggcagcacct ctagcccctg   145980
ccttccctgg ccttggccct gaccccaccc tgctctgctc cctacagagc aaaccctgga   146040
agaagctgaa gacagttctg aagtattcac cctttgtggt ctccttccga aaacactacc   146100
cttgggtcca gctttctgga catgctggta agtggggtgg tggtggacag agctgggcag   146160
agtctcctgg gccagggaaa gggatgttct ctgtagttta gttcccccac ctagtgatgg   146220
gcttggtgac agtccccacc ttatgggact gttatgggca gtgcttaggc ctgggcctgg   146280
cccttcgtat gtcagggcag agggctattc cttgttattc tggtggagag agggagcttc   146340
agacggacct gagctcaaac cctagttctg ctctgtattc atgggtgacc ttgggcaagt   146400
tactttcctt tactgggcct cagctgcccc atctgttaat gtggagataa ccttacctcc   146460
cttgcaggat taaccgaaga gttaaaatca aaatgtatat aaagattgag gccaggcacg   146520
gtggcttaca tctgtaatcc tagcactttg gcaggccaaa acaggaggat cgcttgagcc   146580
caggagttta agaccaacct aggcaatata gtgagacccc gtttcaatta aaaaaaaaaa   146640
aagattggct gggcgcagtg gctcatgcct gtaatcccag cctttggga ggccgaggtg   146700
ggtggatccc ctgaggtcag gagtttaaga ccagcctggc caatgtggtg aaatcccttc   146760
tctactaaaa ataaaaaaat tagccaggca tggtggcggg tgcctgtaat cccagctact   146820
caggaggctg aggcaggaga atcacttgaa cccgggaggt gaaggttgca gtgagccaag   146880
atcgcagcat tgcactgcag cctgagtgac aagagcgaaa cttcgtctca aaaaaaaaaa   146940
agactgaggc acaggactct tatgaatgga aatgatcact ccttgccttc tccgcgtgtt   147000
cagagcatag caggccttca gtaagtagca gctgtaacat tttgccccca ggaccttgca   147060
aatgcctgca gcacagagta gcacaatggt ggcatatagt gctcttttga aaggctaggc   147120
```

```
cataaatatc ttaggttttg tgggcctatg gtctctgtcg caactactca gctctgctgt  147180
tacagcagga aagctgccat agacactatg taaacatatg agtgtgtctg tattccaata  147240
aaactttatt tgcaaaaacc agcagcaggc tggactagaa aagtgtgccc attggcaaat  147300
ggcgacagta agagaatttg tctgccttgt ttgtctttag atctgacctg gaaataaggc  147360
aagaccccct aaaactgtgt caacacaagt ttgccatcta tatgtgttct ggttactatt  147420
gctgagttta ttaaaaaaac aaaactcagc agagcacagc ggctcatggc tgtagttcta  147480
gcactttggg aggctgaggt gggaggatca cttgagccca ggagtttgag accagcctgg  147540
gtgacatagt gagaccttgt ctctacgaaa aataaagaaa ttaactgggc atggtggcat  147600
gcacctgtgg tcccaggtac ttgggagctg agggtgggaa gatcacttga gtccaggagg  147660
tctgggatgc agtgagcctt gatcgcacca cagtactcta gcctagatga ccgagtgaga  147720
ccctgtctca aaaataaata cgccaggggc ggtggctcac gcctgtaatc ccagcacttt  147780
gggaggccaa ggcaggcgga tcacgaggtc aggagatcga gaccatcctg gctaacaaag  147840 tgaaacccg tctctactaa aaatacaaaa aattagccgg gcatggtggc gggcgcctgt  147900
aatcccagct actcgggagg ctgaggcagg agaatggcgt gaacccggga ggcggaggtt  147960
gcagtgagcc gagatagcac cactgcactc cagcctgggt gacagagcga gactctgtct  148020
caaaaataaa taaataaata aaataaatac aaaacaaaac ccaaaaccc   148080 caagacttag tgatggttaa aaaaaataac ttagtagaat aaaacaatca ttttattgac  148140
ctcagaagtt ttgggtcagc aattcagaca ggatggcagg gatggctttt cactgctcca  148200
caatatctgg gaactcagct agggacacct ggaggctaca agctgaaaac ttttggaggt  148260
tcattcactt gcatgcgtgg tgattgatgc tggctattgg ctggggtctc agatggggct  148320
gccacgtggc tttgccatgt agctccttga gcttcctcac agtatggtgg cctcagagta  148380
ctcagatttc taacaagaca gctcaggact accttgaagg taagtgtctc tgccaacaga  148440
agtcatgcag tagcacttct gccataaacc gtcccatatt taatgggaga gcaatctatt  148500
ttttatttat tcatttaatt ttgagatagg atctcagtgt tgcccaggcg ggagtgcagt  148560
ggtgcagtca tagctcattg cagccttgaa ctcctggcct taaggatcc tcctgcctca  148620 acctcccaga gtgttgggat tataggcatg agccactgca cccagcttgg gagagcaatt  148680
aagagtatac tccttgatgg gaaaattcta taagagcagg atcaggaatg ggtctgagac  148740
ccactgtgat caggagatac tgttgtagcc aactttggaa aatgtaatcc aggctggaca  148800
taatcacagc actttgggag gctgagatgg gaggatcatt tgaggccagg agttcgagac  148860
cagcctgggc atcatagcaa cactacccca acccgacatt acacattttt ttttttaga  148920 ttagctggga gtggtgggg tgcacacctg tagtcctagc tactctggtg gttgaggtgg  148980
gaggatcacc tgaatctagg agcttgaggc tgcagtgagc tatgattata ccactcaatt  149040
tcagcctggg tgacagagtg agatcctctc aaataaaaaa agaaaaagaa atataatct  149100 gaaaatacag ctggccacta gaagaaatta gaattattat aatctataca ctctgcgtgg  149160
tccaggaaat gcttgatcta taaattaact taaataggcc ctggttgtta gcaccttggg  149220
attccaggca gcagcaaaag caaatccact ctggagagtg acgctctgga cttagatctc  149280
acagaattcc cacagatgat cacatgtgta caatcaaaaa ttacaaaaca aattaggata  149340
tcctgtgctg ggaacaggac ttggtttaag caacagagaa cagaaattcg ccctttcctt  149400 accaaccct gggcaagact tttaagagtt gcggcctggg cacagtggct cacgcttgta  149460
```

```
atcccagcac tttgggaggc caaggcgggt ggatcatctg aggtcaggag ttcaagacca    149520
gcctgaccaa caaggtgaaa ccctgtctct actaaaaata caaaaattag ctgggcttgg    149580
tggtgtgcac ctgtaatccc agctacttga gaggctgaag caggagaatt gcttgaaccc    149640
gggaggcgga ggttgcagtg agccgagatc gcaccattgc actccagcct gggcaacaga    149700
gtgggactcc atctcaaaaa aataaaataa aatcttaaaa tcattaaaaa aaaagttgca    149760
gggagagaaa gcattgcagg agggtcgggc aagataatgg tggccaggat ctgatgcaaa    149820
caggcagctg cggagaggtt ctcttcctga tccagttcct gatcctctca tttattctac    149880
cacctttagg gaacttccag gcaggagagg atggtcggat tctgaaacgt ttctgtcagt    149940
gtgagcagcg cagcctggag cagctgatga agacccgct gcgacctttc gtgcctgcct    150000
actatggcat ggtgctgcag gatgccagaa ccttcaacca gatggaagac ctcctggctg    150060
actttgaggg cccctccatt atggactgca agatgggcag caggtggggc tggggcagcc    150120
ctggggcagg gatggagggc aggggtgggc cattattgaa aatattggcc tggcaggcgg    150180
cggtggctca cgcctgtaat cccagcactt tgggaggccg aggctggtgg atcacctgag    150240
gttgggagtt ccaaaccagc ctgaccaacg tggtgaagcc ctgtctctac taaaaataca    150300
aaaaattagc caggcgtggt ggtgcatgcc tgtaatccca gctactcagg aggctgaggc    150360
aggagaattg cctgaacctg ggaggtggag gttgcggtga gctgagattg agccattgca    150420
ctccagcctg gcaacaaga gtggaaccct gtctcaaaaa aaagaaaaga aaagaaaaga    150480
aaatagcgcc aagtccattt tcaaagtggt tgtaccagtg taccttccca ccaccatgta    150540
tgagtgttac agtcgtccca gattctcacc ggtgcttggt actgtctgtt ttattaactt    150600
aaaccattcc gatgggtttg gaataggatc ccttttttc ctctttgaga cagagtctta    150660
ctctatcgcc caggctggag tgcagtggca cgatctcggc tcactgcaat ctccacctcc    150720
tgggtttaag tgattctcct gtgtaaacca agtagctagg attacaagcg cccgccacca    150780
cacctggcta ttttttgtat tattagtaga gatggggttt caccatgttg gccaggctgg    150840
tctggaactc ctgacctcag atgatccacc cactacggcc tcccagaatg ctgggattat    150900
aggcgtgagc caccacgcct agtctgcaag aagtgaactc taattgcttt ctccagctgg    150960
gttcagtggc tctcacctat aatcccaaca ctctgggagg ctgtatacac acacacac      151020 agacacacac acacagacac acacatagtc ttcaactctc ccatttcatt cttttagtag    151080
tcttttgata aacatatttt tataaacaaa atagtatttg tattattact ctttttgag     151140 acagagtctc attctgttgc cccgactgaa gtgaaggagc atgattatag ctcacagtag    151200
ccttgaactc ctgggctcag gcggtccttt caccttagcc tccagagtag ctgggactat    151260
aggtatgtcc caccaggctt ggctatattt tattttttat agagacatgg tctccctgta    151320
ctgcccaggc tggtcttgaa cccctgagct caagtgatcc tccttcttct gcccctgag     151380 tagctgggac tgtaggtgca tactatcaca cctagctaat tttcaatttt ttgtagagac    151440
aggctattta ggaaaagctc tgaatccatg ctttccgtt ctcacaccac tgccacaaca     151500
atgagagcac agaagacttc tgtgaccaaa tgtttaggtt ttttaacccc acacaccaag    151560
caacggacac cagctggatg tcctccaatt caagtctaaa accatctacc tggaaatagt    151620
gtcagatccc acaggttggg gactcagtcc ccaagactgc cccccagtta cagacaccag    151680
tcataagttc aggccttcga aacttctgac tgattggctc caagttggag ttcccatgtc    151740
ctcctctttg ggttcaaata atttgctgga gtggctcaaa taactcaggg ggatacttac    151800
ttacctttac tggtttaata taaagcaggg gtccccaacc cctgggccgc agaccagtac    151860
```

-continued

```
cggtccatgg cctcttagga acggggcccc accgtaggag gccagcgagc attaccgctt 151920
gaactccacc tcctgtcaga ctagcgggca ggagattctc tggagggcga accctattgt 151980
gaactgtgcc tgcaagggat ctagattgta tgctcctatg agaatctaat tgatacttga 152040
tgacctgagg tagaagagtt tcatccagaa accatccccc tcacagtctg tgggaaaaat 152100
tatcttctac aaaaccagtc cctggttggg tactgctaca aaggatactg caaagatga 152160
agagaagtgt agggcaaggt atgggggaag gggtacggag cttccatgcc ctccctgggc 152220
gcaccacgct ccaggaacct ccacagggtc agctatctgg aagctcctga gcccaatcct 152280
tggttttttt tttttttttt tttttttga gagggagtct tgctctgtgt cccaggctgg 152340
aatgcagtgg cctgatccgc ccgccttggc ctcccaaagt gctgggatta gagatgtgag 152400
ccaccatgcc cagcctaatc cttgggtttt tatggaggct ttaagacacc agcattcctt 152460
cccccagagt atagggtggg atcctctctg gggagggtcc taagacccac agtcaggaag 152520
gtggggaaag attagagtcc tgccttgggg caggtgaaag gagggcagga ggaggtcaga 152580
gattttggtt tcttgagcca gcttctgaga tctaacacac ctaaaattat aacaaaagat 152640
tgtggctggg cgcagtggct catgcctgta atcccagcac tttgggaggc caaggcaggc 152700
agatcacttg aggccagttc aagacaagcc tgggcaacat ggtgaaactc tgactctact 152760
aaaaaaatac aaaaatgtgc caggtgtggt ggtatactct tgtaattcca gctactcagg 152820
aggctgaggt gggaggatca cttgaacccg ggaggtccta gaagttgcag tgagccaaga 152880
tcacgccact gtactccagc cttggtgaca gagcaagact ccatctcaaa aaaaaaaaaa 152940
aaaaaggct gggcgtagtg gctcacactt gtaaatggga ggcagaggca ggccgatcac 153000
gaggtcagga gttcgagacc agcctggcca acatcgtgaa accccatctc tactaaaaat 153060
acaaaaaatt atccgggtgt ggtggcgggc acctgtaatc ccagctactc aggaggctga 153120
ggcaggagaa tcgcttgaat ccgcgaggca gaggttgcag tgacccgaga tcaccaccat 153180
tccattgcac tctagctcgg gcgggcgtca aaaaaaaaa aaaaaaaaa aaaaagattg 153240
taacaagggc tatgagagtt accagccagg aaccatagag ggaaaccaat atacattgta 153300
actaacaccg ggtctcgcta tgttgccgag gctgatcttg actttctggg ctcaagtgaa 153360
cctcctgcct tggcctccca aagtgttggg gttacagatg tgaacactgc acctggccct 153420
acctttaatt tagtccagtt tgtcagtttt tttcattgtg tttaagaaat cttttcctac 153480
tccaagatca tgcaaatatt atgttttctt ctacaagctt tattgtttta gctttcatat 153540
ttagacctac attccagata gaattaatgt ttctgtgtgt gggaggtagg gatcaggttc 153600
atttttttcc atatggattg ttgacccagc actgtttatt gaaaagactt cccttttcccc 153660
actgaattgc agtgcctagt cataactgca caactctacg tgtgtgtctt tgtggactct 153720
gttgtattct gtgcattgat ttgcccattc ttgtgccaca ctgtggcttt atgtcttaat 153780
atcaggaagg gtaagccctc cagtttgttc tacataattt cctttgtcac atcctctgtg 153840
tgctcaggac ctatctggaa gaggagctag tgaaggcacg ggaacgtccc cgtccccgga 153900
aggacatgta tgagaagatg gtggctgtgg accctggggc ccctacccct gaggagcatg 153960
cccagggtgc agtcaccaag ccccgctaca tgcagtggag ggaaaccatg agctccacct 154020
ctaccctggg cttccggatc gagggcatca aggtgaggac caggaaccgc ctggcctgtc 154080
ccgggaaggc ctatagccag atcccaggca gggcttcttg gggaaagcca cgagagagtg 154140
caggagacgg cgtgggatga aaggctgggg ctggggaagc ccagcctctt tcttacctcc 154200
```

-continued

```
atacccatca gagcccaggt tctgtttatc cgtctgcctg agcatctcct gagtccatct   154260
tttcctcctc tccttctcca tggtcatgtc ctagtccagc cccatcttct cctgcctctg   154320
tctccctggg catcctggcc ctggtctccc tgcagcacaa gagctggagg gatcccttc    154380 ccccagctat ggagaaggtt tctctttttc tttcttgcat tccttttct ttgtcaaatt    154440 aaatataatt gtatgaatag gccaggcatg gtggctcatg cctgtaatcc cagcactttg   154500
ggaggccaag gcaggaggat tgcttgaggc caggagtagt tcaggactaa gctgccaac    154560 atagggagct tctgtttcta gaagaaaaaa aaattgtttg aatagctagt cacacagttc   154620
aaaagtcaaa ataatattat aaagggtaa atgtggagaa atttctctcc caactctgct    154680
gctgtccttc ccattctgtc cctctatccc tctacctgct catggggaac cactttgtca   154740
gtttcttgta tttcttcctg ttagtgccag taaatggagt tgtagatccg aaatgttcct   154800
cagtacgcat actgattggt actttgctat tttcacttaa tagtaacacc ctgcagagtt   154860
ttccacatca ttccatagaa agcttcctct ttctgttttt ttttccccca cagctatgta   154920
acactgtttt tgtgactgtg cctggtcccc tatagacaga cacctgggtt gtttccattt   154980
tttgccatta gcaggcctca agaatcact ttgtatataa gacattttgc aagtatgcag    155040
attgagctgt agatttccag aagcaggact cctgggtcaa agctt                   155085
```

<210> SEQ ID NO 8
<211> LENGTH: 85
<212> TYPE: PRT
<213> ORGANISM: Mus musculus

<400> SEQUENCE: 8

Gly Phe Leu Pro Thr Arg Arg Pro Glu Pro Arg Pro Asp Pro Gly Pro
1               5                   10                  15

Gln Pro Glu Pro Arg Pro Arg Pro Glu Pro Arg Pro Arg Pro Glu Ser
            20                  25                  30

Arg Pro Arg Pro Glu Pro Arg Pro Arg Pro Glu Pro Arg Pro Gln Pro
        35                  40                  45

Glu Ser Gln Pro Arg Pro Glu Ser Arg Pro Arg Pro Glu Ser Gln Pro
    50                  55                  60

Trp Pro Glu Phe Pro Leu Pro Ser Ile Pro Ala Trp Thr Gly Pro Glu
65                  70                  75                  80

Ile Pro Glu Ser Gly
            85

<210> SEQ ID NO 9
<211> LENGTH: 73
<212> TYPE: PRT
<213> ORGANISM: Mus musculus

<400> SEQUENCE: 9

Gly Phe Leu Pro Thr Arg Arg Pro Glu Pro Arg Pro Asp Pro Gly Pro
1               5                   10                  15

Gln Pro Glu Pro Arg Pro Arg Pro Glu Pro Arg Pro Arg Pro Glu Ser
            20                  25                  30

Arg Pro Arg Pro Glu Pro Arg Pro Arg Pro Glu Pro Arg Pro Gln Pro
        35                  40                  45

Glu Ser Gln Pro Trp Pro Glu Phe Pro Leu Pro Ser Ile Pro Ala Trp
    50                  55                  60

Thr Gly Pro Glu Ile Pro Glu Ser Gly
65                  70

<210> SEQ ID NO 10
<211> LENGTH: 47
<212> TYPE: PRT
<213> ORGANISM: Rattus norvegicus

<400> SEQUENCE: 10

Gly Phe Leu Pro Thr Arg Arg Pro Glu Pro Arg Pro Asp Pro Gly Pro
1               5                   10                  15

Gln Pro Glu Leu Arg Pro Glu Pro Gln Pro Arg Pro Glu Phe Pro Leu
            20                  25                  30

Pro Ser Ile Pro Ala Trp Thr Gly Pro Glu Ile Pro Glu Ser Gly
        35                  40                  45

<210> SEQ ID NO 11
<211> LENGTH: 37
<212> TYPE: PRT
<213> ORGANISM: Canis lupus

<400> SEQUENCE: 11

Gly Phe Leu Pro Thr His Arg Pro Glu Pro Pro Glu Pro Arg Pro
1               5                   10                  15

Gly Pro Glu Leu Pro Leu Pro Ser Ile Pro Ala Trp Ser Gly Pro Glu
            20                  25                  30

Ile Ser Glu Ser Gly
        35

<210> SEQ ID NO 12
<211> LENGTH: 37
<212> TYPE: PRT
<213> ORGANISM: Bos taurus

<400> SEQUENCE: 12

Gly Phe Leu Pro Thr His Arg Pro Glu Pro Arg Pro Glu Pro Arg Pro
1               5                   10                  15

Gly Pro Glu Leu Pro Leu Pro Ser Ile Pro Ala Trp Thr Gly Pro Gly
            20                  25                  30

Ile Pro Glu Ser Gly
        35

<210> SEQ ID NO 13
<211> LENGTH: 41
<212> TYPE: PRT
<213> ORGANISM: Homo sapiens

<400> SEQUENCE: 13

Gly Phe Leu Pro Thr His Arg Leu Glu Pro Arg Pro Glu Pro Arg Pro
1               5                   10                  15

Asp Pro Arg Pro Gly Pro Glu Leu Pro Leu Pro Ser Ile Pro Ala Trp
            20                  25                  30

Thr Gly Pro Glu Ile Pro Glu Ser Gly
        35                  40

MITIGATING TISSUE DAMAGE AND FIBROSIS VIA LATENT TRANSFORMING GROWTH FACTOR BETA BINDING PROTEIN (LTBP4)

CROSS REFERENCE TO RELATED APPLICATIONS

This application claims the priority benefit under 35 U.S.C. §119(e) of Provisional U.S. Patent Application No. 61/678,564, filed Aug. 1, 2012, the disclosure of which is incorporated herein by reference in its entirety.

STATEMENT OF GOVERNMENT INTEREST

This invention was made with government support under Grant Number HL61322, awarded by the National Institutes of Health (NIH). The government has certain rights in the invention.

FIELD

The disclosure relates to compositions and methods of mitigating tissue damage and fibrosis in a patient via latent transforming growth factor beta binding protein (LTBP4).

SEQUENCE LISTING

This application contains, as a separate part of the disclosure, a Sequence Listing in computer-readable form (filename: 46577A_SubSeqListing.txt; created: Oct. 31, 2014; 220,653 bytes—ASCII text file) which is incorporated by reference in its entirety.

BACKGROUND

The transforming growth factor (TGF) beta superfamily proteins are key regulators of fibrosis in all parenchymal organs [Kisseleva et al., *Proc Am Thorac Soc.* 5: 338-42 (2008)]. Duchenne Muscular Dystrophy (DMD) is characterized by progressive fibrosis that is accompanied by increased TGFβ signaling [Bernasconi et al., *J Clin Invest.* 96: 1137-44 (1995); Chen et al., *Neurology* 65: 826-34 (2005)]. In DMD, fibrosis not only contributes directly to muscle dysfunction but also inhibits regeneration. DMD is characterized by muscle membrane fragility that leads to progressive myofiber loss. With disease progression, DMD muscle is replaced by fibrosis. Although muscle is highly regenerative, regeneration in DMD is not sufficient to offset degeneration leading to muscle weakness. Glucocorticoid steroids are used to slow progression in DMD, but use of steroids is complicated by side effects including osteoporosis and weight gain (Bushby et al., 2010). Experimental therapies for DMD include approaches to increase dystrophin expression, modulate the inflammatory response, promote muscle growth and reduce fibrosis [Bushby et al., *Lancet* 374: 1849-56 (2009)].

In recent years, biological compounds such as antibodies have shown efficacy for treating chronic diseases. For example, antibodies directed against TNFα (infliximab) or anti-TNF receptor (etanercept) are now in wide use for rheumatoid arthritis and other related disorders. While initially developed for its anti-cancer activity, the anti-VEGF antibody is now used to treat macular degeneration (bevacizumab). Thus, long-term use with biological compounds can be effective and safe. Consistent with therapeutic approaches comprising the administration of a biological compound such as an antibody is the fact that antibodies are readily detected in the matrix of dystrophic muscle, such as the muscle of DMD patients.

A number of approaches, including but not limited to angiotensin inhibition, either through the converting enzyme or the angiotensin receptor, aldosterone inhibition, and inhibition by antibodies directed against TGFβ have been or are being tested to reduce fibrosis in DMD. [Cohn et al., *Nat. Med.* 13: 204-10 (2007); Rafael-Fortney et al., *Circulation.* 124: 582-8 (2011); Nelson et al., *Am J. Pathol.* 178: 2611-21 (2011)]. A major limitation of these approaches is that these drugs are systemically active and often have unwanted effects such as reduced blood pressure. Given the relative hypotension of DMD patients, especially advanced DMD patients, such approaches are limited.

SUMMARY

Disclosed herein are compositions and methods for treating a transforming growth factor beta superfamily protein-related disease. Compositions according to the disclosure modulate the activity and/or proteolysis of latent TGFβ binding protein 4 (LTBP4). Methods according to the disclosure comprise administration of an effective amount of a modulator of LTBP4, with that effective amount being an amount sufficient to prevent, delay onset and/or treat a disorder according to the disclosure. The compositions and methods provided by the disclosure will improve one or more symptoms associated with disorders according to the disclosure in afflicted individuals, thereby improving their quality of life while alleviating the financial, psychological and physical burdens imposed on modern healthcare systems.

Accordingly, in one aspect the disclosure provides a method of treating a patient having a transforming growth factor beta (TGFβ) superfamily protein-related disease, comprising administering an effective amount of an agent that modulates proteolysis of latent TGFβ binding protein 4 (LTBP4) to a patient in need thereof.

A related aspect of the disclosure provides methods of delaying onset or preventing a transforming growth factor beta (TGFβ) superfamily protein-related disease, comprising administering an effective amount of an agent that modulates proteolysis of latent TGFβ binding protein 4 (LTBP4) to a patient in need thereof.

In various embodiments of the foregoing methods, the patient has a disease selected from the group consisting of Duchenne Muscular Dystrophy, Limb Girdle Muscular Dystrophy, Becker Muscular Dystrophy, myopathy, cystic fibrosis, pulmonary fibrosis, cardiomyopathy, acute lung injury, acute muscle injury, acute myocardial injury, radiation-induced injury and colon cancer.

In further embodiments, the agent is selected from the group consisting of an antibody, an inhibitory nucleic acid and a peptide.

In further aspects of the disclosure, the methods disclosed herein further comprise administering an effective amount of a second agent, wherein the second agent is selected from the group consisting of a modulator of an inflammatory response, a promoter of muscle growth, a chemotherapeutic agent and a modulator of fibrosis.

Another aspect of the disclosure is drawn to a method of treating a patient having a transforming growth factor beta (TGFβ)-related disease, comprising administering to the patient an effective amount of an agent that upregulates the activity of latent TGFβ binding protein 4 (LTBP4).

A further aspect of the disclosure provides a method of delaying onset or preventing a transforming growth factor beta (TGFβ)-related disease, comprising administering to the patient an effective amount of an agent that upregulates the activity of latent TGFβ binding protein 4 (LTBP4).

In some embodiments of the methods, LTBP4 interacts with a TGFβ superfamily protein, and in still further embodiments the TGFβ superfamily protein is selected from the group consisting of TGFβ, a growth and differentiation factor (GDF), activin, inhibin, and a bone morphogenetic protein. In specific embodiments, the GDF is myostatin.

In additional embodiments, the agent is selected from the group consisting of a peptide, an antibody and a polynucleotide capable of expressing a protein having LTBP4 activity, each as disclosed herein. In some embodiments, the polynucleotide is contained in a vector and in further embodiments the vector is a viral vector. The disclosure further contemplates embodiments wherein the viral vector is selected from the group consisting of a herpes virus vector, an adeno-associated virus (AAV) vector, an adeno virus vector, and a lentiviral vector. In one embodiment, the AAV vector is recombinant AAV9.

In some embodiments, the compositions and methods disclosed herein are for treating a transforming growth factor beta-related disease in a patient. In particular embodiments, the patient suffers from a disease selected from the group consisting of Duchenne Muscular Dystrophy (DMD), Limb Girdle Muscular Dystrophy (LGMD), Becker Muscular Dystrophy (BMD), myopathy, cystic fibrosis, pulmonary fibrosis, cardiomyopathy, acute lung injury, acute muscle injury, acute myocardial injury, radiation-induced injury and colon cancer.

An additional aspect of the disclosure is drawn to methods as disclosed above that further comprise administering a therapeutically effective amount of a second agent that is selected from the group consisting of a modulator of an inflammatory response, a promoter of muscle growth, a chemotherapeutic agent and a modulator of fibrosis.

In some embodiments, an isolated antibody is provided that specifically binds to a peptide comprising any one of the sequences set forth in SEQ ID NOs: 2-5. In further embodiments, the disclosure provides an isolated antibody that specifically binds to a peptide that is at least 70% identical to a peptide comprising any one of the sequences set forth in SEQ ID NOs: 2-5, wherein the antibody retains an ability to specifically bind to LTBP4 and to decrease the susceptibility of LTBP4 to proteolysis.

Still further embodiments of the disclosure provide a peptide comprising the sequence as set out in SEQ ID NOs: 2-5, or a peptide that is at least 70% identical to any one of the sequences as set out in SEQ ID NO: 2-5 that retains an ability to act as a substrate for a protease.

In another aspect, a pharmaceutical formulation is provided comprising an effective amount, such as a therapeutically effective amount, of an antibody and/or peptide of the disclosure, and a pharmaceutically acceptable carrier or diluent.

A further aspect of the disclosure provides a kit comprising an effective amount, such as a therapeutically effective amount, of an antibody and/or peptide of the disclosure, a pharmaceutically acceptable carrier or diluent and instructions for use.

In some embodiments, the formulation or the kit of the disclosure further comprises an effective amount, such as a therapeutically effective amount, of a second agent, wherein the second agent is selected from the group consisting of a modulator of an inflammatory response, a promoter of muscle growth, a chemotherapeutic agent and a modulator of fibrosis.

Other features and advantages of the present disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

hLTBP4/mdx mice are weaker than mdx littermates (*). Grip strength was measured using the Treat NMD standard protocols.

Figure 8:
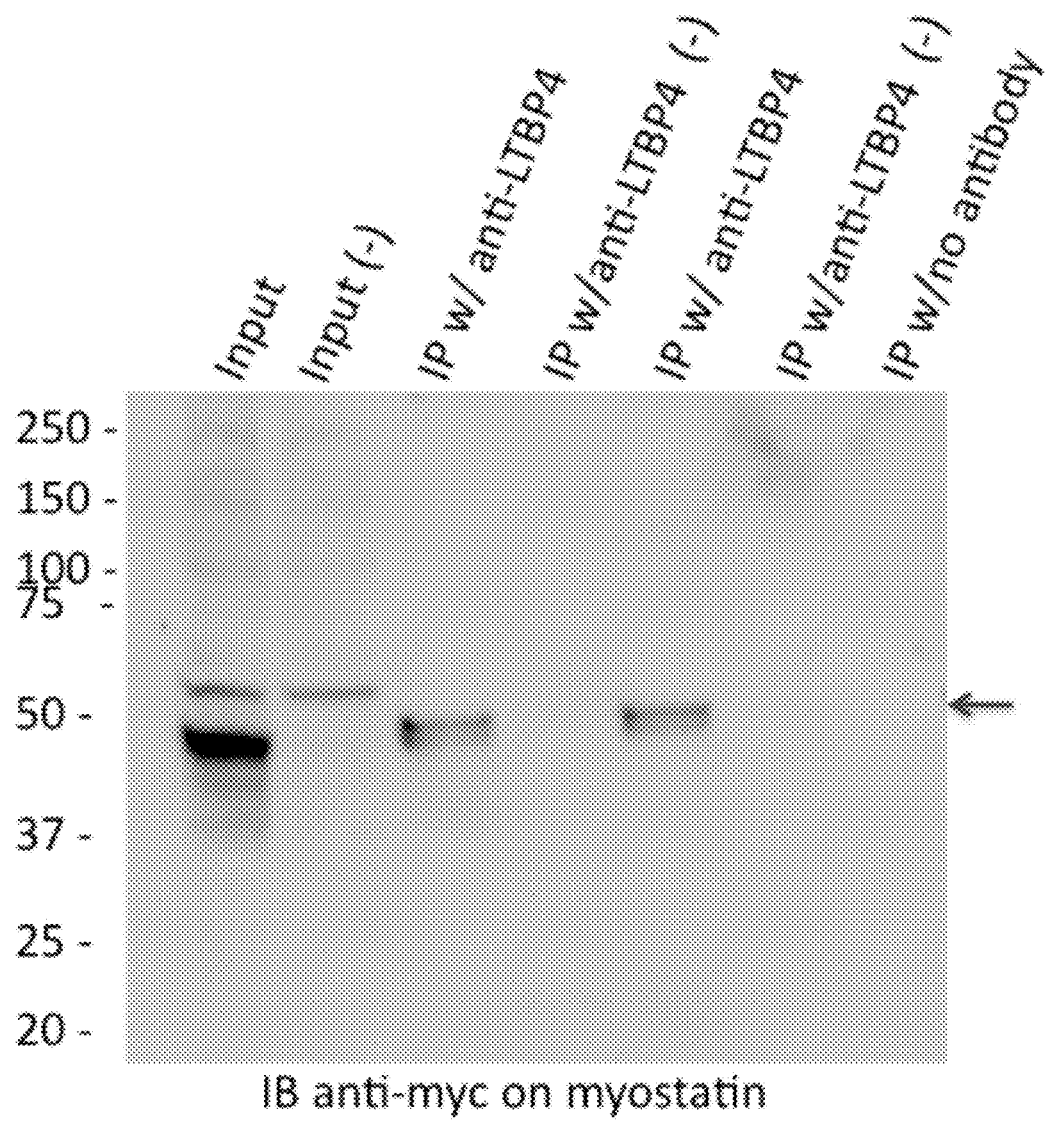

FIG. 8 shows that LTBP4 forms a complex with myostatin. HEK293 cells were transfected with LTBP4 and epitope-tagged myostatin. LTBP4 was precipitated with two different anti-LTBP4 antibodies (lanes 3 and 5), and the precipitate was then immunoblotted with anti-myc antibody. Unprocessed myostatin was detected in the immunoprecipitate (arrow). The upper band in lanes 1 and 2 that migrates above 50 KDa is endogenous c-myc, which is 63 KDa.

Figure 9:
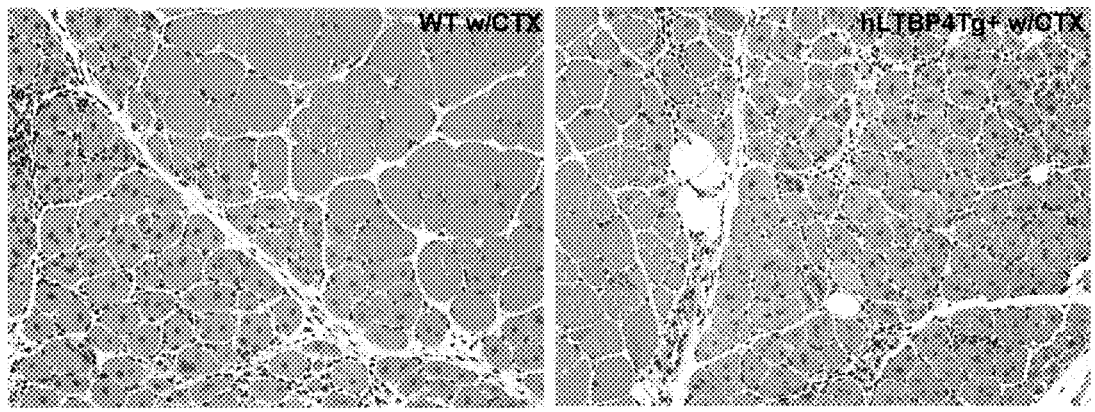
Figure 9:
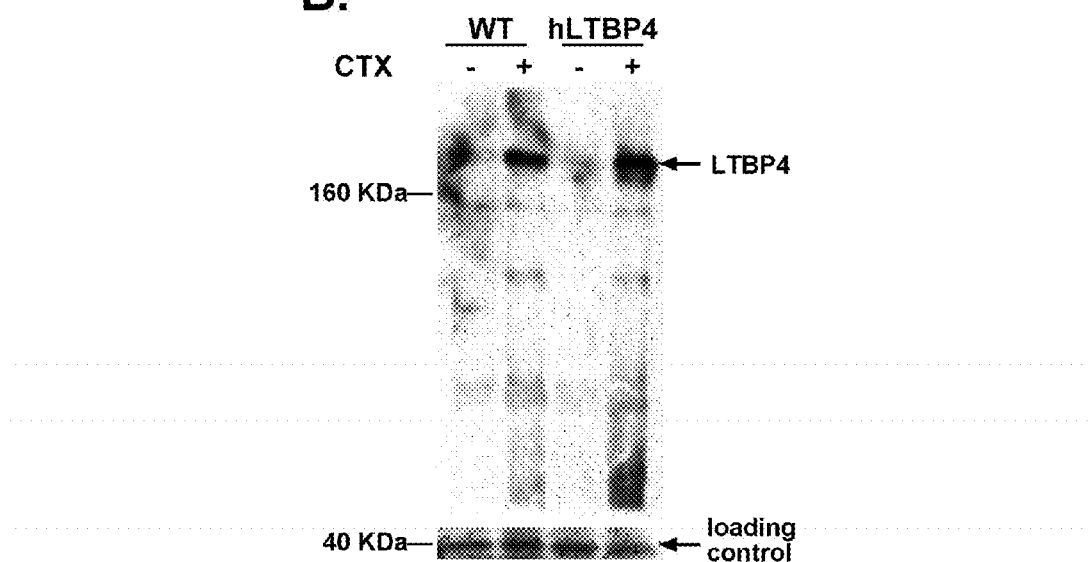

FIG. 9 depicts the results of experiments testing the effects of cardiotoxin on both wild-type mice and transgenic mice that express human LTBP4. A) transgenic mice displayed enhanced injury after cardiotoxin injury seen as greater inflammatory mononuclear cell infiltrate and fibrosis and fat deposition into the injured muscle. B) LTBP4 protein levels are increased after injury.

Figure 10:
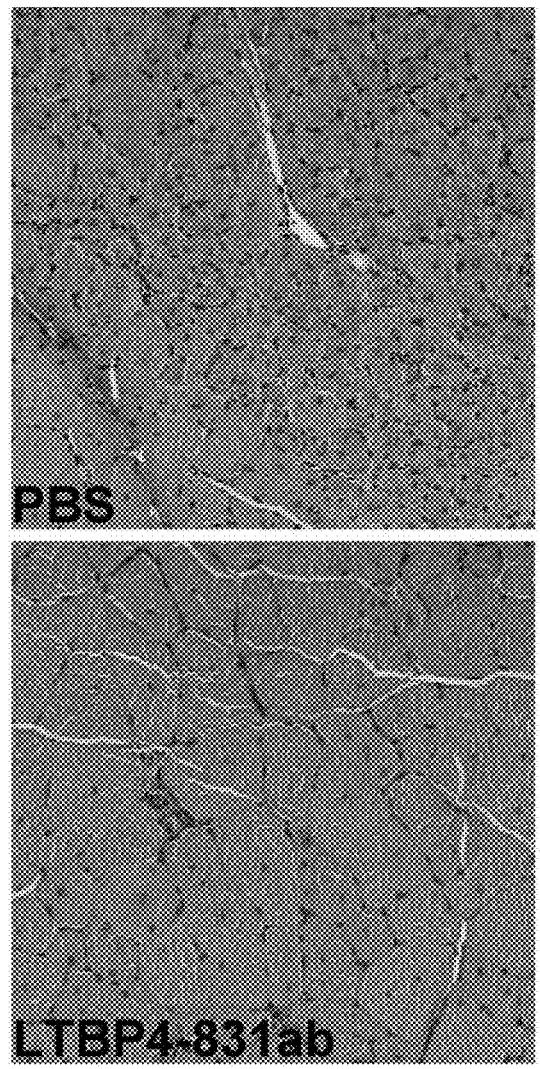
Figure 10:
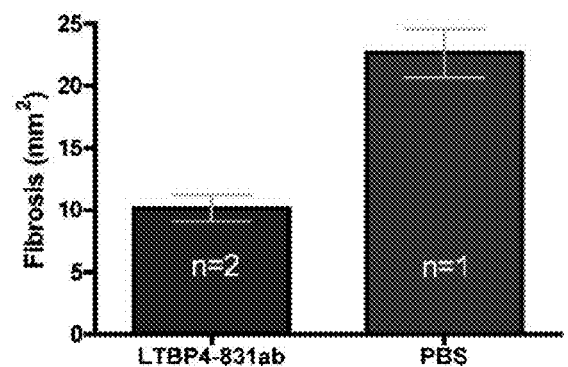

FIG. 10 shows that anti-LTBP4 antibodies mitigate muscle injury in vivo. Compared to PBS-injected mice, LTBP4-831 antibody-treated mice showed reduced central nucleation (panel A) and reduced fibrosis (panel B) following cardiotoxin injection.

Figure 11:
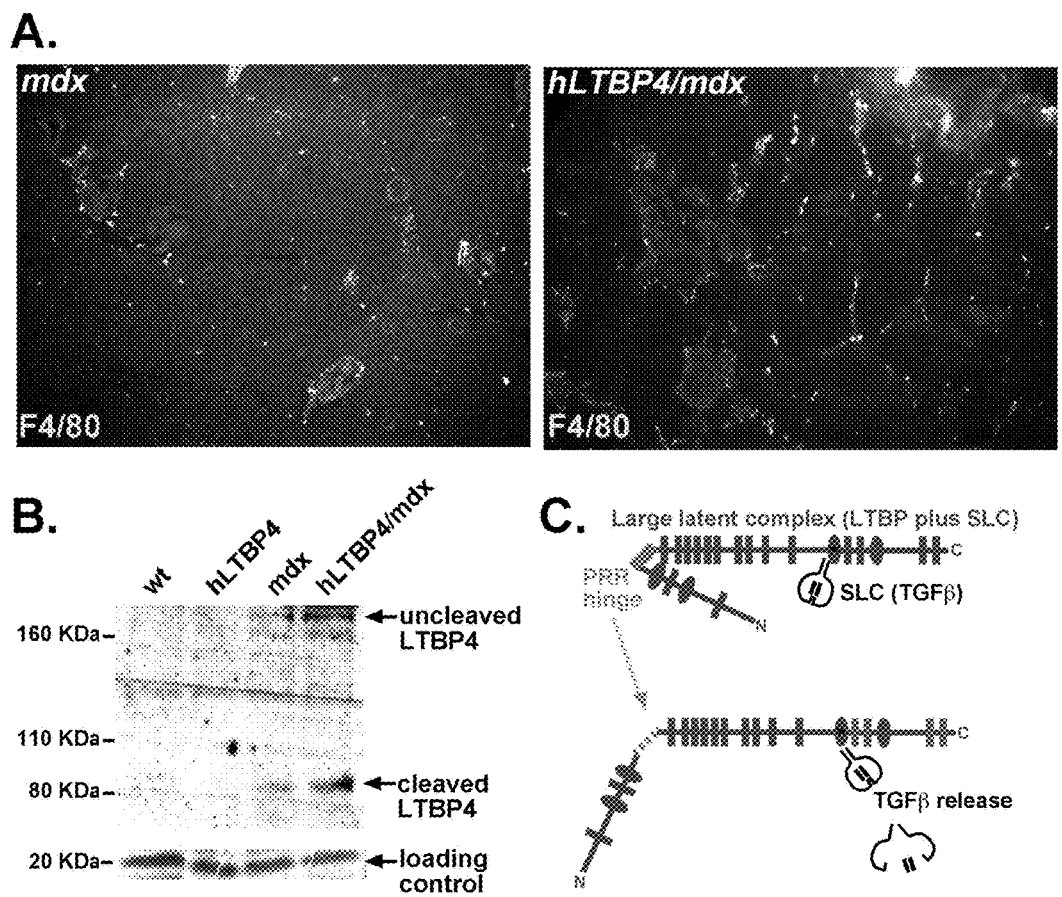

FIG. 11 shows that increased TGFβ signaling is associated with increased macrophage infiltration in hLTBP4/mdx muscle compared to mdx muscle. A) Muscles were stained with antibodies to activated macrophages using the F4/80 antibody. B) hLTBP4/mdx muscle shows an increase in cleaved LTBP4 protein compared to mdx, while little LTBP4 protein is seen in wild type and hLTBP4 muscle in the absence of injury or muscular dystrophy. C) Proteolytic cleavage and a conformational change in LTBP4 is associated with TGFβ release.

DETAILED DESCRIPTION

The transforming growth factor beta (TGFβ) superfamily consists of more than 40 members including TGFβ, activins, inhibins, growth differentiation factors and bone morphogenetic proteins (BMPs). All members of this family share common sequence elements and structural motifs. They are multifunctional regulators of cell division, differentiation, migration, adhesion, organization and death, promoting extracellular matrix (ECM) production, tissue homeostasis and embryogenesis [Massague et al., *Genes Dev* 19: 2783-810 (2005); Javelaud et al., *Int J Biochem Cell Biol* 36: 1161-5 (2004); Moustakas et al., *Immunol Lett* 82: 85-91 (2002)]. Among these proteins, TGFβ has a crucial role in tissue homeostasis and the disruption of the TGFβ pathway has been implicated in many human diseases, including cancer, autoimmune, fibrotic, and cardiovascular diseases [Ruiz-Ortega et al., *Cardiovascular Research* 74: 196-206 (2007)].

TGFβ is synthesized as an inactive protein, named latent TGFβ, which consists of a main region and a latency associated peptide (LAP). This protein interacts with the latent TGFβ binding proteins (e.g., LTBP4) and is anchored in the extracellular matrix (ECM). TGFβ is activated following proteolysis of LTBP4, which results in release of TGFβ. Specifically, and as disclosed herein, the proline-rich region of LTBP4 is susceptible to proteolysis by a protease, and this proteolysis leads to release and activation of TGFβ.

Active TGFβ then binds its receptors and functions in autocrine and paracrine manners to exert its biological and pathological activities via Smad-dependent and independent signaling pathways [Lan, *Int J Biol Sci* 7(7): 1056-1067 (2011); Derynck et al., *Nature.* 425: 577-84 (2003)].

Thus, inhibition of the proteolysis of LTBP4 will inhibit the release of bound TGFβ, and the resulting sequestration of TGFβ will inhibit the downstream signaling effects of TGFβ, resulting in mitigation of TGFβ-related disease.

The working examples and experimental data disclosed therein demonstrate that the proline-rich region of LTBP4 is susceptible to proteolysis. These results support therapeutics and therapies directed to modulating the proteolysis of LTBP4 in a patient having a TGFβ-related disease.

The experimental results disclosed herein also demonstrate that proteolysis of LTBP4 can be inhibited by antibodies. Inhibition of LTBP4 proteolysis using pharmacological approaches is expected to provide an effective approach to the treatment of TGFβ-related diseases.

Experimental results disclosed herein additionally demonstrate that a fragment of human LTBP4 is more susceptible to proteolysis than the mouse LTBP4 sequence. Consequently, a phenomenon elucidated in the mouse is mirrored in humans, and inhibition of LTPB4 proteolysis is expected to provide an effective treatment for TGFβ-related diseases.

Unless otherwise defined herein, scientific and technical terms employed in the disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

As used in the disclosure, the term "treating" or "treatment" refers to an intervention performed with the intention of preventing the further development of or altering the pathology of a disease or infection. Accordingly, "treatment" refers to both therapeutic treatment and prophylactic or preventative measures. Of course, when "treatment" is used in conjunction with a form of the separate term "prophylaxis," it is understood that "treatment" refers to the narrower meaning of altering the pathology of a disease or condition. "Preventing" refers to a preventative measure taken with a subject not having a condition or disease. A therapeutic agent may directly decrease the pathology of a disease, or render the disease more susceptible to treatment by another therapeutic agent(s) or, for example, the host's immune system. Treatment of patients suffering from clinical, biochemical, or subjective symptoms of a disease may include alleviating one or more of such symptoms or reducing the predisposition to the disease. Improvement after treatment may be manifested as a decrease or elimination of one or more of such symptoms.

As used herein, the phrase "effective amount" is meant to refer to an amount of a therapeutic (i.e., a therapeutically effective amount), prophylactic (i.e., a prophylactically effective amount), or symptom-mitigating (i.e., a symptom-mitigating effective amount) compound (e.g., agent or second agent) sufficient to modulate proteolysis of latent TGFβ binding protein 4 (LTBP4), such as would be appropriate for an embodiment of the disclosure in eliciting the desired therapeutic, prophylactic, or symptom-mitigating effect or response, including alleviating one or more of such symptoms of disease or reducing the predisposition to the disease.

As used herein, "hybridization" means the pairing of substantially complementary strands of polymeric compounds. One mechanism of pairing involves hydrogen bonding, which may be Watson-Crick, Hoogsteen or reversed Hoogsteen hydrogen bonding, between complementary nucleotide bases (nucleotides) of the strands of polymeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo applications such as therapeutic treatment, and under conditions in which assays are performed in the case of in vitro assays.

As used herein, the phrase "stringent hybridization conditions" or "stringent conditions" refers to conditions under which a compound (e.g., agent) disclosed herein will hybridize to its target sequence, but to a minimal number of other sequences. Stringent conditions are sequence-dependent and will be different in different circumstances and in the context of this disclosure, "stringent conditions" under which polymeric compounds hybridize to a target sequence are determined by the nature and composition of the polymeric compounds and by the application(s) involved. In general, stringent hybridization conditions comprise low concentrations (<0.15M) of salts with inorganic cations such as Na$^{++}$ or K$^{++}$ (i.e., low ionic strength), temperatures higher than 20° C.-25° C. below the $T_m$ of the polymeric compound: target sequence complex, and the presence of denaturants such as formamide, dimethylformamide, dimethyl sulfoxide, or the detergent sodium dodecyl sulfate (SDS). An example of a set of high stringency hybridization conditions is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two polymeric strands. Consistent with Watson-Crick base pairing rules (A binds T or U; G binds C; where A, G, C, T and U are the conventional ribo-, or deoxyribo-, nucleotide monophosphates). "Specifically hybridizable" and "complementary" are terms which are used to indicate a sufficient degree of precise nucleotide pairing or complementarity over a sufficient number of nucleotides such that stable and specific binding occurs between the polymeric compound and a target nucleic acid. The terms thus allow for base pairing gaps, but not to the extent that it prevents stable and specific binding.

It is understood in the art that the sequence of a polymeric compound need not be 100% complementary to that of its target nucleic acid to be specifically hybridizable. Moreover, a polynucleotide may hybridize over one or more segments such that intervening or adjacent segments are not involved in the hybridization event (e.g., a loop structure, mismatch or hairpin structure). The polymeric compounds of the present disclosure comprise at least about 70%, or at least about 75%, or at least about 80%, or at least about 85%, or at least about 90%, or at least about 95%, or at least about 99% sequence complementarity to a target region, within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present disclosure. Percent complementarity of an antisense compound with a region of a target nucleic acid can be determined by use of routine sequence comparison software and algorithms, e.g., BLAST programs (basic local alignment search tools) and PowerBLAST programs known in the art [Altschul et al., *J. Mol. Biol.*, 215: 403-410 (1990); Zhang and Madden, *Genome Res.*, 7: 649-656 (1997)]. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman [*Adv. Appl. Math.*, 2: 482-489 (1981)].

As used herein, the term "($T_m$)" means melting temperature and refers to the temperature, under defined ionic strength, pH, and nucleic acid concentration, at which 50% of the polynucleotides complementary to the target sequence hybridize to the target sequence at equilibrium. Typically, stringent conditions will be those in which the salt concentration is at least about 0.01 to 1.0 M sodium ion concentration (or other salts) at pH 7.0 to 8.3 and the temperature is at least about 30° C. for short polynucleotides (e.g., 10 to 50 nucleotides). Stringent conditions may also be achieved with the addition of destabilizing agents such as formamide.

As used herein, "modulation" of an activity means either an increase (stimulation) or a decrease (inhibition) in that activity. For example, and without limitation, a modulation of proteolysis can mean either an increase in proteolysis or a decrease in proteolysis.

Latent TGFβ Binding Protein 4 (LTBP4)

The present disclosure is directed in part to Ltbp4, the gene encoding latent TGFβ binding protein (LTBP4; GenBank Accession Number NP_001036009.1; SEQ ID NO: 1), which was identified in a genetic screen as a major genetic modifier of muscular dystrophy [Heydemann et al., *J Clin Invest.* 119: 3703-12 (2009)]. This genetic screen was conducted using mice lacking the dystrophin-associated protein, γ-sarcoglycan (Sgcg null mice). The Sgcg model of limb girdle muscular dystrophy (LGMD) was selected because there was ample evidence from human LGMD of the importance of genetic modifiers affecting the severity of this disease [McNally et al., *Am J Hum Genet.* 59:1040-7 (1996)]. It was surprisingly found that modifiers identified for sarcoglycan-mediated muscular dystrophy similarly modify DMD. Disruption of the dystrophin glycoprotein complex, either in DMD or the sarcoglycan-associated LGMDs, leads to a fragile muscle membrane, enhanced myofiber breakdown, and replacement of normal muscle tissue by fibrosis. Early in pathology, fibrotic replacement is minimal, but in the advanced DMD patient, the muscle is nearly completely replaced by fibrosis.

Figure 1:
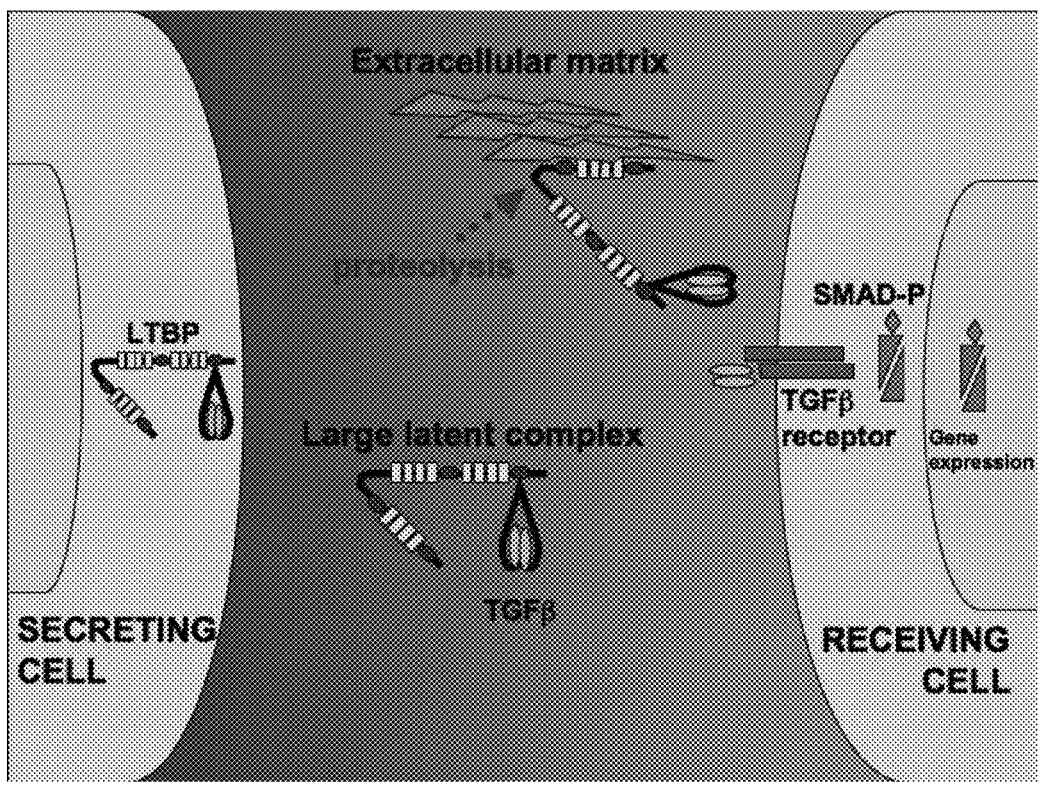
FIG. 1 depicts a model for action of LTBP4 (latent TGFβ binding protein 4). LTBP4 binds directly to TGFβ family member proteins. In the extracellular matrix, the complex of LTBP4 protein and TGFβ forms the large latent complex. With proteolysis, LTBP4 undergoes a conformational change which releases TGFβ, thereby making it available for release and binding TGFβ receptors on neighboring cells. TGFβ binding to its receptor results in TGFβ signaling in cells.
Figure 2:
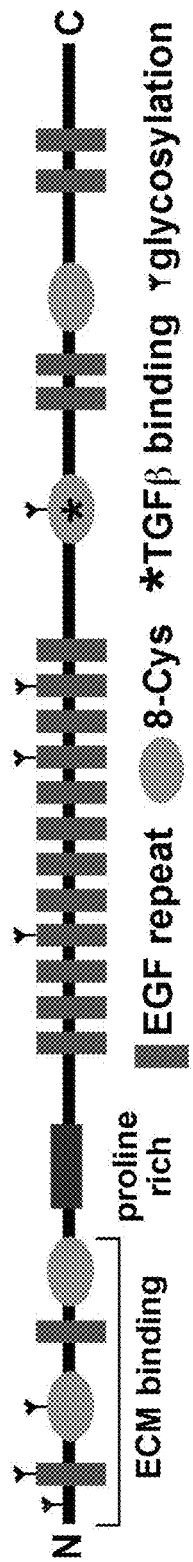
FIG. 2 depicts the gene structure of LTBP4. An insertion deletion polymorphism in Ltbp4 alters the proline-rich region in mice. The N-terminus of LTBP binds the extracellular matrix (ECM). The LTBP4 protein is composed of multiple epidermal growth factor (EGF) repeats interspersed with motifs containing 8 cysteine residues (8-Cys). The third 8-cys repeat binds TGFβ directly. The proline-rich region (labeled horizontal rectangle) separates the matrix-binding domain from the remainder of the protein. Mouse129 is protected against muscular dystrophy because of insertion of 12 amino acids in the proline-rich region. Muscular dystrophy in D2 strains of mice is more severe. Rat, dog, cow, and humans each harbor a larger deletion of the proline-rich region of LTBP4.

LTBP4 is located on human chromosome 19q13.1-q13.2, and is an extracellular matrix protein that binds and sequesters TGFβ (FIG. 1). LTBP4 modifies murine muscular dystrophy through a polymorphism in the Ltbp4 gene. There are two common variants of the Ltbp4 gene in mice. Most strains of mice, including the mdx mouse, have the Ltbp4 insertion allele (Ltbp4$^{I/I}$). Insertion of 36 base pairs (12 amino acids) into the proline-rich region of LTBP4 encoded by Ltbp4$^{I/I}$ leads to milder disease. Deletion of 36 bp/12aa in the proline-rich region is associated with more severe disease (Ltbp4$^{D/D}$) (FIG. 2). It was found that the Ltbp4 genotype correlated strongly with two different aspects of muscular dystrophy pathology, i.e., membrane leakage and fibrosis, and these features define DMD pathology.

To assess muscle membrane leakage, Evans blue dye (EBD), which can complex with serum albumin, and thus is a measure of membrane permeability, was used. EBD is injected intraperitoneally and muscles from the injected animals are harvested approximately 8-40 hours later. Muscle membrane leakage was assessed by determining the amount of EBD in multiple different muscle groups, including quadriceps and other skeletal muscles. Hydroxyproline content was measured to quantify fibrosis, and this assay was also performed on multiple different muscle groups. The Ltbp4 genotype was found to account for nearly 40% of the variance in membrane leakage in quadriceps muscle [Swaggart et al., *Physiol Genomics* 43: 24-31 (2011)]. Similarly, the Ltbp4 genotype also highly correlated with fibrosis in limb-based skeletal muscles where it also accounted for a significant amount of the variance. Ltbp4 is an unusually strong genetic modifier and acts both on membrane fragility as well as fibrosis. Accordingly, the present disclosure identifies LTBP4 as a target for therapy because it will stabilize the plasma membrane in addition to reducing fibrosis in patients in need thereof.

As discussed hereinabove, LTBP4 is a matrix-associated protein that binds and sequesters TGFβ. TGFβ in this form is the large latent complex, which requires further proteolysis to become fully active. It is expected that matrix-bound latent TGFβ is the least active form with regard to receptor engagement, and therefore represents an ideal step at which to inhibit TGFβ release. LTBP4, the fourth member of the LTBP carrier protein family, is highly expressed in heart, muscle, lung and colon [Saharinen et al., *J Biol. Chem.* 273: 18459-69 (1998)]. LTBP4 protein, like other members of this family, can be proteolyzed with plasmin, which results in TGFβ release [Saharinen et al., *J Biol. Chem.* 273: 18459-69 (1998); Ge et al., *J. Cell Biol.* 175: 111-20 (2006)]. The 12-amino-acid insertion/deletion alters the susceptibility of LTBP4 to proteolysis, which in turn alters TGFβ release and its ability to bind TGFβ receptors and activate signaling. It is disclosed herein that inhibiting LTBP4 cleavage will hold TGFβ inactive and limit the downstream effects of TGFβ release.

Agents

Methods of the disclosure contemplate treating a patient having a TGFβ-related disease comprising administering to the patient an effective amount of an agent that modulates proteolysis of LTBP4.

The term "agent" in this context refers to an antibody, an inhibitory nucleic acid, a peptide, and combinations thereof.

Antibodies

The term "antibody" is used in the broadest sense and includes fully assembled antibodies, monoclonal antibodies, polyclonal antibodies, multispecific antibodies (e.g., bispecific antibodies), antibody fragments that can bind antigen (e.g., Fab', F(ab)$_2$, Fv, single chain antibodies, diabodies), camel bodies and recombinant peptides comprising the foregoing provided they exhibit the desired biological activity. Antibody fragments may be produced using recombinant DNA techniques or by enzymatic or chemical cleavage of intact antibodies and are described further below. Non-limiting examples of monoclonal antibodies include murine, chimeric, humanized, human, and human-engineered immunoglobulins, antibodies, chimeric fusion proteins having sequences derived from immunoglobulins, or muteins or derivatives thereof, each described further below. Multimers or aggregates of intact molecules and/or fragments, including chemically derivatized antibodies, are contemplated. Antibodies of any isotype class or subclass are contemplated.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. In contrast to conventional (polyclonal) antibody preparations that typically include different antibodies directed against different determinants (epitopes), each monoclonal antibody is directed against a single determinant on the antigen. In addition to their specificity, monoclonal antibodies are advantageous in that they are synthesized in a homogeneous culture, uncontaminated by other immunoglobulins with different specificities and characteristics.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the disclosure may be made by the hybridoma method first described by Kohler et al., *Nature* 256: 495 (1975), or may be made by recombinant DNA methods (see, e.g., U.S. Pat. No. 4,816,567, incorporated herein by reference). The "monoclonal antibodies" may also be recombinant, chimeric, humanized, human, Human Engineered™, or antibody fragments, for example.

Antibodies described herein are discussed in Example 3. In certain embodiments, a variant of an antibody of the disclosure is contemplated. By "variant" is meant an antibody comprising one or more amino acid substitutions, amino acid deletions, or amino acid additions to a reference amino acid sequence. Variants include, but are not limited to, antibodies having an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to any of the amino acid sequences of an antibody provided herein, provided that the antibody variant retains the ability to block and/or inhibit the proteolysis of LTBP4.

In further embodiments, an anti-LTBP4 antibody described herein specifically binds at least one peptide selected from the group consisting of peptides having a sequence set forth in SEQ ID NOs: 2-5, or a peptide selected from the group consisting of peptides having a sequence at least 70% identical to a peptide having a sequence set forth in SEQ ID NOs: 2-5. In additional embodiments, an anti-LTBP4 antibody described herein binds at least one epitope of LTBP4 with an affinity of $10^{-6}$ M, $10^{-7}$ M, $10^{-8}$ M, $10^{-9}$ M, $10^{-10}$ M, $10^{-11}$ M, or $10^{-12}$ M or less (lower meaning higher binding affinity), or optionally binds all of LTBP4 with an affinity of $10^{-6}$ M, $10^{-7}$ M, $10^{-8}$ M, $10^{-9}$ M $10^{-10}$ M, $10^{-11}$ M, or $10^{-12}$ M or less. In other embodiments, an antibody described herein "specifically binds" to LTBP4 with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% higher affinity compared to binding to a non-target protein.

Antibodies described hereinbelow are suitable for use in the methods described herein. Additional antibodies are also contemplated, provided the antibody possesses the property of modulating the proteolysis or upregulating the activity of LTBP4. Such antibodies may, for example, be humanized according to known techniques and modified and/or formulated to allow delivery and intracellular contact with LTBP4.

Peptides

The disclosure provides peptides that have the ability to act as a substrate for a protease (i.e., "a protease-substrate peptide"). The protease, as discussed herein, means a protease that can cleave LTBP4. In one embodiment, the protease is a serine protease. In further embodiments, the protease is selected from the group consisting of plasmin, leukocyte elastase, pancreatic elastase, human mast cell chymase, trypsin, chymotrypsin, pepsin and papain.

The ability of a peptide to act as a substrate for a protease can be readily determined by one of ordinary skill in the art. By way of non-limiting example, a peptide can be tested in vitro by incubating a labeled LTBP4 protein (or a labeled fragment thereof) with a candidate peptide and a serine protease. The label can be any detectable label known in the art, and in one embodiment is a radioactive label. Following incubation and subsequent gel electrophoresis, it can be determined whether the LTBP4 protein (or fragment thereof) was refractory to proteolysis based on the size of the protein on the gel. If the LTBP4 protein was not protected from proteolysis by the peptide, the radioactive band on the gel will be smaller than one would expect for a full-length LTBP4 protein. Thus, while peptide sequences disclosed herein are contemplated for use according to the methods of the disclosure, additional peptides are also contemplated, with the proviso being their ability to act as a substrate for a protease in a manner that renders them an inhibitor of LTBP4 proteolysis.

Use of one or more peptides or antibodies of the disclosure, each of which has an ability to act either as a substrate for a protease (peptide) or to act as an inhibitor of proteolysis (antibody), is expected to upregulate the activity of LTBP4 compared to the activity of LTBP4 in the absence of the one or more peptides. In this context, upregulation of LTBP4 activity results from its protection from proteolysis via the action of the one or more peptides and/or antibodies of the disclosure. The downstream effect of this upregulation of LTBP4 activity is the concomitant downregulation of TGFβ signaling. Intact LTBP4 will continue to bind and sequester TGFβ and thus prevent its release and subsequent downstream effects. Thus, in various embodiments, the upregulation of LTBP4 activity is measured by quantitating TGFβ signaling. Methods of quantitating TGFβ signaling are known to those of skill in the art, and include determination of Smad signaling from a biological sample obtained from a patient. It is contemplated that, in some embodiments, Smad signaling in a patient being administered one or more agent(s) and/or additional agent(s) of the disclosure is reduced by at least about 1% and up to about 5%, about 10%, about 20%, about 30%, about 40% or about 50% relative to a patient not so treated. In further embodiments, Smad signaling in a patient being administered one or more agent(s) and/or additional agent(s) of the disclosure is reduced by at least about 10% and up to about 20%, about 50%, about 70%, about 80%, about 90%, about 99% or more relative to a patient not so treated. In specific embodiments, Smad signaling in a patient being administered one or more agent(s) and/or additional agent(s) of the disclosure is reduced by at least about 1%, about 2%, about 5%, about 10%, about 20%, about 25%, about 30%, about 35%, about 40%, about 50%, about 60%, about 70%, about 80%, about 90%, about 95%, about 99% or more relative to a patient not so treated.

Peptides described above (i.e., peptide inhibitors of LTBP4 proteolysis) are set forth in Example 3 and Table 1. Thus, in certain embodiments, the peptide comprises or consists of the amino acid sequence of any one of SEQ ID NOs: 2-5 or a variant of any of the foregoing. By "variant" is meant a peptide comprising one or more amino acid substitutions, amino acid deletions, or amino acid additions to a reference amino acid sequence (e.g., any one of SEQ ID NOs: 2-5). Variants include, but are not limited to, peptides having an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to any of the amino acid sequences provided herein while retaining the ability to act as a substrate for a protease.

In one aspect, the peptide consists of 35 amino acids or less. In various embodiments, the peptide comprises 15-35 amino acid residues (e.g., 15, 16, 17, 18, 19, 20, 21, 22, 23, 24, 25, 26, 27, 28, 29, 30, 31, 32, 33, 34, or 35 amino acid residues). It is also contemplated that a peptide described herein comprising one or more deletions is suitable in the context of the disclosure so long as the peptide can act as a substrate for a protease. In some embodiments, amino acids are removed from within the amino acid sequence, at the N-terminus, and/or at the C-terminus. Such peptide fragments can comprise 3-14 amino acid residues (e.g., 3, 4, 5, 6, 7, 8, 9, 10, 11, 12, 13, or 14 amino acid residues).

Optionally, the peptide comprises one or more amino acid substitutions (with reference to any of the amino acid sequences provided herein) that do not destroy the ability of the peptide to act as a substrate for a protease. Amino acid substitutions include, but are not limited to, those which: (1) reduce susceptibility to proteolysis, (2) reduce susceptibility to oxidation, (3) alter binding affinities, and/or (4) confer or modify other physiochemical or functional properties on a peptide. In one aspect, the substitution is a conservative substitution, wherein an amino acid residue is replaced with an amino acid residue having a similar side chain. Families of amino acid residues having similar side chains have been defined within the art, and include amino acids with basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), beta-branched side chains (e.g., threonine, valine, and isoleucine) and side chains with aromatic character (e.g., tyrosine, phenylalanine, tryptophan, and histidine). It will be appreciated, however, that a practitioner is not limited to conservative substitutions, so long as the resulting peptide retains the ability to act as a substrate, in whole or in part, for a protease. The disclosure also embraces protease-substrate peptides comprising atypical, non-naturally occurring amino acids, which are well known in the art. The individual amino acids may have either L or D stereochemistry when appropriate, although the L stereochemistry is typically employed for all of the amino acids in the peptide.

The disclosure further includes protease-substrate peptide variants comprising one or more amino acids inserted within an amino acid sequence provided herein and/or attached to the N-terminus or C-terminus. In some embodiments, the peptide further comprises one or more amino acids that facilitate synthesis, handling, or use of the peptide including, but not limited to, one or two lysines at the N-terminus and/or C-terminus to increase solubility of the peptide. Suitable fusion proteins include, but are not limited to, proteins comprising a peptide linked to another polypeptide, a polypeptide fragment, or amino acids not generally recognized to be part of the protein sequence. In some embodiments, a fusion peptide comprises the entire amino acid sequences of two or more peptides or, alternatively, comprises portions (fragments) of two or more peptides. In addition to all or part of the peptides described herein, a fusion protein optionally includes all or part of any suitable peptide comprising a desired biological activity/function. Indeed, in some embodiments, a peptide is operably linked to, for instance, one or more of the following: a peptide with long circulating half-life, a marker protein, a peptide that facilitates purification of the protease-substrate peptide, a peptide sequence that promotes formation of multimeric proteins, or a fragment of any of the foregoing. In one embodiment, two or more protease-substrate peptides are fused together, linked by a multimerization domain, or attached via chemical linkage to generate a protease-substrate peptide complex. The protease-substrate peptides may be the same or different.

"Derivatives" are also contemplated by the disclosure and include protease-substrate peptides that have been chemically modified in some manner distinct from addition, deletion, or substitution of amino acids. In this regard, a peptide provided herein is chemically bonded with polymers, lipids, other organic moieties, and/or inorganic moieties. Derivatives are prepared in some situations to increase solubility, absorption, or circulating half-life. Various chemical modifications eliminate or attenuate any undesirable side effect of the agent. In this regard, the disclosure provides protease-substrate peptides covalently modified to include one or more water-soluble polymer attachments. Useful polymers known in the art include, but are not limited to, polyethylene glycol, polyoxyethylene glycol, polypropylene glycol, monomethoxy-polyethylene glycol, dextran, cellulose, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of any of the foregoing. For further discussion of water soluble polymer attachments, see U.S. Pat. Nos. 4,640,835; 4,496,689; 4,301,144; 4,670,417; 4,791,192; and 4,179,337, incorporated herein by reference. In other embodiments, a peptide derivative includes a targeting moiety specific for a particular cell type, tissue, and/or organ. Alternatively, the peptide is linked to one or more chemical moieties that facilitate purification, detection, multimerization, and/or characterization of peptide activity.

Derivatives also include peptides comprising modified or non-proteinogenic amino acids or a modified linker group [see, e.g., Grant, *Synthetic Peptides: A User's Guide*, Oxford University Press (1992)]. Modified amino acids include, for example, amino acids wherein the amino and/or carboxyl group is replaced by another group. Non-limiting examples include modified amino acids incorporating thioamides, ureas, thioureas, acylhydrazides, esters, olefines, sulfonamides, phosphoric acid amides, ketones, alcohols, boronic acid amides, benzodiazepines and other aromatic or non-aromatic heterocycles [see Estiarte et al., *Burgers Medicinal Chemistry*, 6th edition, Volume 1, Part 4, John Wiley & Sons, New York (2002)]. Modified amino acids are often connected to the peptide with at least one of the above-mentioned functional groups instead of an amide bond. Non-proteinogenic amino acids include, but are not limited, to β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (orn), hydroxyproline (Hyp), sarcosine, citrulline, cysteic acid (Coh), cyclohexylalanine, methioninesulfoxide (Meo), methioninesulfone (Moo), homoserinemethylester (Hsm), propargylglycine (Eag), 5-fluorotryptophan (5Fw), 6-fluorotryptophan (6Fw), 3',4'-dimethoxyphenyl-alanine (Ear), 3',4'-difluorophenylalanine (Dff), 4'-fluorophenyl-alanine (Pff), 1-naphthyl-alanine (1Ni), 1-methyltryptophan (1Mw), penicillamine (Pen), homoserine (HSe), α-amino isobutyric acid, t-butylglycine, t-butylalanine, phenylglycine (Phg), benzothienylalanine (Bta), L-homo-cysteine (L-Hcys), N-methyl-phenylalanine (NMF), 2-thienylalanine (Thi), 3,3-diphenylalanine (Ebw), homophenylalanine (Hfe), s-benzyl-L-cysteine (Ece) and cyclohexylalanine (Cha). These and other non-proteinogenic amino acids may exist as D- or L-isomers and D-isomers of proteinogenic amino acids may also be found in derivatives.

Examples of modified linkers include, but are not limited to, the flexible linker 4,7,10-trioxa-1,13-tridecanediamine (Ttds), glycine, 6-aminohexanoic acid, beta-alanine, and combinations of Ttds, glycine, 6-aminohexanoic acid and beta-alanine.

Protease-substrate peptides are made in a variety of ways. In some embodiments, the peptides are synthesized by solid-phase synthesis techniques including those described in Merrifield, *J. Am. Chem. Soc.* 85: 2149 (1963); Davis et al., *Biochem. Intl.* 10: 394-414 (1985); Larsen et al., *J. Am. Chem. Soc.* 115: 6247 (1993); Smith et al., *J. Peptide Protein Res.* 44:183 (1994); O'Donnell et al., *J. Am. Chem. Soc.* 118: 6070 (1996); Stewart and Young, Solid Phase Peptide Synthesis, Freeman (1969); Finn et al., The Proteins, 3rd ed., vol. 2, pp. 105-253 (1976); and Erickson et al., The Proteins, 3rd ed., vol. 2, pp. 257-527 (1976). Alternatively, the protease-substrate peptide is expressed recombinantly by introducing a nucleic acid encoding a protease-substrate peptide into host cells that are cultured to express the peptide. Such peptides are purified from the cell culture using standard protein purification techniques.

The disclosure also encompasses a nucleic acid comprising a nucleic acid sequence encoding an antibody or protease-substrate peptide. Methods of preparing DNA and/or RNA molecules are well known in the art. In one aspect, a DNA/RNA molecule encoding an antibody or protease-substrate peptide provided herein is generated using chemical synthesis techniques and/or using polymerase chain reaction (PCR). If desired, an antibody and/or protease-substrate peptide coding sequence is incorporated into an expression vector. One of ordinary skill in the art will appreciate that any of a number of expression vectors known in the art are suitable in the context of the disclosure, such as, but not limited to, plasmids, plasmid-liposome complexes, and viral vectors. Any of these expression vectors are prepared using standard recombinant DNA techniques described in, e.g., Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994). Optionally, the nucleic acid is operably linked to one or more regulatory sequences, such as a promoter, activator, enhancer, cap signal, polyadenylation signal, or other signal involved in the control of transcription or translation.

As with all binding agents and binding assays, one of skill in this art recognizes that the various moieties to which a binding agent should not detectably bind in order to be biologically (e.g., therapeutically) effective would be exhaustive and impractical to list. Therefore, when discussing a peptide, the term "specifically binds" refers to the ability of a peptide to bind (or otherwise inhibit) a protease involved in cleavage of LTBP4 with greater affinity than it binds to a non-target control protein that is not the protease. For example, the peptide may bind to the protease with an affinity that is at least, 5, 10, 15, 25, 50, 100, 250, 500, 1000, or 10,000 times greater than the affinity for a control protein. In some embodiments, the peptide binds the protease with greater affinity than it binds to an "anti-target," a protein or other naturally occurring substance in humans wherein binding of the peptide might lead to adverse effects. Several classes of peptides are potential anti-targets. Because protease-substrate peptides are expected to exert their activity in the extracellular matrix, ECM proteins are contemplated as anti-targets.

Also specifically contemplated by the disclosure are peptides that elicit an immune response to LTBP4 in methods to modulate LTBP4 that involve the host immune system. Thus, in some aspects, a composition is provided that comprises a peptide of the disclosure for use as a vaccine in an individual. Vaccines often include an adjuvant. The compositions comprising one or more peptides described herein may also contain an adjuvant, or be administered with an adjuvant. Thus, the adjuvant may be administered with the peptide compositions or as part of the peptide compositions, before the peptide compositions, or after the peptide compositions.

A variety of adjuvants are suitable for use in combination with the peptide composition to elicit an immune response to the peptide. Preferred adjuvants augment the intrinsic response to an antigen without causing conformational changes in the antigen that affect the qualitative form of the response. Adjuvants for use in the methods disclosed herein include, but are not limited to, keyhole limpet hemocyanin (KLH), forms of alum (see below) and 3 De-O-acylated monophosphoryl lipid A (MPL or 3-DMP) [see GB 2220211]. Other suitable adjuvant include QS21, which is a triterpene glycoside or saponin isolated from the bark of the *Quillaja Saponaria* Molina tree found in South America [see Kensil et al., in Vaccine Design: The Subunit and Adjuvant Approach (eds. Powell and Newman, Plenum Press, NY, 1995); U.S. Pat. No. 5,057,540] and CpG [Bioworld Today, Nov. 15, 1998]. Still other suitable adjuvants are described in the following paragraph.

One class of suitable adjuvants, noted briefly above, is aluminum salts (alum), such as aluminum hydroxide, aluminum phosphate, and aluminum sulfate. Such adjuvants can be used with or without other specific immunostimulating agents such as MPL or 3-DMP, QS21, polymeric or monomeric amino acids such as polyglutamic acid or polylysine. Another class of suitable adjuvants is oil-in-water emulsion formulations [such as squalene or peanut oil], optionally in combination with immunological stimulants, such as monophosphoryl lipid A [see Stoute et al., N. Engl. J. Med. 336, 86-91 (1997)]. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetyl-muramyl-L-alanyl-D-isoglutaminyl-L-alanine-2-(1,2-dipalmitoyl-sn-glycero-3-(hydroxyphosphoryloxy)) ethylamide (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Additional oil-in-water emulsions include (a) MF59 (WO 90/14837), containing 5% Squalene, 0.5% polyoxyethylene sorbitan monostearate 80 (TWEEN® 80), and 0.5% Span 85 (optionally containing various amounts of MTP-PE) formulated into submicron particles using a microfluidizer such as a Model 110Y microfluidizer (Microfluidics, Newton Mass.), (b) SAF, containing 10% Squalane, 0.4% polyoxyethylene sorbitan monostearate 80 (TWEEN® 80), 5% block copolymers of polyethylene oxide and polypropylene oxide (PLURONIC®) blocked polymer L121, and thr-MDP, either microfluidized into a submicron emulsion or vortexed to generate a larger particle size emulsion, and (c) the RIBI® adjuvant system (RAS), (Ribi Immunochem, Hamilton, Mont.) containing 2% squalene, 0.2% polyoxyethylene sorbitan monostearate 80 (TWEEN® 80), and one or more bacterial cell wall components from the group consisting of monophosphoryl lipid A (MPL), trehalose dimycolate (TDM), and cell wall skeleton (CWS), preferably MPL+CWS (Detox™). Another class of suitable adjuvants is saponin adjuvants, such as Stimulon™ (QS21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Any of the suitable adjuvants may include a cytokine, such as an interleukin (IL-1, IL-2, or IL-12), macrophage colony stimulating factor (M-CSF), tumor necrosis factor (TNF), or combinations of cytokines.

An adjuvant can be administered with a peptide composition of the disclosure as a single composition, or can be administered before, concurrent with or after administration of a peptide composition of the disclosure. Immunogen and adjuvant can be packaged and supplied in the same vial or can be packaged in separate vials and mixed before use. Immunogen and adjuvant are typically packaged with a label indicating the intended application, such as a therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory agencies. For example, Complete Freund's adjuvant is not suitable for human administration, while alum, MPL and QS21 are suitable. Optionally, two or more different adjuvants can be used simultaneously, such as alum with MPL, alum with QS21, MPL with QS21, and alum, QS21 and MPL together. Also, Incomplete Freund's adjuvant can be used [Chang et al., Advanced Drug Delivery Reviews 32, 173-186 (1998)], optionally in combination with any of alum, QS21, and MPL and all combinations thereof.

Inhibitory Nucleic Acids

By "inhibitory nucleic acid" is meant an RNA or DNA polynucleotide that binds to another RNA or DNA (target RNA, DNA). An inhibitory nucleic acid down-regulates expression and/or function of a particular target polynucleotide. The definition is meant to include any foreign RNA or DNA molecule which is useful from a therapeutic, diagnostic, or other viewpoint. Such molecules include, for example, antisense polynucleotides such as RNA or DNA molecules, interference RNA (RNAi), micro RNA (miRNA), siRNA, enzymatic RNA, aptamers, ribozymes and other polymeric compounds that hybridize to at least a portion of the target polynucleotide or target polypeptide. As such, these compounds may be introduced in the form of single-stranded, double-stranded, triple-stranded, or partially single-stranded molecules, and the molecules may be linear or circular polymeric compounds.

The production and use of aptamers is known to those of ordinary skill in the art. In general, aptamers are nucleic acid- or peptide-binding species capable of tightly binding to and discreetly distinguishing target ligands [Yan et al., RNA Biol. 6(3): 316-320 (2009), incorporated by reference herein in its entirety]. Aptamers, in some embodiments, may be obtained by a technique called the systematic evolution of ligands by exponential enrichment (SELEX) process [Tuerk et al., Science 249: 505-10 (1990), U.S. Pat. No. 5,270,163, and U.S. Pat. No. 5,637,459, each of which is incorporated herein by reference in its entirety]. General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). In various aspects, an aptamer is between 10-100 nucleotides in length.

As used herein, the term "target polynucleotide" encompasses DNA, RNA (comprising pre-mRNA and mRNA) transcribed from such DNA, and also cDNA derived from such RNA, coding sequences, noncoding sequences, sense polynucleotides or antisense polynucleotides. The specific hybridization of a polymeric compound with its target nucleic acid interferes with the normal function of the target nucleic acid. This modulation of function of a target nucleic acid or polynucleotide by compounds that specifically hybridize to it is generally referred to as antisense modulation or inhibition. The functions of DNA to be interfered include, for example, replication and transcription. The functions of RNA to be interfered include all vital functions such as, for example and without limitation, translocation of the RNA to the site of protein translation, translation of protein from the RNA, splicing of the RNA to yield one or more mRNA species, catalytic activity which may be engaged in or facilitated by the RNA, and/or translation to express an encoded polypeptide. The overall effect of such modulation (e.g., inhibition) with target polynucleotide function is modulation of the expression of an encoded product or activity of the polynucleotide itself.

RNA interference "RNAi" is mediated by double-stranded RNA (dsRNA) molecules that have sequence-specific homology to their target nucleic acid sequence(s) [Caplen et al., Proc. Natl. Acad. Sci. USA 98: 9742-9747 (2001)]. In certain embodiments of the present disclosure, the mediators are "small interfering" RNA duplexes (siRNAs) of 5-25 nucleotides. The siRNAs are derived from the processing of dsRNA by an RNase enzyme known as Dicer [Bernstein et al., Nature 409: 363-366 (2001)]. The siRNA duplex products are recruited into a multi-protein siRNA complex termed RISC(RNA-Induced Silencing Complex). Small interfering RNAs that can be used in accordance with the present disclosure can be synthesized and used according to procedures that are well known in the art and that will be familiar to the ordinarily skilled artisan. The siRNAs for use in the methods of the present disclosure suitably comprise between about 1 to about 50 nucleotides (nt). In non-limiting embodiments, siRNAs comprise about 5 to about 40 nt, about 5 to about 30 nt, about 10 to about 30 nt, about 15 to about 25 nt, or about 20-25 nucleotides.

Methods for inhibiting target polynucleotide expression are provided that include those wherein expression of the target polynucleotide is inhibited by at least about 5% and up to about 10%, 20%, 50% or 100%, at least about 5% and up to about 30%, 60%, 70% or 90%, or at least 10% and up to about 50%, 60%, 70%, 80%, 90% or 100%. In additional embodiments, expression of the target polynucleotide is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to target polynucleotide expression in the absence of an inhibitory nucleic acid. In other words, methods of inhibiting the expression or activity of a polynucleotide according to the disclosure result in essentially any degree of inhibition of expression of a target polynucleotide.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of specific inhibitory nucleic acid.

Exon Skipping

Inhibitory nucleic acids are also contemplated for use in exon skipping. In general, exon skipping is a method in which inhibitory nucleic acids are designed to modulate the splicing of a gene of interest, resulting in mRNA transcripts that are able to make some level of gene product with some function. The inhibitory nucleic acids are, in various embodiments, short nucleic acid sequences designed to selectively bind to specific mRNA or pre-mRNA sequences to generate small double-stranded regions of the target mRNA. By binding to these regions and forming double strands at key sites where the spliceosome or proteins of the spliceosome would normally bind, mutated (frameshifting) exons are skipped and the remainder of the pre-mRNA is edited correctly in frame, albeit shorter.

Exon skipping is generally described in Hoffman et al. [The American J. of Path. 179(1): 12-22 (2010], Lu et al. [The American Soc. of Gene and Cell Therapy 19(1): 9-15 (2010], and U.S. Pat. Nos. 8,084,601, 7,960,541 and 7,973,015, all of which are incorporated herein by reference in their entireties.

Thus, the disclosure contemplates that skipping exons that encode the proline-rich region of LTBP4 will generate a protease-resistant protein. In some embodiments, one or more of exons 11, 12 and 13 of mouse LTBP4 (corresponding to exons 11, 12 and 13 in human LTBP4) are targeted for exon skipping. It is expected that skipping of the exons that encode part or all of the proline-rich region of LTBP4 will generate a protein that is resistant to protease activity.

Compositions

Any of the agents and/or additional agents described herein (or nucleic acids encoding any of the agents and/or additional agents described herein) also is provided in a composition. In this regard, the agent and/or additional agent is formulated with a physiologically-acceptable (i.e., pharmacologically acceptable) carrier, buffer, or diluent, as described further herein. Optionally, the peptide is in the form of a physiologically acceptable salt, which is encompassed by the disclosure. "Physiologically acceptable salts" means any salts that are pharmaceutically acceptable. Some examples of appropriate salts include acetate, trifluoroacetate, hydrochloride, hydrobromide, sulfate, citrate, tartrate, glycolate, and oxalate.

TGFβ-Related Diseases

TGFβ-related diseases contemplated for treatment according to the disclosure include Duchenne Muscular Dystrophy, Limb Girdle Muscular Dystrophy, Becker Muscular Dystrophy, myopathy, cystic fibrosis, pulmonary fibrosis, cardiomyopathy, acute lung injury, acute muscle injury, acute myocardial injury, radiation-induced injury, colon cancer, idiopathic pulmonary fibrosis, idiopathic interstitial pneumonia, autoimmune lung diseases, benign prostate hypertrophy, cerebral infarction, musculoskeletal fibrosis, post-surgical adhesions, liver cirrhosis, renal fibrotic disease, fibrotic vascular disease, neurofibromatosis, Alzheimer's disease, diabetic retinopathy, skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; renal fibrosis, irritable bowel syndrome; pyresis; restenosis; cerebral malaria; stroke and ischemic injury; neural trauma; Huntington's disease; Parkinson's disease; allergies, including allergic rhinitis and allergic conjunctivitis; cachexia; Reiter's syndrome; acute synoviitis; muscle degeneration, bursitis; tendonitis; tenosynoviitis; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as multiple sclerosis, lupus and fibromyalgia; viral diseases such as Herpes Zoster, Herpes Simplex I or II, influenza virus, Severe Acute Respiratory Syndrome (SARS) and cytomegalovirus.

As used herein, "cardiomyopathy" refers to any disease or dysfunction of the myocardium (heart muscle) in which the heart is abnormally enlarged, thickened and/or stiffened. As a result, the heart muscle's ability to pump blood is usually weakened, often leading to congestive heart failure. The disease or disorder can be, for example, inflammatory, metabolic, toxic, infiltrative, fibrotic, hematological, genetic, or unknown in origin. Such cardiomyopathies may result from a lack of oxygen. Other diseases include those that result from myocardial injury which involves damage to the muscle or the myocardium in the wall of the heart as a result of disease or trauma. Myocardial injury can be attributed to many things such as, but not limited to, cardiomyopathy, myocardial infarction, or congenital heart disease. The cardiac disorder may be pediatric in origin. Cardiomyopathy includes, but is not limited to, cardiomyopathy (dilated, hypertrophic, restrictive, arrhythmogenic, genetic, idiopathic and unclassified cardiomyopathy), sporadic dilated cardiomyopathy, X-linked Dilated Cardiomyopathy (XLDC), acute and chronic heart failure, right heart failure, left heart failure, biventricular heart failure, congenital heart defects, myocardiac fibrosis, mitral valve stenosis, mitral valve insufficiency, aortic valve stenosis, aortic valve insufficiency, tricuspidal valve stenosis, tricuspidal valve insufficiency, pulmonal valve stenosis, pulmonal valve insufficiency, combined valve defects, myocarditis, acute myocarditis, chronic myocarditis, viral myocarditis, diastolic heart failure, systolic heart failure, diabetic heart failure and accumulation diseases.

TGFβ Proteins

The disclosure provides compositions and methods directed to modulating the activity, including the expression, of LTBP4, which is a protein that interacts with TGFβ proteins. Modulation of the activity of any protein that interacts with LTBP4 is contemplated by the disclosure, and in various embodiments the TGFβ protein is selected from the group consisting of a growth and differentiation factor (GDF), activin, inhibin, and a bone morphogenetic protein. TGFβ proteins are known in the art and are discussed, for example and without limitation, in Schmierer et al. (*Nature Reviews Molecular Cell Biology* 8: 970-982 (2007)], incorporated herein by reference. In addition, isoforms of TGFβ proteins are contemplated and include, without limitation, TGFβ1, TGFβ2, TGFβ3, GDF 8, and GDF 11.

Practice of methods of the disclosure wherein a patient is administered one or more agent(s) and optionally additional agent(s) is expected to result in modulation of the activity of a TGFβ protein by at least about 1% relative to a patient not so treated. In further embodiments, the activity of a TGFβ protein in a patient that is administered one or more agent(s) and/or additional agent(s) is modulated by at least about 1% and up to any one of about 2%, about 5%, about 10% or about 15% TGFβ activity relative to a patient not so treated. In still further embodiments, the activity of a TGFβ protein in a patient that is administered one or more agent(s) and optionally additional agent(s) is modulated by at least about 10% and up to any one of about 15%, about 20%, about 25% or about 30% TGFβ activity relative to a patient not so treated. In further embodiments, the activity of a TGFβ protein in a patient that is administered one or more agent(s) and/or additional agent(s) is modulated by at least about 10% and up to any one of about 40%, about 50%, about 60%, about 70%, about 80%, about 90%, about 95%, about 99% or more TGFβ activity relative to a patient not so treated. In specific embodiments, the activity of a TGFβ protein in a patient that is administered one or more agent(s) and optionally additional agent(s) is modulated by at least about 1%, about 2%, about 5%, about 10%, about 20%, about 25%, about 30%, about 35%, about 40%, about 50%, about 60%, about 70%, about 80%, about 90%, about 95%, about 99% TGFβ activity or more relative to a patient not so treated. Protein activity may be quantitated by methods generally known to those of skill in the art.

Additional (Second) Agents

In various embodiments of the disclosure it is contemplated that a second agent is administered with the agent that modulates LTBP4 activity by modulating the proteolysis of LTBP4. Nonlimiting examples of the second agent are a modulator of an inflammatory response, a promoter of muscle growth, a chemotherapeutic agent and a modulator of fibrosis. Further, the methods disclosed herein can, in various embodiments, encompass one or more of such agents, or one or more of such agents in composition with any other active agent(s).

Chemotherapeutic Agents

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, docetaxel ((2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate; TAXOTERE®), estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Modulators of Fibrosis

A "modulator of fibrosis" as used herein is synonymous with antifibrotic agent. The term "antifibrotic agent" refers to a chemical compound that has antifibrotic activity (i.e., prevents or reduces fibrosis) in mammals. This takes into account the abnormal formation of fibrous connective tissue, which is typically comprised of collagen. These compounds may have different mechanisms of action, some reducing the formation of collagen or another protein, others enhancing the catabolism or removal of collagen in the affected area of the body. All such compounds having activity in the reduction of the presence of fibrotic tissue are included herein, without regard to the particular mechanism of action by which each such drug functions. Antifibrotic agents useful in the methods and compositions of the disclosure include those described in U.S. Pat. No. 5,720,950, incorporated herein by reference. Additional antifibrotic agents contemplated by the disclosure include, but are not limited to, Type II interferon receptor agonists (e.g., interferon-gamma); pirfenidone and pirfenidone analogs; anti-angiogenic agents, such as VEGF antagonists, VEGF receptor antagonists, bFGF antagonists, bFGF receptor antagonists, TGFβ antagonists, TGFβ receptor antagonists; anti-inflammatory agents, IL-1 antagonists, such as IL-1Ra, angiotensin-converting-enzyme (ACE) inhibitors, angiotensin receptor blockers and aldosterone antagonists.

Modulators of an Inflammatory Response

A modulator of an inflammatory response includes the following agents. In one embodiment of the disclosure, the modulator of an inflammatory response is a beta2-adrenergic receptor agonist (e.g., albuterol). The term beta2-adrenergic receptor agonist is used herein to define a class of drugs which act on the β2-adrenergic receptor, thereby causing smooth muscle relaxation resulting in dilation of bronchial passages, vasodilation in muscle and liver, relaxation of uterine muscle and release of insulin. In one embodiment, the beta2-adrenergic receptor agonist for use according to the disclosure is albuterol, an immunosuppressant drug that is widely used in inhalant form for asthmatics. Albuterol is thought to slow disease progression by suppressing the infiltration of macrophages and other immune cells that contribute to inflammatory tissue loss. Albuterol also appears to have some anabolic effects and promotes the growth of muscle tissue. Albuterol may also suppress protein degradation (possibly via calpain inhibition).

In DMD, the loss of dystrophin leads to breaks in muscle cell membrane, and destabilizes neuronal nitric oxide synthase (nNOS), a protein that normally generates nitric oxide (NO). It is thought that at least part of the muscle degeneration observed in DMD patients may result from the reduced production of muscle membrane-associated neuronal nitric oxide synthase. This reduction may lead to impaired regulation of the vasoconstrictor response and eventual muscle damage.

In one embodiment, modulators of an inflammatory response suitable for use in compositions of the disclosure are Nuclear Factor Kappa-B (NF-κB) inhibitors. NF-κB is a major transcription factor modulating cellular immune, inflammatory and proliferative responses. NF-κB functions in activated macrophages to promote inflammation and muscle necrosis and in skeletal muscle fibers to limit regeneration through the inhibition of muscle progenitor cells. The activation of this factor in DMD contributes to diseases pathology. Thus, NF-kB plays an important role in the progression of muscular dystrophy and the IKK/NF-κB signaling pathway is a potential therapeutic target for the treatment of a TGFβ-related disease. Inhibitors of NF-κB (for example, IRFI 042, a vitamin E analog) enhance muscle function, decrease serum creatine kinase (CK) level and muscle necrosis and enhance muscle regeneration. Furthermore, specific inhibition of NF-κB-mediated signaling by IKK has similar benefits.

In a further embodiment, the modulator of an inflammatory response is a tumor necrosis factor alpha antagonist. TNF-α is one of the key cytokines that triggers and sustains the inflammation response. In one specific embodiment of the disclosure, the modulator of an inflammatory response is the TNF-α antagonist infliximab.

TNF-α antagonists for use according to the disclosure include, in addition to infliximab (Remicade™), a chimeric monoclonal antibody comprising murine VK and VH domains and human constant Fc domains. The drug blocks the action of TNF-α by binding to it and preventing it from signaling the receptors for TNF-α on the surface of cells. Another TNF-α antagonist for use according to the disclosure is adalimumab (Humira™) Adalimumab is a fully human monoclonal antibody. Another TNF-α antagonist for use according to the disclosure is etanercept (Enbrel™). Etanercept is a dimeric fusion protein comprising soluble human TNF receptor linked to an Fc portion of an IgG1. It is a large molecule that binds to TNF-α and thereby blocks its action. Etanercept mimics the inhibitory effects of naturally occurring soluble TNF receptors, but as a fusion protein it has a greatly extended half-life in the bloodstream and therefore a more profound and long-lasting inhibitory effect.

Another TNF-α antagonist for use according to the disclosure is pentoxifylline (Trental™), chemical name 1-(5-oxohexyl)-3,7-dimethylxanthine. The usual dosage in controlled-release tablet form is one tablet (400 mg) three times a day with meals.

Dosing: Remicade is administered by intravenous infusion, typically at 2-month intervals. The recommended dose is 3 mg/kg given as an intravenous infusion followed with additional similar doses at 2 and 6 weeks after the first infusion, then every 8 weeks thereafter. For patients who have an incomplete response, consideration may be given to adjusting the dose up to 10 mg/kg or treating as often as every 4 weeks. Humira is marketed in both preloaded 0.8 ml (40 mg) syringes and also in preloaded pen devices, both injected subcutaneously, typically by the patient at home. Etanercept can be administered at a dose of 25 mg (twice weekly) or 50 mg (once weekly).

In another embodiment of the disclosure, the modulator of an inflammatory response is cyclosporin. Cyclosporin A, the main form of the drug, is a cyclic nonribosomal peptide of 11 amino acids produced by the fungus *Tolypocladium inflatum*. Cyclosporin is thought to bind to the cytosolic protein cyclophilin (immunophilin) of immunocompetent lymphocytes (especially T-lymphocytes). This complex of cyclosporin and cyclophylin inhibits calcineurin, which under normal circumstances is responsible for activating the transcription of interleukin-2. It also inhibits lymphokine production and interleukin release and therefore leads to a reduced function of effector T-cells. It does not affect cytostatic activity. It has also an effect on mitochondria, preventing the mitochondrial PT pore from opening, thus inhibiting cytochrome c release (a potent apoptotic stimulation factor). Cyclosporin may be administered at a dose of 1-10 mg/kg/day.

A Promoter of Muscle Growth

In some embodiments of the disclosure, a therapeutically effective amount of a promoter of muscle growth is administered to a patient. Promoters of muscle growth contemplated by the disclosure include, but are not limited to, insulin-like growth factor-1 (IGF-1), Akt/protein kinase B, clenbuterol, creatine, decorin (see U.S. Patent Publication Number 20120058955), a steroid (for example and without limitation, a corticosteroid or a glucocorticoid steroid), testosterone and a myostatin antagonist.

Myostatin Antagonist

Another class of promoters of muscle growth suitable for use in the combinations of the disclosure is myostatin antagonists. Myostatin, also known as growth/differentiation factor 8 (GDF-8) is a transforming growth factor-β (TGFβ) superfamily member involved in the regulation of skeletal muscle mass. Most members of the TGF-β-GDF family are widely expressed and are pleiotropic; however, myostatin is primarily expressed in skeletal muscle tissue where it negatively controls skeletal muscle growth. Myostatin is synthesized as an inactive preproprotein which is activated by proteolyic cleavage. The precurser protein is cleaved to produce an approximately 109-amino-acid COOH-terminal protein which, in the form of a homodimer of about 25 kDa, is the mature, active form. The mature dimer appears to circulate in the blood as an inactive latent complex bound to the propeptide. As used herein the term "myostatin antagonist" defines a class of agents that inhibits or blocks at least one activity of myostatin, or alternatively, blocks or reduces the expression of myostatin or its receptor (for example, by interference with the binding of myostatin to its receptor and/or blocking signal transduction resulting from the binding of myostatin to its receptor). Such agents therefore include agents which bind to myostatin itself or to its receptor.

Myostatin antagonists for use according to the disclosure include antibodies to GDF-8; antibodies to GDF-8 receptors; soluble GDF-8 receptors and fragments thereof (e.g., the ActRIIB fusion polypeptides as described in U.S. Patent Publication Number 2004/0223966, which is incorporated herein by reference in its entirety, including soluble ActRIIB receptors in which ActRIIB is joined to the Fc portion of an immunoglobulin); GDF-8 propeptide and modified forms thereof (e.g., as described in WO 2002/068650 or U.S. Pat. No. 7,202,210, including forms in which GDF-8 propeptide is joined to the Fc portion of an immunoglobulin and/or form in which GDF-8 is mutated at an aspartate (asp) residue, e.g., asp-99 in murine GDF-8 propeptide and asp-100 in human GDF-8 propeptide); a small molecule inhibitor of GDF-8; follistatin (e.g., as described in U.S. Pat. No. 6,004,937, incorporated herein by reference) or follistatin-domain-containing proteins (e.g., GASP-1 or other proteins as described in U.S. Pat. No. 7,192,717 and U.S. Pat. No. 7,572,763, each incorporated herein by reference); and modulators of metalloprotease activity that affect GDF-8 activation, as described in U.S. Patent Publication Number 2004/0138118, incorporated herein by reference.

Additional myostatin antagonists include myostatin antibodies which bind to and inhibit or neutralize myostatin (including the myostatin proprotein and/or mature protein, in monomeric or dimeric form). Myostatin antibodies are mammalian or non-mammalian derived antibodies, for example an IgNAR antibody derived from sharks, or humanized antibodies, or comprise a functional fragment derived from antibodies. Such antibodies are described, for example, in WO 2005/094446 and WO 2006/116269, the content of which is incorporated herein by reference. Myostatin antibodies also include those antibodies that bind to the myostatin proprotein and prevent cleavage into the mature active form. Additional antibody antagonists include the antibodies described in U.S. Pat. No. 6,096,506 and U.S. Pat. No. 6,468,535 (each of which is incorporated herein by reference). In some embodiments, the GDF-8 inhibitor is a monoclonal antibody or a fragment thereof that blocks GDF-8 binding to its receptor. Further embodiments include murine monoclonal antibody JA-16 (as described in U.S. Pat. No. 7,320,789 (ATCC Deposit No. PTA-4236); humanized derivatives thereof and fully human monoclonal anti-GDF-8 antibodies (e.g., Myo29, Myo28 and Myo22, ATCC Deposit Nos. PTA-4741, PTA-4740, and PTA-4739, respectively, or derivatives thereof) as described in U.S. Pat. No. 7,261,893 and incorporated herein by reference.

In still further embodiments, myostatin antagonists include soluble receptors which bind to myostatin and inhibit at least one activity thereof. The term "soluble receptor" herein includes truncated versions or fragments of the myostatin receptor that specifically bind myostatin thereby blocking or inhibiting myostatin signal transduction. Truncated versions of the myostatin receptor, for example, include the naturally occurring soluble domains, as well as variations produced by proteolysis of the N- or C-termini. The soluble domain includes all or part of the extracellular domain of the receptor, either alone or attached to additional peptides or other moieties. Because myostatin binds activin receptors (including the activin type IEB receptor (ActRHB) and activin type HA receptor (ActRHA)), activin receptors can form the basis of soluble receptor antagonists. Soluble receptor fusion proteins can also be used, including soluble receptor Fc (see U.S. Patent Publication Number 2004/0223966 and WO 2006/012627, both of which are incorporated herein by reference in their entireties).

Other myostatin antagonists based on the myostatin receptors are ALK-5 and/or ALK-7 inhibitors (see for example WO 2006/025988 and WO 2005/084699, each incorporated herein by reference). As a TGF-β cytokine, myostatin signals through a family of single transmembrane serine/threonine kinase receptors. These receptors can be divided in two classes, the type I or activin-like kinase (ALK) receptors and type II receptors. The ALK receptors are distinguished from the Type II receptors in that the ALK receptors (a) lack the serine/threonine-rich intracellular tail, (b) possess serine/threonine kinase domains that are highly homologous among Type I receptors, and (c) share a common sequence motif called the GS domain, consisting of a region rich in glycine and serine residues. The GS domain is at the amino terminal end of the intracellular kinase domain and is believed to be critical for activation by the Type II receptor. Several studies have shown that TGF-β signaling requires both the ALK (Type I) and Type II receptors. Specifically, the Type II receptor phosphorylates the GS domain of the Type 1 receptor for TGFβ ALK5, in the presence of TGFβ. The ALK5, in turn, phosphorylates the cytoplasmic proteins smad2 and smad3 at two carboxy terminal serines. Generally, it is believed that in many species, the Type II receptors regulate cell proliferation and the Type I receptors regulate matrix production. Various ALK5 receptor inhibitors have been described (see, for example, U.S. Pat. No. 6,465,493, U.S. Pat. No. 6,906,089, U.S. Patent Publication Numbers 2003/0166633, 2004/0063745 and 2004/0039198, the disclosures of which are incorporated herein by reference). Thus, the myostatin antagonists for use according to the disclosure may comprise the myostatin binding domain of an ALK5 and/or ALK7 receptor.

Other myostatin antagonists include soluble ligand antagonists that compete with myostatin for binding to myostatin receptors. The term "soluble ligand antagonist" herein refers to soluble peptides, polypeptides or peptidomimetics capable of non-productively binding the myostatin receptor(s) (e.g., the activin type HB receptor (ActRHA)) and thereby competitively blocking myostatin-receptor signal transduction. Soluble ligand antagonists include variants of myostatin, also referred to as "myostatin analogs" that have homology to, but not the activity of, myostatin. Such analogs include truncates (such as N- or C-terminal truncations, substitutions, deletions, and other alterations in the amino acid sequence, such as variants having non-amino acid substitutions).

Additional myostatin antagonists contemplated by the disclosure include inhibitory nucleic acids as described herein. These antagonists include antisense or sense polynucleotides comprising a single-stranded polynucleotide sequence (either RNA or DNA) capable of binding to target mRNA (sense) or DNA (antisense) sequences. Thus, RNA interference (RNAi) produced by the introduction of specific small interfering RNA (siRNA), may also be used to inhibit or eliminate the activity of myostatin.

In specific embodiments, myostatin antagonists include, but are not limited to, follistatin, the myostatin prodomain, growth and differentiation factor 11 (GDF-11) prodomain, prodomain fusion proteins, antagonistic antibodies or antibody fragments that bind to myostatin, antagonistic antibodies or antibody fragments that bind to the activin type IEB receptor, soluble activin type IHB receptor, soluble activin type IEB receptor fusion proteins, soluble myostatin analogs (soluble ligands), polynucleotides, small molecules, peptidomimetics, and myostatin binding agents. Other antagonists include the peptide immunogens described in U.S. Pat. No. 6,369,201 and WO 2001/05820 (each of which is incorporated herein by reference) and myostatin multimers and immunoconjugates capable of eliciting an immune response and thereby blocking myostatin activity. Other antagonists include the protein inhibitors of myostatin described in WO 2002/085306 (incorporated herein by reference), which include the truncated Activin type II receptor, the myostatin pro-domain, and follistatin. Other myostatin inhibitors include those released into culture from cells overexpressing myostatin (see WO 2000/43781), dominant negative myostatin proteins (see WO 2001/53350) including the protein encoded by the Piedmontese allele, and mature myostatin peptides having a C-terminal truncation at a position either at or between amino acid positions 335 to 375. The small peptides described in U.S. Patent Publication Number 2004/0181033 (incorporated herein by reference) that comprise the amino acid sequence WMCPP, are also suitable for use in the compositions of the disclosure.

Vectors

An appropriate expression vector may be used to deliver exogenous nucleic acid to a recipient muscle cell in the methods of the disclosure. In order to achieve effective gene therapy, the expression vector must be designed for efficient cell uptake and gene product expression. Use of adenovirus or adeno-associated virus (AAV) based vectors for gene delivery have been described [Berkner, *Current Topics in Microbiol. and Immunol.* 158: 39-66 (1992); Stratford-Perricaudet et al., *Hum. Gene Ther.* 1: 241-256 (1990); Rosenfeld et al., *Cell* 8: 143-144 (1992); Stratford-Perricaudet et al., *J. Clin. Invest.* 90: 626-630 (1992)]. In one specific embodiment, the adeno-associated virus vector is AAV9. Specific methods for gene therapy useful in the context of the present disclosure depend largely upon the expression system employed; however, most methods involve insertion of coding sequence at an appropriate position within the expression vector, and subsequent delivery of the expression vector to the target muscle tissue for expression.

Additional delivery systems useful in the practice of the methods of the disclosure are discussed in U.S. Patent Publication Numbers 2012/0046345 and 2012/0039806, each of which is incorporated herein by reference in its entirety.

Therapeutic Endpoints

In various aspects of the disclosure, use of the agent(s) and optional additional agent(s) as described herein provide one or more benefits related to specific therapeutic endpoints relative to a patient not receiving the agent(s) and/or additional agent(s).

In embodiments wherein the TGFβ-related disease is a muscle-related disease (e.g., a muscular dystrophy or cardiomyopathy), therapeutic endpoints include, but are not limited to, length of time until a patient is non-ambulatory, ambulatory capacity as measured by, for example and without limitation, six-minute-walk distance which has been shown to correlate with human LTBP4 SNPs [see, for example, Hersh et al., Am J Respir Crit. Care Med. 173(9): 977-84 (2006)], relative health of heart as determined by, e.g., echocardiography, magnetic resonance imaging (MRI), muscle mechanics, pulmonary function and/or amount of tissue fibrosis.

With respect to the length of time until a patient is non-ambulatory, it is contemplated that, in some embodiments, a patient that is administered one or more agent(s) and, optionally, additional agent(s) remains ambulatory at least 1 day and up to any of about 5, about 10, about 30, about 60 or about 90 days longer than a patient not so treated. In further embodiments, a patient that is administered one or more agent(s) and optional additional agent(s) remains ambulatory at least about 1 month and up to any of about 2, about 4, about 6, about 8, about 10 or about 12 months longer than a patient not so treated. Still further embodiments of the disclosure contemplate that a patient that is administered one or more agent(s) and, optionally, additional agent(s) remains ambulatory at least about 1 year and up to any of about 1.5, about 2, about 3, about 4, about 5, about 6, about 7, about 8, about 9, about 10 or more years longer than a patient not so treated.

In embodiments wherein the TGFβ-related disease is a cancer, therapeutic endpoints include but are not limited to a reduction in tumor volume (i.e., the size of the tumor measured by the amount of space taken up by it expressed in traditional units of volume (e.g., cubic centimeters) or as a percentage of the tissue or organ within which it is found (e.g., the tumor volume of prostate cancer is the percentage of the prostate taken up by the tumor)) and/or a reduction in metastasis. With respect to the reduction in tumor volume and/or a reduction in metastasis, it is contemplated that in some embodiments the tumor volume or amount of metastasis is reduced in a patient that is administered one or more agent(s) and, optionally, additional agent(s) by about 1% relative to a patient not so treated. In further embodiments, the tumor volume or amount of metastasis is reduced in a patient that is administered one or more agent(s) and, optionally, additional agent(s) by at least about 1% and up to any of about 2%, about 5%, about 10% or about 15% relative to a patient not so treated. In still further embodiments, the tumor volume or amount of metastasis is reduced in a patient that is administered one or more agent(s) and, optionally, additional agent(s) by at least about 10% and up to about 15%, about 20%, about 25% or about 30% relative to a patient not so treated. In further embodiments, the tumor volume or amount of metastasis is reduced in a patient that is administered one or more agent(s) and, optionally, additional agent(s) by at least about 10% and up to any of about 40%, about 50%, about 60%, about 70%, about 80%, about 90%, about 95%, about 99% or more relative to a patient not so treated. In specific embodiments, the tumor volume or amount of metastasis is reduced in a patient that is administered one or more agent(s) and, optionally, additional agent(s) by at least about 1%, about 2%, about 5%, about 10%, about 20%, about 25%, about 30%, about 35%, about 40%, about 50%, about 60%, about 70%, about 80%, about 90%, about 95%, about 99% or more relative to a patient not so treated. Methods of measuring tumor volume as well as amount of metastasis are known in the art.

In embodiments wherein the TGFβ-related disease is a viral disease, therapeutic endpoints relate to the viral load in the patient. Methods of determining viral load are well known in the art and can be quantitated using methods such as polymerase chain reaction (PCR), reverse-transcriptase PCR (RT-PCR), probe-specific amplification or by the branched DNA (bDNA) method. In various embodiments, the viral load of a patient being administered one or more agent(s) and, optionally, additional agent(s) of the disclosure is reduced by at least about 1% and up to any of about 5%, about 10%, about 20%, about 30%, about 40% or about 50% relative to a patient not so treated. In further embodiments, the viral load of a patient being administered one or more agent(s) and, optionally, additional agent(s) of the disclosure is reduced by at least about 10% and up to any of about 20%, about 50%, about 70%, about 80%, about 90%, about 99% or more relative to a patient not so treated. In specific embodiments, the viral load of a patient being administered one or more agent(s) and/or additional agent(s) of the disclosure is reduced by at least about 1%, about 2%, about 5%, about 10%, about 20%, about 25%, about 30%, about 35%, about 40%, about 50%, about 60%, about 70%, about 80%, about 90%, about 95%, about 99% or more relative to a patient not so treated.

In general, a therapeutic endpoint achieved by practice of the methods of the disclosure is a reduction in the amount of fibrosis in a patient being administered one or more agent(s) and, optionally, additional agent(s) of the disclosure. Relative amounts of fibrosis in a patient can be quantitated by tissue biopsy and subsequent histology, e.g., by quantifying Evans blue dye uptake as a measure of myofiber or cellular damage [Heydemann et al., Neuromuscular Disorders 15(9-10): 601-9 (2005)], and/or quantitation of hydroxyproline content as described previously [Swaggart et al., *Physiol Genomics* 43: 24-31 (2011)]. In various embodiments, the amount of fibrosis in a patient being administered one or more agent(s) and, optionally, additional agent(s) of the disclosure is reduced by at least about 1% and up to any of about 5%, about 10%, about 20%, about 30%, about 40% or about 50% relative to a patient not so treated. In further embodiments, the amount of fibrosis in a patient being administered one or more agent(s) and, optionally, additional agent(s) of the disclosure is reduced by at least about 10% and up to about 20%, about 50%, about 70%, about 80%, about 90%, about 99% or more relative to a patient not so treated. In specific embodiments, the amount of fibrosis in a patient being administered one or more agent(s) and/or additional agent(s) of the disclosure is reduced by at least about 1%, about 2%, about 5%, about 10%, about 20%, about 25%, about 30%, about 35%, about 40%, about 50%, about 60%, about 70%, about 80%, about 90%, about 95%, about 99% or more relative to a patient not so treated.

The amount of fibrosis in a patient can be routinely determined by one of ordinary skill in the art. For example, and without limitation, the amount of fibrosis can be determined by taking a muscle biopsy from a patient, sectioning the muscle onto slides and assessing the amount of fibrosis as revealed by staining techniques known in the art (e.g., Hematoxylin and Eosin (H&E) staining and/or Masson's trichrome staining). Alternatively, or in addition, the amount of fibrosis can be determined in vivo by using magnetic resonance imaging (MRI).

Dosing/Administration/Kits

A particular administration regimen for a particular subject will depend, in part, upon the agent and optional additional agent used, the amount of the agent and optional additional agent administered, the route of administration, the particular ailment being treated, and the cause and extent of any side effects. The amount of agent and optional additional agent administered to a subject (e.g., a mammal, such as a human) is sufficient to effect the desired response. Dosage typically depends upon a variety of factors, including the particular agent and/or additional agent employed, the age and body weight of the subject, as well as the existence and severity of any disease or disorder in the subject. The size of the dose also will be determined by the route, timing, and frequency of administration. Accordingly, the clinician may titer the dosage and modify the route of administration to obtain optimal therapeutic effect, and conventional range-finding techniques are known to those of ordinary skill in the art. Purely by way of illustration, in some embodiments, the method comprises administering, e.g., from about 0.1 μg/kg up to about 100 mg/kg or more, depending on the factors mentioned above. In other embodiments, the dosage may range from 1 μg/kg up to about 75 mg/kg; or 5 μg/kg up to about 50 mg/kg; or 10 μg/kg up to about 20 mg/kg. In certain embodiments, the dose comprises about 0.5 mg/kg to about 20 mg/kg (e.g., about 1 mg/kg, 1.5 mg/kg, 2 mg/kg, 2.3 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 8 mg/kg, 9 mg/kg, or mg/kg) of agent and optional additional agent. In embodiments in which an agent and additional agent are administered, the above dosages are contemplated to represent the amount of each agent administered, or in further embodiments the dosage represents the total dosage administered. Given the chronic nature of many TGFβ-related disorders, it is envisioned that a subject will receive the agent and/or additional agent over a treatment course lasting weeks, months, or years, and may require one or more doses daily or weekly. Dosages are also contemplated for once daily, twice daily (BID) or three times daily (TID) dosing. A unit dose may be formulated in either capsule or tablet form. In other embodiments, the agent and optional additional agent is administered to treat an acute condition (e.g., acute muscle injury or acute myocardial injury) for a relatively short treatment period, e.g., one to 14 days.

Suitable methods of administering a physiologically-acceptable composition, such as a pharmaceutical composition comprising an agent and optional additional agent described herein, are well known in the art. Although more than one route can be used to administer an agent and/or additional agent, a particular route can provide a more immediate and more effective avenue than another route. Depending on the circumstances, a pharmaceutical composition is applied or instilled into body cavities, absorbed through the skin or mucous membranes, ingested, inhaled, and/or introduced into circulation. In some embodiments, a composition comprising an agent and/or additional agent is administered intravenously, intraarterially, or intraperitoneally to introduce an agent and optional additional agent into circulation. Non-intravenous administration also is appropriate, particularly with respect to low molecular weight therapeutics. In certain circumstances, it is desirable to deliver a pharmaceutical composition comprising the agent and/or additional agent orally, topically, sublingually, vaginally, rectally; through injection by intracerebral (intra-parenchymal), intracerebroventricular, intramuscular, intra-ocular, intraportal, intralesional, intramedullary, intrathecal, intraventricular, transdermal, subcutaneous, intranasal, urethral, or enteral means; by sustained release systems; or by implantation devices. If desired, the agent and/or additional agent is administered regionally via intraarterial or intravenous administration to a region of interest, e.g., via the femoral artery for delivery to the leg. In one embodiment, the composition is administered via implantation of a membrane, sponge, or another appropriate material within or upon which the desired agent and optional additional agent has been absorbed or encapsulated. Where an implantation device is used, the device in one aspect is implanted into any suitable tissue, and delivery of the desired agent and/or additional agent is, in various embodiments, effected via diffusion, time-release bolus, or continuous administration. In other embodiments, the agent and optional additional agent is administered directly to exposed tissue during surgical procedures or treatment of injury, or is administered via transfusion of blood products. Therapeutic delivery approaches are well known to the skilled artisan, some of which are further described, for example, in U.S. Pat. No. 5,399,363.

In some embodiments facilitating administration, the agent and optional additional agent in one embodiment is formulated into a physiologically-acceptable composition comprising a carrier (i.e., vehicle, adjuvant, buffer, or diluent). The particular carrier employed is limited only by chemico-physical considerations, such as solubility and lack of reactivity with the agent and/or additional agent, by the route of administration, and by the requirement of compatibility with the recipient organism. Physiologically acceptable carriers are well known in the art. Illustrative pharmaceutical forms suitable for injectable use include, without limitation, sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers. eds., pages 238-250 (1982), and ASHP Handbook on Injectable Drugs, Toissel, 4th ed., pages 622-630 (1986), incorporated herein by reference).

A pharmaceutical composition comprising an agent and optional additional agent as provided herein is optionally placed within containers/kits, along with packaging material that provides instructions regarding the use of such pharmaceutical compositions. Generally, such instructions include a tangible expression describing the reagent concentration, as well as, in certain embodiments, relative amounts of excipient ingredients or diluents that may be necessary to reconstitute the pharmaceutical composition.

The disclosure thus includes administering to a subject one or more agent(s), in combination with one or more additional agent(s), each being administered according to a regimen suitable for that medicament. Administration strategies include concurrent administration (i.e., substantially simultaneous administration) and non-concurrent administration (i.e., administration at different times, in any order, whether overlapping or not) of the agent and one or more additional agents(s). It will be appreciated that different components are optionally administered in the same or in separate compositions, and by the same or different routes of administration.

All publications, patents and patent applications cited in this specification are herein incorporated by reference as if each individual publication or patent application were specifically and individually indicated to be incorporated by reference. In addition, the entire document is intended to be related as a unified disclosure, and it should be understood that all combinations of features described herein are contemplated, even if the combination of features are not found together in the same sentence, or paragraph, or section of this document. For example, where protein therapy is described, embodiments involving polynucleotide therapy (using polynucleotides/vectors that encode the protein) are specifically contemplated, and the reverse also is true. With respect to elements described as one or more members of a set, it should be understood that all combinations within the set are contemplated.

EXAMPLES

Example 1

Structure-Function Relationship Between the Proline-Rich Region of LTBP4 and Proteolytic Susceptibility The data provided in this Example show that the proline-rich region of LTBP4 contributes to its proteolytic susceptibility.

LTBP4 binds to TGFβ in the extracellular matrix (ECM), where it serves as a readily available TGFβ storage site. A 36-nucleotide deletion was identified in the proline-rich domain of murine LTBP4 that associates with enhanced pathogenic features of muscular dystrophy in mice. This region in murine LTBP4 is associated with variable susceptibility to proteolysis. Sequence comparison analysis between LTBP4 from mouse and humans reveals an even larger deletion in the proline-rich region of human LTBP4. Thus, consistent with the murine deletion being associated with pathogenic features and variable proteolysis [see Heydemann et al., J Clin Invest. 119(12): 3703-12 (2009)], it was contemplated that the larger deletion of the proline-rich region of human LTBP4 was associated with enhanced susceptibility to proteolytic cleavage.

To investigate this possibility, a portion of the human LTBP4 coding region was ligated into an expression vector to express the proline-rich region. The TP fragment (amino acids 483-565 of the human LTBP4 protein (SEQ ID NO: 1)) was expressed and migrated as a 3.5 KDa protein although its predicted molecular mass is 8.9 KDa. A second fragment, TP2E fragment (amino acids 357-586 of the human LTBP4 protein (SEQ ID NO: 1)) was also expressed. Its predicted molecular mass is 24.5 KDa, yet it electrophoretically migrated as a 31 KDa protein. TP2E included the two EGF-like domains that flank the proline-rich region of LTBP4 along with the amino terminal 8-cysteine rich region immediately amino-terminal of the proline-rich region. Murine TP2E and TP each contained an additional 44 amino acids compared to the human sequences, reflecting the larger proline-rich region. The murine TP2E electrophoretically migrates as a 35 KDa protein while its calculated molecular mass is 30.58 KDa.

Susceptibility to Proteolysis In Vitro

Figure 3:
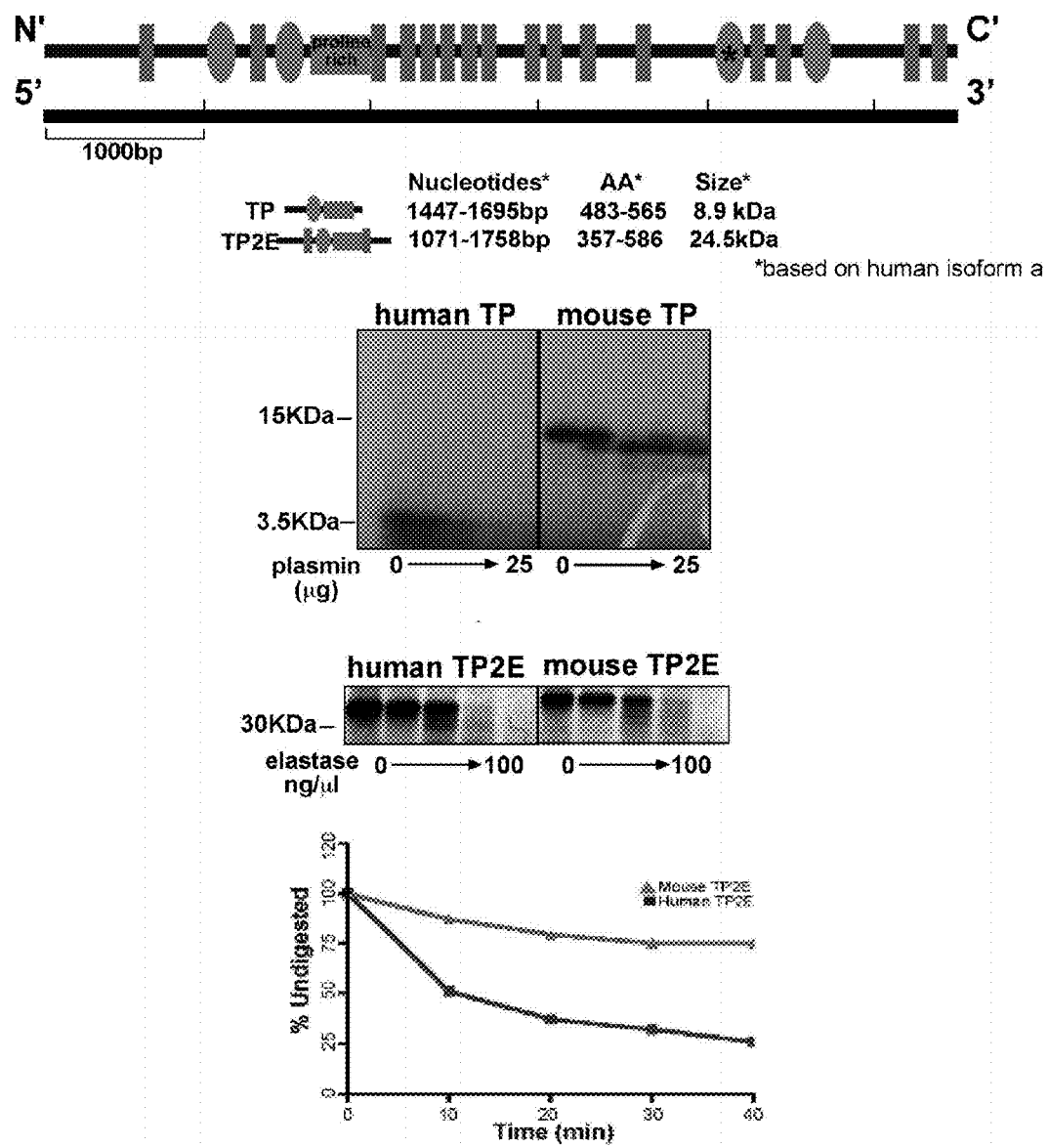
FIG. 3 depicts results of studies using fragments of human and mouse LTBP4 that were expressed and digested. Human LTBP4 is more readily cleaved than murine LTBP4. The amino acid positions indicated for TP and TP2E are based on the human isoform a LTBP4 sequence (SEQ ID NO: 1).

Human and mouse TP2E fragments were expressed in vitro using a transcription-translation coupled assay (Promega TnT® Quick Coupled in vitro Transcription/Translation System) and the expressed fragments were labeled using $^{35}$S-Cysteine. Dose-response and time course experiments were performed with elastase and plasmin, which are both serine proteases that cleave LTBP4, to determine the differential digestion of the human and mouse TP2E fragments. Data from these experiments showed that the human TP2E fragment is more readily cleaved than the mouse LTBP4 sequence (FIG. 3).

Effects of Smaller Fragments of LTBP4 on TGFβ Signaling

Figure 4:
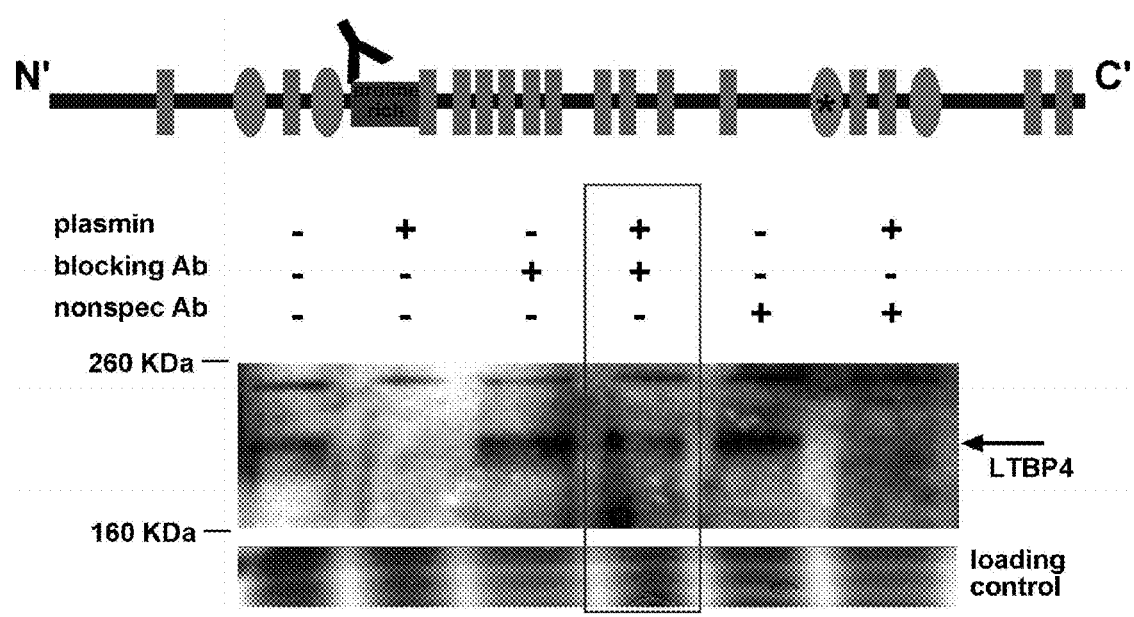
FIG. 4 depicts results of studies using a blocking antibody that was designed to recognize and bind the proline-rich region (Y) of LTBP4. When incubated with cell lysates expressing LTBP4, the presence of the antibody inhibits cleavage by plasmin. A nonspecific antibody did not inhibit cleavage.

An antibody to the proline-rich region of human LTBP4 was generated to inhibit LTBP4 cleavage. This antibody was tested and confirmed to recognize and bind to the full-length human LTBP4 by immunoblot. Conditions were then optimized for the digestion of full-length human LTBP4 by plasmin, and inhibition of proteolysis using the antibody was tested. The data in FIG. 4 show that the anti-LTBP4 antibody specifically inhibited the protein digestion compared to a nonrelated antibody raised in the same species (FIG. 4).

Example 2

Effect of Human LTBP4 Expression on Muscle and Cardiac Phenotypes

LTBP4 plays a critical role in TGFβ secretion and activation in cardiac muscle, skeletal muscle and lung. Human LTBP4 has a larger deletion in the proline-rich region compared to a mutant murine LTBP4, with wild-type murine LTBP4 used as a reference. Thus, it is contemplated that human LTBP4 is associated with increased pathogenic TGFβ signaling and, therefore, will be associated with more severe disease in mice with muscular dystrophy.

Transgenic Mice Expressing Human LTBP4

A mouse harboring the human LTBP4 gene was generated according to standard protocols [see, e.g., Heintz, Nat Rev Neurosci. 2(12):861-70 (2001)]. A bacterial artificial chromosome (BAC) that included the complete human LTBP4 gene; the BAC transgenic-positive (Tg+) mice are referred to as hLTBP4 Tg+. To generate the hLTBP4 Tg+ mice, a single, unmodified BAC clone (clone number CDT-2166J9) was used to inject a fertilized oocyte using conventional methodology [see, e.g., Heintz, Nat Rev Neurosci. 2(12): 861-70 (2001)]. The human sequence of this BAC (Genbank accession number AC010412.9; SEQ ID NO: 7) contains 155085 bp from chromosome 19. The LTBP4 gene spans from 19891 to 57891 bp of this clone. Eleven founder lines were evaluated by PCR and found to contain the full-length human LTBP4, including promoter regions. Six lines were chosen for breeding to ensure that these mice were passing the BAC in their germline. By RT-PCR, it was determined that the human LTBP4 mRNA was expressed in cardiac and skeletal muscle of the transgenic mice. At present, there is no antibody that distinguishes human LTBP4 from mouse LTBP4; human and mouse LTBP4 are 98% similar. Overall, LTBP4 expression may be slightly elevated in hLTBP4 Tg+ mice compared to littermate controls. hLTBP4 Tg+ mice are outwardly normal and breed normally. Histological examination showed grossly normal histology in brain, kidney, lung, heart and muscle. Interestingly, hLTBP4 Tg+ skeletal muscle fibers were significantly larger than littermate control transgene negative mice. It is contemplated that even modest overexpression of LTBP4 may be sufficient to bind other TGFβ superfamily members such as myostatin, and sequestration of myostatin would inhibit myostatin activity and would be expected to result in larger muscle fibers.

Example 3

LTBP4 Peptides and Antibody Generation

Antibodies were generated using multiple different peptides including the mouse and human LTBP4 sequences (see Table 1, below). Each of the peptides in Table 1 cross reacts to the human protein as determined by immunoblotting. A longer LTBP4 peptide, FLPTHRLEPRPEPRPDPRPGPEL-PLPSIPAWTGPEIPESGPSS (SEQ ID NO: 6), is also contemplated for use according to the disclosure. Humanized monoclonal antibodies directed against LTBP4 will also be generated.

TABLE 1

LTBP4 peptides used or antibody generation. "Species" indicates antibody source.

| Antibody Name | Species | Peptide Used | Antigen Source | Western Blot Activity | Results on Proteolysis |
|---|---|---|---|---|---|
| mLTBP4d36-829 | chicken | EPRPRPEPRPQPESQPWP (SEQ ID NO: 2) | Mouse - D2 | +++ | NA |
| mLTBP4d36-830 | chicken | EPRPRPEPRPQPESQPWP (SEQ ID NO: 2) | Mouse - D2 | ++ | NA |
| hLTBP4pr-831 | chicken | EPRPEPRPDPRPGPELP (SEQ ID NO: 3) | Human | ++++ | positive |
| hLTBP4pr-832 | chicken | EPRPEPRPDPRPGPELP (SEQ ID NO: 3) | Human | ++ | NA |
| mLTBP4ins-24226 | rabbit | ESQPRPESRPRPESQPWP (SEQ ID NO: 4) | Mouse - 129 | ++ | NA |
| mLTBP4ins-24226 | rabbit | ESQPRPESRPRPESQPWP (SEQ ID NO: 4) | Mouse - 129 | ++ | NA |
| hLTBP4(511-530) 28200 | rabbit | EPRPEPRPDPRPGPELPLP (SEQ ID NO: 5) | Human | NA | NA |
| hLTBP4(511-530) 28199 | rabbit | EPRPEPRPDPRPGPELPLP (SEQ ID NO: 5) | Human | NA | NA |

The hLTBP4 Tg+ animal will be bred to the mouse mdx model of Duchenne Muscular Dystrophy and the phenotype and TGFβ signaling capacity will be assessed. Ten mice of each genotype (hLTBP4 Tg+/mdx, mdx, hLTBP4+ and WT) will be generated. Basic neuromuscular function will be evaluated using SHIRPA protocols. SHIRPA is a combination of neurological tests that assess neuromuscular function [Rafael et al., Mamm Genome. 11(9): 725-8 (2000)]. For example and without limitation, grip strength, running capacity, wire maneuver and rotorod are basic tests that will be used to assess muscle function. In addition, cardiac function will be assessed using echocardiography, and histology will be performed to evaluate fibrosis and membrane permeability using Evans blue dye uptake. All analyses will be conducted on male mice at 8 weeks of age. A cohort of mice will also be aged to examine the effect on mice at a later time point(s). Fibroblasts will also be isolated from these mice to determine their level of SMAD signaling using methods as previously described [Heydemann et al., J Clin Invest. 119(12): 3703-12 (2009)]. It is expected that insertion of the human LTBP4 will result in increased SMAD signaling and enhancement of the mdx phenotype.

Table 1 shows that each antibody recognized a protein the size of human LTBP4, as determined by immunoblot. The data in the table also indicates that the antibody raised against the human sequence (SEQ ID NO: 3) protects LTBP4 against proteolysis in vitro (FIG. 6, described below) and, given the cross reactivity, the other anti-hLTBP4 antibodies are also expected to protect hLTBP4 from proteolysis. Enzyme-linked immunosorbent assays (ELISA) will also be performed to compare the relative affinity of antibodies to each peptide using serum and purified antibodies.

Proteolysis of LTBP4 can be Inhibited with LTBP4 Antibodies

It was contemplated that the insertion/deletion polymorphism in murine Ltbp4 discussed hereinabove indicated that the proline-rich region is important since the presence or absence of 12 additional amino acids in this region explains its ability to reduce membrane leak and suppress fibrosis, two activities that were attributed to LTBP4's ability to sequester TGFβ. This position is consistent with the differential sensitivity to proteolysis of the various forms of LTBP4 and the associated TGFβ activity in the form of nuclear pSMAD [Heydemann et al., *J Clin Invest.* 119: 3703-12 (2009)].

Figure 5:
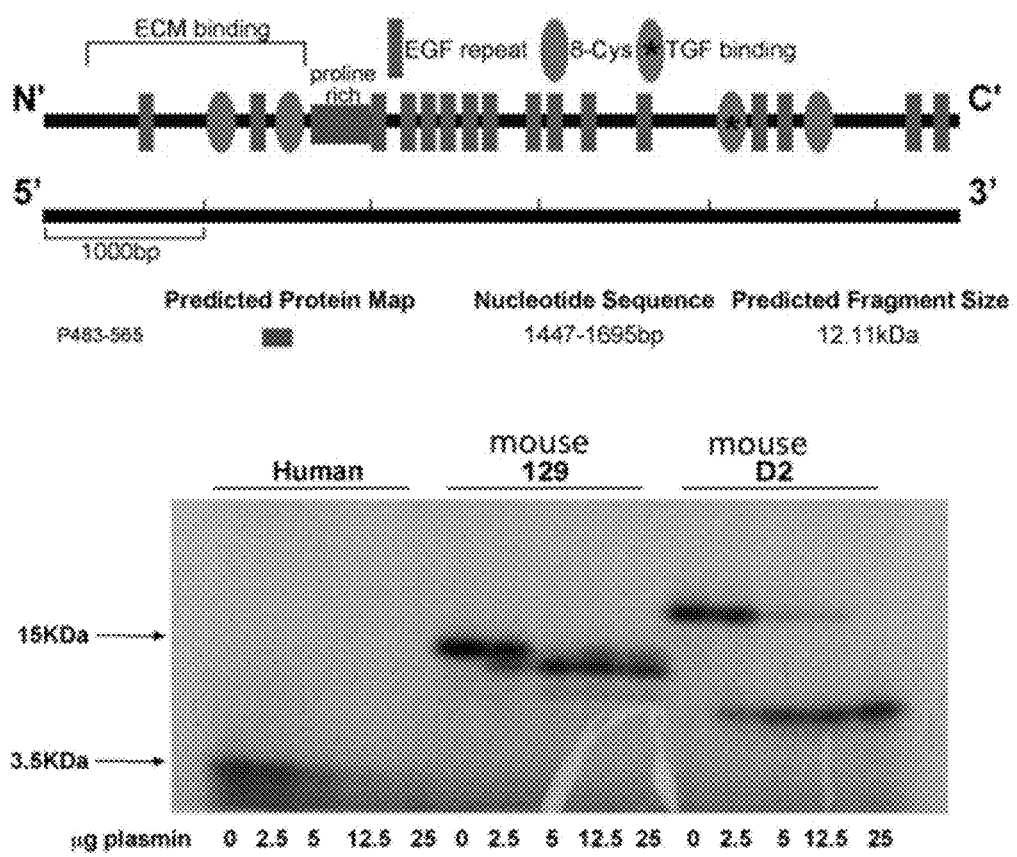
FIG. 5 depicts that the proline-rich region of human LTBP4 is more easily cleaved than murine LTBP4.
Figure 6:
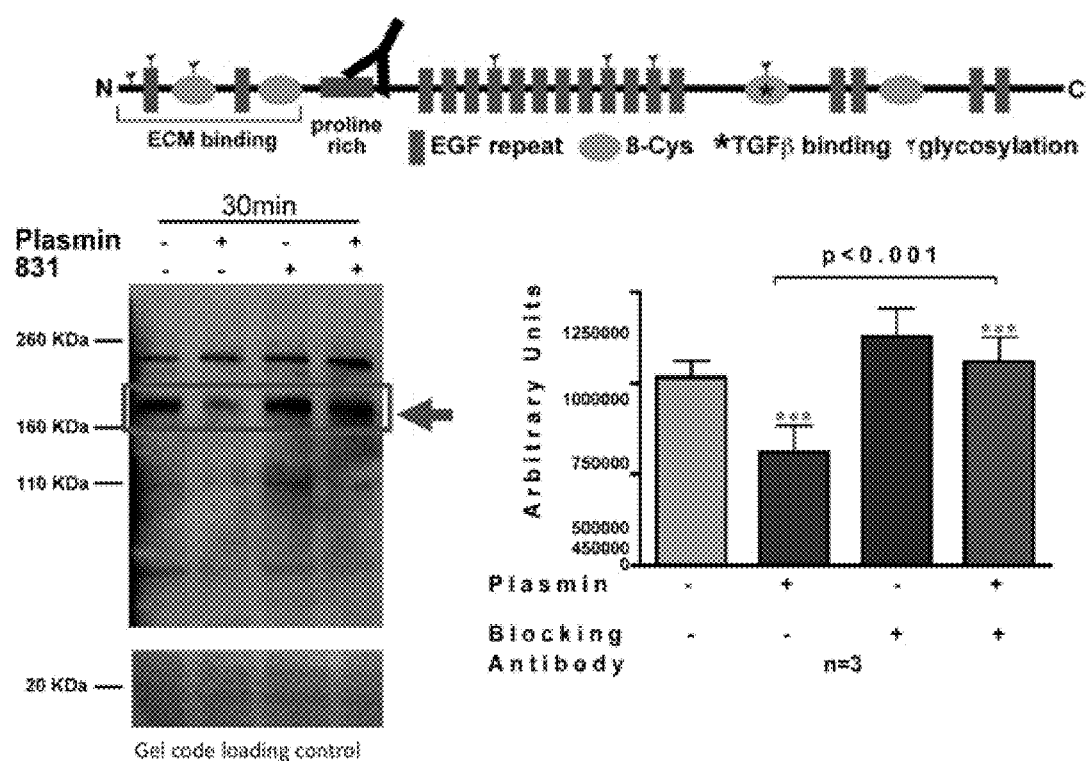
FIG. 6 shows results of a study using a blocking antibody that inhibited cleavage of full-length LTBP4. A nonspecific blocking antibody showed no effect. Assays were conducted in triplicate with significant inhibition of proteolysis observed.

To demonstrate that the proline-rich region of human LTBP4 was susceptible to proteolysis, protein domains were expressed using in vitro transcription and translation according to methods as previously described [Heydemann et al., J Clin Invest. 119(12): 3703-12 (2009)]. By design, only the carboxy-terminus of these expressed proteins was labeled. The expressed fragments were exposed to plasmin. Murine LTBP4 with the 12-amino-acid insertion was largely resistant to proteolysis while the murine LTBP4 deleted for the 12 amino acids was readily degraded (FIG. 5, middle and right lanes). The human LTBP4 was most readily degraded (FIG. 5, left lanes). Similar results were obtained with elastase. It is contemplated that this region (i.e., the region included in the TP and TP2E sequences) is a general serine protease target. Antibodies were generated that were directed at the proline-rich region and it was found that these antibodies inhibited LTBP4 cleavage in vitro (FIG. 6). A nonspecific antibody generated from the same species showed no blocking effect. Additional anti-LTBP4 antibodies have been generated, and Fab fragments will be purified and tested because these fragments are expected to be more useful for in vivo delivery.

Full-length LTBP4 protein, produced from cultured cells, is also susceptible to plasmin proteolysis (FIG. 6). With muscle injury, such as the injury that occurs in DMD, release of proteases into the extracellular matrix is expected to result in LTBP4 cleavage. The sources of these proteases in vivo may be inflammatory cells, fibroblasts or the myofibers. Increased LTBP4 cleavage was shown to correlate with increased fibrosis, increased muscle membrane leak, increased muscle weakness and increased TGFβ signaling [Heydemann et al., J Clin Invest. 119(12): 3703-12 (2009)]. Reduction of TGFβ signaling was shown to improve outcome in muscular dystrophy [Cohn et al., Nat. Med. 13(2): 204-10 (2007); Goldstein et al., Hum Mol. Genet. 20(5): 894-904 (2011)].

This example demonstrates that proteolysis of the proline-rich region of LTBP4 can be inhibited by antibodies provided herein.

Example 4

Transgenic Mice Harboring Human Ltbp4

Figure 7:
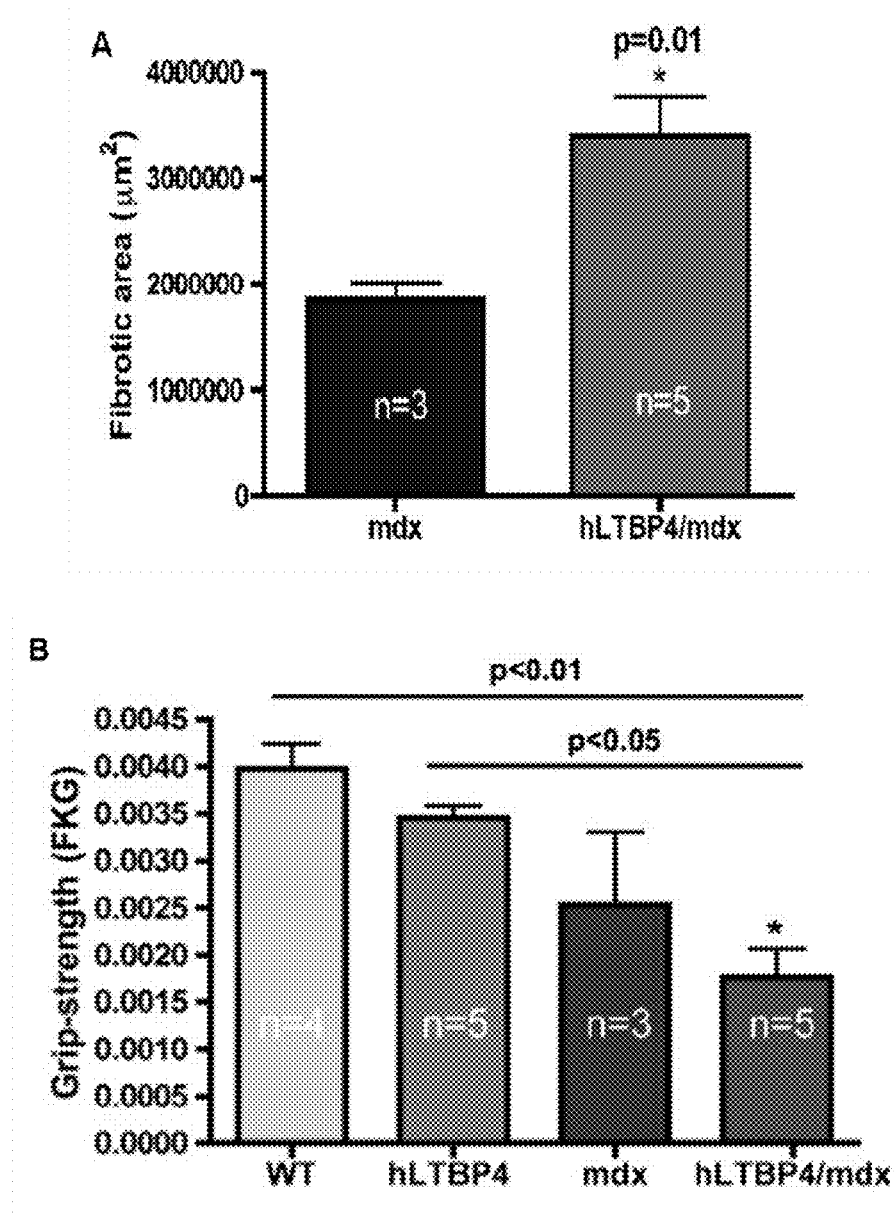
FIG. 7 shows results of a study wherein a bacterial artificial transgene expressing human LTBP4 (hLTBP4 Tg) was crossed into the mouse mdx model of Duchenne Muscular Dystrophy. (A) hLTBP4/mdx mice have enhanced fibrosis in their muscles as determined grossly through histology and by direct quantitation. When quantified, fibrotic area was increased in hLTBP4/mdx mice compared to littermate mdx mice. (B) hLTBP4/mdx mice have reduced grip strength. Grip strength was compared between hLTBP4/mdx mice and mdx mice to determine whether the human LTBP4 gene worsens the muscle disease seen in mdx mice.

A human bacterial artificial chromosome (BAC) carrying the full length human LTBP4 gene was isolated and characterized. This BAC was injected into mice and several lines of transgenic mice were characterized. Human LTBP4 (hLTBP4-BAC) transgenic mice were bred to mdx mice. The human LTBP4 BAC in the normal background resulted in larger myofiber diameter, a sign of hypertrophy. When the human LTBP4 BAC was in the mdx background, it resulted in enhanced fibrosis in skeletal and cardiac muscle as well as reduced grip strength, relative to control mice that did not carry the transgene (FIG. 7). This supports the observation that the human LTBP4 sequence, with its larger deletion in the proline-rich region, enhances the muscular dystrophy phenotype. These mice will be further used to test whether antibodies directed against human LTBP4 can reduce muscular dystrophy fibrosis and muscle membrane leakage.

Example 5

In Vivo Studies

Short-term studies are conducted in dystrophic mice (i.e., mdx and limb girdle muscular dystrophy (LGMD)) to determine safety and efficacy of inhibiting LTBP4 cleavage in vivo. Animals are treated from 3 weeks to 8 weeks of age with antibody injections, three times weekly, delivered via intraperitoneal injection. Dose responsiveness is determined. Echocardiography, plethysmography, muscle harvest and ex vivo muscle mechanics are conducted on treated animals and controls. Target tissues are studied, including heart, diaphragm, quadriceps, gluteus/hamstrings, gastrocnemius/soleus, triceps and abdominal muscles, according to previously identified protocols [Heydemann et al., Neuromuscul Disord. 15: 601-9 (2005); Heydemann, et al., J Clin Invest. 119: 3703-12 (2009); Swaggart et al., *Physiol Genomics*. 43: 24-31 (2011)]. TGFβ signaling is also determined.

Long-term studies are conducted in dystrophic mice to determine the safety and efficacy of the treatment. Once dosing has been determined, cohorts of mice are treated from 3 weeks until 1 year of age. A similar analysis of efficacy are undertaken, as discussed above (i.e., echocardiography, plethysmography, muscle harvest and ex vivo muscle mechanics). Analysis of other organs, including lung, colon, kidney, brain, and other tissues, is included. Mice that are null for LTBP4 develop cardiomyopathy, pulmonary fibrosis and colon cancer. Because LTBP4 is not ablated in these studies, these cardiomyopathy, pulmonary fibrosis and colon cancer defects are not expected, consistent with the results of the genetic studies described above. Nonetheless, off-target tissues are also analyzed.

The studies described above are expected to show that inhibition of LTBP4 cleavage in vivo results in decreased TGFβ signaling, which is further expected to lead to a decrease in membrane permeability as well as a decrease in fibrosis in the muscles of dystrophic mice. These results will be evidenced by an improvement or lack of decline in therapeutic endpoints as described herein, thereby establishing that blockage of LTBP4 proteolysis is a robust therapeutic in the treatment of TGFβ superfamily protein-related diseases.

Example 6

LTBP4 Interacts with Myostatin In Vitro

The ability of LTBP4 to directly interact with myostatin, a TGF-β superfamily member, was also investigated. The methods used to investigate the interaction were as follows. Full length LTBP4 was cloned into an expression vector (pcDNA3.1, Life Technologies (Invitrogen), Grand Island, N.Y.) and the XPRESS™ epitope tag (Life Technologies (Invitrogen), Grand Island, N.Y.) was added to its 5' end/amino terminus. Full-length myostatin, encoding the propeptide and mature regions, was tagged at its 3' end/carboxy terminus with the myc epitope tag. Both plasmids were introduced into HEK293 (Human Embryonic Kidney 293) cells. The cells were lysed and the proteins were blotted or immunoprecipitated with either antibody 28200 or, in a separate experiment, antibody 28199 (see Table 1). Both of these rabbit polyclonal antibodies are directed at the LTBP4 proline-rich region. The immunoprecipitated material was then blotted with the anti-myc antibody, showing that myostatin associates with LTBP4 (FIG. 8).

This Example shows that LTBP4 is able to directly interact with myostatin. The results indicate that, by inhibiting the proteolysis of LTBP4 according to the present disclosure, one can sequester myostatin and prevent its activation and resultant downstream signaling. Because myostatin is a known negative regulator of muscle growth, the inhibition of myostatin signaling is expected to result in increased muscle growth and increased muscle strength.

Example 7

Expression of Human LTBP4 in Mice Leads to Enhanced Damage after Cardiotoxin Injury Mice were generated to express the human LTBP4 gene on a bacterial artificial chromosome, and these transgenic mice were referred to as hLTBP4 Tg+ mice. The human LTBP4 protein is more readily proteolyzed because of its shorter proline-rich region. This increased proteolysis leads to enhanced damage in muscle due to increased TGFβ release. Cardiotoxin was injected into the tibialis anterior muscle of normal (WT w/CTX) and hLTBP4 transgenic mice (hLTBP4 Tg+ w/CTX). Transgenic mice displayed enhanced injury after cardiotoxin injury seen as greater inflammatory mononuclear cell infiltrate and fibrosis and fat deposition into the injured muscle (FIG. 9A), similar to what is seen in muscular dystrophy.

Normal (WT) and hLTBP4 muscle were injected with cardiotoxin to induce injury. Immunoblotting with an anti-LTBP4 antibody showed increased levels of LTBP4 protein induced by injury in both normal and in hLTBP4 transgenic muscle (FIG. 9B). hLTBP4 muscle was also found to be associated with increased TGFβ signaling seen as nuclear localized phosphorylated SMAD.

The results showed that expression of human LTBP4 protein in muscle leads to enhanced muscle damage following cardiotoxin injury.

Example 8

Anti-LTBP4 Antibodies Mitigate Muscle Injury In Vivo

To test whether anti-LTBP4 antibody mitigated skeletal muscle injury in muscular dystrophy, experiments were carried out using hLTBP4/mdx mice. Cardiotoxin, which is known to cause necrosis of skeletal muscle cells, was injected into the tibialis anterior muscle to induce enhanced injury. This injury model resolves within 2 weeks because a low-volume injection of 10 µl is used. hLTBP4/mdx mice (8 weeks of age) were pretreated on day 0 with either (i) PBS or (ii) antibody to LTBP4-831 antibody at 5 mg/Kg intraperitoneally. On day 1, cardiotoxin was injected into the tibialis anterior muscle. LTBP4-831 antibody was injected on days 1, 3, and 5, each time delivering a 5 mg/Kg dose intraperitoneally. Mice were sacrificed on day 7 and tibialis anterior muscle was harvested for study. The experimental design of sacrificing the mice on day 7 was used because the LTBP4-831 antibody is a chicken antibody that was expected to be recognized as foreign after 2-3 weeks.

Following harvest, the muscle was processed for analysis by snap-freezing in liquid nitrogen-cooled isopentane. The frozen muscle was sectioned and the sections were subjected to hematoxylin and eosin (H&E) staining.

Results of the experiment showed that, compared to PBS-injected mice, LTBP4-831 antibody-treated mice showed reduced central nucleation and reduced fibrosis (FIGS. 10A and 10B). Centralized nuclei are indicative of newly formed (i.e., regenerating) myofibers, and reduced central nucleation in the muscle of animals that were administered LTBP4-831 antibody provides evidence that the antibody mitigated muscle injury in the mice.

Example 9

Increased Inflammatory Infiltrate in hLTBP4/Mdx Mice Compared to Mdx Mice

Quadriceps muscles obtained from both mdx and hLTPB4/mdx mice were stained with F4/80 antibodies that recognize and bind to activated macrophages (shown as speckles throughout the muscle). The immunofluorescent staining showed an increase in activated macrophages in hLTBP4/mdx muscle compared to mdx muscle (FIG. 11A). hLTBP4/mdx muscle showed an increase in cleaved LTBP4 protein compared to mdx, while little LTBP4 protein was seen in wild-type and hLTBP4 muscle in the absence of injury or muscular dystrophy (FIG. 11B).

The results showed that there is an increase in inflammatory cell infiltrate in the muscle of hLTBP4/mdx mice versus mdx mice. The results also showed that hLTBP4/mdx muscle possessed increased cleaved LTBP4 protein relative to mdx muscle.

The disclosed subject matter has been described with reference to various specific and preferred embodiments and techniques. It should be understood, however, that many variations and modifications may be made while remaining within the spirit and scope of the disclosed subject matter. All references cited herein are hereby incorporated by reference in their entireties, or to the extent that they provide relevant disclosure, as would be ascertained from context.

What is claimed is:

1. An isolated antibody that specifically binds to the sequence set forth in SEQ ID NO: 6.

2. A pharmaceutical formulation comprising the antibody of claim 1 and a pharmaceutically acceptable carrier or diluent.

3. The formulation of claim 2, further comprising a second agent, wherein the second agent is selected from the group consisting of a modulator of an inflammatory response, a promoter of muscle growth, a chemotherapeutic agent and a modulator of fibrosis.

4. A kit comprising the antibody of claim 1, a pharmaceutically acceptable carrier or diluent, and instructions for use.

5. The kit of claim 4, further comprising a second agent, wherein the second agent is selected from the group consisting of a modulator of an inflammatory response, a promoter of muscle growth, a chemotherapeutic agent and a modulator of fibrosis.

6. A method of treating a patient having Duchenne Muscular Dystrophy, Limb Girdle Muscular Dystrophy, Becker Muscular Dystrophy, myopathy, pulmonary fibrosis, cardiomyopathy, acute lung injury, acute skeletal muscle injury, or acute myocardial injury, comprising administering the antibody of claim 1 to the patient.

7. The method of claim 6 further comprising administering a second agent, wherein the second agent is selected from the group consisting of a modulator of an inflammatory response, a promoter of muscle growth, a chemotherapeutic agent, and a modulator of fibrosis.

8. The method of claim 7 wherein the promoter of muscle growth is selected from the group consisting of insulin-like growth factor-1 (IGF-1), Akt/protein kinase B, clenbuterol, creatine, decorin, a steroid, and testosterone.

9. The method of claim 7 wherein the second agent is selected from the group consisting of an antibody to growth and differentiation factor-8 (GDF-8), an antibody to a GDF-8 receptor, a soluble GDF-8 receptor, a GDF-8 propeptide, follistatin, and a follistatin-domain-containing protein.

10. The method of claim 7 wherein the modulator of an inflammatory response is cyclosporin.

11. The method of claim 7 wherein the chemotherapeutic agent is selected from the group consisting of an alkylating agent, a nitrosourea, a ethylenimines/methylmelamine, an alkyl sulfonate, a triazine, an antimetabolite, a pyrimidine analog, a purine analog, an antimitotic drug, an epipodophylotoxin, an antibiotic, L-asparaginase, interferon-alpha, interleukin-2 (IL-2), granulocyte colony stimulating factor (G-CSF), granulocyte macrophage colony stimulating factor (GM-CSF), cisplatin, carboplatin, en anthracenedione, substituted urea, a methylhydrazine derivative, an adrenocortical suppressant, an adrenocorticosteroid antagonist, progestin, estrogen, antiestrogen, an androgen, an antiandrogen, a gonadotropin-releasing hormone analog, and a non-steroidal antiandrogen.

12. The method of claim 7 wherein the modulator of fibrosis is selected from the group consisting of pirfenidone, an angiotensin-converting-enzyme (ACE) inhibitor, an angiotensin receptor blocker, and an aldosterone antagonist.

* * * * *

UNITED STATES PATENT AND TRADEMARK OFFICE
CERTIFICATE OF CORRECTION

PATENT NO. : 9,873,739 B2
APPLICATION NO. : 13/957100
DATED : January 23, 2018
INVENTOR(S) : Elizabeth M. McNally et al.

Page 1 of 1

It is certified that error appears in the above-identified patent and that said Letters Patent is hereby corrected as shown below:

On the Title Page

At item (72), Line 1, "Elizabeth McNally," should be -- Elizabeth M. McNally, --.

In the Claims

At Column 184, Line 15, "a ethylenimines/methylmelamine," should be -- an ethylenimine/methylmelamine, --.

At Column 184, Lines 17-18, "epipodophylotoxin," should be -- epipodophyllotoxin, --.

At Column 184, Line 21, "en anthracenedione," should be -- an anthracenedione, --.

Signed and Sealed this
Twelfth Day of June, 2018

Andrei Iancu
*Director of the United States Patent and Trademark Office*